US012649756B2

(12) United States Patent
Han et al.

(10) Patent No.: US 12,649,756 B2
(45) Date of Patent: Jun. 9, 2026

(54) ORGANOMETALLIC COMPOUND AND LIGHT-EMITTING DEVICE INCLUDING THE SAME

(71) Applicant: Samsung Display Co., Ltd., Yongin-si (KR)

(72) Inventors: Junghoon Han, Yongin-si (KR); Iljoon Kang, Yongin-si (KR); Soobyung Ko, Yongin-si (KR); Eunsoo Ahn, Yongin-si (KR); Jaesung Lee, Yongin-si (KR); Hyunjung Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 947 days.

(21) Appl. No.: 17/824,147

(22) Filed: May 25, 2022

(65) Prior Publication Data

US 2023/0139906 A1 May 4, 2023

(30) Foreign Application Priority Data

Sep. 10, 2021 (KR) ........................ 10-2021-0121196

(51) Int. Cl.

| | |
|---|---|
| ***H01L 51/54*** | (2006.01) |
| ***C07C 13/62*** | (2006.01) |
| ***C07C 15/28*** | (2006.01) |
| ***C07C 15/30*** | (2006.01) |
| ***C07C 15/38*** | (2006.01) |
| ***C07C 211/54*** | (2006.01) |
| ***C07D 213/38*** | (2006.01) |
| ***C07D 235/08*** | (2006.01) |
| ***C07D 239/26*** | (2006.01) |
| ***C07D 249/08*** | (2006.01) |
| ***C07D 251/24*** | (2006.01) |
| ***C07D 307/91*** | (2006.01) |
| ***C07D 333/76*** | (2006.01) |
| ***C07D 401/04*** | (2006.01) |
| ***C07D 401/10*** | (2006.01) |
| ***C07D 401/14*** | (2006.01) |

(Continued)

(52) U.S. Cl.

CPC .......... *C07F 15/0086* (2013.01); *C07C 13/62* (2013.01); *C07C 15/28* (2013.01); *C07C 15/30* (2013.01); *C07C 15/38* (2013.01); *C07C 211/54* (2013.01); *C07D 213/38* (2013.01); *C07D 235/08* (2013.01); *C07D 239/26* (2013.01); *C07D 249/08* (2013.01); *C07D 251/24* (2013.01); *C07D 307/91* (2013.01); *C07D 333/76* (2013.01); *C07D 401/04* (2013.01); *C07D 401/10* (2013.01); *C07D 401/14* (2013.01); *C07D 403/10* (2013.01); *C07D 403/14* (2013.01); *C07D 487/04* (2013.01); *C07D 491/048* (2013.01); *C07D 495/04* (2013.01); *C07D 519/00* (2013.01); *H10K 85/342* (2023.02); *H10K 85/346* (2023.02); *H10K 85/615* (2023.02); *H10K 85/622* (2023.02); *H10K 85/624* (2023.02); *H10K 85/631* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 50/11* (2023.02); *H10K 50/155* (2023.02); *H10K 50/165* (2023.02); *H10K 2102/351* (2023.02); *H10K 2102/361* (2023.02)

(58) Field of Classification Search

None

See application file for complete search history.

(56) References Cited

U.S. PATENT DOCUMENTS 7,381,479 B2 6/2008 Lamansky et al.
7,393,599 B2 7/2008 Thompson et al.

(Continued)

FOREIGN PATENT DOCUMENTS

CN 104370974 2/2015
CN 109748938 A 5/2019

(Continued)

OTHER PUBLICATIONS

Notice of Allowance dated Nov. 27, 2025 for corresponding KR Patent Application No. 10-2021-0121196, 3pp.

*Primary Examiner* — Andrew K Bohaty

(74) *Attorney, Agent, or Firm* — Womble Bond Dickinson (US) LLP

(57) ABSTRACT

An organometallic compound represented by Formula 1, which is explained in the specification, is provided. A light-emitting device is provided, which includes a first electrode, a second electrode facing the first electrode, an interlayer between the first electrode and the second electrode and including an emission layer, and the organometallic compound. An electronic apparatus including the light-emitting device is also provided:

[Formula 1]

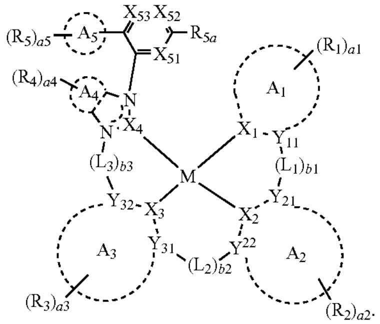

20 Claims, 3 Drawing Sheets

(51) Int. Cl.

| | |
|---|---|
| ***C07D 403/10*** | (2006.01) |
| ***C07D 403/14*** | (2006.01) |
| ***C07D 487/04*** | (2006.01) |
| ***C07D 491/048*** | (2006.01) |
| ***C07D 495/04*** | (2006.01) |
| ***C07D 519/00*** | (2006.01) |
| ***C07F 15/00*** | (2006.01) |
| ***H10K 85/30*** | (2023.01) |
| ***H10K 85/60*** | (2023.01) |
| *H10K 50/11* | (2023.01) |
| *H10K 50/155* | (2023.01) |
| *H10K 50/165* | (2023.01) |
| *H10K 102/00* | (2023.01) |

(56) References Cited

U.S. PATENT DOCUMENTS

| | | | |
|---|---|---|---|
| 7,585,573 | B2 | 9/2009 | Lee et al. |
| 7,776,458 | B2 | 8/2010 | Ragini et al. |
| 8,106,199 | B2 | 1/2012 | Jabbour et al. |
| 8,389,725 | B2 | 3/2013 | Li et al. |
| 8,669,364 | B2 | 3/2014 | Li et al. |
| 8,680,760 | B2 | 3/2014 | Cheng et al. |
| 8,816,080 | B2 | 8/2014 | Li et al. |
| 8,846,940 | B2 | 9/2014 | Li et al. |
| 8,946,417 | B2 | 2/2015 | Jian et al. |
| 9,051,344 | B2 | 6/2015 | Lin et al. |
| 9,076,974 | B2 | 7/2015 | Li et al. |
| 9,203,039 | B2 | 12/2015 | Li et al. |
| 9,221,857 | B2 | 12/2015 | Li et al. |
| 9,224,963 | B2 | 12/2015 | Li et al. |
| 9,238,668 | B2 | 1/2016 | Li et al. |
| 9,312,502 | B2 | 4/2016 | Li et al. |
| 9,324,957 | B2 | 4/2016 | Li et al. |
| 9,382,273 | B2 | 7/2016 | Li et al. |
| 9,425,415 | B2 | 8/2016 | Li et al. |
| 9,698,359 | B2 | 7/2017 | Li et al. |
| 9,899,614 | B2 | 2/2018 | Li et al. |
| 2005/0287394 | A1 | 12/2005 | Yang et al. |
| 2008/0018221 | A1 | 1/2008 | Egen et al. |
| 2012/0121936 | A1 | 5/2012 | Baek et al. |
| 2014/0309428 | A1 | 10/2014 | Egen et al. |
| 2015/0010555 | A1 | 1/2015 | Seehra et al. |
| 2015/0105556 | A1 | 4/2015 | Li et al. |
| 2018/0037503 | A1 | 2/2018 | Dhyllon |
| 2018/0375036 | A1 | 12/2018 | Chen et al. |
| 2019/0119312 | A1 | 4/2019 | Chen et al. |
| 2020/0119289 | A1 | 4/2020 | Lin et al. |
| 2020/0392173 | A1 | 12/2020 | Bae et al. |
| 2021/0050530 | A1 | 2/2021 | Wu et al. |
| 2021/0104691 | A1 | 4/2021 | Lee et al. |

FOREIGN PATENT DOCUMENTS

| | | | |
|---|---|---|---|
| EP | 3 715 353 | A1 | 9/2020 |
| JP | 2007-45742 | | 2/2007 |
| KR | 10-0730115 | | 6/2007 |
| KR | 10-2015-0043225 | A | 4/2015 |
| KR | 10-2020-0116039 | A | 10/2020 |
| KR | 10-2020-0143236 | | 12/2020 |
| KR | 10-2021-0036829 | | 4/2021 |
| WO | 2012/121936 | | 9/2012 |

ORGANOMETALLIC COMPOUND AND LIGHT-EMITTING DEVICE INCLUDING THE SAME

CROSS-REFERENCE TO RELATED APPLICATION(S)

This application claims priority to and benefits of Korean Patent Application No. 10-2021-0121196 under 35 U.S.C. § 119, filed on Sep. 10, 2021 in the Korean Intellectual Property Office, the entire contents of which are incorporated herein by reference.

BACKGROUND

1. Technical Field

Embodiments relate to an organometallic compound and a light-emitting device including the organometallic compound.

2. Description of the Related Art

Among light-emitting devices, organic light-emitting devices are self-emissive devices that have wide viewing angles, high contrast ratios, short response times, and excellent characteristics in terms of luminance, driving voltage, and response speed, compared to devices in the art.

Organic light-emitting devices may include a first electrode located on a substrate, and a hole transport region, an emission layer, an electron transport region, and a second electrode sequentially stacked on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. These excitons transition from an excited state to a ground state to thereby generate light.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Provided are an organometallic compound having low driving voltage, excellent luminescence efficiency, long lifespan, and excellent color purity, and a light-emitting device using the same.

Additional aspects will be set forth in part in the description which follows and, in part, will be apparent from the description, or may be learned by practice of the embodiments of the disclosure.

According to embodiment, provided is a light-emitting device which may include a first electrode, a second electrode facing the first electrode, an interlayer arranged between the first electrode and the second electrode and including an emission layer, and an organometallic compound represented by Formula 1.

[Formula 1]

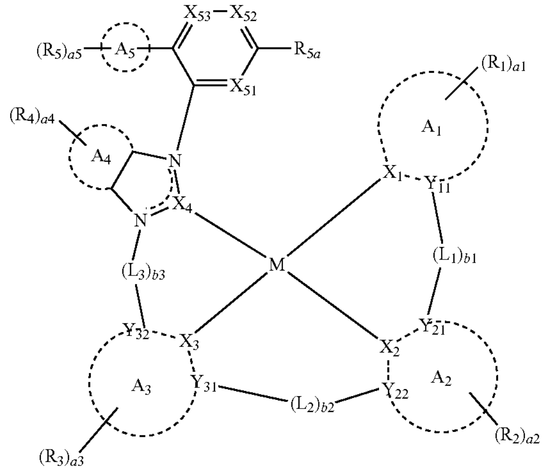

In Formula 1,

M may be platinum (Pt), palladium (Pd), nickel (Ni), copper (Cu), silver (Ag), gold (Au), rhodium (Rh), iridium (Ir), ruthenium (Ru), osmium (Os), titanium (Ti), zirconium (Zr), hafnium (Hf), europium (Eu), terbium (Tb), or thulium (Tm), $X_1$ may be C, N, O, or S, $X_2$ to $X_4$, $Y_{11}$, $Y_{21}$, $Y_{22}$, $Y_{31}$, and $Y_{32}$ may each independently be C or N, $X_{51}$ may be $C(R_{51})$ or N, $X_{52}$ may be $C(R_{52})$ or N, and $X_{53}$ may be $C(R_{53})$ or N, $A_1$ to $A_5$ may each independently be a $C_3$-$C_{60}$ carbocyclic group or a $C_1$-$C_{60}$ heterocyclic group, $L_1$ to $L_3$ may each independently be a single bond, a double bond, *—$N(Z_{11})$—*', *—$B(Z_{11})$—*', *—$P(Z_{11})$—*', *—$C(Z_{11})(Z_{12})$—*', *—$Si(Z_{11})(Z_{12})$—*', *—$Ge(Z_{11})(Z_{12})$—*', *—S—*'*—Se—*'*—O—*', *—C(=O)—*', *—S(=O)—*', *—$S(=O)_2$—*'*—$C(Z_{11})$=*', *=$C(Z_{11})$—*', *—$C(Z_{11})=C(Z_{12})$—*', *—C(=S)—*', or *—C≡C—*',

* and *' each indicate a binding site to a neighboring atom, b1 to b3 may each independently be an integer from 1 to 3, $R_1$ to $R_5$, $R_{51}$ to $R_{53}$, $Z_{11}$, and $Z_{12}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$, $R_{5a}$ may be deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$, a1 to a5 may each independently be an integer from 0 to 10, when a1 is 2 or more, two $R_1$(s) of two or more $R_1$(s) may optionally be bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a2 is 2 or more, two $R_2$(s) of two or more $R_2$(s) may optionally be bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{10a}$ may be:

deuterium, —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{11})(Q_{12})(Q_{13})$, —$N(Q_{11})(Q_{12})$, —$B(Q_{11})(Q_{12})$, —$P(Q_{11})(Q_{12})$, —$C(=O)(Q_{11})$, —$S(=O)(Q_{11})$, —$S(=O)_2(Q_{11})$, —$P(=O)(Q_{11})(Q_{12})$, —$P(=S)(Q_{11})(Q_{12})$, or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{21})(Q_{22})(Q_{23})$, —$N(Q_{21})(Q_{22})$, —$B(Q_{21})(Q_{22})$, —$P(Q_{21})(Q_{22})$, —$C(=O)(Q_{21})$, —$S(=O)(Q_{21})$, —$S(=O)_2(Q_{21})$, —$P(=O)(Q_{21})(Q_{22})$, —$P(=S)(Q_{21})(Q_{22})$, or any combination thereof, or —$Si(Q_{31})(Q_{32})(Q_{33})$, —$N(Q_{31})(Q_{32})$, —$B(Q_{31})(Q_{32})$, —$P(Q_{31})(Q_{32})$, —$C(=O)(Q_{31})$, —$S(=O)(Q_{31})$, —$S(=O)_2(Q_{31})$, —$P(=O)(Q_{31})(Q_{32})$, or —$P(=S)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be hydrogen, deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, the interlayer may further include a hole transport region between the first electrode and the emission layer and an electron transport region between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In an embodiment, the emission layer may include the organometallic compound represented by Formula 1.

In an embodiment, the emission layer may emit blue light having a maximum emission wavelength in a range of about 410 nm to about 500 nm.

In an embodiment, the interlayer may include a first compound which is the organometallic compound represented by Formula 1; and a second compound including a group represented by Formula 2, a third compound represented by Formula 3, a fourth compound including a group represented by Formula 4, or any combination thereof. Formula 2, Formula 3, and Formula 4 are explained below. The first compound, the second compound, and the third compound may be different from one another.

The first compound, the second compound, and the fourth compound may be different from one another. The third compound and the fourth compound may be identical to or different from each other.

In an embodiment, the emission layer may include a dopant and a host, the dopant may include the first compound, and the host may include the second compound, the third compound, the fourth compound, or any combination thereof.

In an embodiment, the emission layer may include a dopant and a host, and the dopant may include the first compound. The host may include the second compound; and at least one of the third compound and the fourth compound.

According to embodiments, provided is an electronic apparatus which may include the light-emitting device and a thin-film transistor. The thin-film transistor may include a source electrode and a drain electrode, and the first electrode of the light-emitting device may be electrically connected to at least one of the source electrode and the drain electrode of the thin-film transistor.

In an embodiment, the electronic apparatus may further include a color filter, a color conversion layer, a touch screen layer, a polarizing layer, or any combination thereof.

According to embodiments, provided is an organometallic compound which may be represented by Formula 1.

In an embodiment, $X_1$ may be N, and $X_2$ to $X_4$ may each be C; or $X_1$ may be O or S, and $X_2$ to $X_4$ may each be C; or $X_1$ to $X_4$ may each be C; or $X_1$, $X_3$, and $X_4$ may each be C, and $X_2$ may be N.

In an embodiment, a bond between $X_1$ and M may be a covalent bond or a coordinate bond, a bond between $X_2$ and M may be a covalent bond, a bond between $X_3$ and M may be a covalent bond, and a bond between $X_4$ and M may be a coordinate bond.

In an embodiment, $X_{51}$ may be $C(R_{51})$, $X_{52}$ may be $C(R_{52})$, and $X_{53}$ may be $C(R_{53})$.

In an embodiment, $A_1$ may be an $X_1$-containing 6-membered ring, an $X_1$-containing 6-membered ring condensed with at least one 5-membered ring, an $X_1$-containing 5-membered ring, or an $X_1$-containing 5-membered ring condensed with at least one 6-membered ring; $A_2$ may be an $X_2$-containing 6-membered ring or an $X_2$-containing 6-membered ring condensed with at least one 5-membered ring; $A_3$ may be an $X_3$-containing 6-membered ring; and $A_4$ may be an $X_4$-containing 6-membered ring.

In an embodiment, an $X_1$-containing 6-membered ring in $A_1$, an $X_1$-containing 6-membered ring condensed with at least one 5-membered ring in $A_1$, an $X_2$-containing 6-membered ring in $A_2$, an $X_2$-containing 6-membered ring condensed with at least one 5-membered ring in $A_1$, an $X_3$-containing 6-membered ring in $A_3$, and an $X_4$-containing 6-membered ring in $A_4$ may each independently be a benzene group, a pyridine group, a pyrimidine group, a pyridazine group, or a pyrazine group; and an $X_1$-containing 5-membered ring in $A_1$ and an $X_1$-containing 5-membered ring condensed with at least one 6-membered ring in $A_1$ may each independently be a pyrrole group, a pyrazole group, an imidazole group, a triazole group, a furan group, an oxazole group, an iso-oxazole group, a thiazole group, an isothiazole group, an oxadiazole group, or a thiadiazole group.

In an embodiment, in organometallic compound represented by Formula 1, at least one of Condition 1 to Condition 4 may be satisfied. Condition 1 to Condition 4 will be explained below.

In an embodiment, $A_5$ may be a $C_6$-$C_{60}$ aryl group or a $C_1$-$C_{60}$ heteroaryl group.

In an embodiment, $L_1$ may be a single bond or *—N($Z_{11}$)—*'; $L_2$ may be *—N($Z_{11}$)—*', *—B($Z_{11}$)—*', *—Si($Z_{11}$)($Z_{12}$)—*', *—S—*', or *—O—*'; $L_3$ may be a single bond; or any combination thereof.

In an embodiment, $R_{5a}$ may be:

deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, an adamantanyl group, a norbornanyl group, a norbornenyl group, a cyclopentenyl group, a cyclohexenyl group, a phenyl group, a naphthyl group, a pyridinyl group, a pyrimidinyl group, or any combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, or a benzocarbazolyl group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, or any combination thereof.

In an embodiment, the organometallic compound may be selected from Compounds 1 to 150, which are explained below.

It is to be understood that the embodiments above are described in a generic and explanatory sense only and not for the purpose of limitation, and the disclosure is not limited to the embodiments described above.

BRIEF DESCRIPTION OF THE DRAWINGS

The above and other aspects, features, and advantages of embodiments of the disclosure will be more apparent from the following description taken in conjunction with the accompanying drawings, in which.

DETAILED DESCRIPTION OF THE EMBODIMENTS

Figure 1:
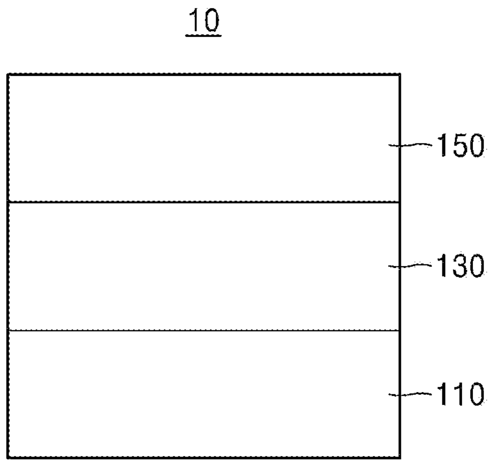
FIG. 1 shows a schematic cross-sectional view of a light-emitting device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

In the specification and the claims, the term "at least one of" is intended to include the meaning of "at least one selected from the group of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element.

Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

According to embodiments, an organometallic compound may be represented by Formula 1:

[Formula 1]

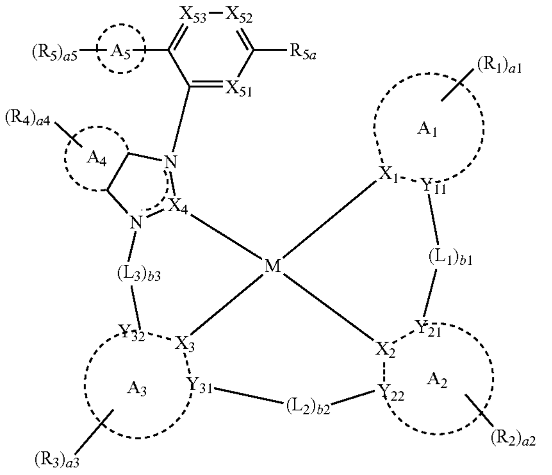

In Formula 1, M may be platinum (Pt), palladium (Pd), nickel (Ni), copper (Cu), silver (Ag), gold (Au), rhodium (Rh), iridium (Ir), ruthenium (Ru), osmium (Os), titanium (Ti), zirconium (Zr), hafnium (Hf), europium (Eu), terbium (Tb), or thulium (Tm).

In an embodiment, M may be platinum (Pt), palladium (Pd), copper (Cu), silver (Ag), gold (Au), rhodium (Rh), iridium (Ir), ruthenium (Ru), or osmium (Os).

In Formula 1, $X_1$ may be C, N, O, or S.

In Formula 1, $X_2$ to $X_4$, $Y_{11}$, $Y_{21}$, $Y_{22}$, $Y_{31}$, and $Y_{32}$ may each independently be C or N.

In an embodiment, $X_1$ may be N, and $X_2$ to $X_4$ may each be C; or $X_1$ may be O or S, and $X_2$ to $X_4$ may each be C; or $X_1$ to $X_4$ may each be C; or $X_1$, $X_3$, and $X_4$ may each be C, and $X_2$ may be N.

In an embodiment, $Y_{11}$ may be C, and $Y_{21}$ may be N; or $Y_{21}$ may be N, and $Y_{21}$ may be C.

In an embodiment, a bond between $X_1$ and M, a bond between $X_2$ and M, and a bond between $X_3$ and M may each independently be a covalent bond or a coordinate bond, and a bond between $X_4$ and M may be a coordinate bond.

In an embodiment, a bond between $X_1$ and M may be a covalent bond or a coordinate bond, a bond between $X_2$ and M may be a covalent bond, a bond between $X_3$ and M may be a covalent bond, and a bond between $X_4$ and M may be a coordinate bond.

In Formula 1, $X_{51}$ may be $C(R_{51})$ or N, $X_{52}$ may be $C(R_{52})$ or N, and $X_{53}$ may be $C(R_{53})$ or N. $R_{51}$ to $R_{53}$ are respectively the same as those described in the specification.

In an embodiment, $X_{51}$ may be $C(R_{51})$, $X_{52}$ may be $C(R_{52})$, and $X_{53}$ may be $C(R_{53})$. $R_{51}$ to $R_{53}$ are respectively the same as those described in the specification.

In Formula 1, $A_1$ to $A_5$ may each independently be a $C_3$-$C_{60}$ carbocyclic group or a $C_1$-$C_{60}$ heterocyclic group.

In an embodiment, $A_1$ may be an $X_1$-containing 6-membered ring, an $X_1$-containing 6-membered ring condensed with at least one 5-membered ring, an $X_1$-containing 5-membered ring, or an $X_1$-containing 5-membered ring condensed with at least one 6-membered ring, $A_2$ may be an $X_2$-containing 6-membered ring or an $X_2$-containing 6-membered ring condensed with at least one 5-membered ring, $A_3$ may be an $X_3$-containing 6-membered ring, and $A_4$ may be an $X_4$-containing 6-membered ring.

In an embodiment, an $X_1$-containing 6-membered ring in $A_1$, an $X_1$-containing 6-membered ring condensed with at least one 5-membered ring in $A_1$, an $X_2$-containing 6-membered ring in $A_2$, an $X_2$-containing 6-membered ring condensed with at least one 5-membered ring in $A_1$, an $X_3$-containing 6-membered ring in $A_3$, and an $X_4$-containing 6-membered ring in $A_4$ may each independently be a benzene group, a pyridine group, a pyrimidine group, a pyridazine group, or a pyrazine group, and a $X_1$-containing 5-membered ring in $A_1$ and an $X_1$-containing 5-membered ring condensed with at least one 6-membered ring in $A_1$ may each independently be a pyrrole group, a pyrazole group, an imidazole group, a triazole group, a furan group, an oxazole group, an iso-oxazole group, a thiazole group, an isothiazole group, an oxadiazole group, or thiadiazole group.

In an embodiment, the organometallic compound may satisfy at least one of Condition 1 to Condition 4:

[Condition 1]

A group represented by

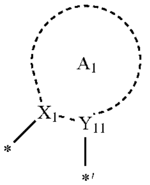

in Formula 1 may be represented by one of Formulae A1(1) to A1(44):

A1(1)

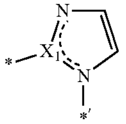

A1(2)

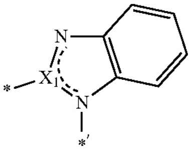

A1(3)

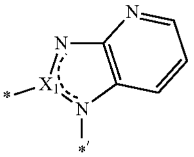

A1(4)

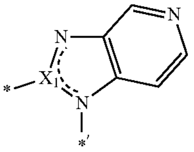

-continued

A1(5)

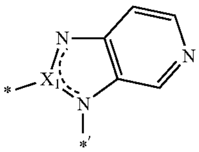

A1(6)

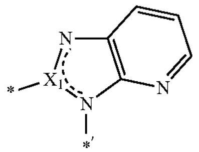

A1(7)

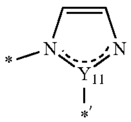

A1(8)

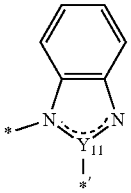

A1(9)

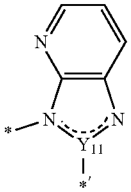

A1(10)

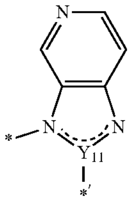

A1(11)

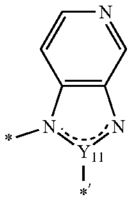

A1(12)

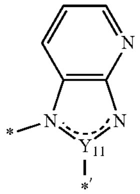

A1(13)

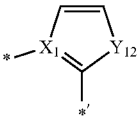

-continued
A1(14)
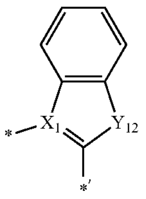
A1(15)
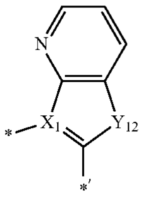
A1(16)
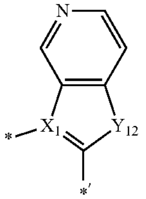
A1(17)
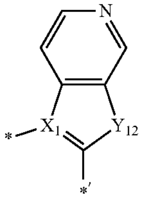
A1(18)
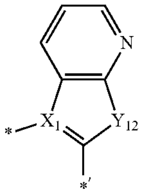
A1(19)
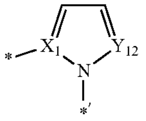
A1(20)
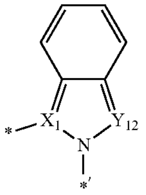
A1(21)
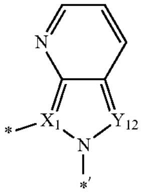
-continued
A1(22)
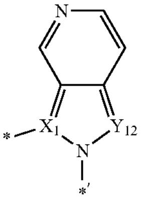
A1(23)
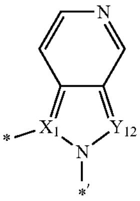
A1(24)
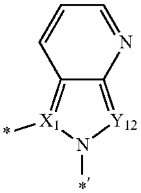
A1(25)
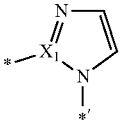
A1(26)
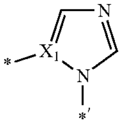
A1(27)
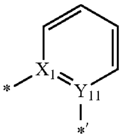
A1(28)
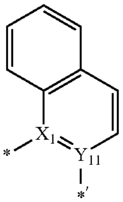
A1(29)
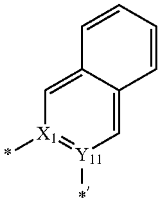
A1(30)
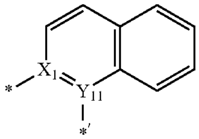

-continued
A1(31)
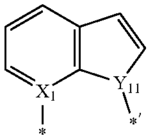
A1(32)
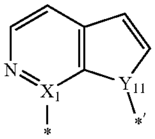
A1(33)
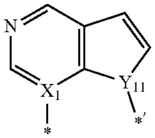
A1(34)
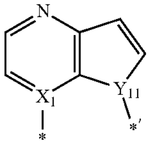
A1(35)
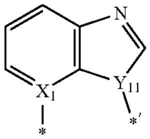
A1(36)
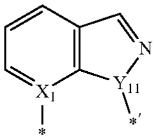
A1(37)
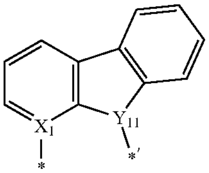
A1(38)
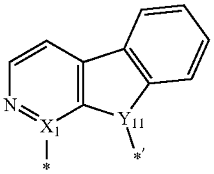
A1(39)
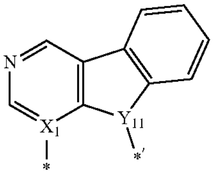
-continued
A1(40)
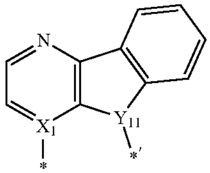
A1(41)
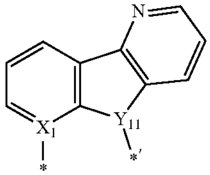
A1(42)
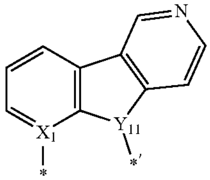
A1(43)
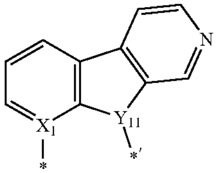
A1(44)
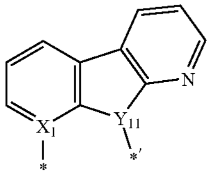
In Formulae A1(1) to A1(44),
$X_1$ and $Y_{11}$ are respectively the same as those described in the specification,
$Y_{12}$ may be C, N, O, or S,
* indicates a binding site to M, and
* ' indicates a binding site to $(L_1)_{b1}$.
[Condition 2]
A group represented by
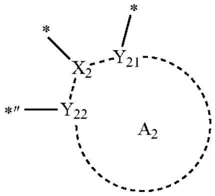
in Formula 1 may be represented by one of Formulae A2(1) to A2(11):

A2(1)
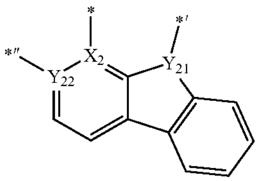
A2(2)
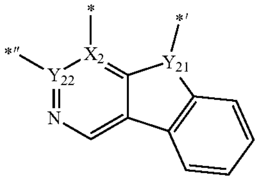
A2(3)
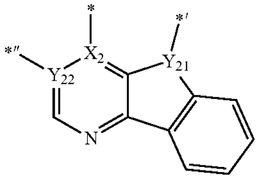
A2(4)
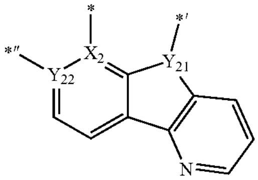
A2(5)
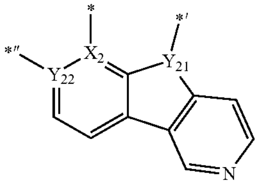
A2(6)
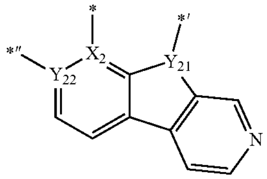
A2(7)
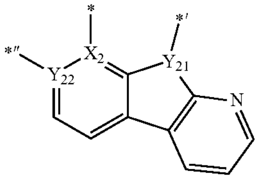
A2(8)
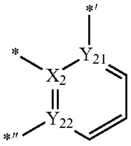
-continued
A2(9)
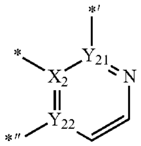
A2(10)
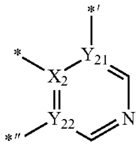
A2(11)
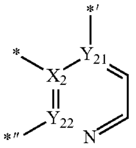
In Formulae A2(1) to A2(11),
$X_2$, $Y_{21}$, and $Y_{22}$ are respectively the same as those described in the specification,
* indicates a binding site to M,
*' indicates a binding site to $(L_1)_{b1}$, and
*" indicates a binding site to $(L_2)_{b2}$.
[Condition 3]
A group represented by
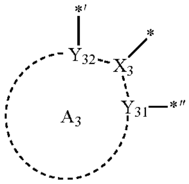
in Formula 1 may be represented by one of Formulae A3(1) to A3(4):
A3(1)
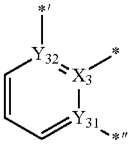
A3(2)
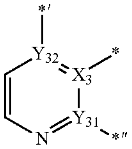
A3(3)
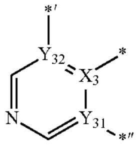

-continued

A3(4)

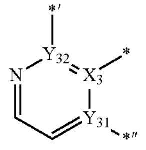

In Formulae A3(1) to A3(4), $X_3$, $Y_{31}$, and $Y_{32}$ are respectively the same as those described in the specification,

* indicates a binding site to M,

*' indicates a binding site to $(L_3)_{b3}$, and

*" indicates a binding site to $(L_2)_{b2}$.

[Condition 4]

A group represented by

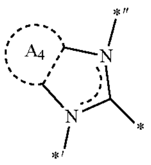

in Formula 1 may be represented by one of Formulae A4(1) to A4(13):

A4(1)

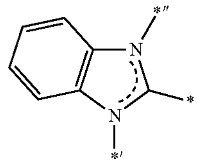

A4(2)

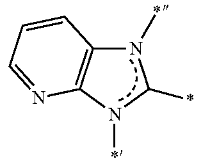

A4(3)

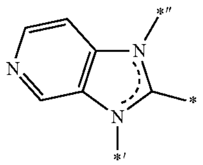

A4(4)

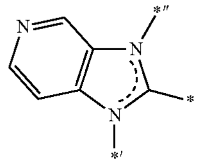

A4(5)

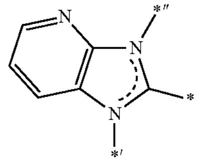

-continued

A4(6)

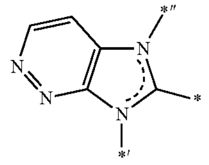

A4(7)

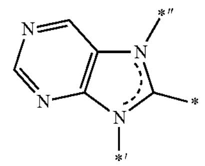

A4(8)

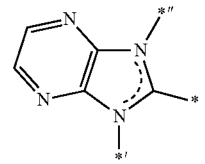

A4(9)

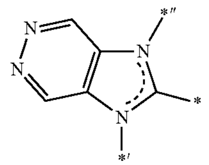

A4(10)

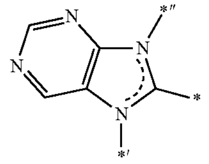

A4(11)

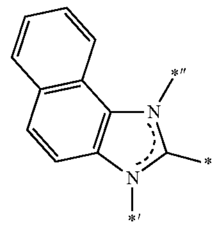

A4(12)

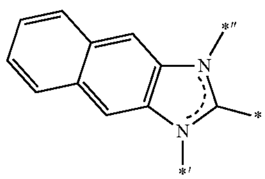

A4(13)

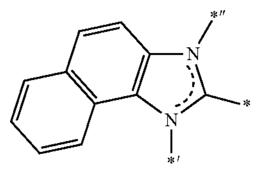

In Formulae A4(1) to A4(13),

* indicates a binding site to M,

*' indicates a binding site to $(L_3)_{b3}$, and

*" indicates a binding site to a neighboring atom.

In an embodiment, $A_5$ may be a $C_6$-$C_{60}$ aryl group or a $C_1$-$C_{60}$ heteroaryl group.

In an embodiment, $A_1$ to $A_5$ may each independently be a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indeno phenanthrene group, an indenoanthracene group, a pyrrole group, a thiophene group, a furan group, an indole group, a benzoindole group, a naphtho indole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, a thiepine group, an oxepine group, cycloocta-1,3,5,7-tetraene, pyrido[2,3-b]indole, pyrido[3,4-b]indole, pyrido[4,3-b]indole, pyrido[3,2-b]indole, or pyrrolo[2,3-b]pyridine.

In an embodiment, $A_1$ to $A_4$ may each independently be a benzene group, an indole group, a benzoindole group, a naphtho indole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, a pyrazole group, an imidazole group, a triazole group, an oxazole group, an isoxazole group, a thiazole group, an isothiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, pyrido[2,3-b]indole, pyrido[3,4-b]indole, pyrido[4,3-b]indole, pyrido[3,2-b]indole, or pyrrolo[2,3-b]pyridine.

In an embodiment, $A_5$ may be a benzene group, a naphthalene group, an azulene group, an indacene group, a phenanthrene group, an anthracene group, a triphenylene group, a pyrene group, a chrysene group, an indene group, a fluorene group, a spiro-bifluorene group, a benzofluorene group, a pyrrole group, a thiophene group, a furan group, an indole group, a benzoindole group, a naphtho indole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, a pyrazole group, an imidazole group, a triazole group, an oxazole group, an isoxazole group, a thiazole group, an isothiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a thiepine group, an oxepine group, or cycloocta-1,3,5,7-tetraene.

In Formula 1, $L_1$ to $L_3$ may each independently be a single bond, a double bond, *—$N(Z_{11})$—*', *—$B(Z_{11})$—*', *—$P(Z_{11})$—*', *—$C(Z_{11})(Z_{12})$—*', *—$Si(Z_{11})(Z_{12})$—*', *—$Ge(Z_{11})(Z_{12})$—*', *—S—*', *—Se—*', *—O—*', *—C(=O)—*', *—S(=O)—*', *—$S(=O)_2$—*', *—$C(Z_{11})$=*', *=$C(Z_{11})$—*', *—$C(Z_{11})=C(Z_{12})$—*', *—C(=S)—*', or *—C≡C—*', and * and *' each indicate a binding site to a neighboring atom. $Z_{11}$ and $Z_{12}$ are respectively the same as those described in the specification.

In an embodiment, $L_1$ may be a single bond or *—$N(Z_{11})$—*';

$L_2$ may be *—$N(Z_{11})$—*', *—$B(Z_{11})$—*', *—$Si(Z_{11})(Z_{12})$—*', *—S—*', or *—O—*';

$L_3$ may be a single bond; or any combination thereof. $Z_{11}$ and $Z_{12}$ are respectively the same as those described in the specification.

In Formula 1, b1 to b3 may each independently be an integer from 1 to 3. In Formula 1, b1 indicates the number of $L_1$, wherein, when b1 is 2 or more, two or more of $L_1$(s) may be identical to or different from each other. In Formula 1, b2 indicates the number of $L_2$, wherein, when b2 is 2 or more, two or more of $L_2$(s) may be identical to or different from each other. In Formula 1, b3 indicates the number of $L_3$, wherein, when b3 is 2 or more, two or more of $L_3$(s) may be identical to or different from each other.

In Formula 1, $R_1$ to $R_5$, $R_{51}$ to $R_{53}$, $Z_{11}$, and $Z_{12}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$. $R_{10a}$ and $Q_1$ to $Q_3$ are respectively the same as those described in the specification.

In an embodiment, $R_1$ to $R_5$, $R_{51}$ to $R_{53}$, $Z_{11}$, and $Z_{12}$ may each independently be:

hydrogen, deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), —P(═O)($Q_{31}$)($Q_{32}$), or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), —P(═O)($Q_{31}$)($Q_{32}$), or any combination thereof; or —B($Q_1$)($Q_2$), —P($Q_1$)($Q_2$), or —C(═O)($Q_1$). $Q_1$, $Q_2$, and $Q_{31}$ to $Q_{33}$ are respectively the same as those described in the specification.

In an embodiment, $R_1$ to $R_5$, $R_{51}$ to $R_{53}$, $Z_{11}$, and $Z_{12}$ may each independently be:

hydrogen, deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a phenyl group, a naphthyl group, a pyridinyl group, a pyrimidinyl group, or any combination thereof; or a phenyl group, a naphthyl group, a pyrrolyl group, a pyridinyl group, a pyrazinyl group, or a pyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, a pyrrolyl group, a pyridinyl group, a pyrazinyl group, a pyrimidinyl group, or any combination thereof.

In an embodiment, $R_{51}$ to $R_{53}$ may each independently be:

hydrogen, deuterium, —F, —Cl, —Br, —I, a hydroxyl group, a cyano group, or a nitro group; or a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, —Si($Q_{31}$)($Q_{32}$)($Q_{33}$), —N($Q_{31}$)($Q_{32}$), —B($Q_{31}$)($Q_{32}$), or any combination thereof.

In an embodiment, $R_{51}$ to $R_{53}$ may each independently be:

hydrogen, deuterium, —F, —Cl, —Br, —I, a hydroxyl group, a cyano group, or a nitro group; or a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, or any combination thereof.

In Formula 1, $R_{5a}$ may be deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —P($Q_1$)($Q_2$), —C(═O)($Q_1$), —S(═O)($Q_1$), —S(═O)$_2$($Q_1$), —P(═O)($Q_1$)($Q_2$), or —P(═S)($Q_1$)($Q_2$). $R_{10a}$ and $Q_1$ to $Q_3$ are respectively the same as those described in the specification.

In an embodiment, $R_{5a}$ may be:

deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), —P(═O)($Q_{31}$)($Q_{32}$), or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), —P(═O)($Q_{31}$)($Q_{32}$), or any combination thereof; or —B($Q_1$)($Q_2$), —P($Q_1$)($Q_2$), or —C(═O)($Q_1$). $Q_1$, $Q_2$, and $Q_{31}$ to $Q_{33}$ are respectively the same as those described in the specification.

In an embodiment, $R_{5a}$ may be:

deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, an adamantanyl group, a norbornanyl group, a norbornenyl group, a cyclopentenyl group, a cyclohexenyl group, a phenyl group, a naphthyl group, a pyridinyl group, a pyrimidinyl group, or any combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, or a benzocarbazolyl group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, or any combination thereof.

In an embodiment, $R_{5a}$ may be:

deuterium, —F, —Cl, —Br, —I, a hydroxyl group, a cyano group, or a nitro group; or a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, an adamantanyl group, a norbornanyl group, a norbornenyl group, a cyclopentenyl group, a cyclohexenyl group, a phenyl group, a naphthyl group, a pyridinyl group, a pyrimidinyl group, or any combination thereof.

In Formula 1, a1 to a5 may each independently be an integer from 0 to 10.

In Formula 1, when a1 is 2 or more, two $R_1$(s) of two or more $R_1$(s) may be optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and when a2 is 2 or more, two $R_2$(s) of two or more $R_2$(s) may be optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$. $R_{10a}$ is the same as described in the specification.

In an embodiment, the organometallic compound represented by Formula 1 may be selected from Compounds 1 to 150:

1

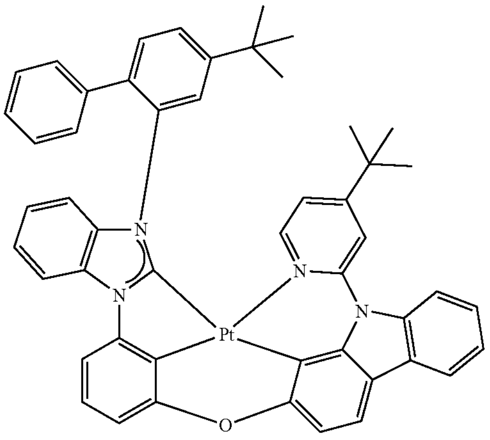

2

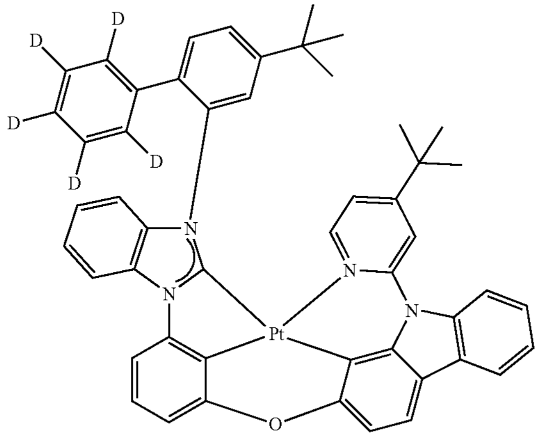

-continued

3

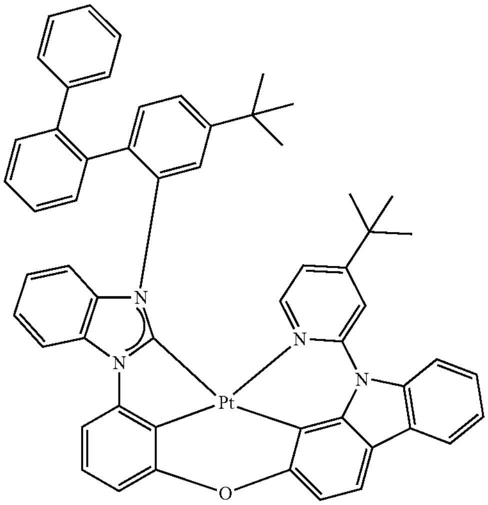

4

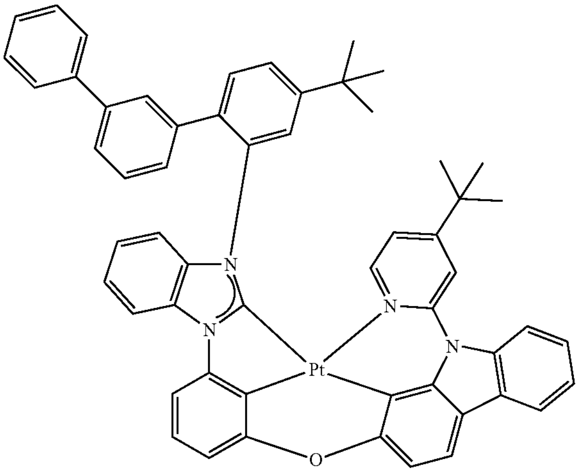

5

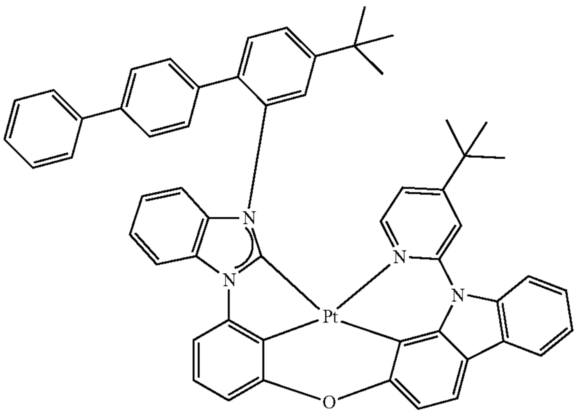

-continued
6
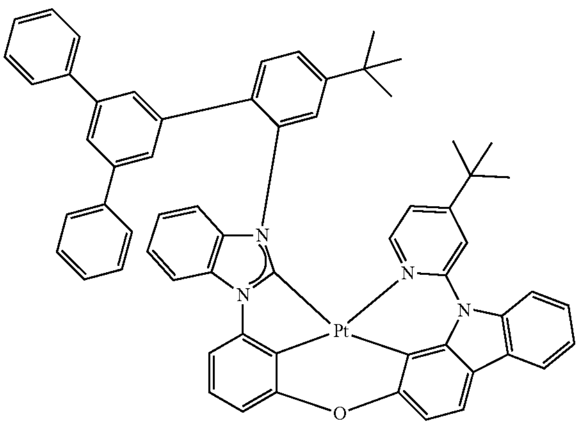
7
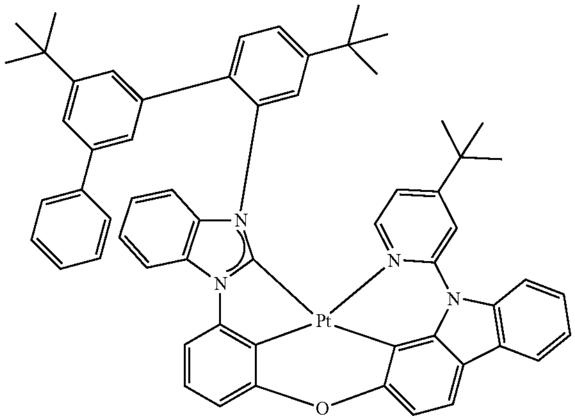
8
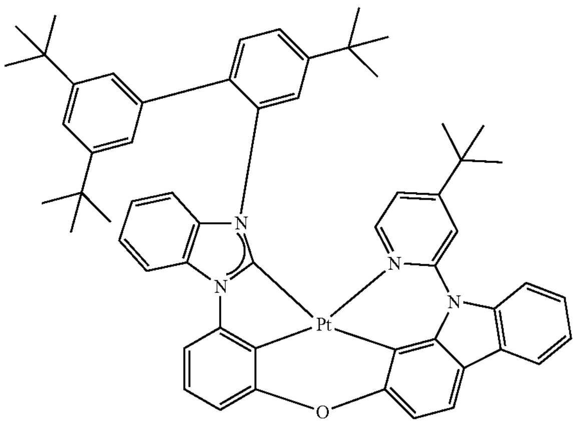
-continued
9
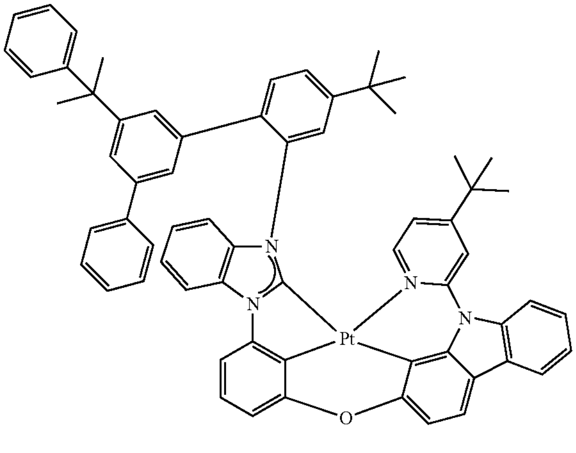
10
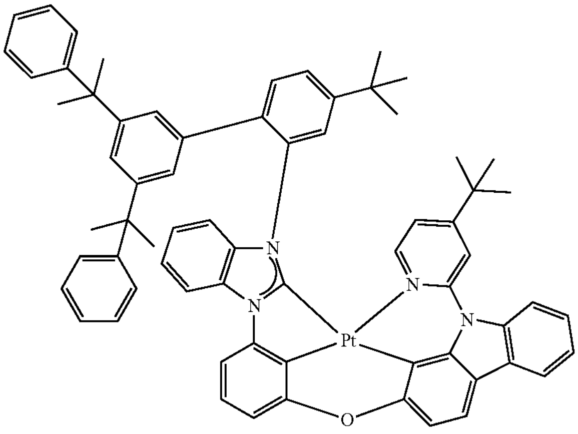
11
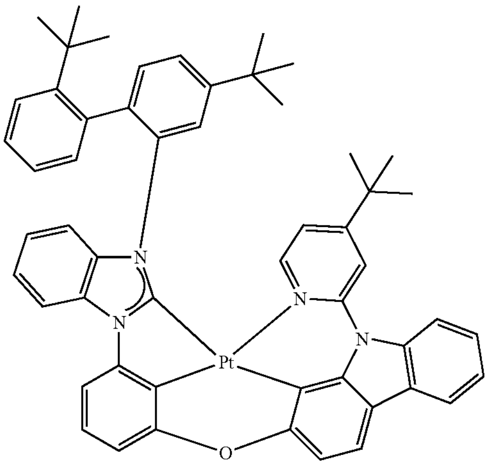

-continued
12
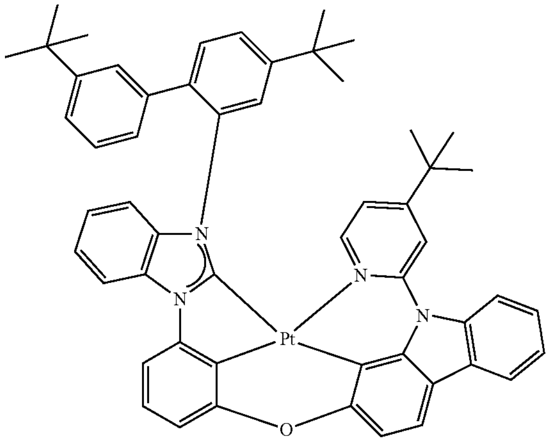
13
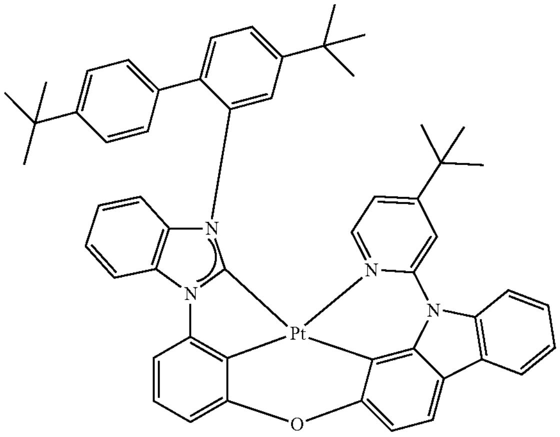
14
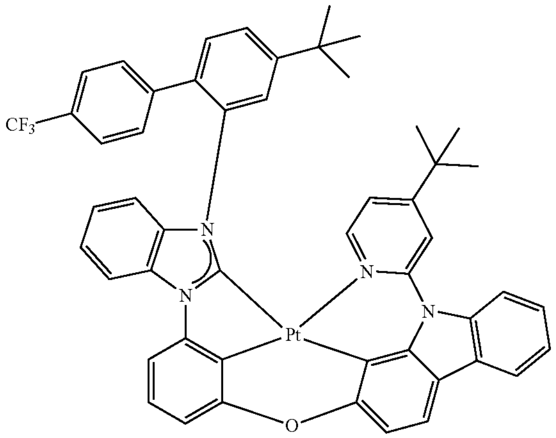
-continued
15
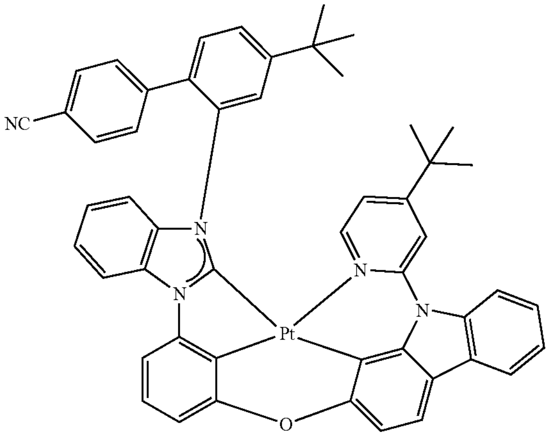
16
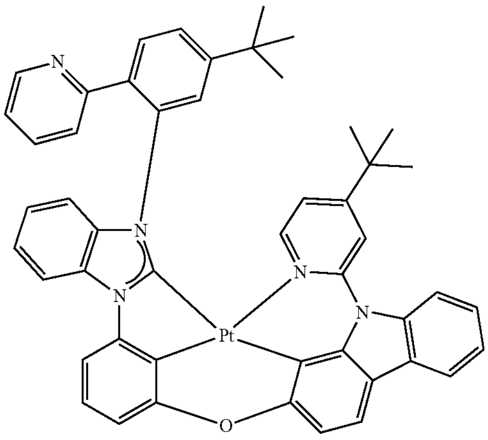
17
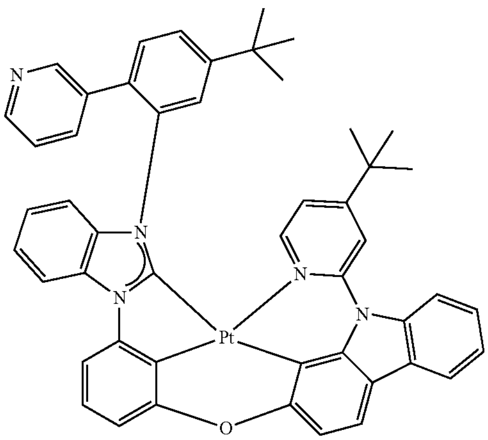

18
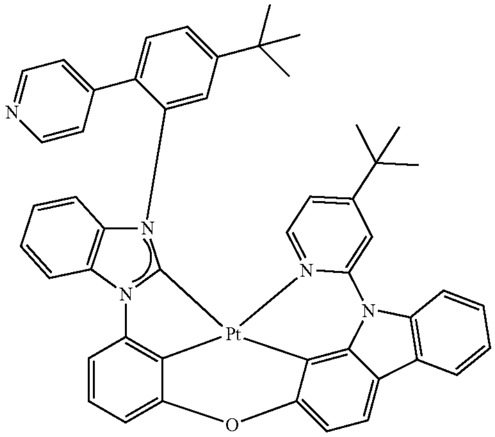
19
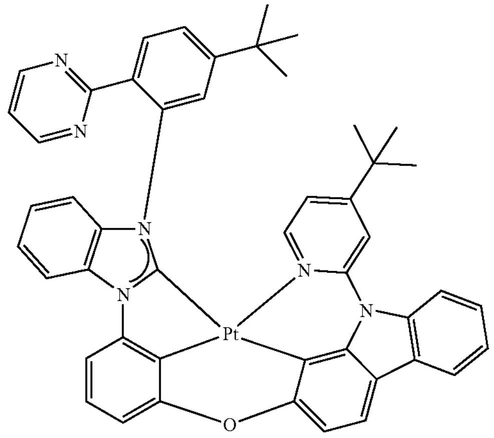
20
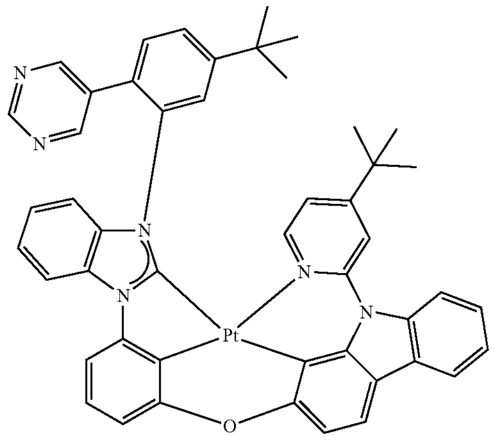
21
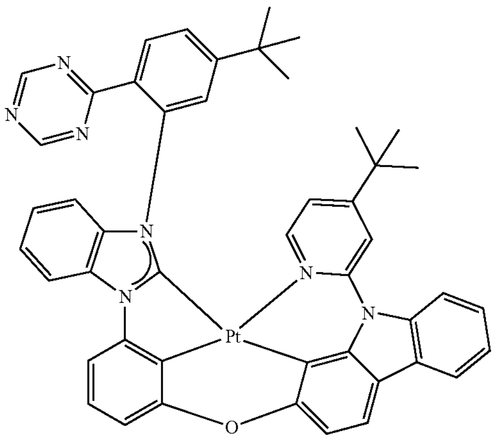
22
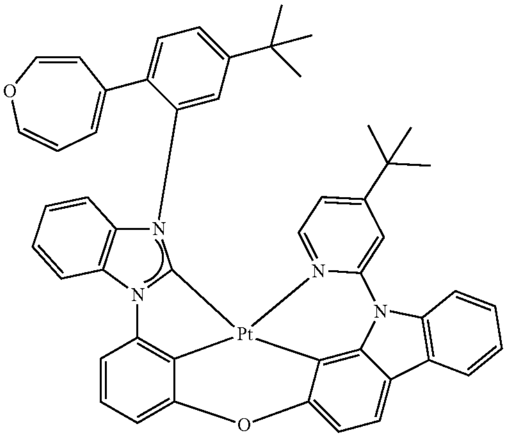
23
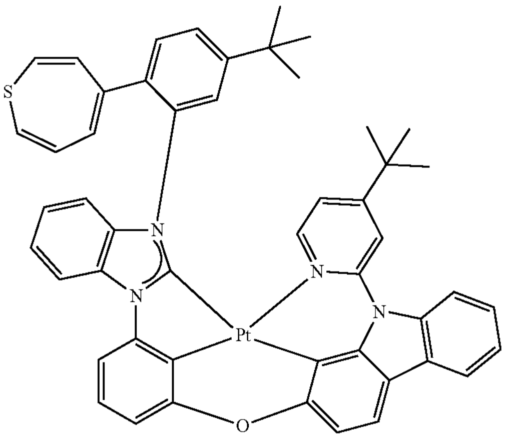

-continued
24
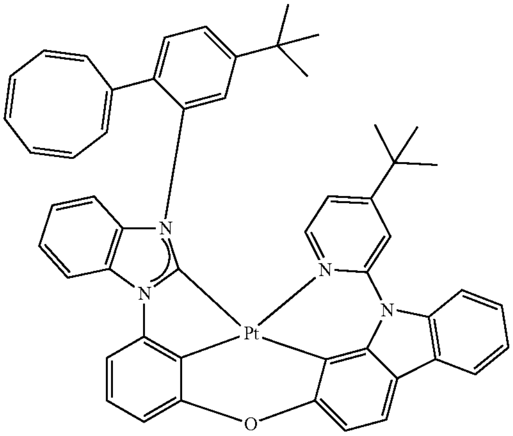
25
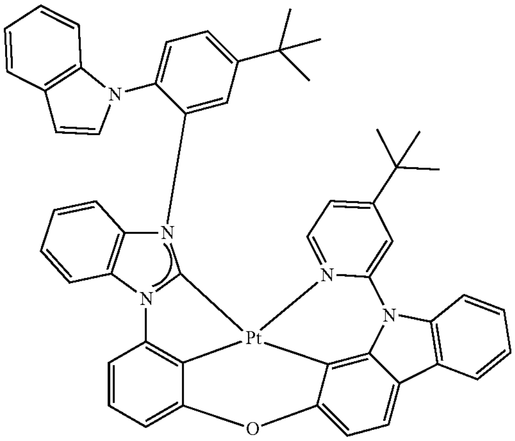
26
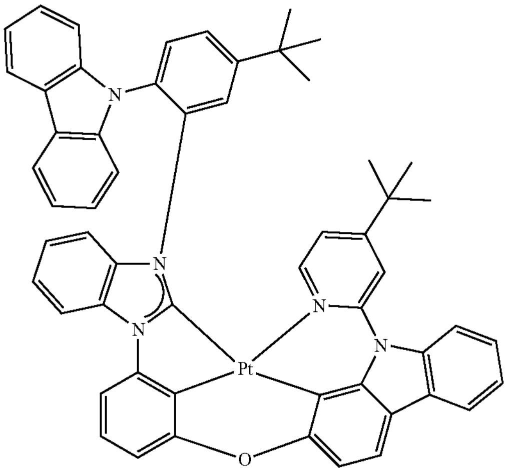
-continued
27
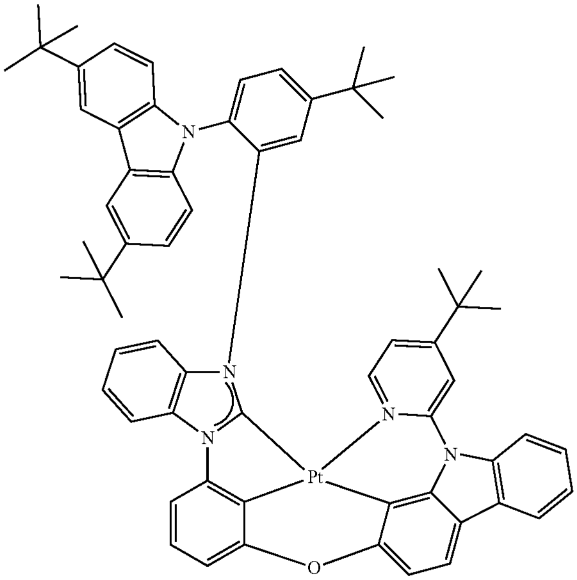
28
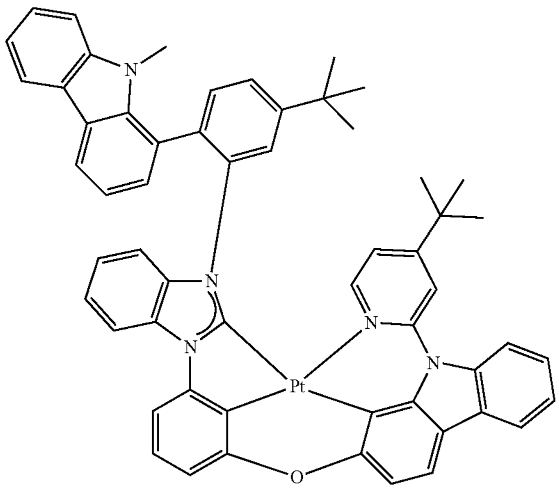

-continued
29
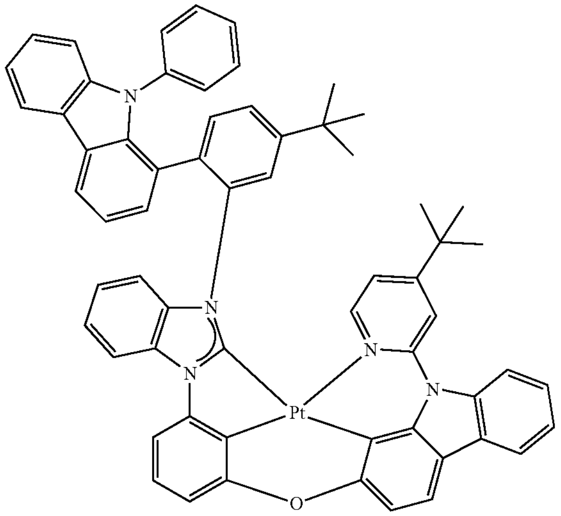
30
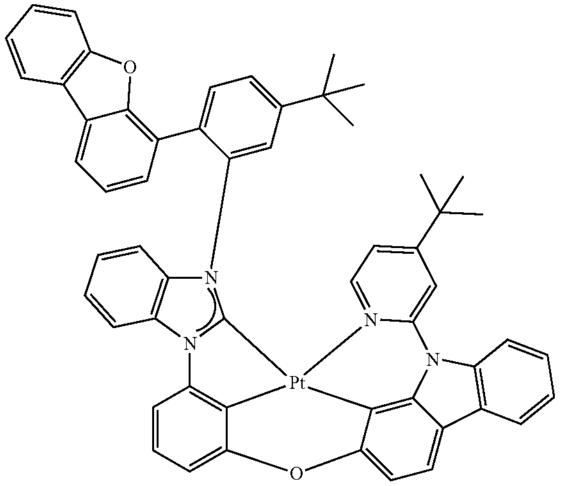
31
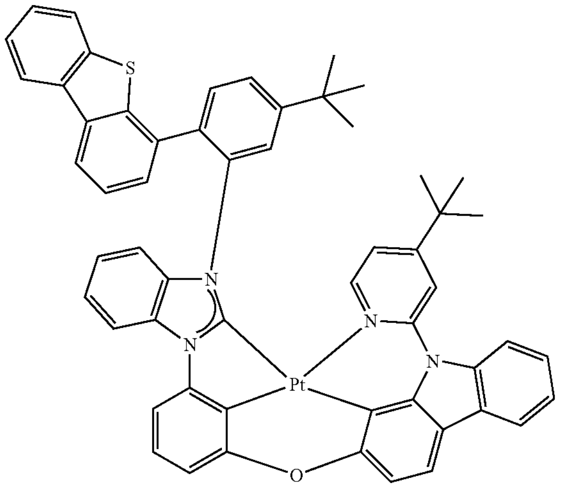
-continued
32
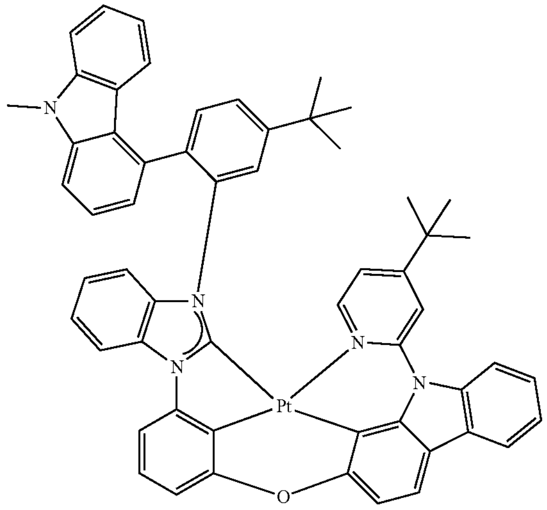
33
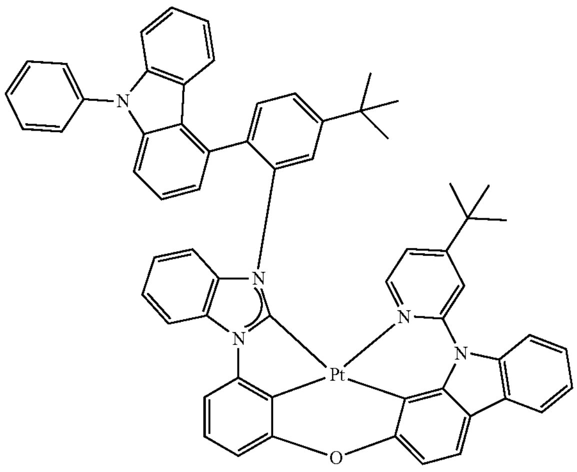
34
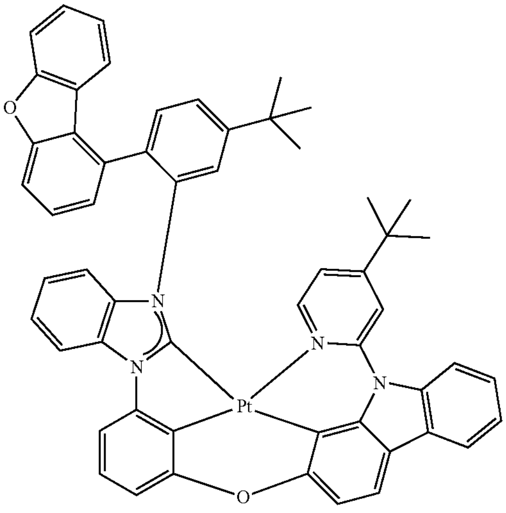

-continued
35
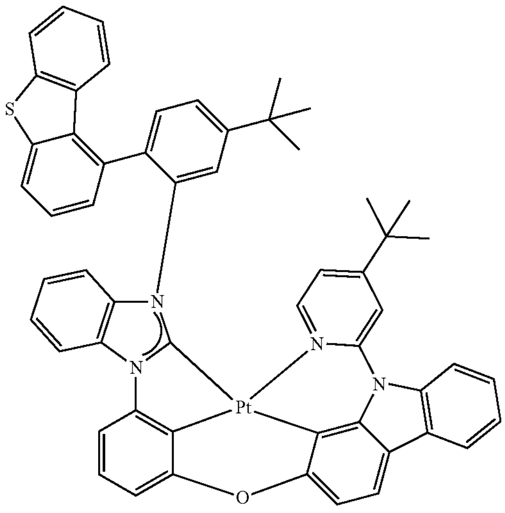
36
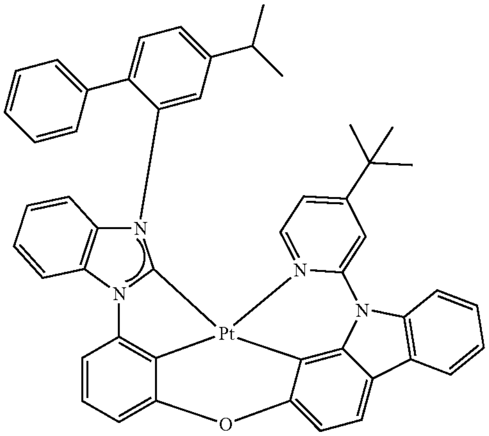
37
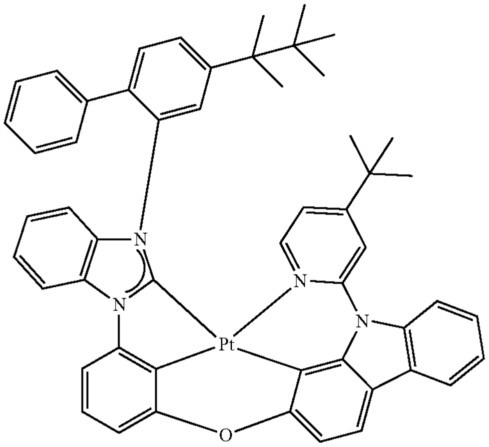
-continued
38
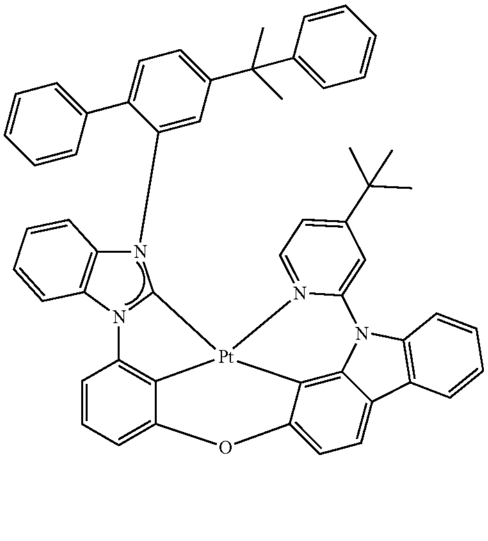
39
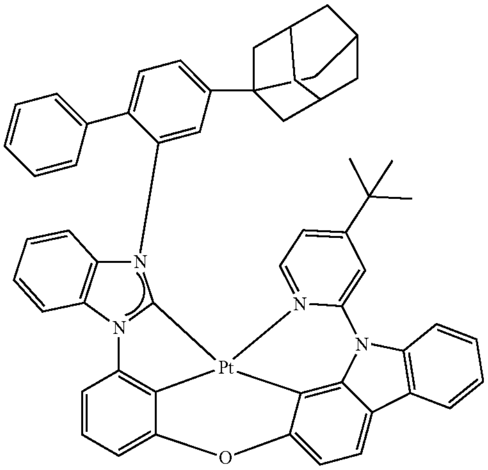
40
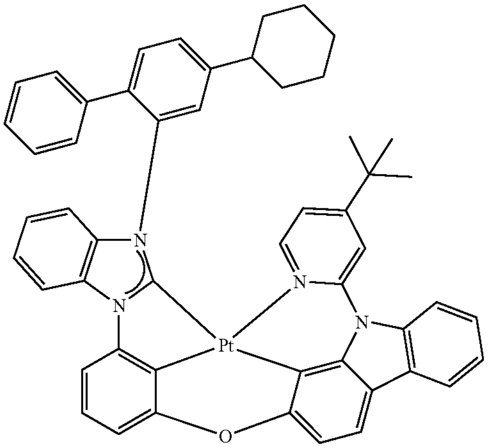

-continued
41
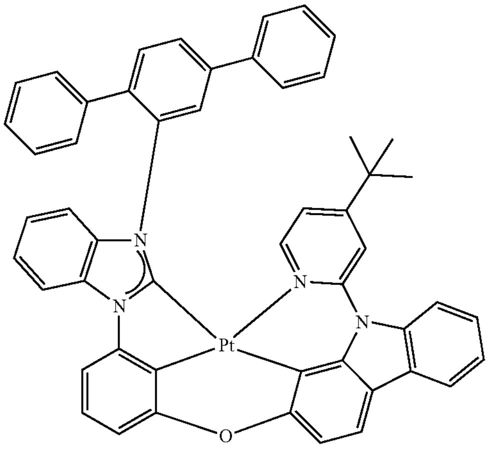
42
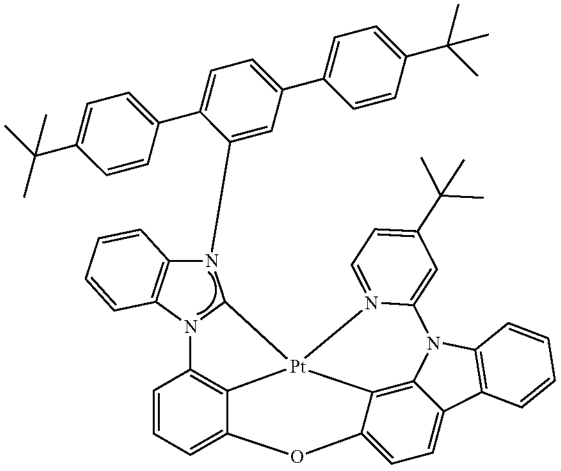
43
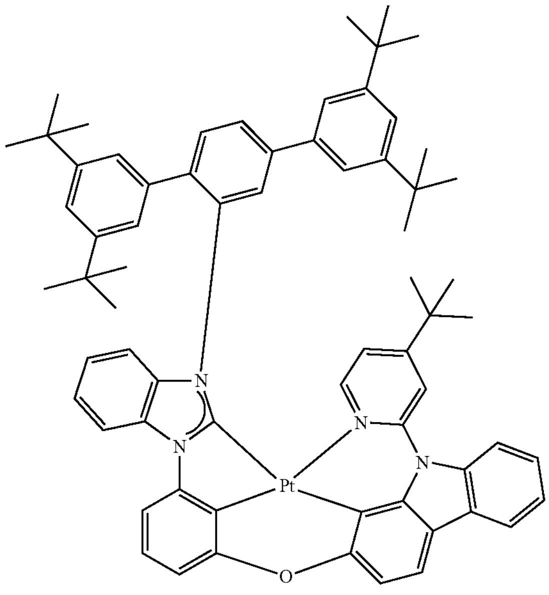
-continued
44
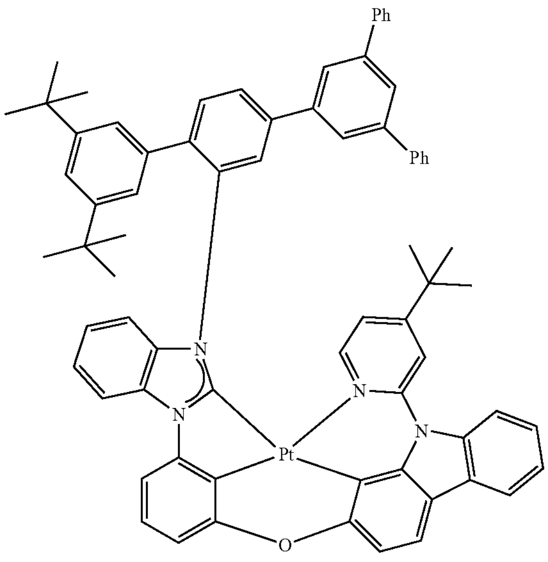
45
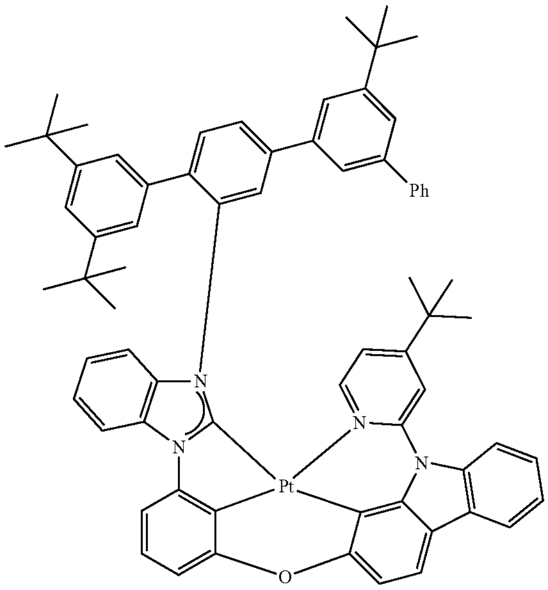
46
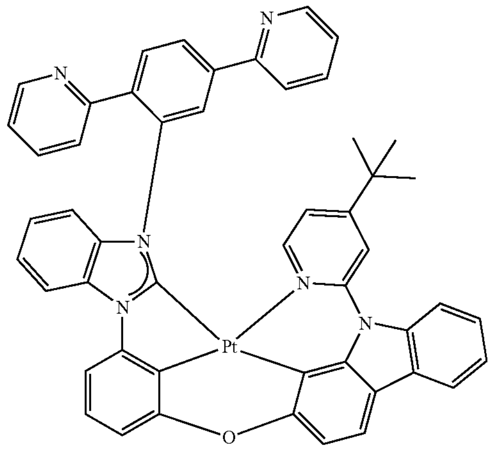

-continued
47
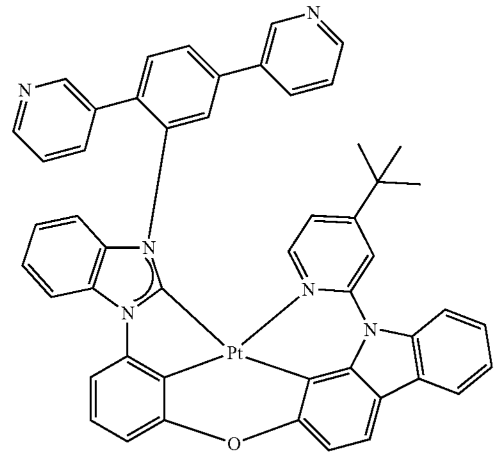
48
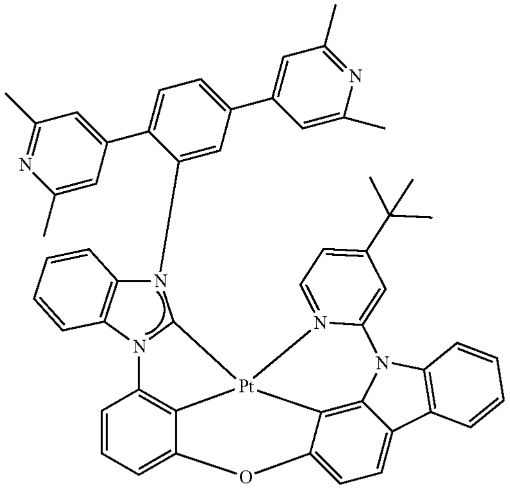
49
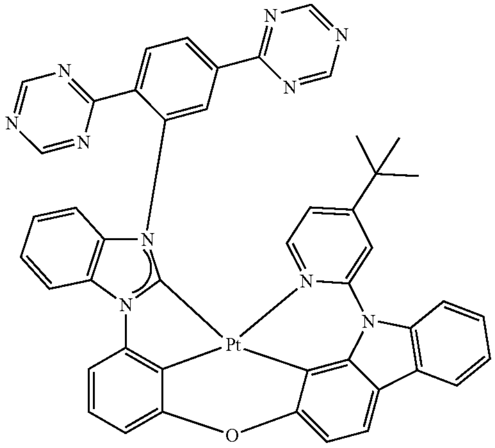
-continued
50
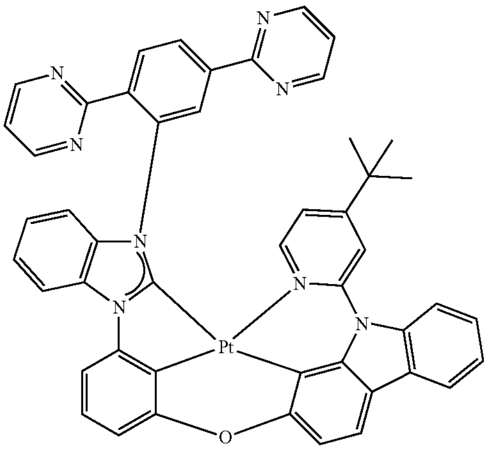
51
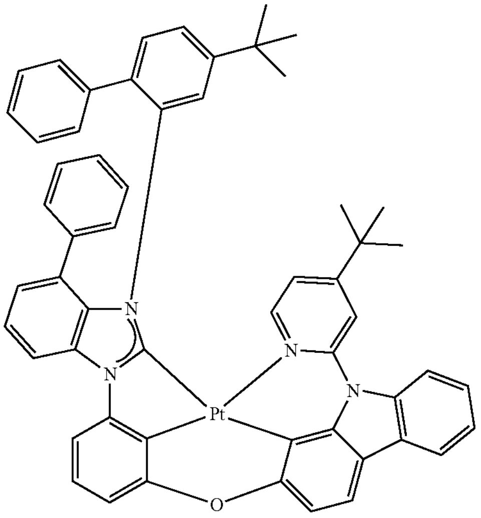
52
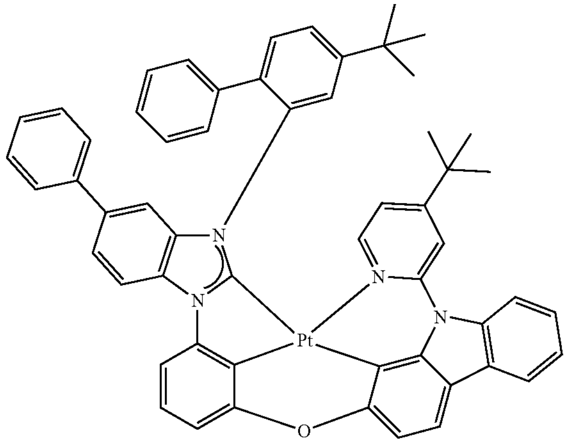

-continued
53
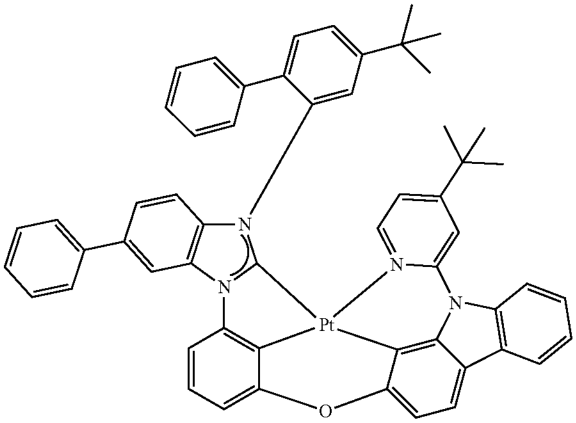
54
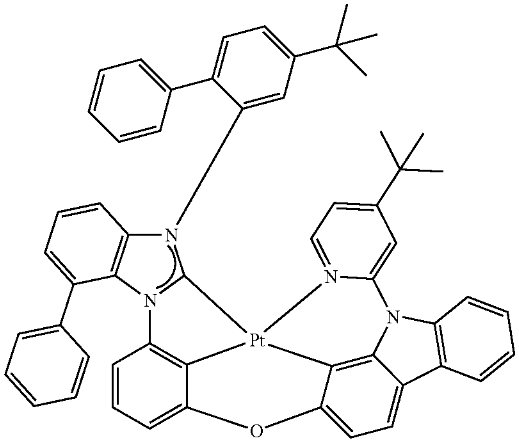
55
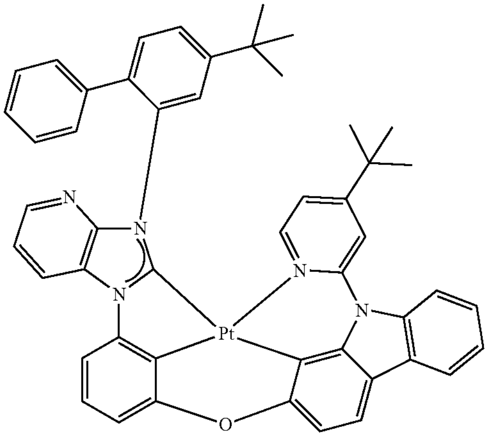
-continued
56
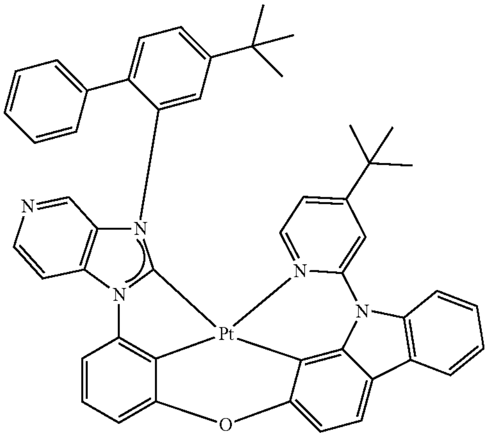
57
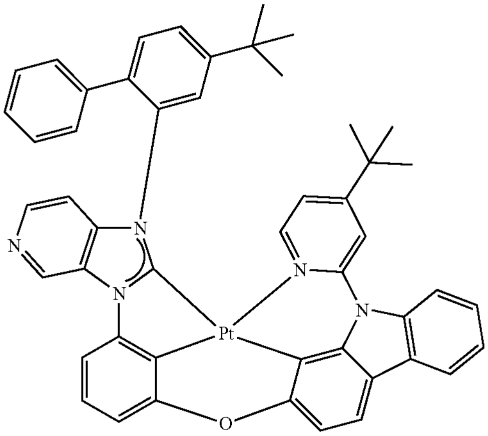
58
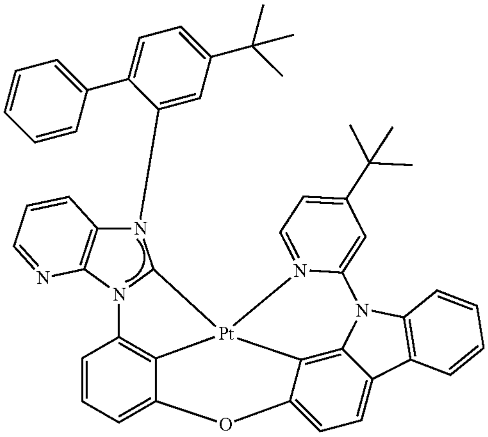

-continued
59
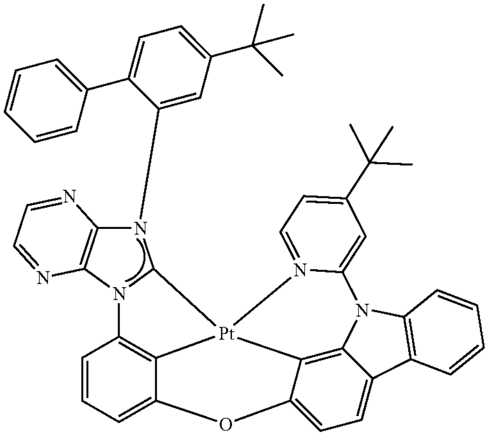
60
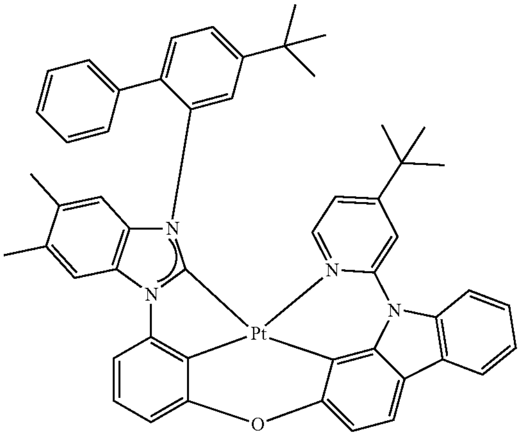
61
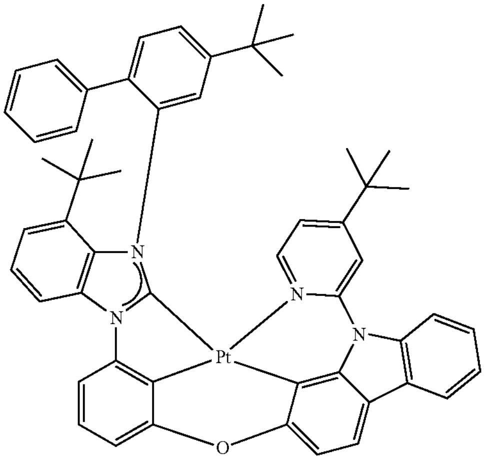
-continued
62
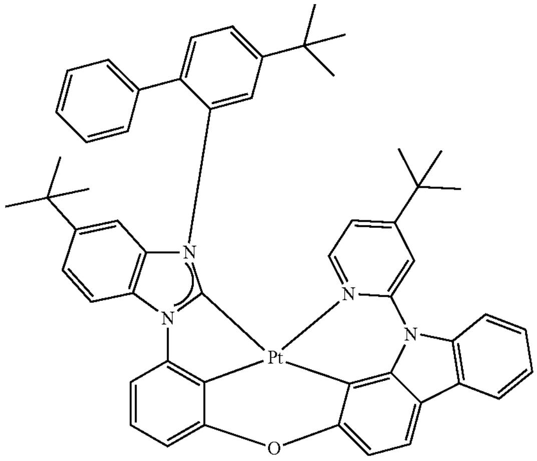
63
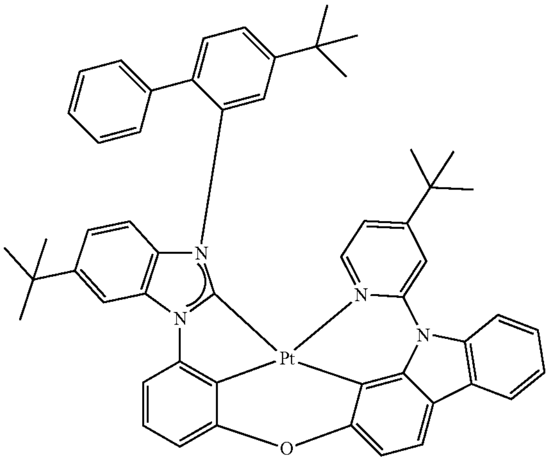
64
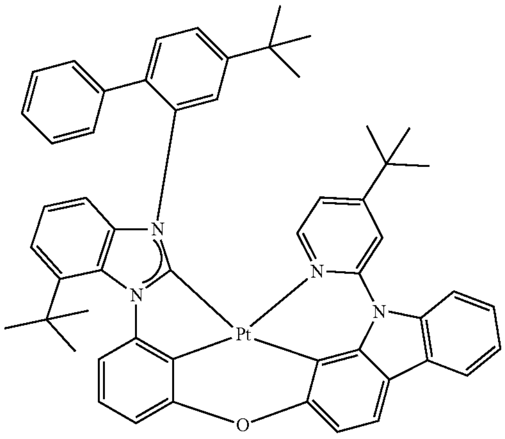

65
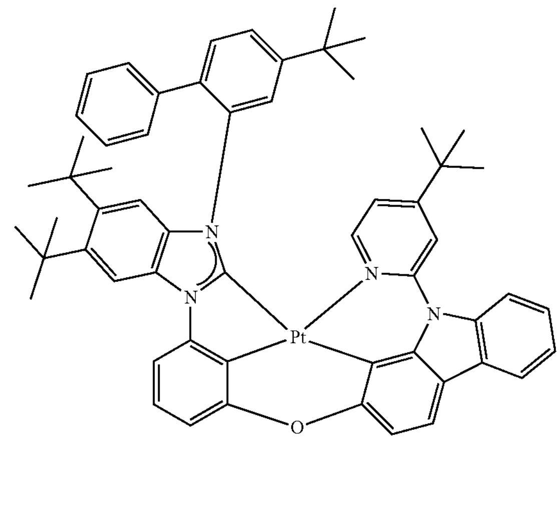
66
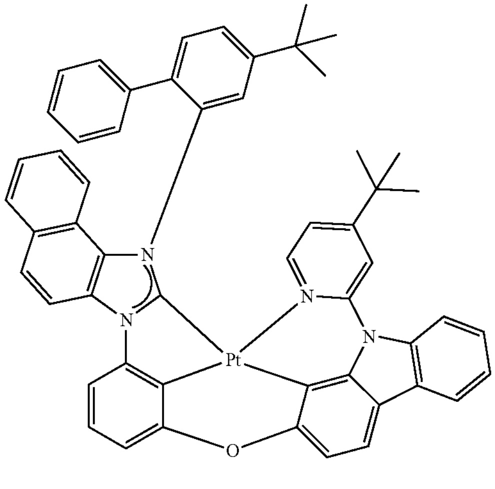
67
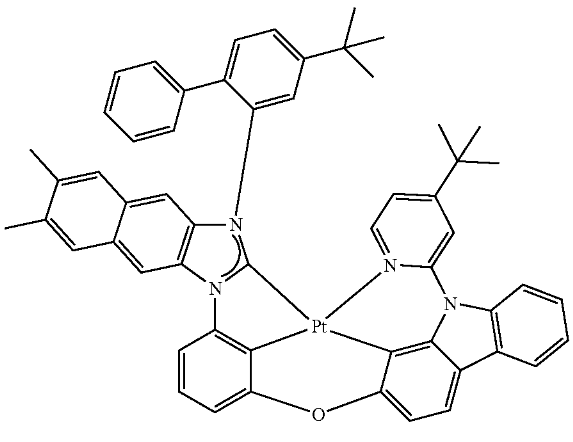
68
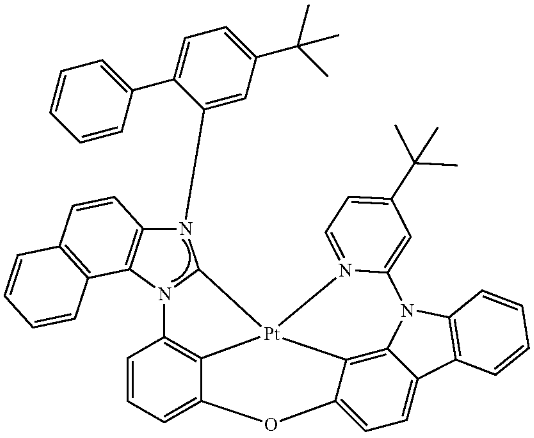
69
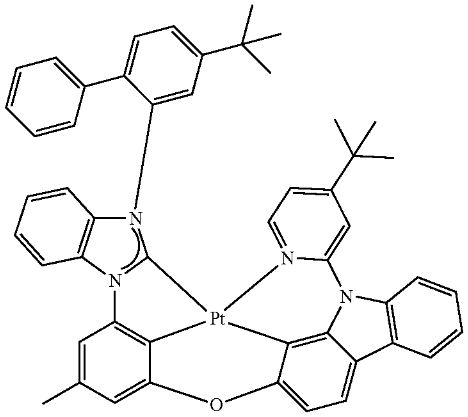
70
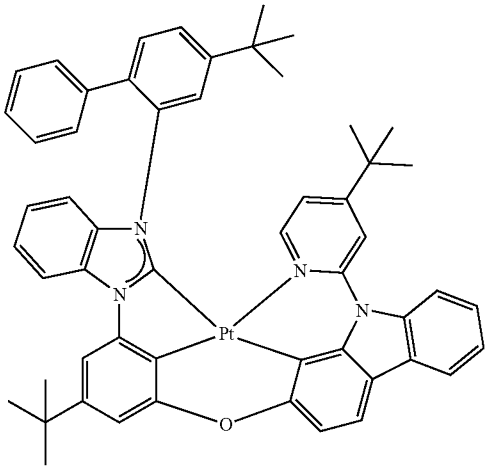

-continued
71
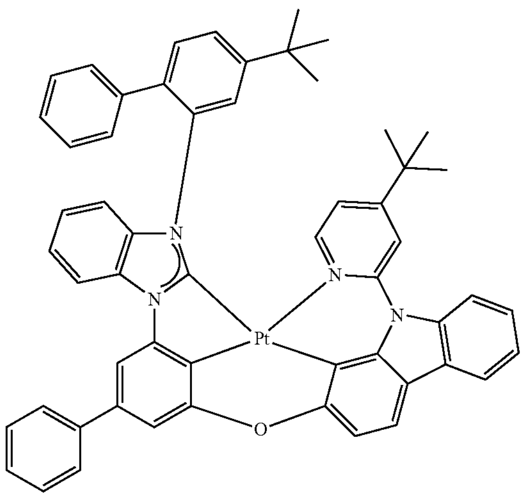
72
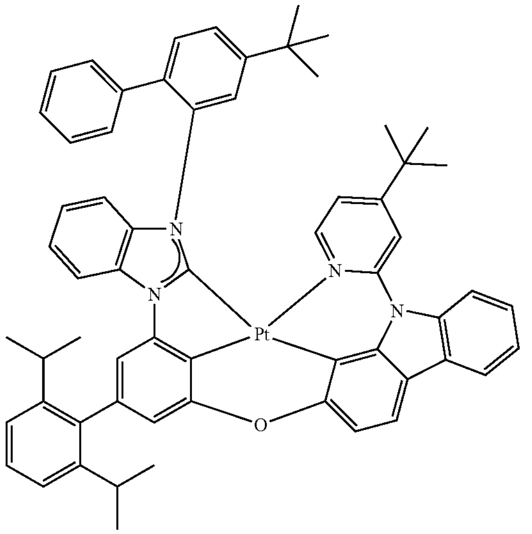
73
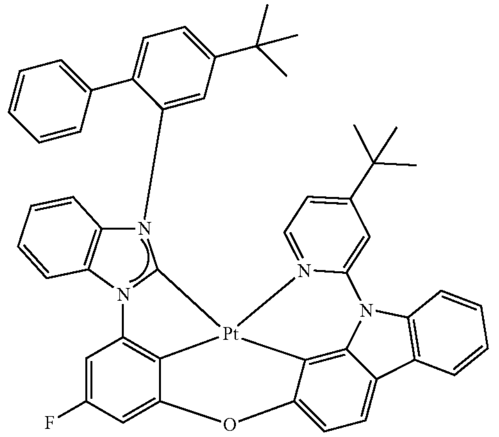
-continued
74
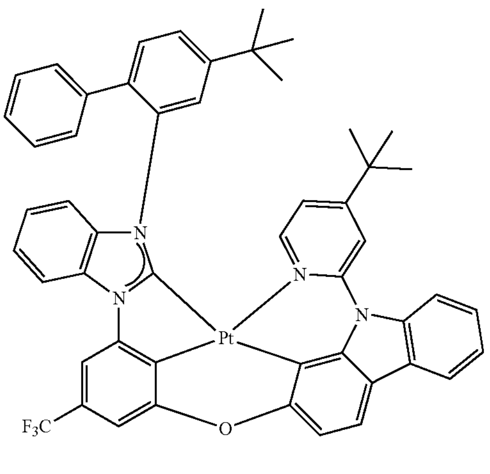
75
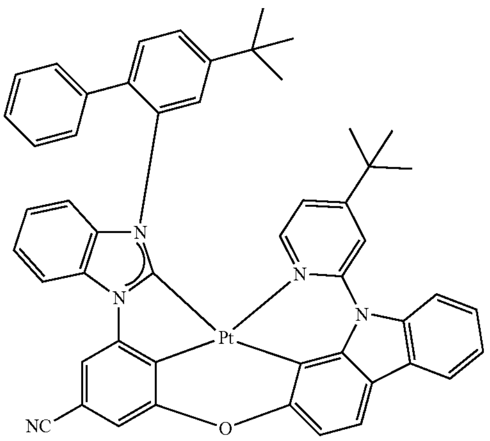
76
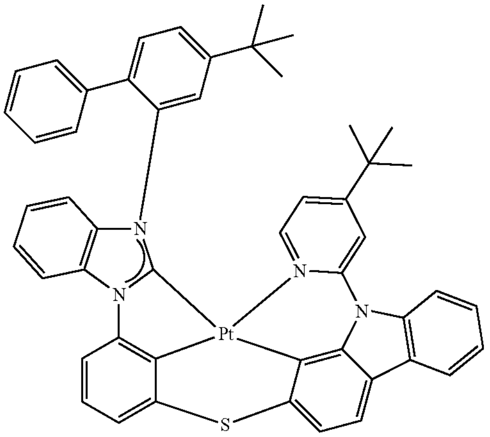

-continued
77
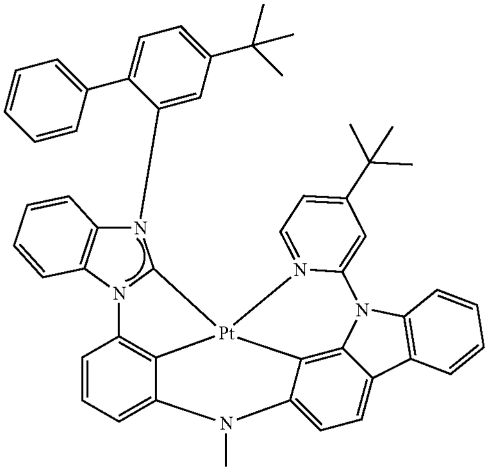
78
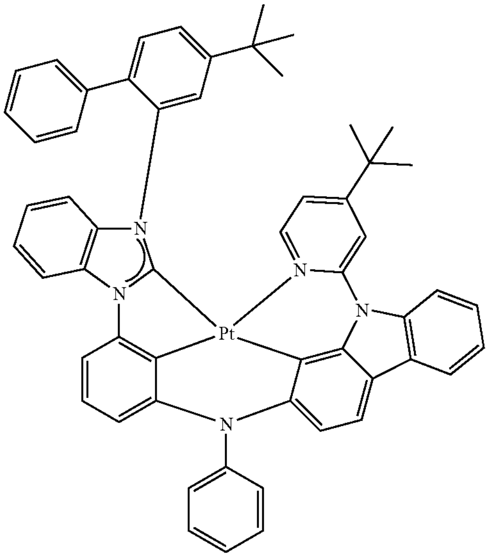
79
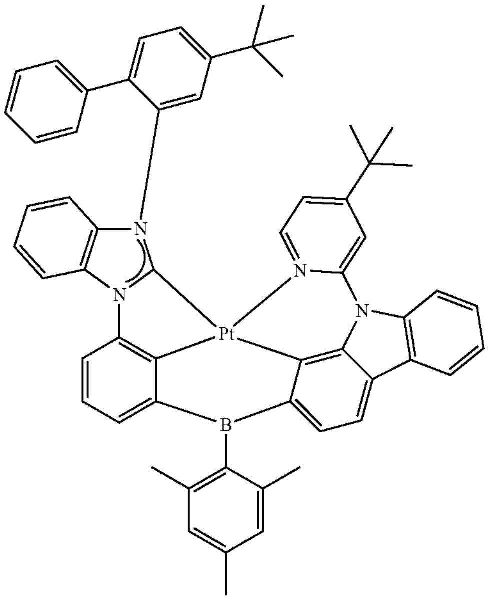
-continued
80
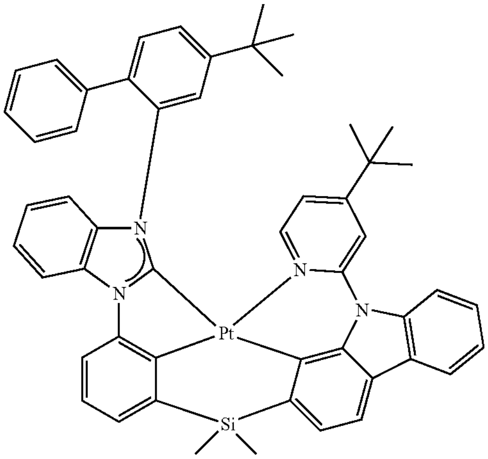
81
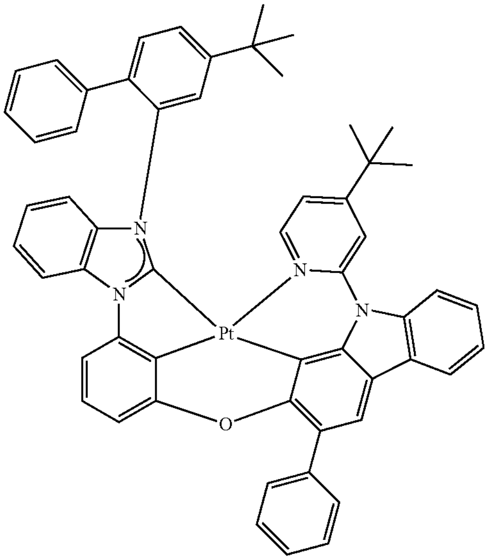
82
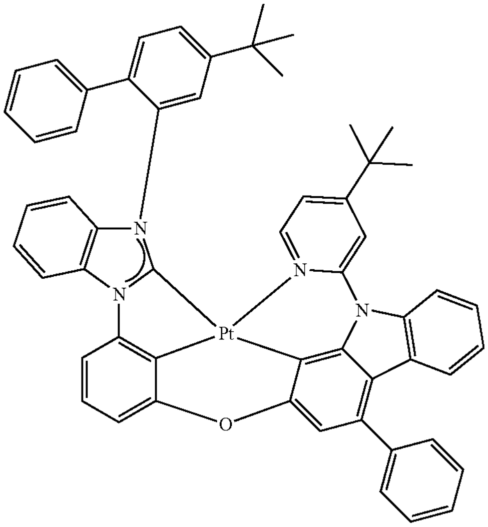

-continued
83
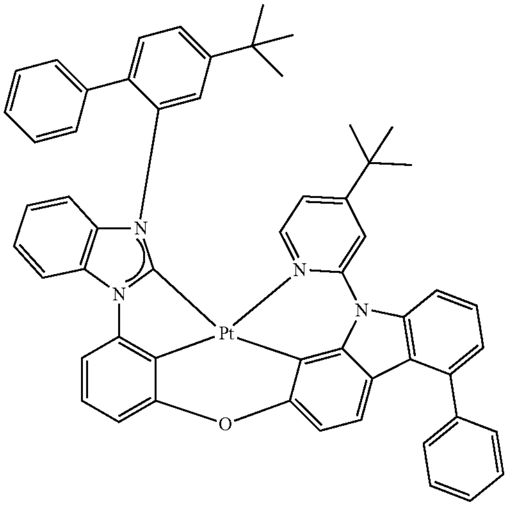
84
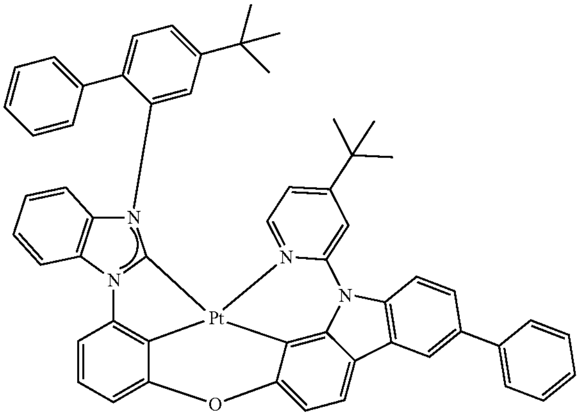
85
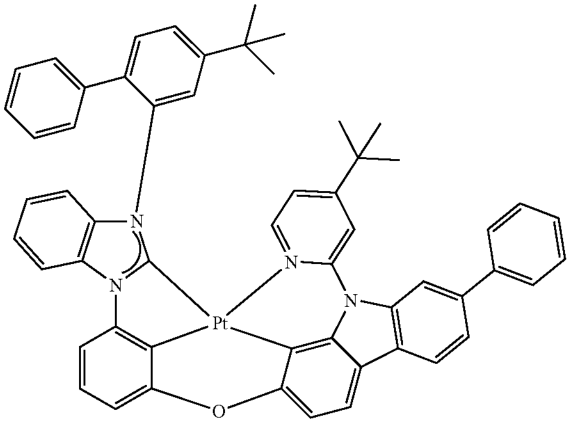
-continued
86
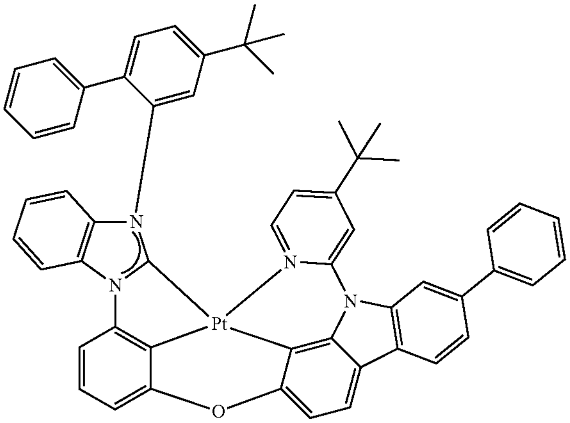
87
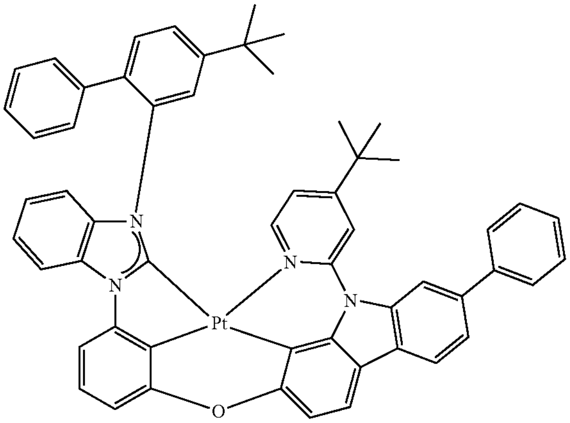
88
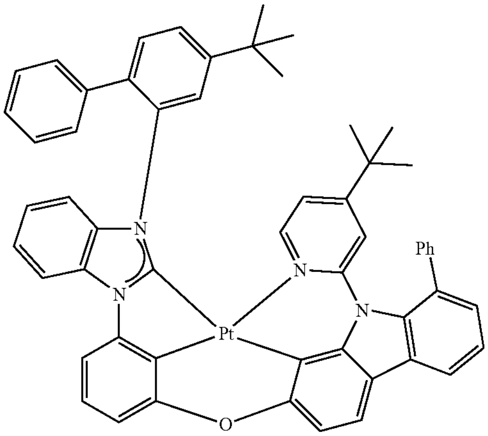

-continued
89
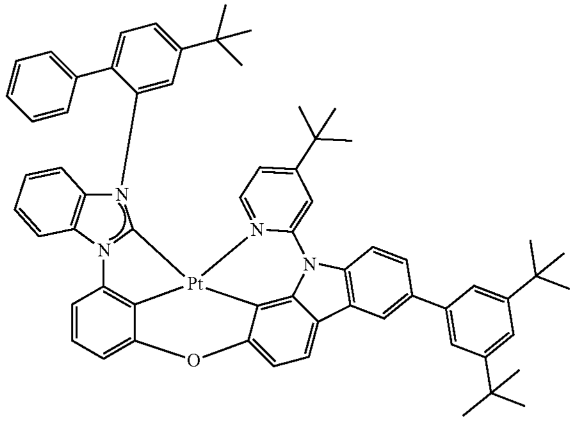
90
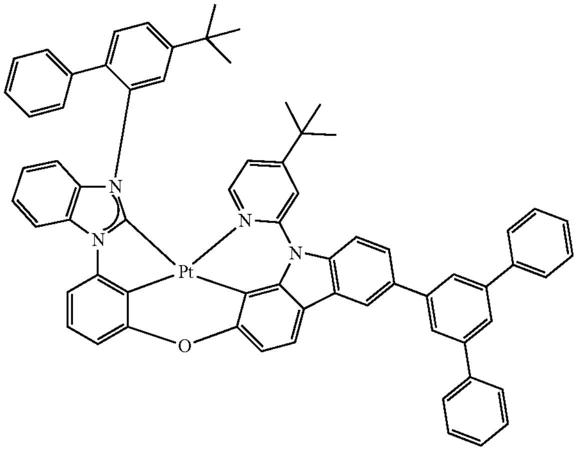
91
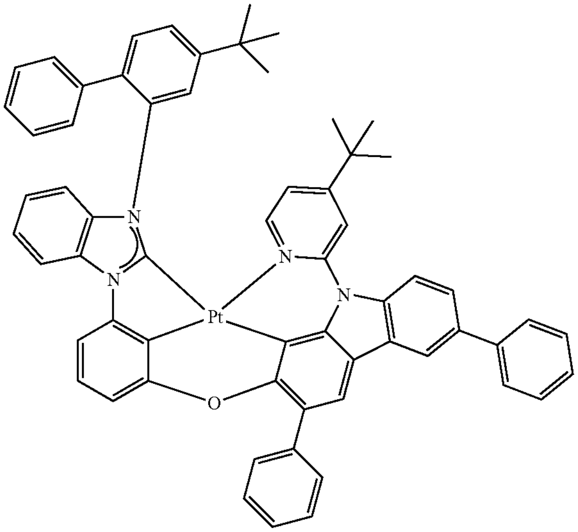
-continued
92
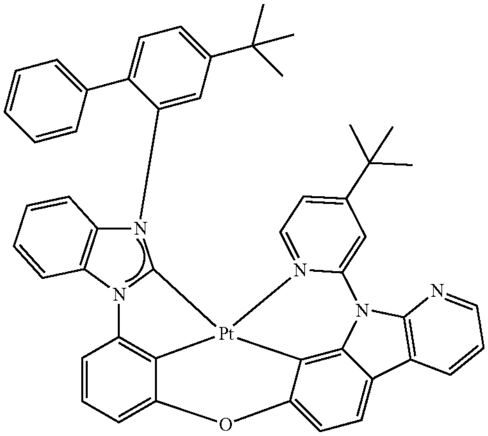
93
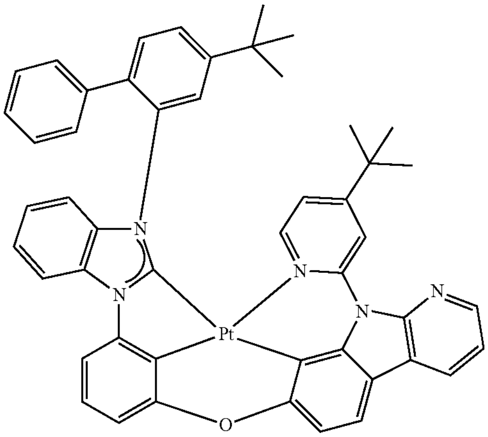
94
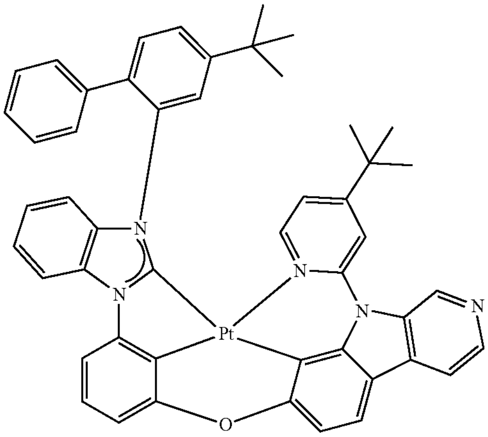

-continued
95
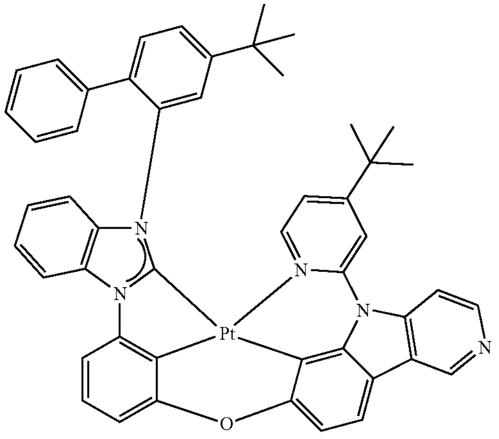
96
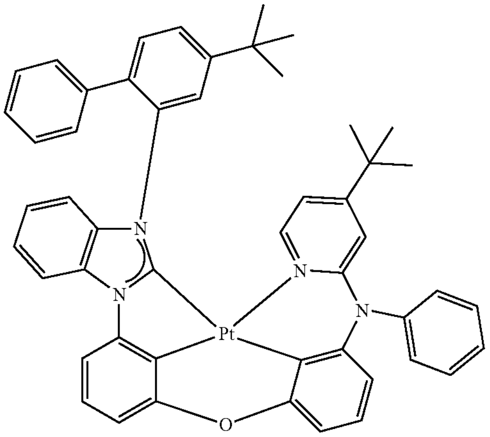
97
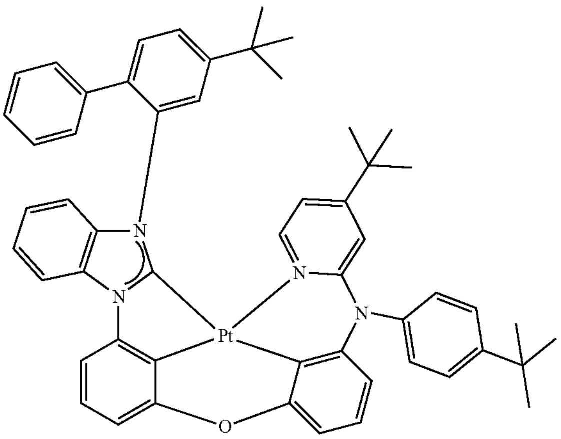
-continued
98
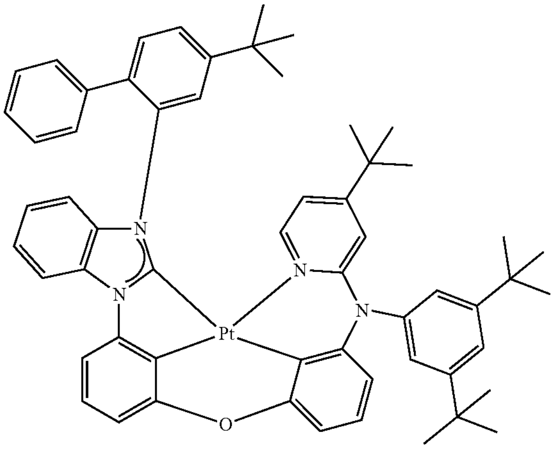
99
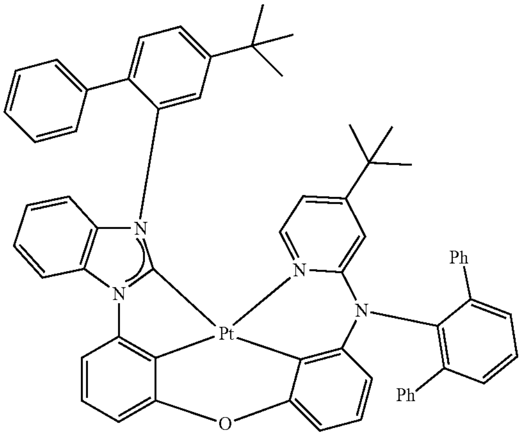
100
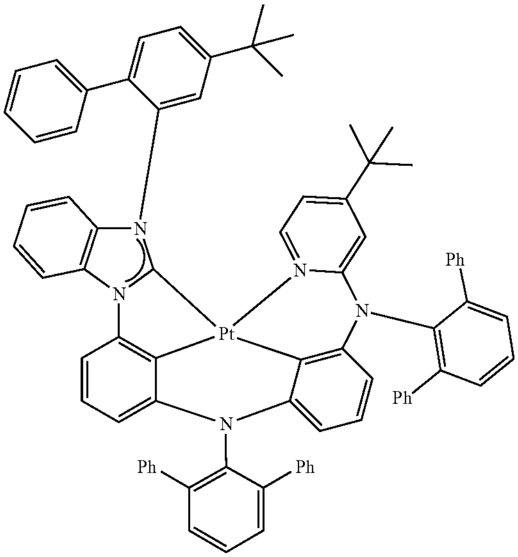

-continued
101
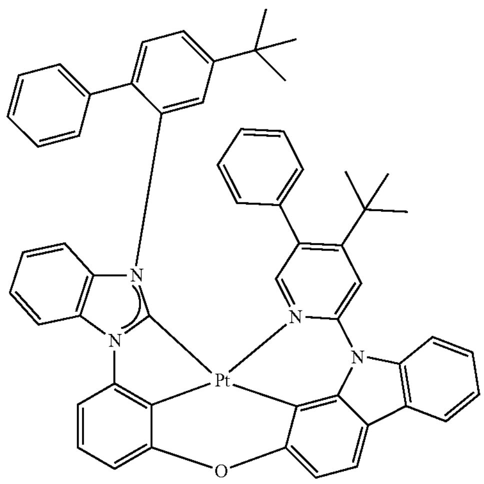
102
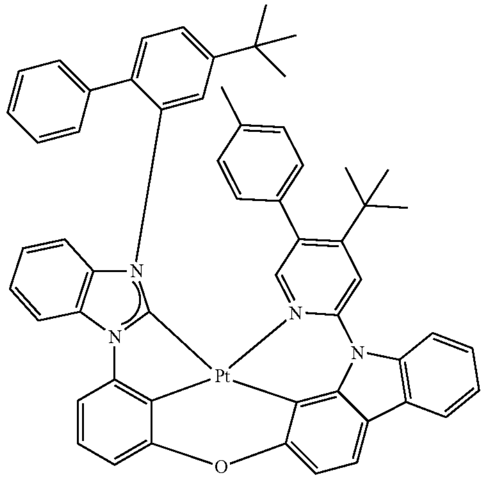
103
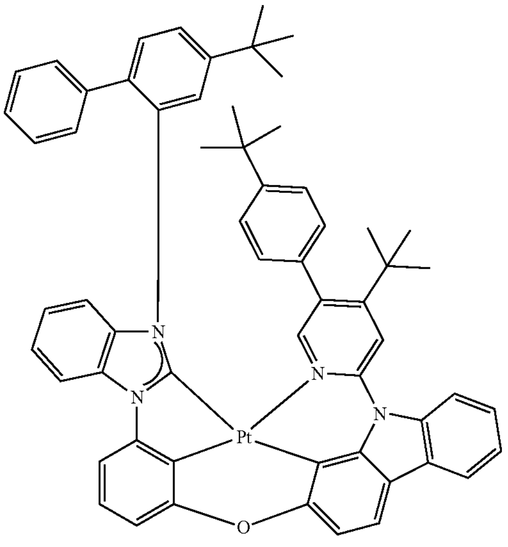
-continued
104
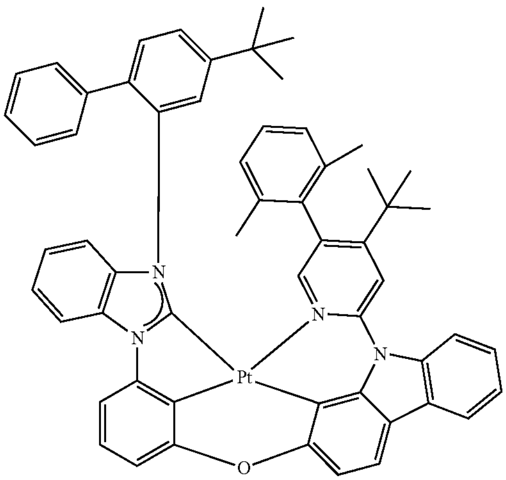
105
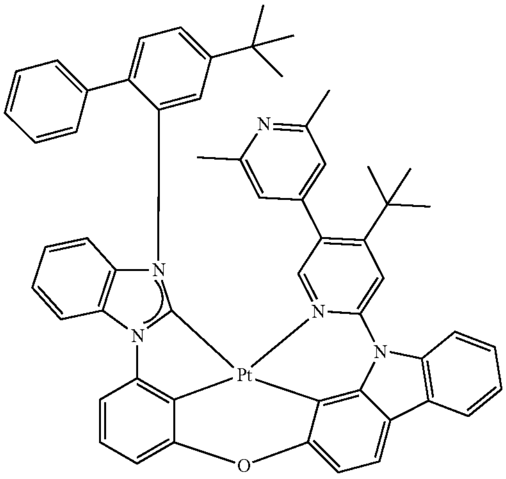
106
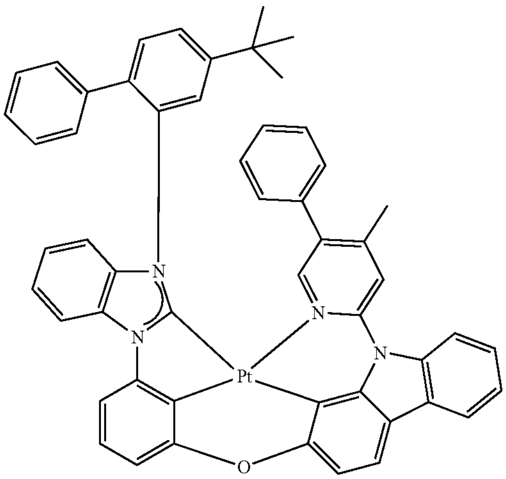

-continued
107
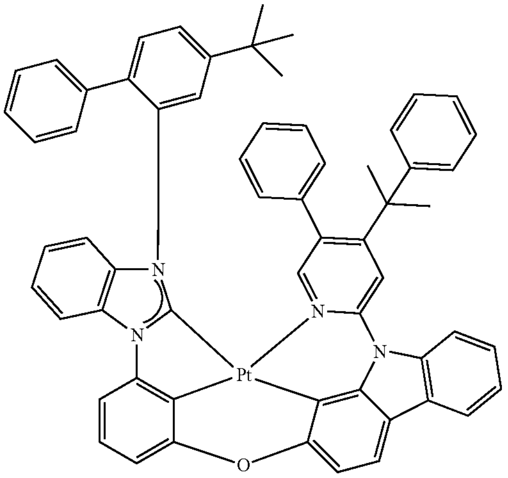
108
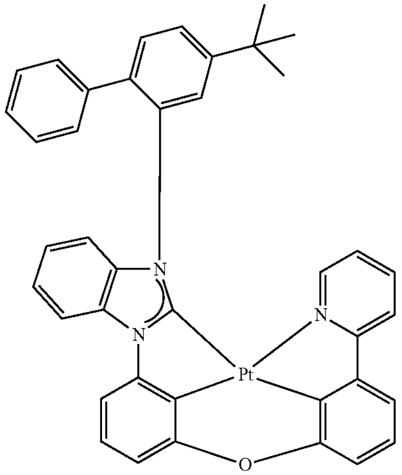
109
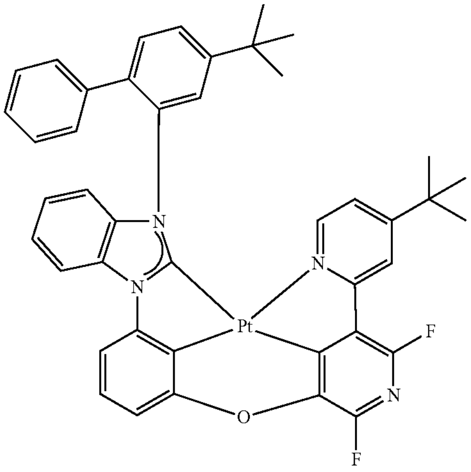
-continued
110
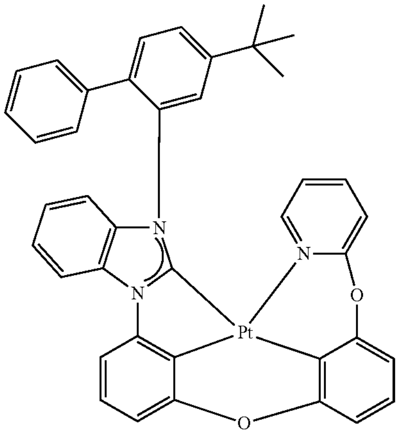
111
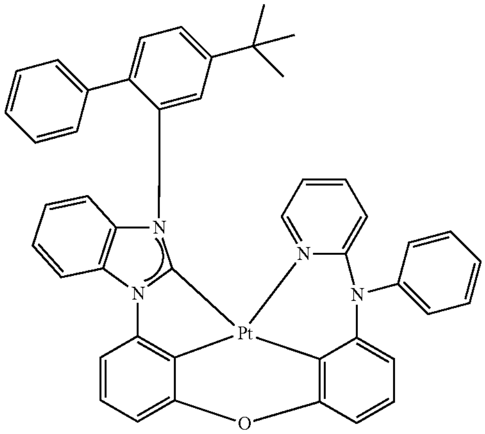
112
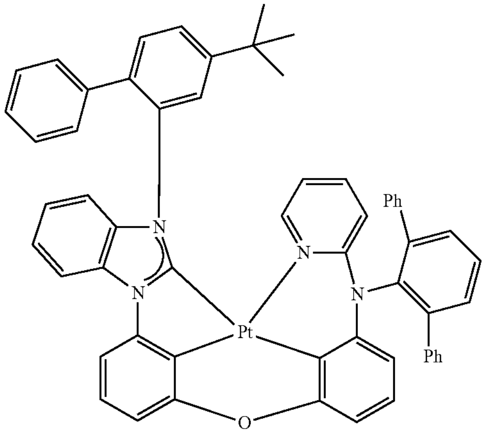

-continued
113
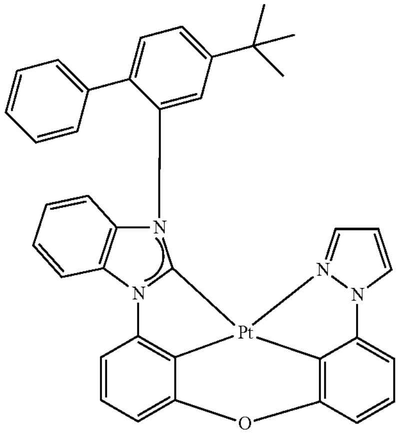
114
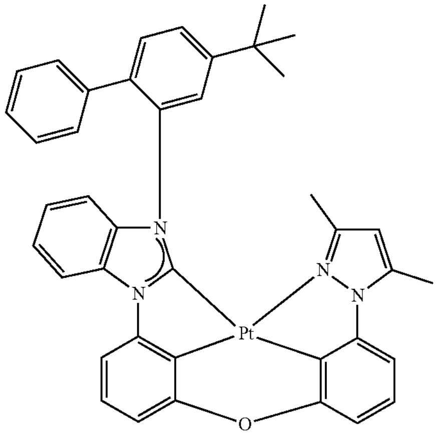
115
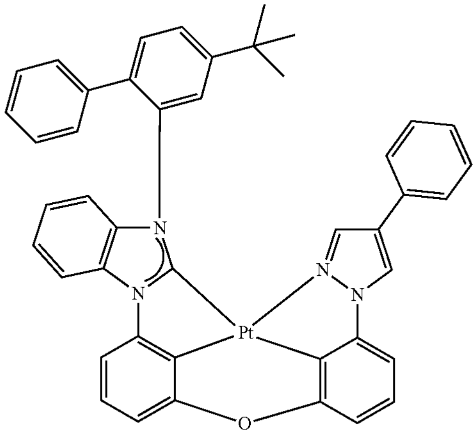
-continued
116
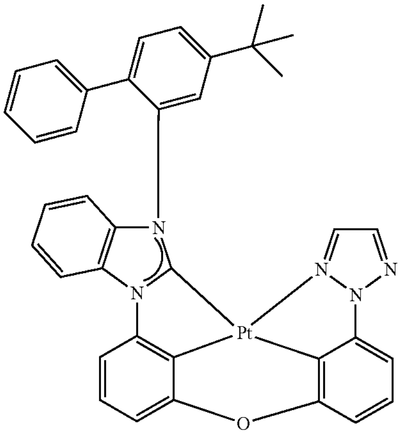
117
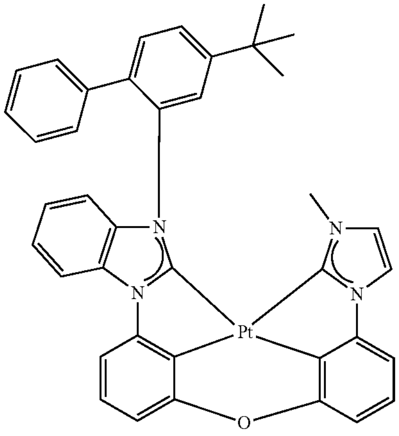
118
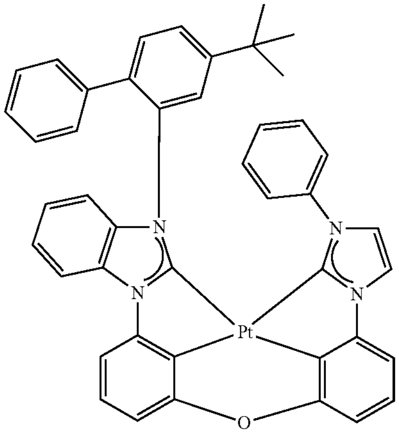

-continued
119
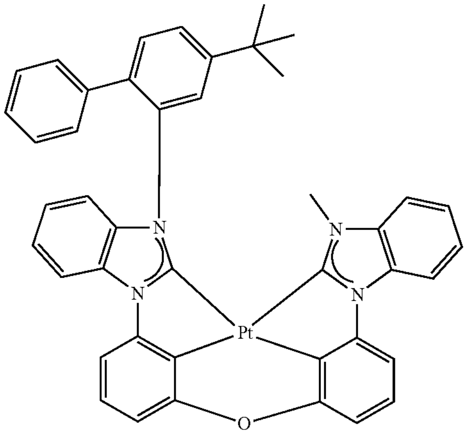
120
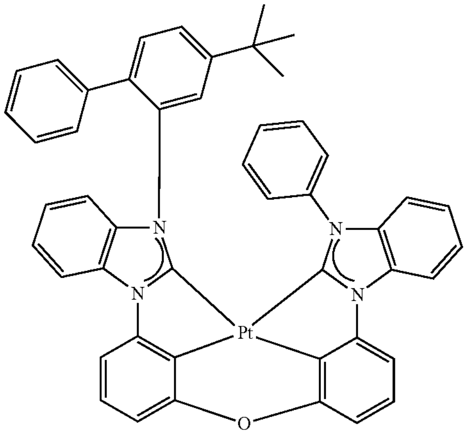
121
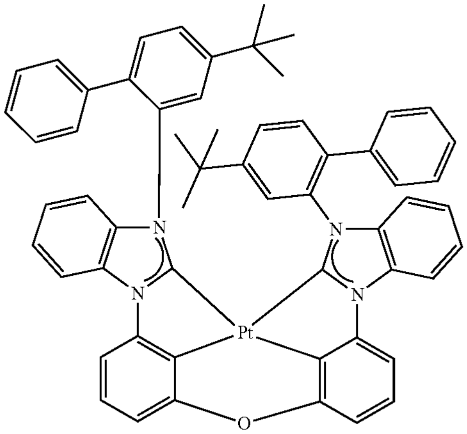
-continued
122
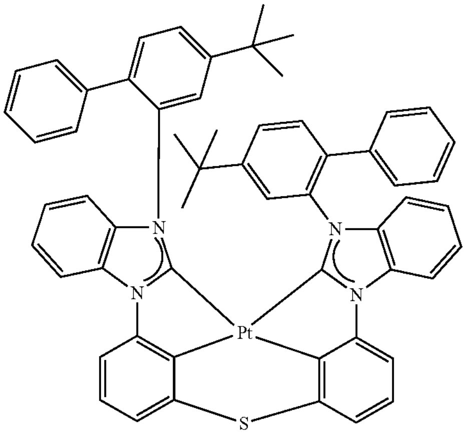
123
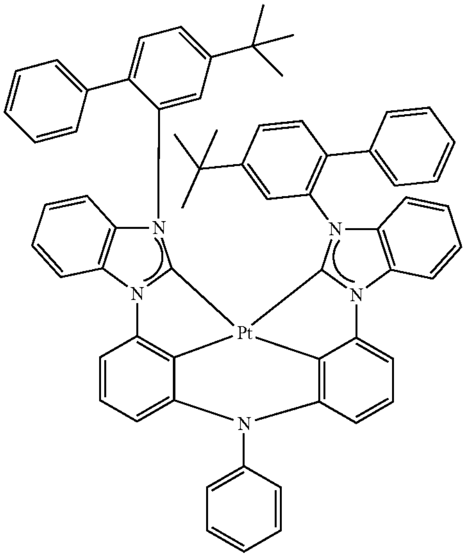
124
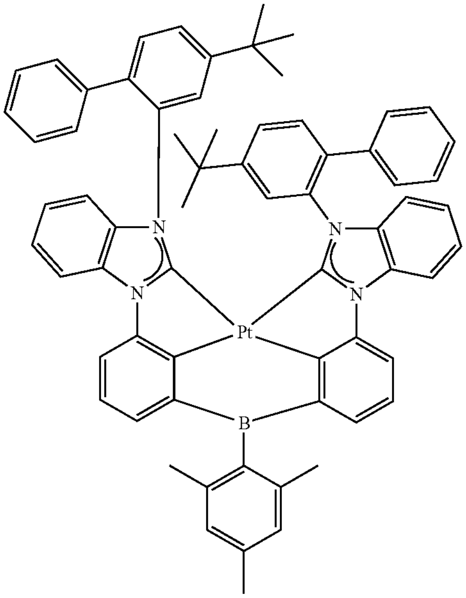

-continued
125
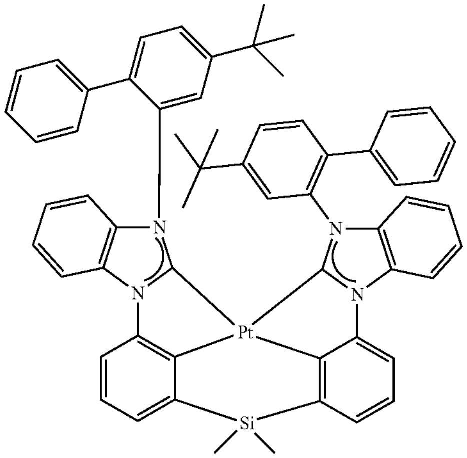
126
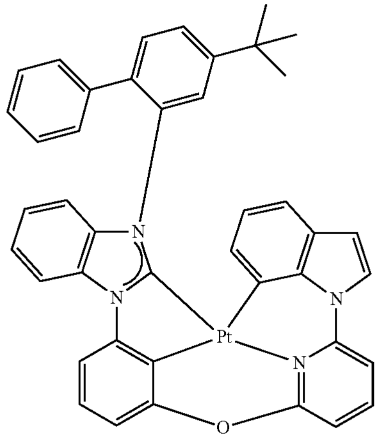
127
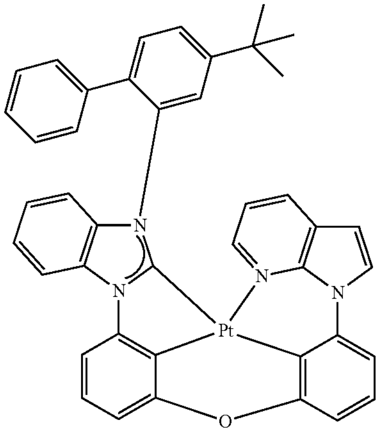
-continued
128
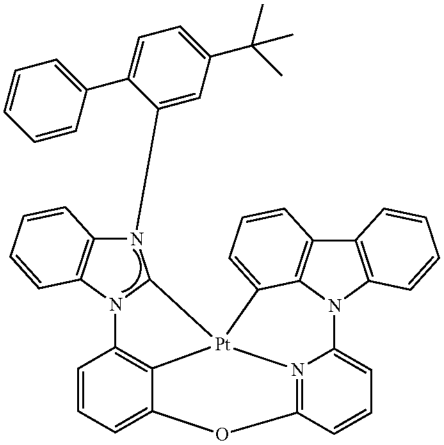
129
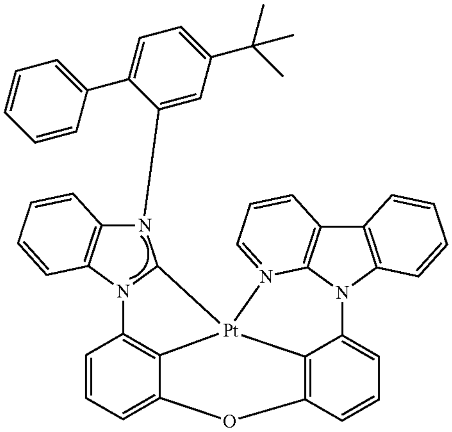
130
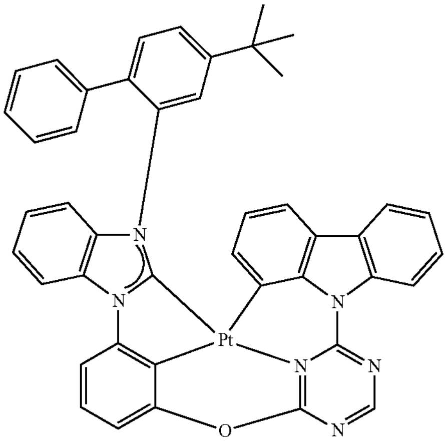

-continued
131
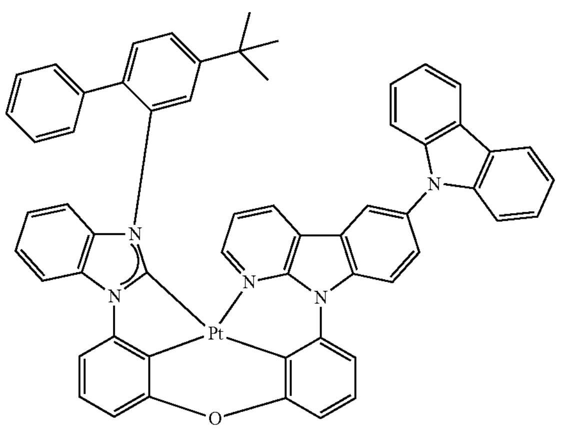
132
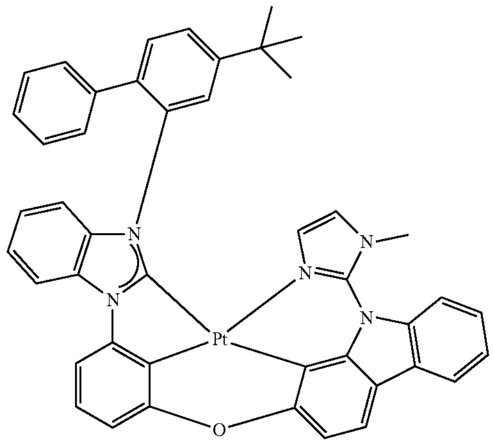
133
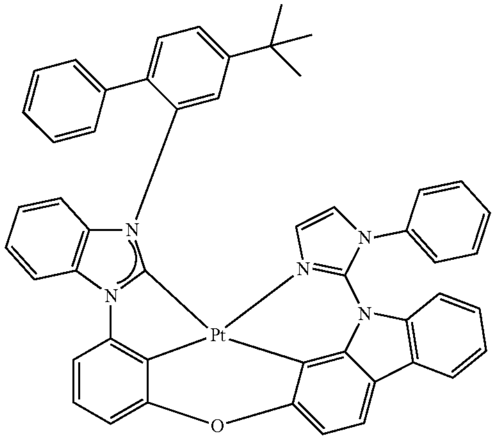
-continued
134
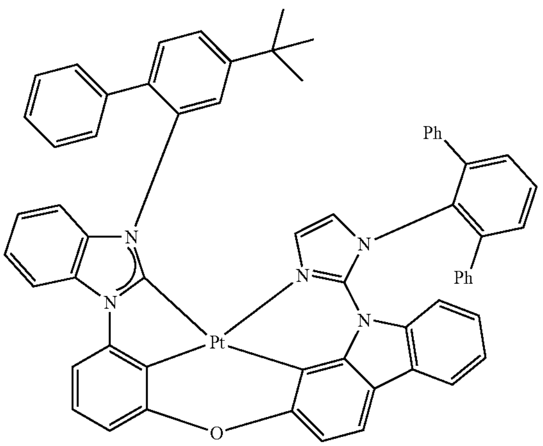
135
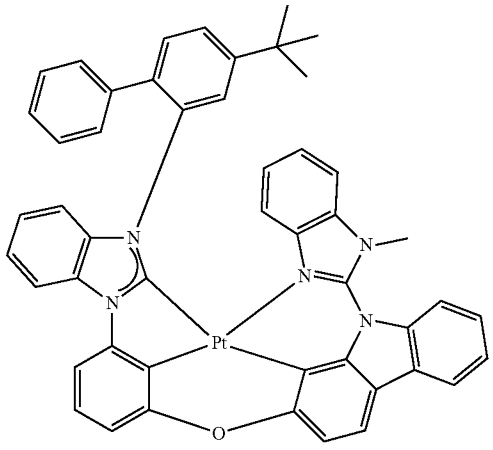
136
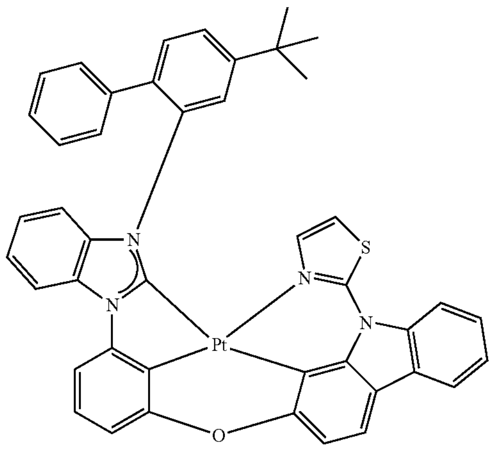

-continued
137
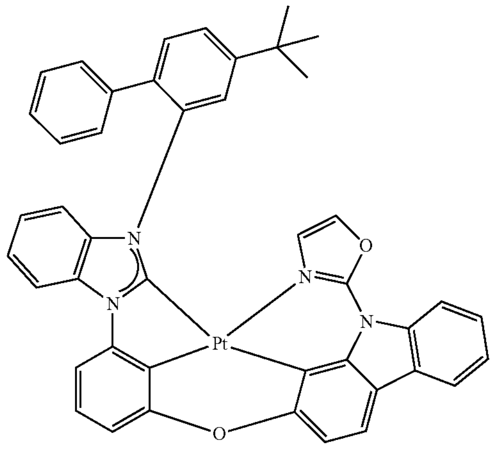
138
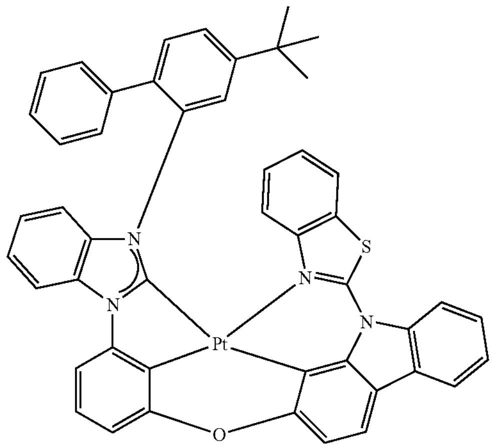
139
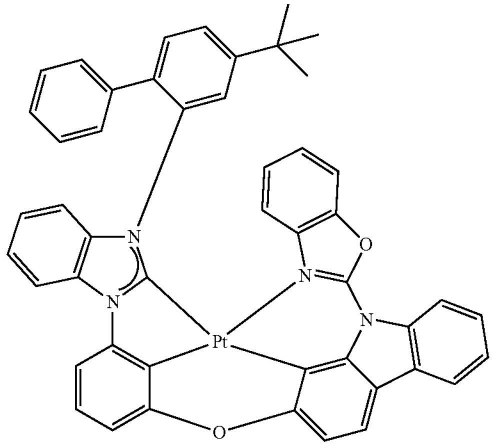
-continued
140
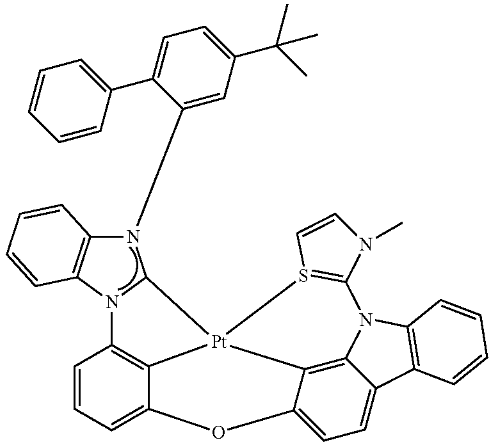
141
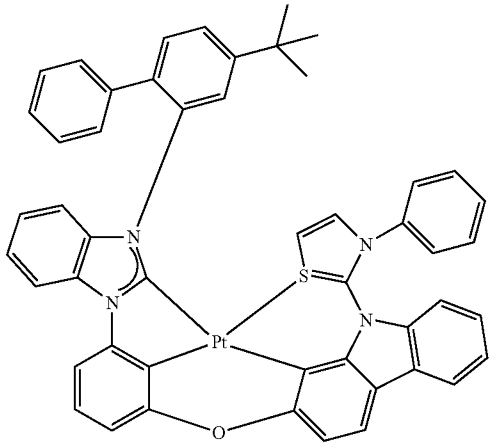
142
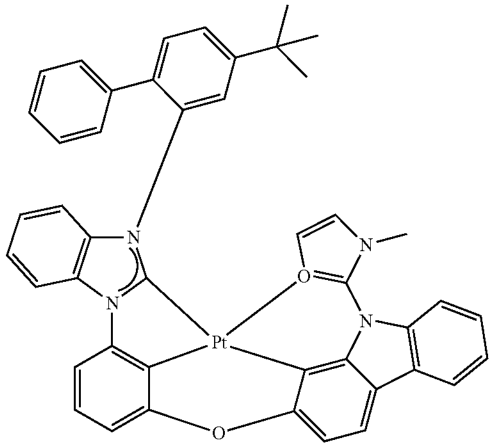

-continued
143
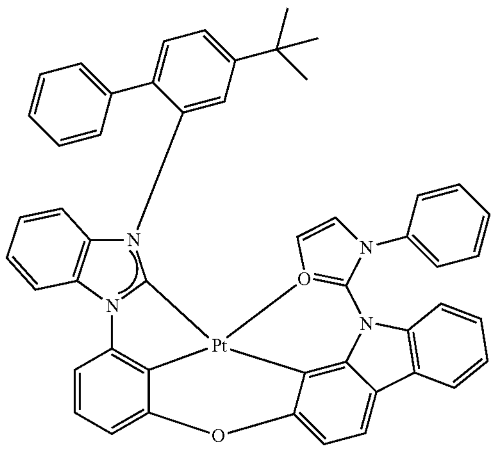
144
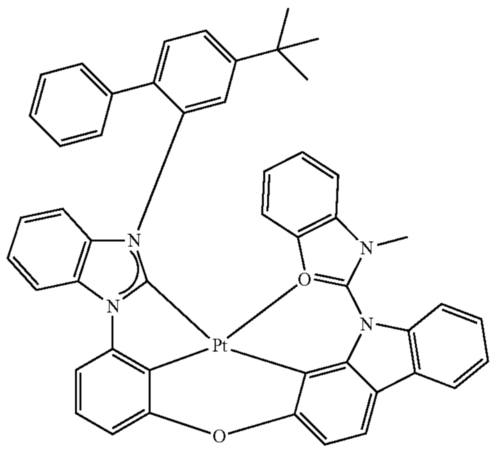
145
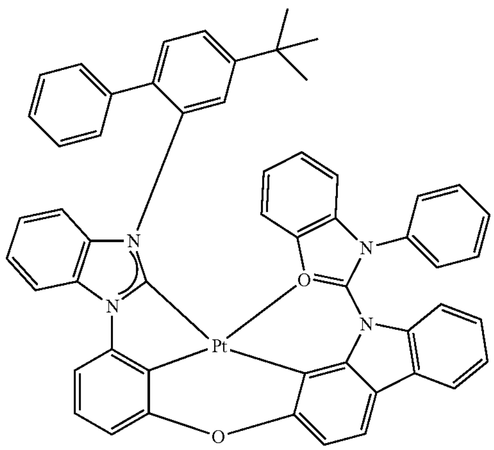
-continued
146
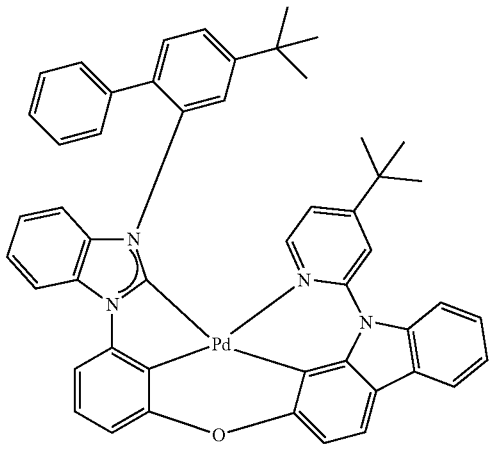
147
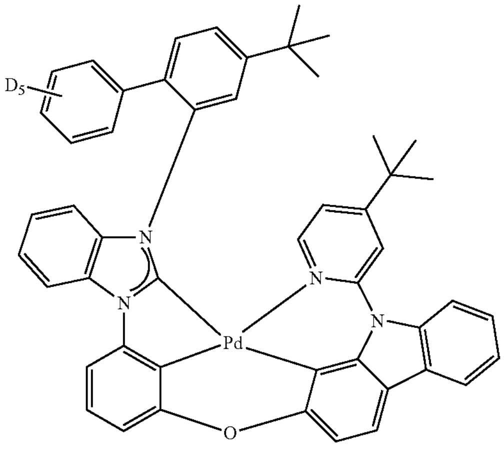
148
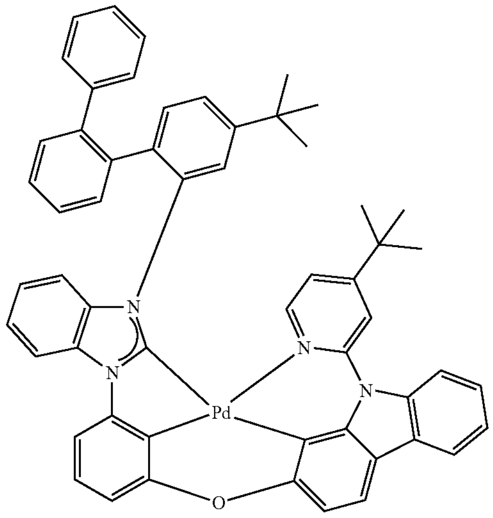

-continued

149

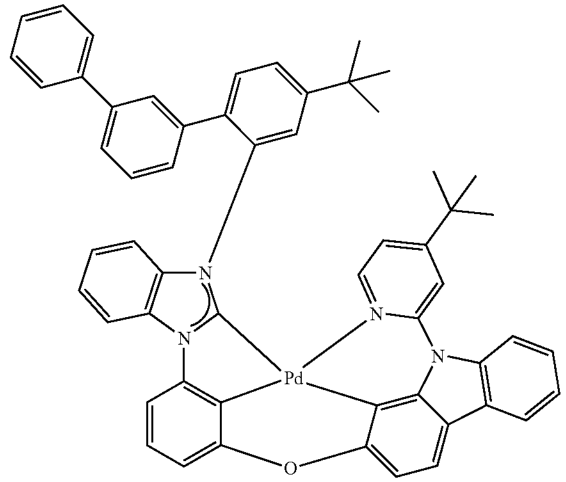

150

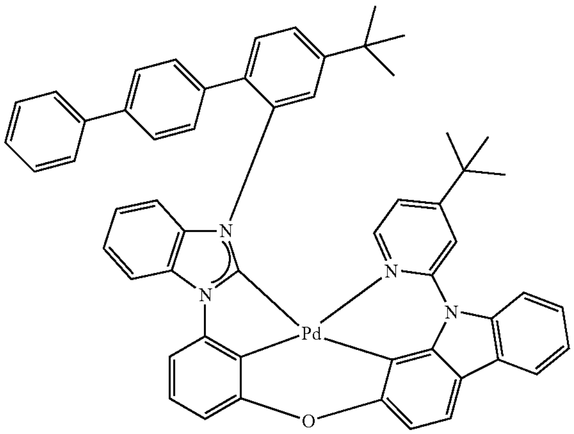

In Compounds 1 to 150, $D_5$ represents substitution with five deuterium atoms, and Ph is a phenyl group. For example, a group represented by

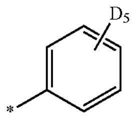

is identical to a group represented by

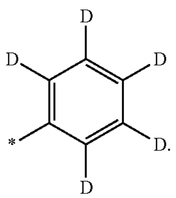

The organometallic compound represented by Formula 1 may have a strong steric shielding effect due to an N-containing core structure being bonded at an ortho position to $A_5$ in Formula 1, and may have a relatively weak steric shielding effect due to $R_{5a}$ being bonded at a para position to $A_5$, and thus, the organometallic compound may have high color purity and high stability due to a steric shielding effect.

When $A_5$ is a $C_6$-$C_{60}$ aryl group or a $C_1$-$C_{60}$ heteroaryl group, an inductive effect in a core may decrease, thereby increasing stability of the organometallic compound.

Thus, an electronic device, for example, an organic light-emitting device including the organometallic compound, may have low driving voltage, excellent luminescence efficiency, long lifespan, and excellent color purity, and thus, may be used in the manufacture of a high-quality electronic apparatus.

Methods of synthesizing the organometallic compound represented by Formula 1 may be readily understood by those of ordinary skill in the art by referring to Synthesis Examples and Examples described herein.

At least one organometallic compound represented by Formula 1 may be used in a light-emitting device (for example, an organic light-emitting device). Thus, provided is a light-emitting device which may include a first electrode, a second electrode facing the first electrode, an interlayer between the first electrode and the second electrode and including an emission layer, and the organometallic compound represented by Formula 1 as described in the specification.

In an embodiment, the interlayer of the light-emitting device may further include a hole transport region between the first electrode and the emission layer and an electron transport region between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In an embodiment, the first electrode of the light-emitting device may be an anode, and the second electrode of the light-emitting device may be a cathode.

In an embodiment, the organometallic compound may be included between the first electrode and the second electrode of the light-emitting device. Therefore, the organometallic compound may be included in the interlayer of the light-emitting device, for example, in the emission layer of the interlayer.

In an embodiment, the emission layer in the interlayer of the light-emitting device may include a dopant and a host, and the host may include the organometallic compound. For example, the organometallic compound may serve as a dopant. The emission layer may emit red light, green light, blue light, and/or white light. In an embodiment, the emission layer may emit blue light, and the blue light may have a maximum emission wavelength in a range of, for example, about 410 nm to about 500 nm.

In an embodiment, the interlayer of the light-emitting device may include:

a first compound which is the organometallic compound represented by Formula 1; and a second compound including a group represented by Formula 2, a third compound represented by Formula 3, a fourth compound including a group represented by Formula 4, or any combination thereof, the first compound, the second compound, and the third compound may be different from one another, the first compound, the second compound, and the fourth compound may be different from one another, and the third compound and the fourth compound may be identical to or different from each other:

[Formula 2]

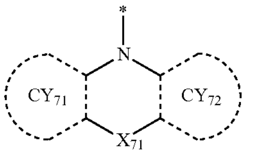

In Formula 2, ring CY71 and ring CY72 may each independently be a π electron-rich $C_3$-$C_{60}$ cyclic group or a pyridine group, $X_{71}$ may be: a single bond; or a linking group including O, S, N, B, C, Si, or any combination thereof,

* indicates a binding site to a neighboring atom in the second compound, and

CBP and mCBP are excluded from the second compound:

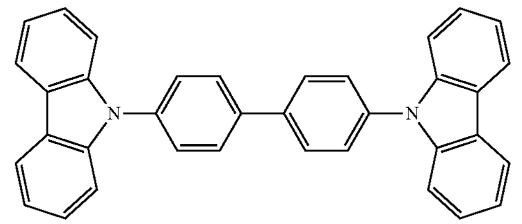

CBP

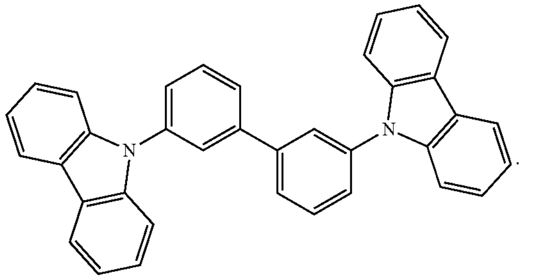

mCBP

[Formula 3]

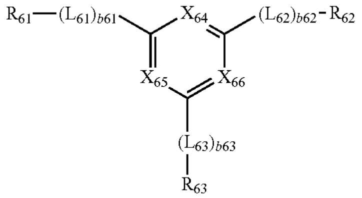

In Formula 3, $L_{61}$ to $L_{63}$ may each independently be a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, b61 to b63 may each independently be an integer from 1 to 5, $X_{64}$ may be N or $C(R_{64})$, $X_{65}$ may be N or $C(R_{65})$, $X_{66}$ may be N or $C(R_{66})$, and at least one of $X_{64}$ to $X_{66}$ may be N, $R_{61}$ to $R_{66}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$C(Q_1)(Q_2)(Q_3)$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, and $R_{10a}$ and $Q_1$ to $Q_3$ are respectively the same as those described in the specification.

[Formula 4]

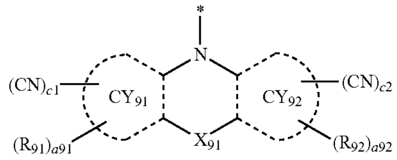

In Formula 4, ring CY91 and ring CY92 may each independently be a π electron-rich $C_3$-$C_{60}$ cyclic group or a pyridine group, $X_{91}$ may be: a single bond; or a linking group including O, S, N, B, C, Si, or any combination thereof, $R_{91}$ and $R_{92}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$C(Q_1)(Q_2)(Q_3)$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, a91 and a92 may each independently be an integer from 0 to 5, c1 and c2 may each independently be an integer from 0 to 5, wherein the sum of c1 and c2 is 1 or more, $R_{10a}$ and $Q_1$ to $Q_3$ are respectively the same as those described in the specification, and

* indicates a binding site to a neighboring atom in the fourth compound.

In an embodiment, the emission layer of the light-emitting device may include a dopant and a host, the dopant may include the first compound, and the host may include the second compound, the third compound, the fourth compound, or any combination thereof.

In an embodiment, the emission layer of the light-emitting device may include a dopant and a host, the dopant may include the first compound, and the host may include: the second compound; and at least one of the third compound and the fourth compound.

In an embodiment, the emission layer may emit phosphorescent or fluorescent light emitted from the first compound. In an embodiment, the phosphorescent or fluorescent light emitted from the first compound may be blue light.

In an embodiment, the second compound may include a compound represented by Formula 2-1, a compound represented by Formula 2-2, a compound represented by Formula 2-3, a compound represented by Formula 2-4, a compound represented by Formula 2-5, or any combination thereof:

[Formula 2-1]

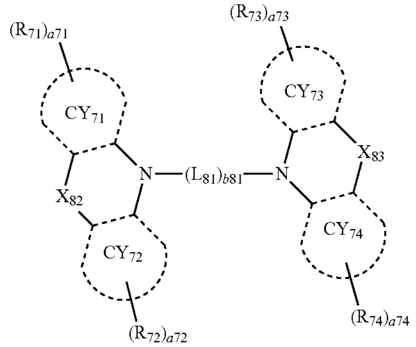

[Formula 2-2]

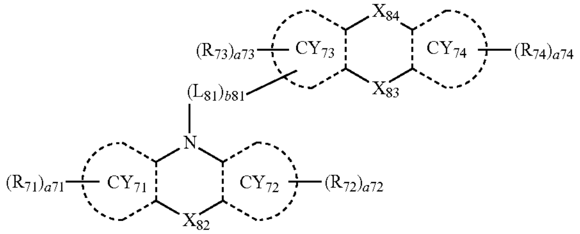

[Formula 2-3]

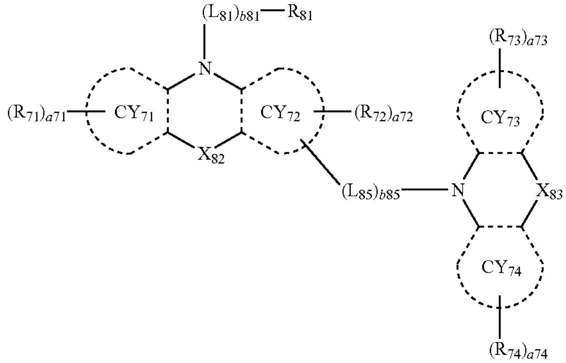

[Formula 2-4]

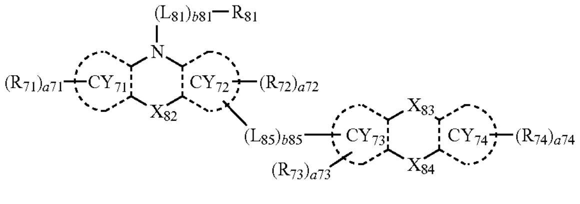

-continued

[Formula 2-5]

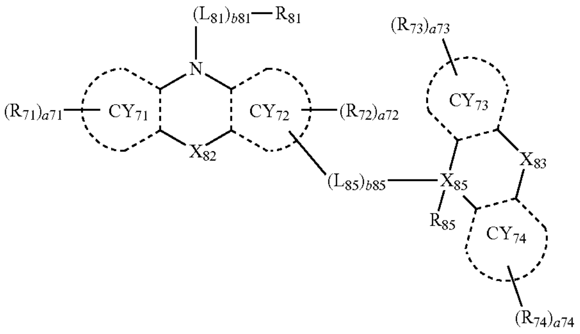

In Formulae 2-1 to 2-5, ring CY71 to ring CY74 may each independently be a π electron-rich $C_3$-$C_{60}$ cyclic group or a pyridine group, $X_{82}$ may be a single bond, O, S, N-[$(L_{82})_{b82}$-$R_{82}$], C($R_{82a}$)($R_{82b}$), or Si($R_{82a}$)($R_{82b}$), $X_{83}$ may be a single bond, O, S, N-[$(L_{83})_{b83}$-$R_{83}$], C($R_{83a}$)($R_{83b}$), or Si($R_{83a}$)($R_{83b}$), $X_{84}$ may be O, S, N-[$(L_{84})_{b84}$-$R_{84}$], C($R_{84a}$)($R_{84b}$), or Si($R_{84a}$)($R_{84b}$), $X_{85}$ may be C or Si, $L_{81}$ to $L_{85}$ may each independently be a single bond, *—C($Q_4$)($Q_5$)-*', *—Si($Q_4$)($Q_5$)-*', a π electron-rich $C_3$-$C_{60}$ cyclic group unsubstituted or substituted with at least one $R_{10a}$, or a pyridine group unsubstituted or substituted with at least one $R_{10a}$, wherein $Q_4$ and $Q_5$ are each independently the same as described in connection with $Q_1$ in the specification, b81 to b85 may each independently be an integer from 1 to 5, $R_{71}$ to $R_{74}$, $R_{81}$ to $R_{85}$, $R_{82a}$, $R_{82b}$, $R_{83a}$, $R_{83b}$, $R_{84a}$, and $R_{84b}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), a71 to a74 may each independently be an integer from 0 to 20, and $R_{10a}$ and $Q_1$ to $Q_3$ are respectively the same as those described in connection with Formula 1.

In an embodiment, the second compound may be one of Compounds H1-1 to H1-24:
H1-1
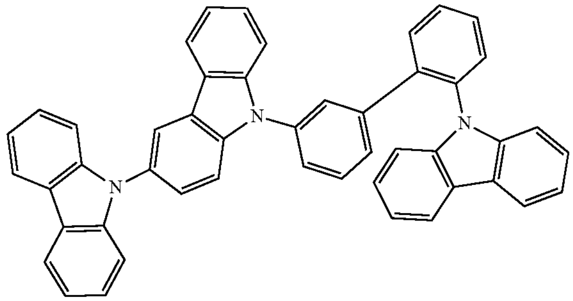
H1-2
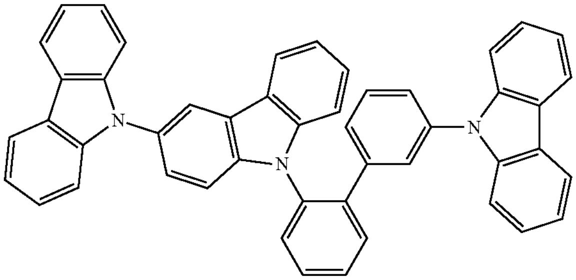
H1-3
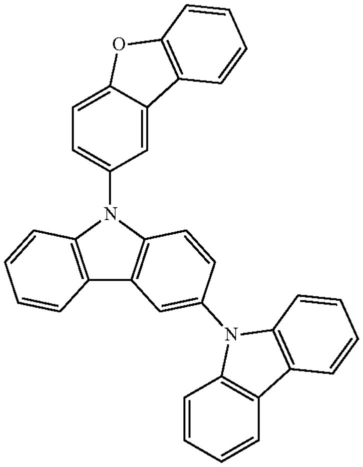
H1-4
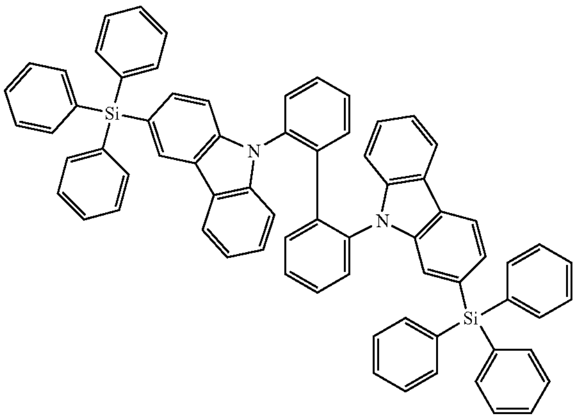
-continued
H1-5
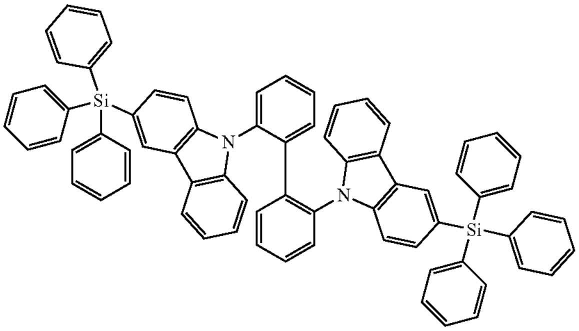
H1-6
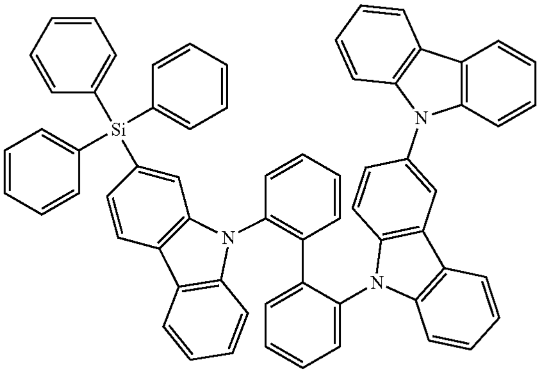
H1-7
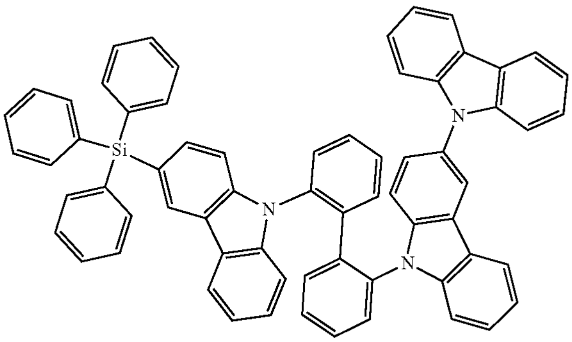
H1-8
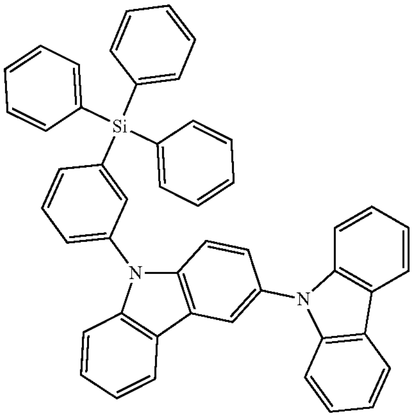

-continued
H1-9
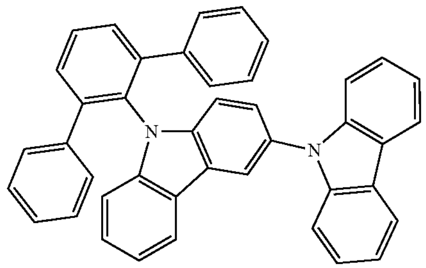
H1-10
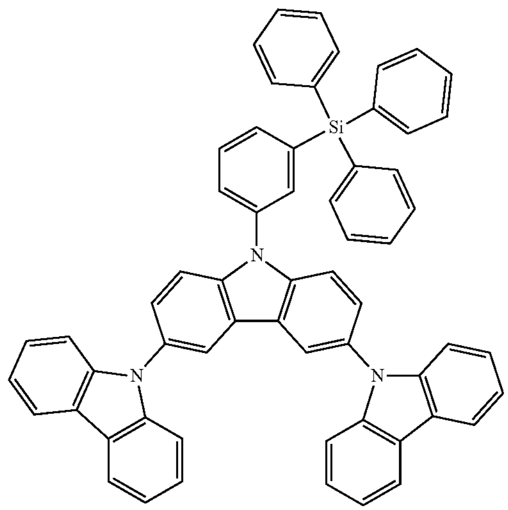
H1-11
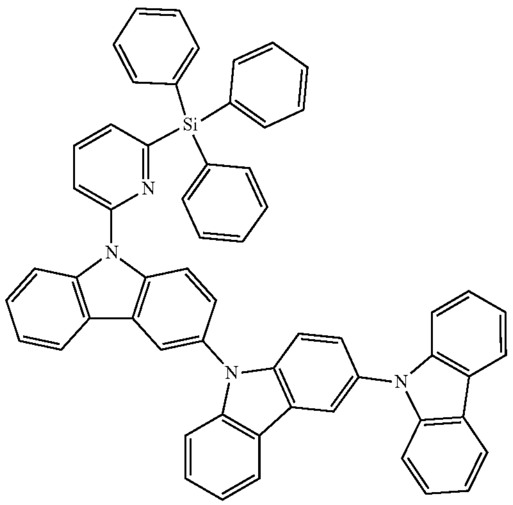
-continued
H1-12
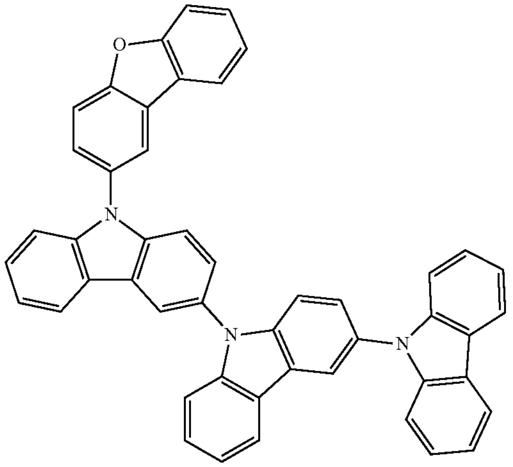
H1-13
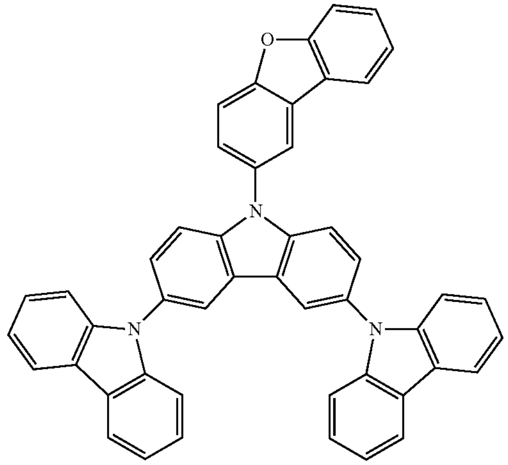
H1-14
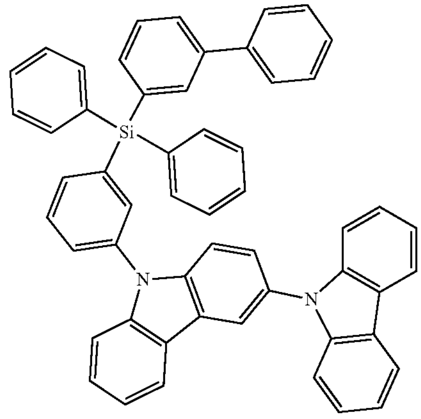

-continued
H1-15
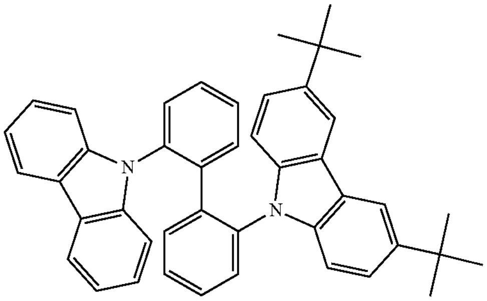
H1-16
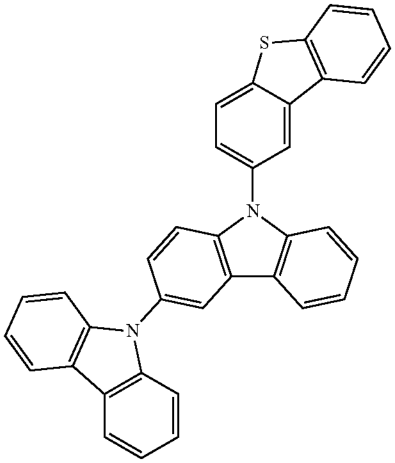
H1-17
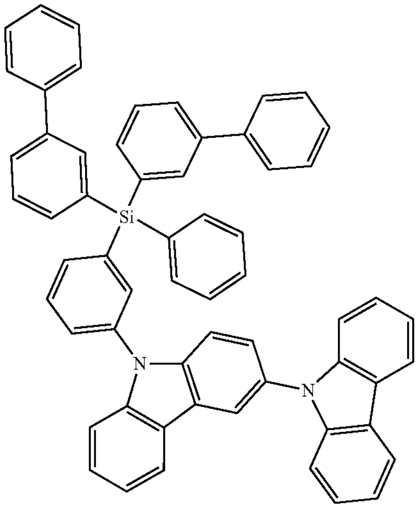
H1-18
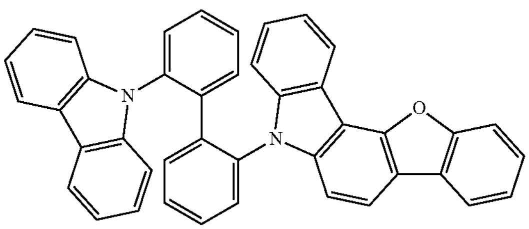
-continued
H1-19
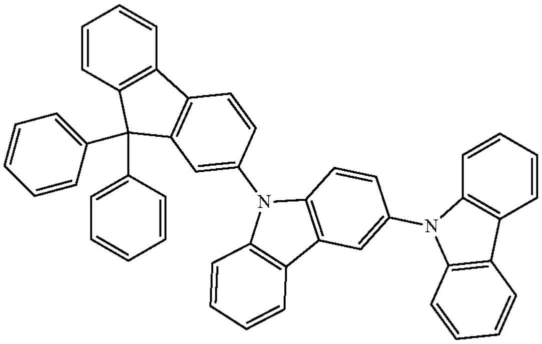
H1-20
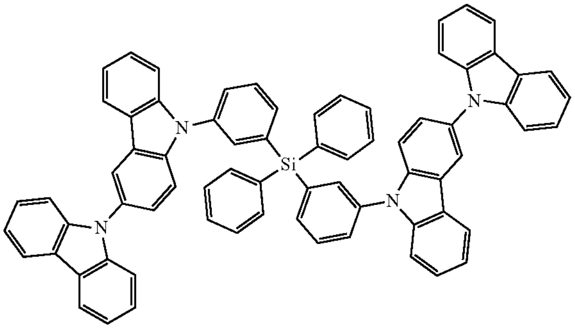
H1-21
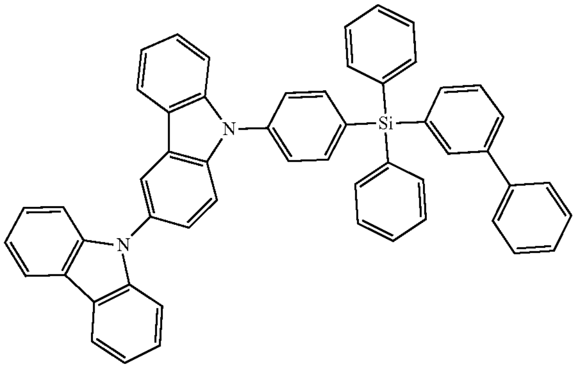
H1-22
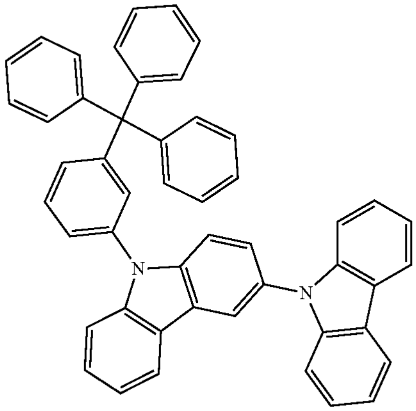

-continued

H1-23

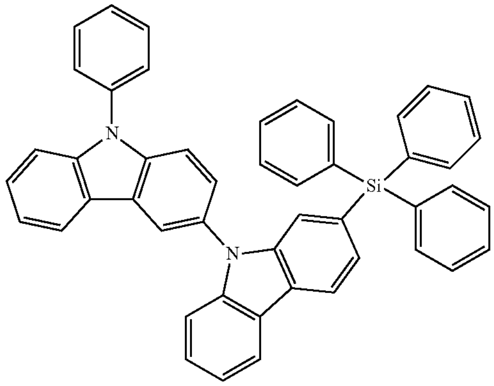

H1-24

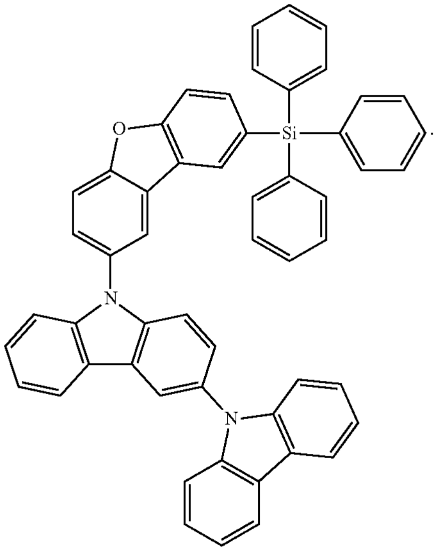

In an embodiment, the fourth compound may include a group represented by Formula 4-1:

[Formula 4-1]

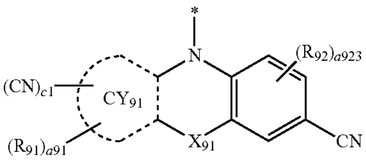

In Formula 4-1,

CY91, $X_{91}$, $R_{91}$, $R_{92}$, a91, and c1 are respectively the same as those described in connection with Formula 4, a923 may be an integer from 0 to 3, and

* indicates a binding site to a neighboring atom in the fourth compound.

In an embodiment, the third compound and the fourth compound may each independently be one of Compounds E1 to E32:

E1

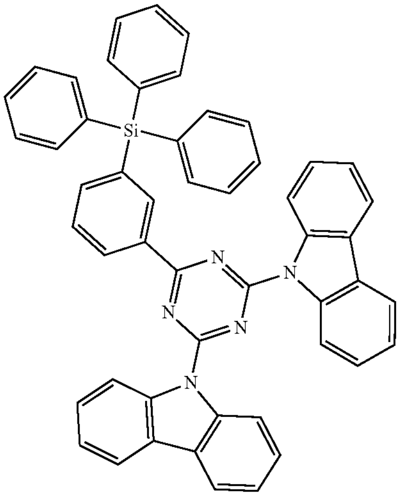

E2

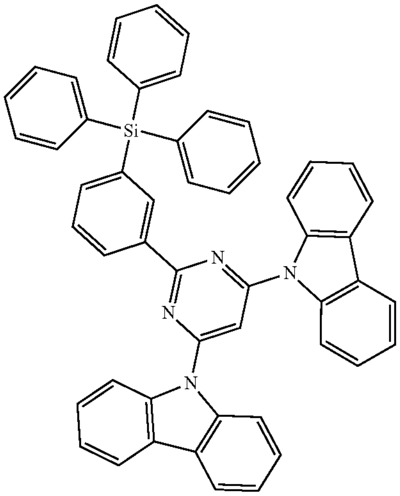

E3

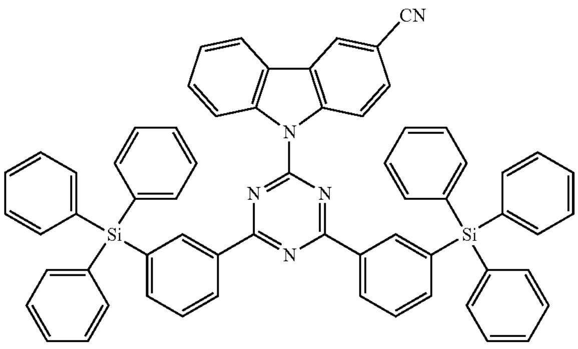

-continued
E4
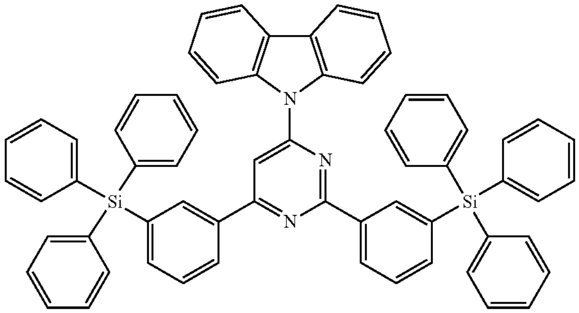
E5
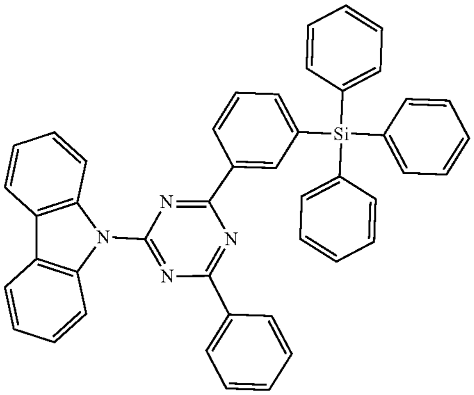
E6
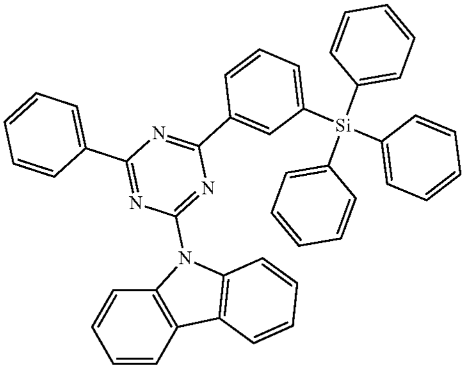
E7
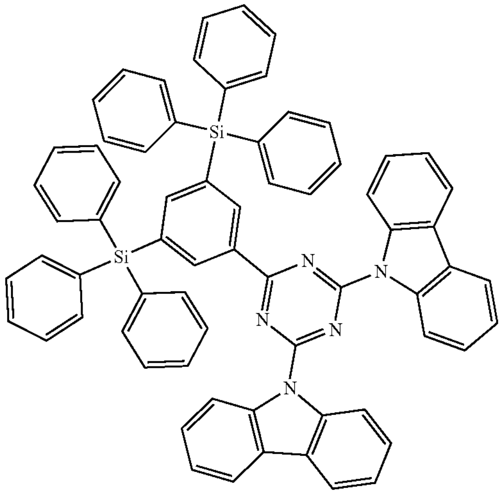
-continued
E8
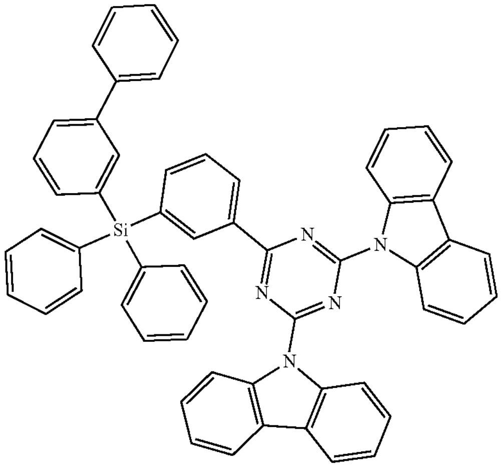
E9
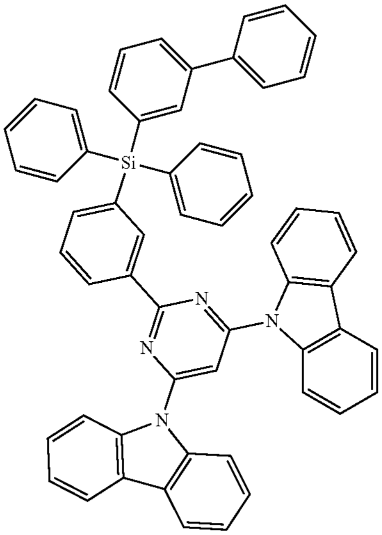
E10
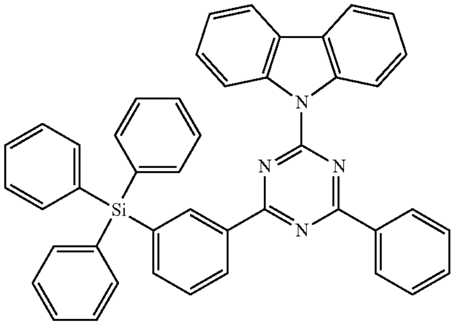

-continued
E11
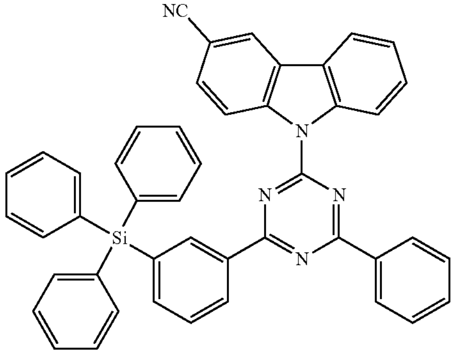
E12
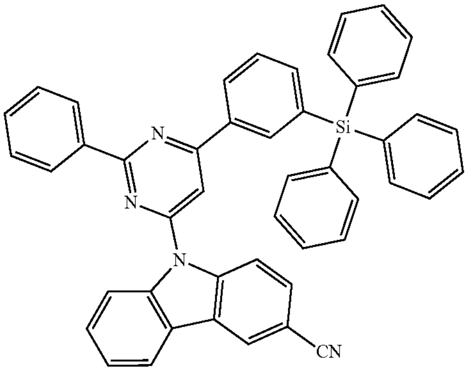
E13
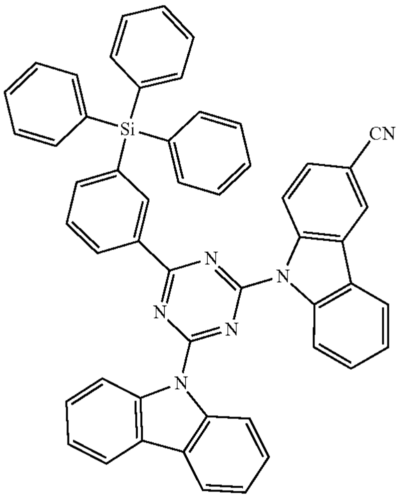
-continued
E14
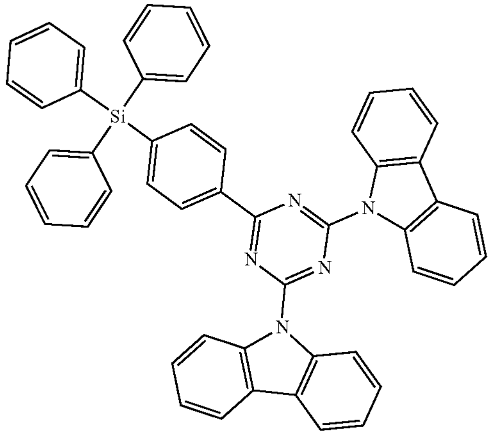
E15
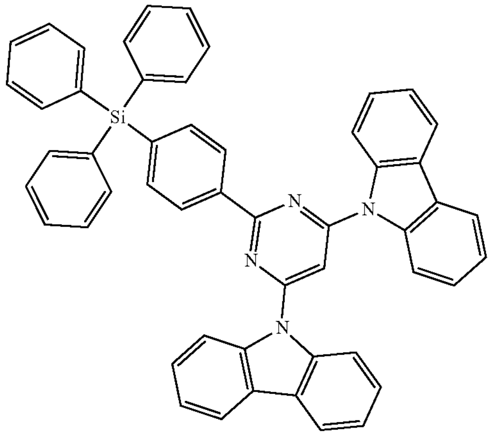
E16
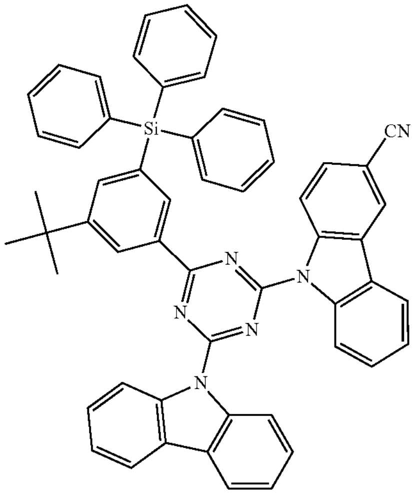

-continued
E17
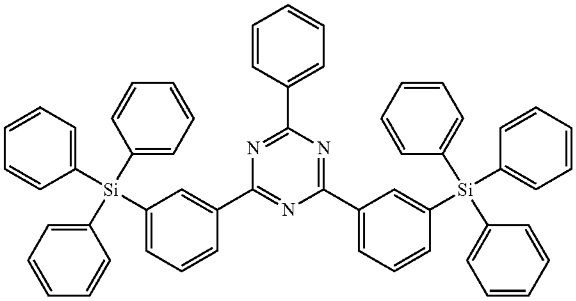
E18
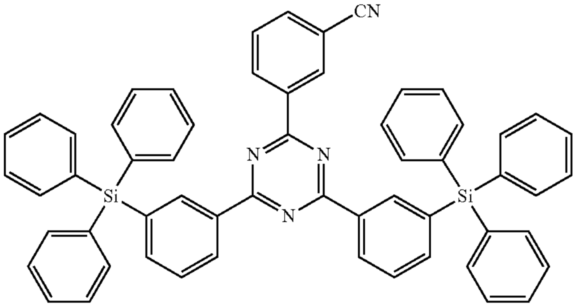
E19
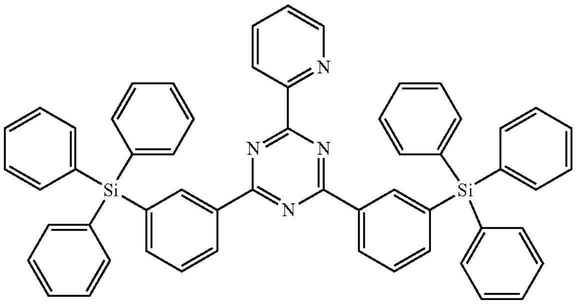
E20
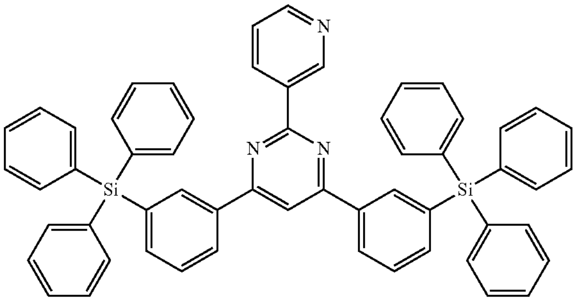
E21
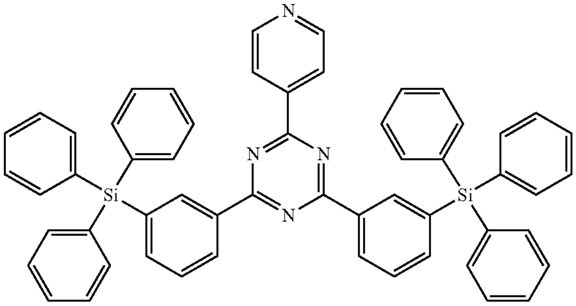
-continued
E22
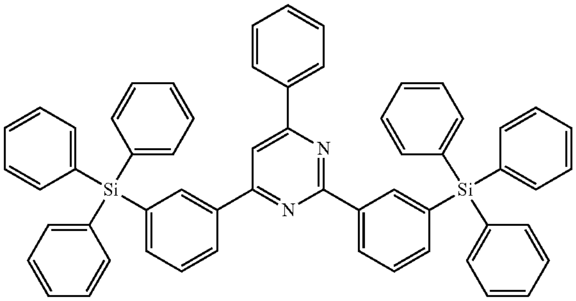
E23
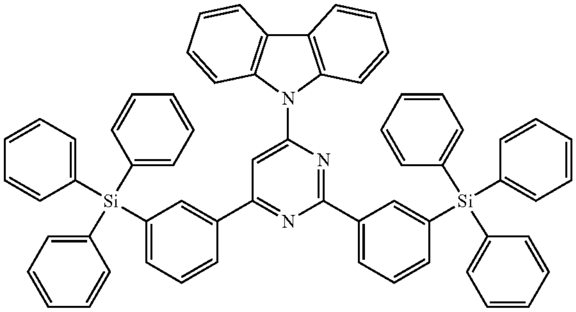
E24
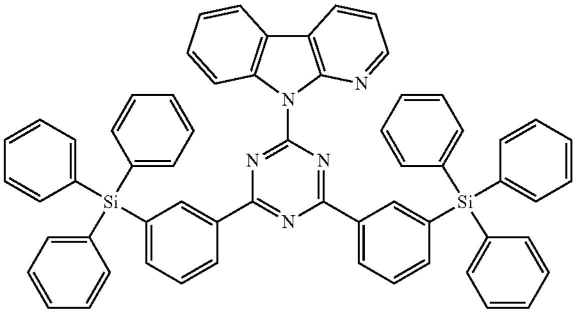
E25
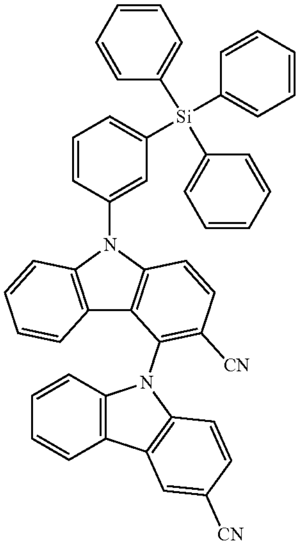

-continued

E26

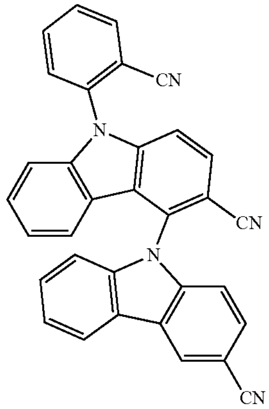

E27

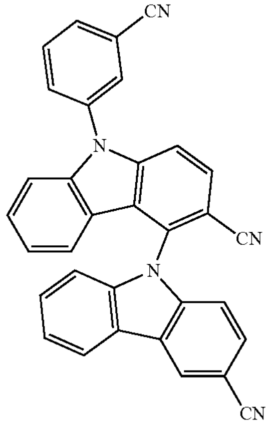

E28

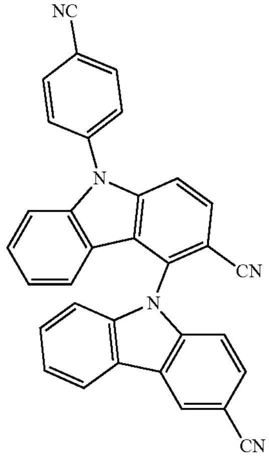

E29

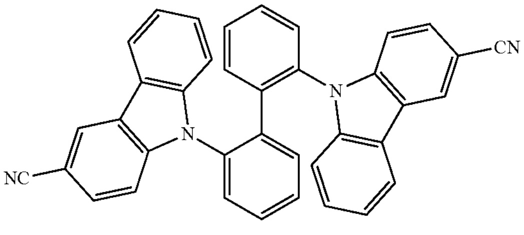

-continued

E30

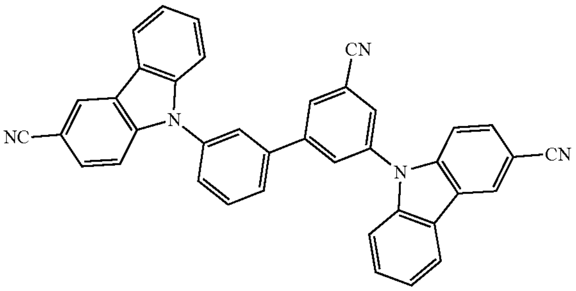

E31

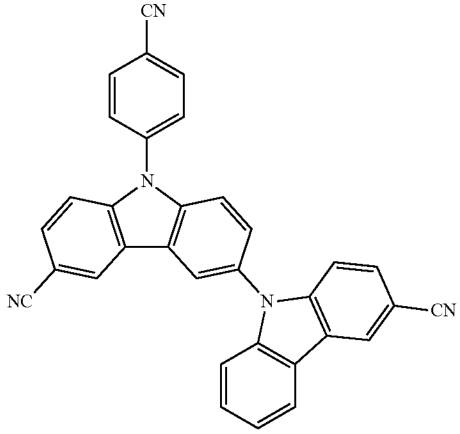

E32

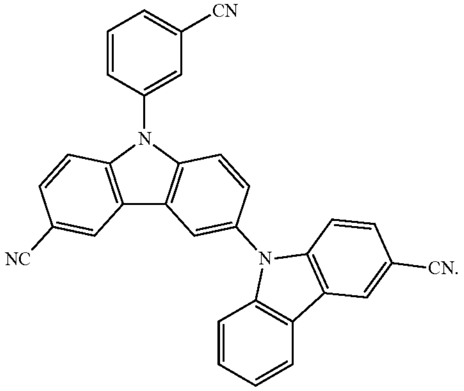

[Descriptions of Formulae 2, 2-1 to 2-5, 3, 4, and 4-1]

In Formula 3, b61 to b63 respectively indicate numbers of $L_{61}$ to $L_{63}$, and may each independently be an integer from 1 to 5. When b61 is 2 or more, two or more of $L_{61}$(s) may be identical to or different from each other, when b62 is 2 or more, two or more of $L_{62}$(s) may be identical to or different from each other, and when b63 is 2 or more, two or more of $L_{63}$(s) may be identical to or different from each other. In an embodiment, b61 to b63 may each independently be 1 or 2.

$L_{61}$ to $L_{63}$ in Formula 3 may each independently be:

a single bond; or a benzene group, a naphthalene group, an anthracene group, a phenanthrene group, a triphenylene group, a pyrene group, a chrysene group, a cyclopentadiene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an iso-oxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a dibenzooxasiline group, a dibenzothiasiline group, a dibenzodihydroazasiline group, a dibenzodihydrodihydrodisiline group, a dibenzodihydrosiline group, a dibenzodioxine group, a dibenzooxathiine group, a dibenzooxazine group, a dibenzopyran group, a dibenzodithiine group, a dibenzothiazine group, a dibenzothiopyran group, a dibenzocyclohexadiene group, a dibenzodihydropyridine group, or a dibenzodihydropyrazine group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a naphthyl group, a pyridinyl group, a pyrimidinyl group, a triazinyl group, a fluorenyl group, a dimethylfluorenyl group, a diphenyl fluorenyl group, a carbazolyl group, a phenylcarbazolyl group, a dibenzofuranyl group, a dibenzothiophenyl group, a dibenzosilolyl group, a dimethyl dibenzosilolyl group, a diphenyl dibenzosilolyl group, —O ($Q_{31}$), —S($Q_{31}$), —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(═O)($Q_{31}$), —S(═O)$_2$($Q_{31}$), —P(═O)($Q_{31}$)($Q_{32}$), or any combination thereof, and $Q_{31}$ to $Q_{33}$ may each independently be hydrogen, deuterium, a $C_1$-$C_{20}$ alkyl group, a $C_1$-$C_{20}$ alkoxy group, a phenyl group, a biphenyl group, a terphenyl group, a pyridinyl group, a pyrimidinyl group, a pyridazinyl group, a pyrazinyl group, or a triazinyl group.

In an embodiment, in Formula 3, a bond between $L_{61}$ and $R_{61}$, a bond between $L_{62}$ and $R_{62}$, a bond between $L_{63}$ and $R_{63}$, a bond between two or more $L_{61}$(s), a bond between two or more $L_{62}$(s), a bond between two or more $L_{63}$(s), a bond between $L_{61}$ and carbon between $X_{64}$ and $X_{65}$ in Formula 2, a bond between $L_{62}$ and carbon between $X_{64}$ and $X_{66}$ in Formula 3, and a bond between $L_{63}$ and carbon between $X_{65}$ and $X_{66}$ in Formula 3 may each be a carbon-carbon single bond.

In Formula 3, $X_{64}$ may be N or C($R_{64}$), $X_{65}$ may be N or C($R_{65}$), $X_{66}$ may be N or C($R_{66}$), and at least one of $X_{64}$ to $X_{66}$ may be N. $R_{64}$ to $R_{66}$ are respectively the same as those described in the specification. In an embodiment, two or three of $X_{64}$ to $X_{66}$ may be N.

$R_{61}$ to $R_{66}$, $R_{71}$ to $R_{74}$, $R_{81}$ to $R_{85}$, $R_{82a}$, $R_{82b}$, $R_{83a}$, $R_{83b}$, $R_{84a}$, $R_{84b}$, $R_{91}$, and $R_{92}$ in the specification may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), —N($Q_1$)($Q_2$), —B($Q_1$)($Q_2$), —C(═O)($Q_1$), —S(═O)$_2$($Q_1$), or —P(═O)($Q_1$)($Q_2$). $Q_1$ to $Q_3$ are respectively the same as those described in the specification.

In an embodiment, $R_{61}$ to $R_{66}$, $R_{71}$ to $R_{74}$, $R_{81}$ to $R_{85}$, $R_{82a}$, $R_{82b}$, $R_{83a}$, $R_{83b}$, $R_{84a}$, $R_{84b}$, $R_{91}$, and $R_{92}$ in Formulae 2, 2-1 to 2-5, 3, 4, and 4-1; and $R_{10a}$ may each independently be:

hydrogen, deuterium, —F, —Cl, —Br, —I, a hydroxyl group, a cyano group, a nitro group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, an azadibenzosilolyl group, or a group represented by Formula 91, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, $-O(Q_{31})$, $-S(Q_{31})$, $-Si(Q_{31})(Q_{32})(Q_{33})$, $-N(Q_{31})(Q_{32})$, $-B(Q_{31})(Q_{32})$, $-P(Q_{31})(Q_{32})$, $-C(=O)(Q_{31})$, $-S(=O)_2(Q_{31})$, $-P(=O)(Q_{31})(Q_{32})$, or any combination thereof; or $-C(Q_1)(Q_2)(Q_3)$, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, or $-P(=O)(Q_1)(Q_2)$, and $Q_1$ to $Q_3$ and $Q_{31}$ to $Q_{33}$ may each independently be:

$-CH_3$, $-CD_3$, $-CD_2H$, $-CDH_2$, $-CH_2CH_3$, $-CH_2CD_3$, $-CH_2CD_2H$, $-CH_2CDH_2$, $-CHDCH_3$, $-CHDCD_2H$, $-CHDCDH_2$, $-CHDCD_3$, $-CD_2CD_3$, $-CD_2CD_2H$, or $-CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{10}$ alkyl group, a phenyl group, a biphenyl group, a pyridinyl group, a pyrimidinyl group, a pyridazinyl group, a pyrazinyl group, a triazinyl group, or any combination thereof:

[Formula 91]

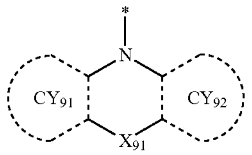

wherein in Formula 91, ring $CY_{91}$ and ring $CY_{92}$ may each independently be a $C_5$-$C_{30}$ carbocyclic group that is unsubstituted or substituted with at least one $R_{10a}$ or a $C_1$-$C_{30}$ heterocyclic group that is unsubstituted or substituted with at least one $R_{10a}$, $X_{91}$ may be a single bond, O, S, $N(Z_{91})$, $B(Z_{91})$, $C(Z_{91a})(Z_{91b})$, or $Si(Z_{91a})(Z_{91b})$, $Z_{91}$, $Z_{91a}$, and $Z_{91b}$ are respectively the same as those described in connection with $R_{82}$, $R_{82a}$, and $R_{82b}$ in the specification, $R_{10a}$ is the same as described in the specification, and

* indicates a binding site to a neighboring atom.

In an embodiment, in Formula 91, ring $CY_{91}$ and ring $CY_{92}$ may each independently be a benzene group, a pyridine group, a pyrimidine group, a pyrazine group, a pyridazine group, or a triazine group, each unsubstituted or substituted with at least one $R_{10a}$, $Z_{91}$, $Z_{91a}$, and $Z_{91b}$ may each independently be:

hydrogen or a $C_1$-$C_{10}$ alkyl group; or a phenyl group, a pyridinyl group, a pyrimidinyl group, a pyridazinyl group, a pyrazinyl group, or a triazinyl group, each unsubstituted or substituted with deuterium, a $C_1$-$C_{10}$ alkyl group, a phenyl group, a biphenyl group, a pyridinyl group, a pyrimidinyl group, a pyridazinyl group, a pyrazinyl group, a triazinyl group, or any combination thereof.

In an embodiment, $R_1$ to $R_5$, $R_{51}$ to $R_{53}$, $R_{5a}$, $Z_{11}$, and $Z_{12}$ in Formula 1; and $R_{61}$ to $R_{66}$, $R_{71}$ to $R_{74}$, $R_{81}$ to $R_{85}$, $R_{82a}$, $R_{82b}$, $R_{83a}$, $R_{83b}$, $R_{84a}$, $R_{84b}$, $R_{91}$, and $R_{92}$ in Formulae 2, 2-1 to 2-5, 3, and 4; and $R_{10a}$ may each independently be hydrogen, deuterium, —F, a cyano group, a nitro group, $-CH_3$, $-CD_3$, $-CD_2H$, $-CDH_2$, $-CF_3$, $-CF_2H$, $-CFH_2$, a group represented by one of Formulae 9-1 to 9-20 in the specification, a group represented by one of Formulae 10-1 to 10-255 in the specification, $-C(Q_1)(Q_2)(Q_3)$, $-Si(Q_1)(Q_2)(Q_3)$, or $-P(=O)(Q_1)(Q_2)$, wherein $Q_1$ to $Q_3$ are respectively the same as those described in the specification; and $R_{5a}$ in Formula 1 may not be hydrogen.

In Formulae 2-1 to 2-5, a71 to a74 respectively indicate numbers of $R_{71}$ to $R_{74}$, and may each independently be an integer from 0 to 20. When a71 is 2 or more, two or more of $R_{71}$(s) may be identical to or different from each other, when a72 is 2 or more, two or more of $R_{72}$(s) may be identical to or different from each other, when a73 is 2 or more, two or more of $R_{73}$(s) may be identical to or different from each other, and when a74 is 2 or more, two or more of $R_{74}$(s) may be identical to or different from each other. In an embodiment, a71 to a74 may each independently be an integer from 0 to 8.

In an embodiment, in Formula 3, a group represented by $*-(L_{61})_{b61}-R_{61}$ and a group represented by $*-(L_{62})_{b62}-R_{62}$ may each not be a phenyl group.

In an embodiment, in Formula 3, a group represented by $*-(L_{61})_{b61}-R_{61}$ and a group represented by $*-(L_{62})_{b62}-R_{62}$ may be identical to each other.

In an embodiment, in Formula 3, a group represented by $*-(L_{61})_{b61}-R_{61}$ and a group represented by $*-(L_{62})_{b62}-R_{62}$ may be different from each other.

In an embodiment, b61 and b62 in Formula 3 may each independently be 1, 2, or 3, and $L_{61}$ and $L_{62}$ may each independently be a benzene group, a pyridine group, a pyrimidine group, a pyridazine group, a pyrazine group, or a triazine group, each unsubstituted or substituted with at least one $R_{10a}$.

In an embodiment, $R_{61}$ and $R_{62}$ in Formula 3 may each independently be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-C(Q_1)(Q_2)(Q_3)$, or $-Si(Q_1)(Q_2)(Q_3)$, and $Q_1$ to $Q_3$ may each independently be a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, a group represented by $*-(L_{61})_{b61}-R_{61}$ in Formula 3 may be a group represented by one of Formulae CY51-1 to CY51-26, and/or a group represented by $*-(L_{62})_{b62}-R_{62}$ in Formula 3 may be a group represented by one of Formulae CY52-1 to CY52-26, and/or a group represented by *-$(L_{63})_{b63}$-$R_{63}$ in Formula 3 may be a group represented by one of Formulae CY53-1 to CY53-27, —$C(Q_1)(Q_2)(Q_3)$, or —$Si(Q_1)(Q_2)(Q_3)$:
CY51-1
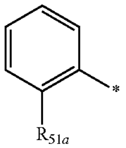
CY51-2
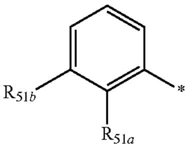
CY51-3
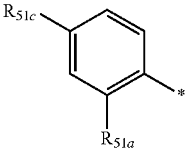
CY51-4
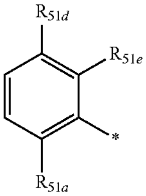
CY51-5
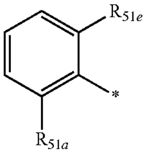
CY51-6
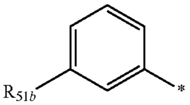
CY51-7
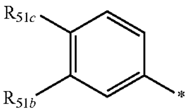
CY51-8
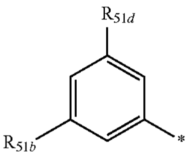
CY51-9
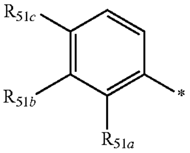
-continued
CY51-10
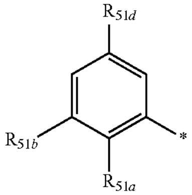
CY51-11
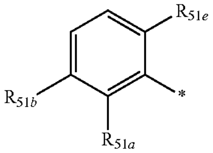
CY51-12
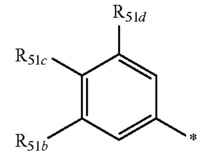
CY51-13
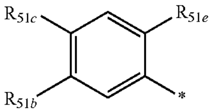
CY51-14
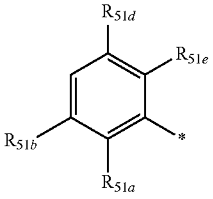
CY51-15
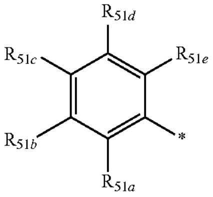
CY51-16
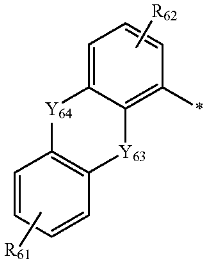
CY51-17
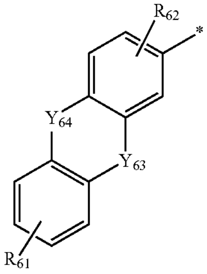

CY51-18
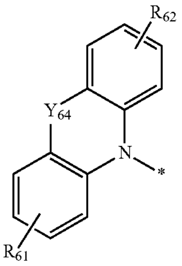
CY51-19
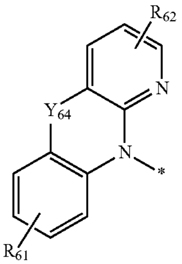
CY51-20
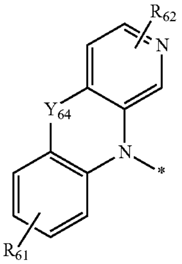
CY51-21
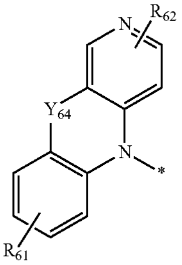
CY51-22
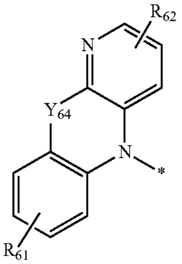
CY51-23
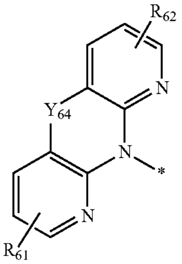
CY51-24
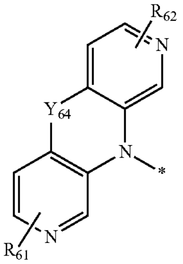
CY51-25
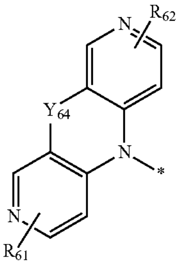
CY51-26
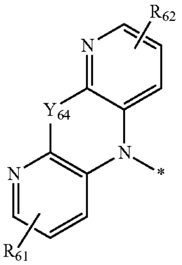
CY52-1
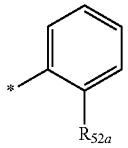
CY52-2
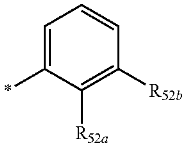
CY52-3
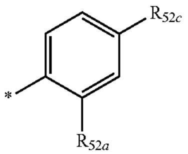
CY52-4
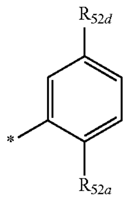

CY52-5
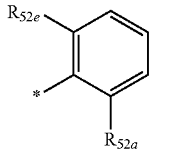
CY52-6
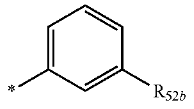
CY52-7
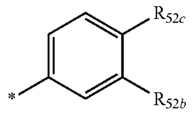
CY52-8
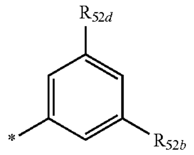
CY52-9
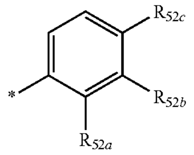
CY52-10
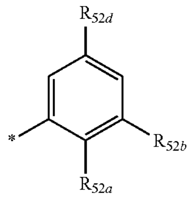
CY52-11
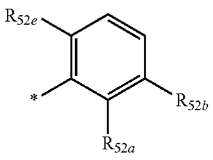
CY52-12
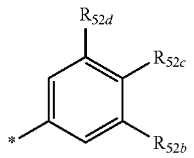
CY52-13
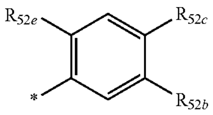
CY52-14
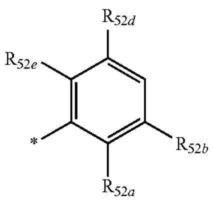
CY52-15
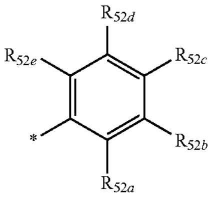
CY52-16
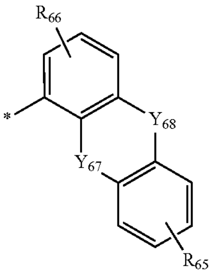
CY52-17
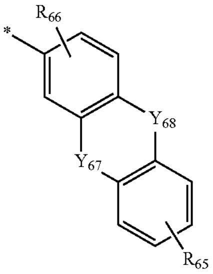
CY52-18
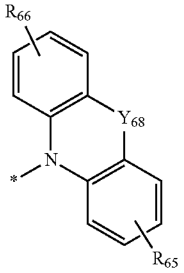
CY52-19
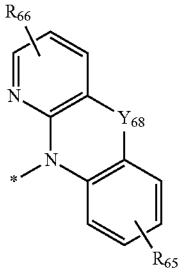
CY52-20
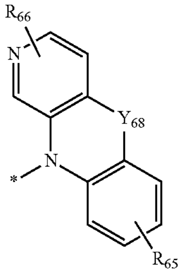

-continued
CY52-21
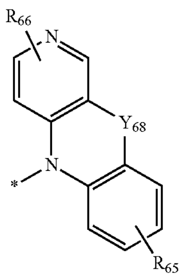
CY52-22
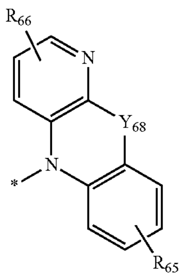
CY52-23
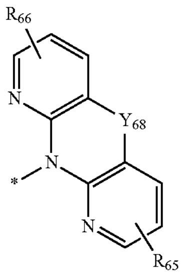
CY52-24
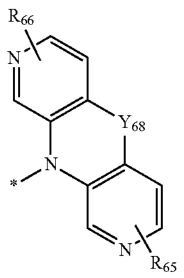
CY52-25
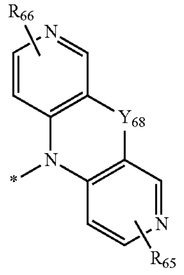
-continued
CY52-26
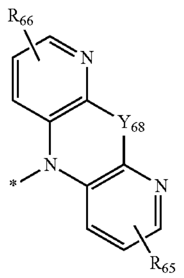
CY53-1
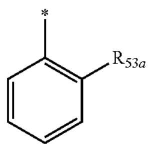
CY53-2
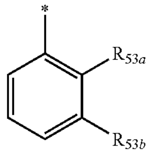
CY53-3
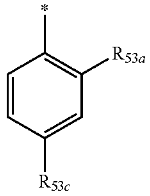
CY53-4
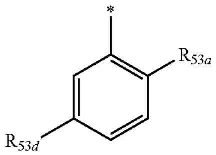
CY53-5
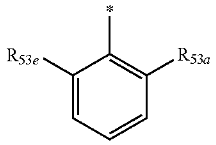
CY53-6
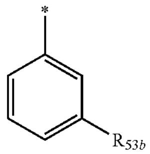
CY53-7
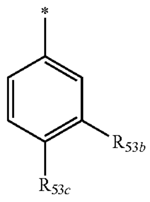

-continued
CY53-8
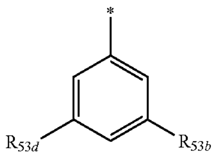
CY53-9
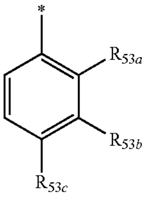
CY53-10
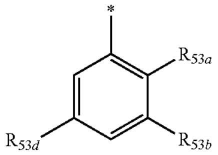
CY53-11
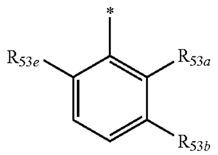
CY53-12
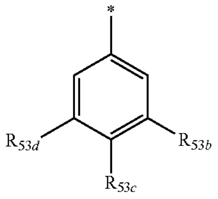
CY53-13
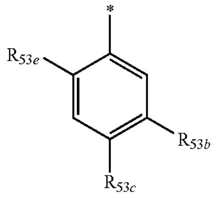
CY53-14
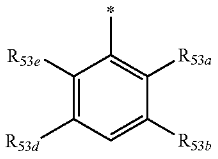
CY53-15
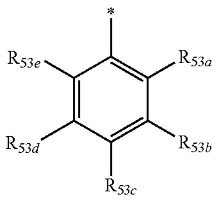
-continued
CY53-16
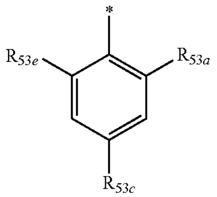
CY53-17
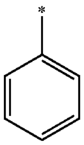
CY53-18
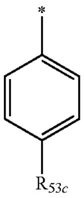
CY53-19
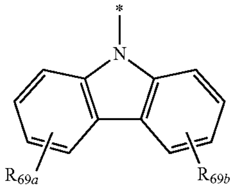
CY53-20
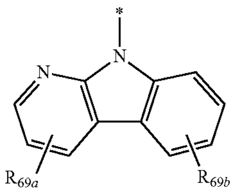
CY53-21
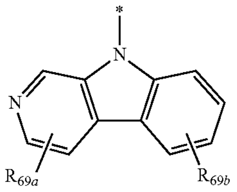
CY53-22
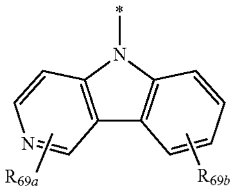
CY53-23
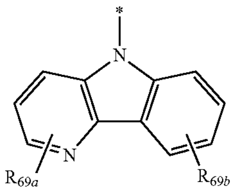

-continued

CY53-24

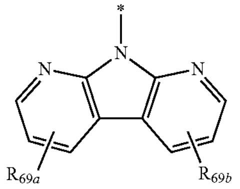

CY53-25

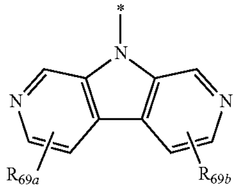

CY53-26

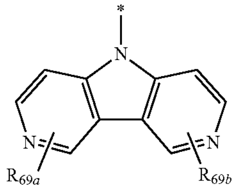

CY53-27

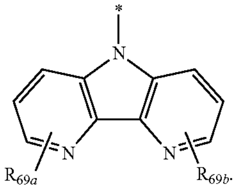

In Formulae CY51-1 to CY51-26, CY52-1 to CY52-26, and CY53-1 to CY53-27, $Y_{63}$ may be a single bond, O, S, $N(R_{63})$, $B(R_{63})$, $C(R_{63a})(R_{63b})$, or $Si(R_{63a})(R_{63b})$, $Y_{64}$ may be a single bond, O, S, $N(R_{64})$, $B(R_{64})$, $C(R_{64a})(R_{64b})$, or $Si(R_{64a})(R_{64b})$, $Y_{67}$ may be a single bond, O, S, $N(R_{67})$, $B(R_{67})$, $C(R_{67a})(R_{67b})$, or $Si(R_{67a})(R_{67b})$, $Y_{68}$ may be a single bond, O, S, $N(R_{68})$, $B(R_{68})$, $C(R_{68a})(R_{68b})$, or $Si(R_{68a})(R_{68b})$, $Y_{63}$ and $Y_{64}$ in Formulae CY51-16 and CY51-17 may not both simultaneously be a single bond, $Y_{67}$ and $Y_{68}$ in Formulae CY52-16 and CY52-17 may not both simultaneously be a single bond, $R_{51a}$ to $R_{51e}$, $R_{61}$ to $R_{64}$, $R_{63a}$, $R_{63b}$, $R_{64a}$, and $R_{64b}$ are each independently the same as described in connection with $R_{61}$ in the specification, wherein $R_{51a}$ to $R_{51e}$ may each not be hydrogen, $R_{52a}$ to $R_{52e}$, $R_{65}$ to $R_{68}$, $R_{67a}$, $R_{67b}$, $R_{68a}$, and $R_{68b}$ are each independently the same as described in connection with $R_{62}$ in the specification, wherein $R_{52a}$ to $R_{52e}$ may each not be hydrogen, $R_{53a}$ to $R_{53e}$, $R_{69a}$ and $R_{69b}$ are each independently the same as described in connection with $R_{63}$, wherein $R_{53a}$ to $R_{53e}$ may each not be hydrogen, and

* indicates a binding site to a neighboring atom.

In an embodiment, $R_{51a}$ to $R_{51e}$ and $R_{52a}$ to $R_{52e}$ in Formulae CY51-1 to CY51-26 and CY52-1 to CY 52-26 may each independently be:

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, an azadibenzosilolyl group, or a group represented by Formula 91, each unsubstituted or substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or any combination thereof; or $—C(Q_1)(Q_2)(Q_3)$ or $—Si(Q_1)(Q_2)(Q_3)$, $Q_1$ to $Q_3$ may each independently be a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{10}$ alkyl group, a phenyl group, a biphenyl group, a pyridinyl group, a pyrimidinyl group, a pyridazinyl group, a pyrazinyl group, a triazinyl group, or any combination thereof, in Formulae CY51-16 and CY51-17, i) $Y_{63}$ may be O or S, and $Y_{64}$ may be $Si(R_{64a})(R_{64b})$, or ii) $Y_{63}$ may be $Si(R_{63a})(R_{63b})$, and $Y_{64}$ may be O or S, and in Formulae CY52-16 and CY52-17, i) $Y_{67}$ may be O or S, and $Y_{68}$ may be $Si(R_{68a})(R_{68b})$, or ii) $Y_{67}$ may be $Si(R_{67a})(R_{67b})$, and $Y_{68}$ may be O or S.

In an embodiment, $L_{81}$ to $L_{85}$ in Formulae 2-1 to 2-5 may each independently be:

a single bond;

*—$C(Q_4)(Q_5)$-*' or *—$Si(Q_4)(Q_5)$-*'; or a benzene group, a naphthalene group, an anthracene group, a phenanthrene group, a triphenylene group, a pyrene group, a chrysene group, a cyclopentadiene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an iso-oxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a naphthyl group, a pyridinyl group, a pyrimidinyl group, a triazinyl group, a fluorenyl group, a dimethylfluorenyl group, a diphenyl fluorenyl group, a carbazolyl group, a phenylcarbazolyl group, a dibenzofuranyl group, a dibenzothiophenyl group, a dibenzosilolyl group, a dimethyl dibenzosilolyl group, a diphenyl dibenzosilolyl group, —O $(Q_{31})$, —$S(Q_{31})$, —$Si(Q_{31})(Q_{32})(Q_{33})$, —$N(Q_{31})(Q_{32})$, —$B(Q_{31})(Q_{32})$, —$P(Q_{31})(Q_{32})$, —$C(=O)(Q_{31})$, —$S(=O)_2(Q_{31})$, —$P(=O)(Q_{31})(Q_{32})$, or any combination thereof, and $Q_4$, $Q_5$, and $Q_{31}$ to $Q_{33}$ may each independently be hydrogen, deuterium, a $C_1$-$C_{20}$ alkyl group, a $C_1$-$C_{20}$ alkoxy group, a phenyl group, a biphenyl group, a terphenyl group, a pyridinyl group, a pyrimidinyl group, a pyridazinyl group, a pyrazinyl group, or a triazinyl group.

In an embodiment, a group represented by

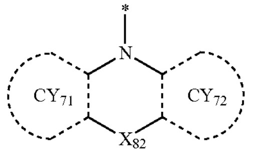

in Formulae 2-1 and 2-2 may be a group represented by one of Formulae CY71-1(1) to CY71-1(8), and/or a group represented by

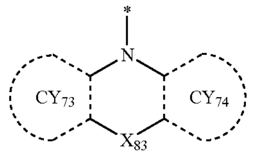

in Formulae 2-1 and 2-3 may be a group represented by one of Formulae CY71-2(1) to CY71-2(8), and/or a group represented by

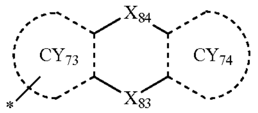

in Formulae 2-2 and 2-4 may be a group represented by one of Formulae CY71-3(1) to CY71-3(32), and/or a group represented by

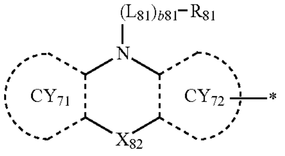

in Formulae 2-3 to 2-5 may be a group represented by one of Formulae CY71-4(1) to CY71-4(32), and/or a group represented by

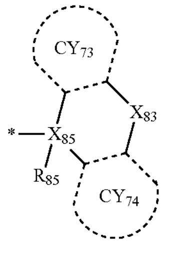

in Formula 2-5 may be a group represented by one of Formulae CY71-5(1) to CY71-5(8):

CY71-1(1)

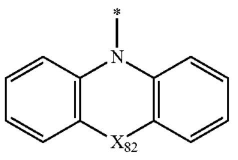

-continued
CY71-1(2)
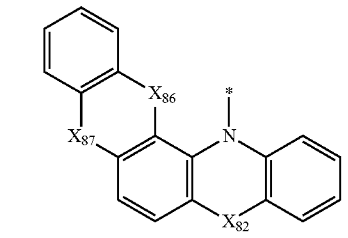
CY71-1(3)
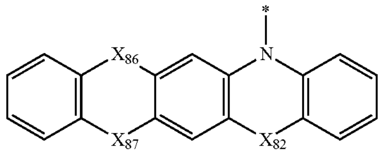
CY71-1(4)
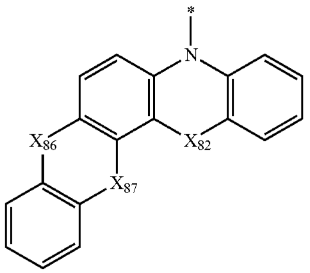
CY71-1(5)
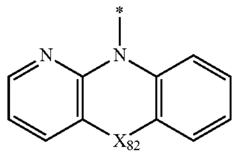
CY71-1(6)
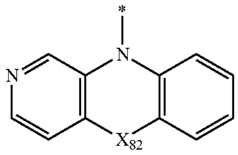
CY71-1(7)
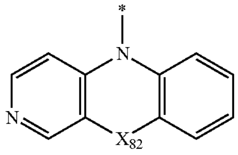
CY71-1(8)
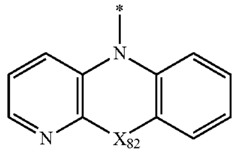
CY71-2(1)
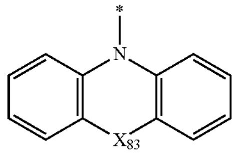
-continued
CY71-2(2)
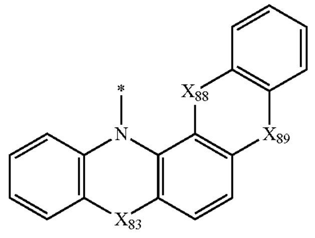
CY71-2(3)
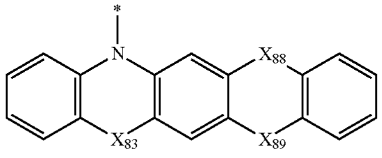
CY71-2(4)
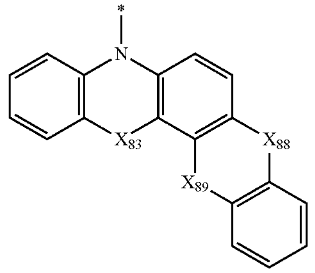
CY71-2(5)
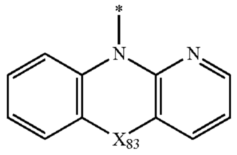
CY71-2(6)
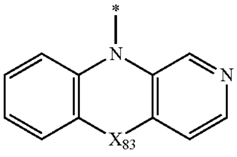
CY71-2(7)
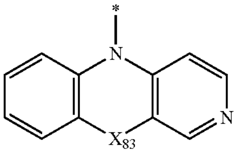
CY71-2(8)
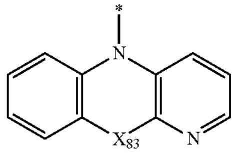
CY71-3(1)
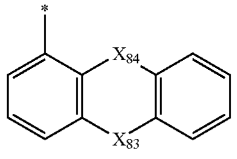

-continued
CY71-3(2)
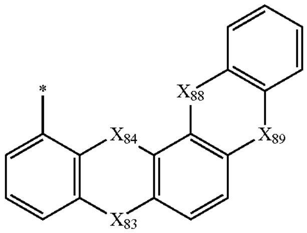
CY71-3(3)
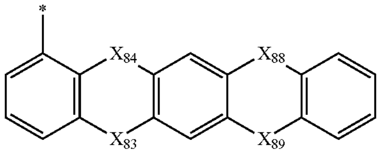
CY71-3(4)
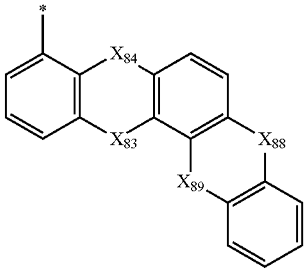
CY71-3(5)
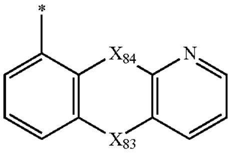
CY71-3(6)
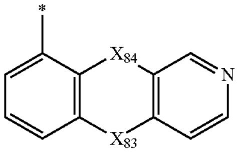
CY71-3(7)
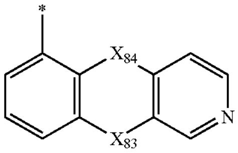
CY71-3(8)
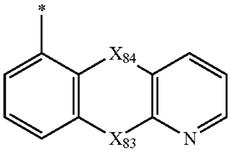
CY71-3(9)
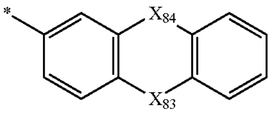
-continued
CY71-3(10)
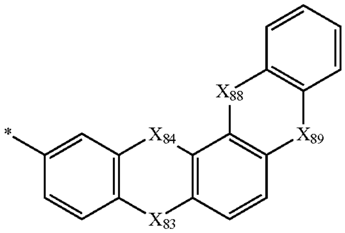
CY71-3(11)
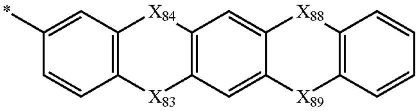
CY71-3(12)
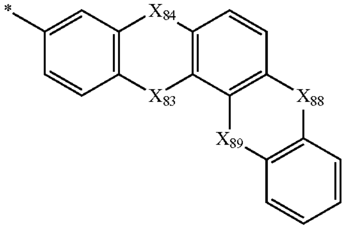
CY71-3(13)
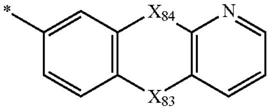
CY71-3(14)
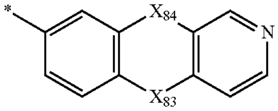
CY71-3(15)
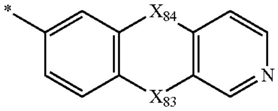
CY71-3(16)
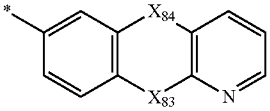
CY71-3(17)
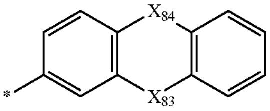
CY71-3(18)
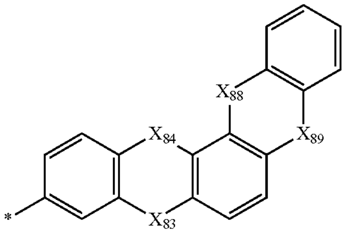
CY71-3(19)
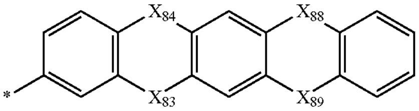

-continued
CY71-3(20)
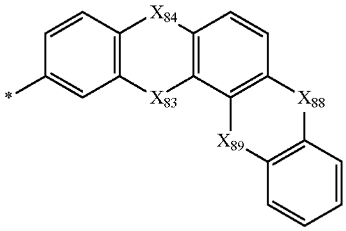
CY71-3(21)
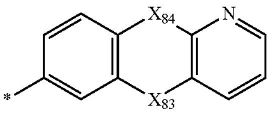
CY71-3(22)
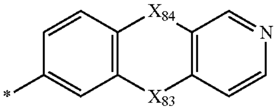
CY71-3(23)
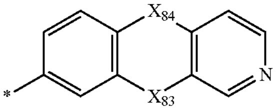
CY71-3(24)
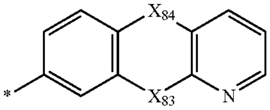
CY71-3(25)
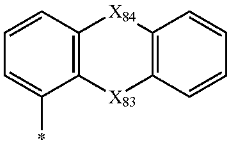
CY71-3(26)
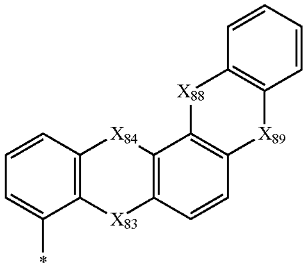
CY71-3(27)
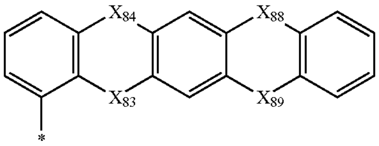
CY71-3(28)
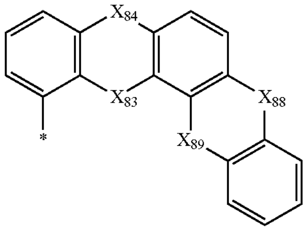
-continued
CY71-3(29)
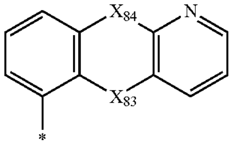
CY71-3(30)
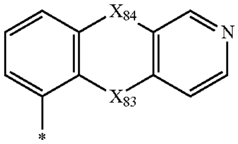
CY71-3(31)
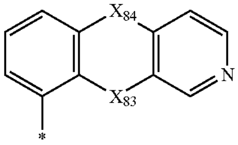
CY71-3(32)
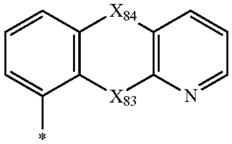
CY71-4(1)
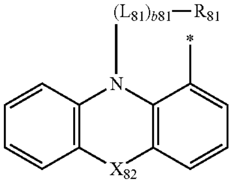
CY71-4(2)
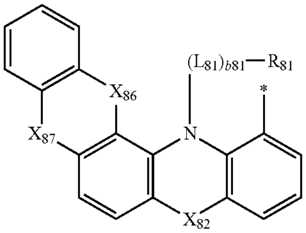
CY71-4(3)
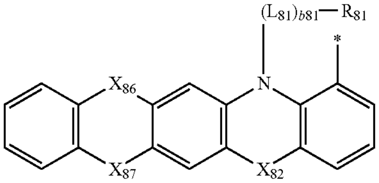
CY71-4(4)
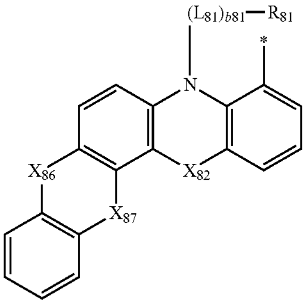

-continued
CY71-4(5)
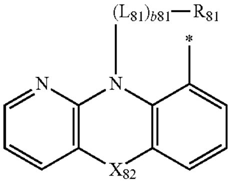
CY71-4(6)
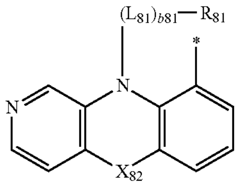
CY71-4(7)
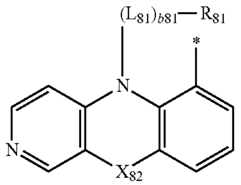
CY71-4(8)
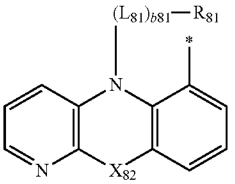
CY71-4(9)
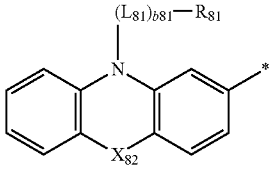
CY71-4(10)
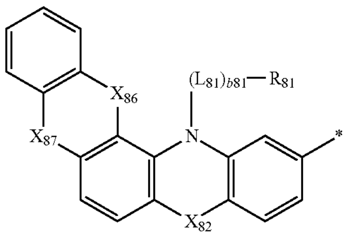
CY71-4(11)
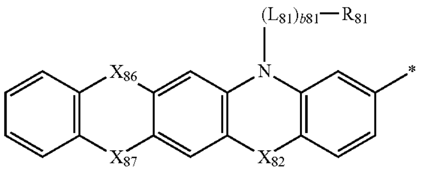
-continued
CY71-4(12)
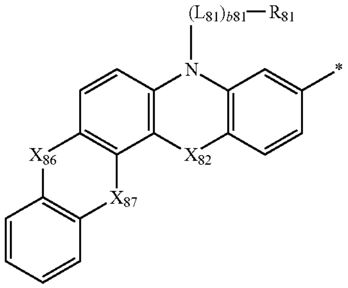
CY71-4(13)
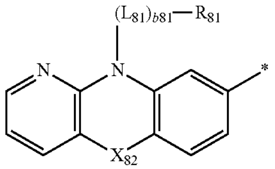
CY71-4(14)
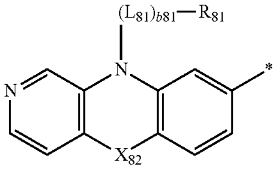
CY71-4(15)
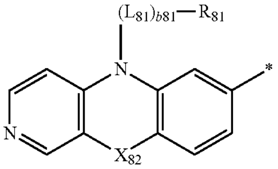
CY71-4(16)
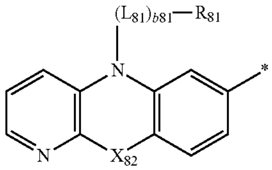
CY71-4(17)
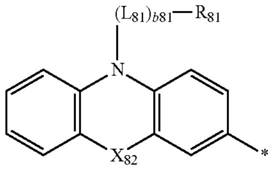
CY71-4(18)
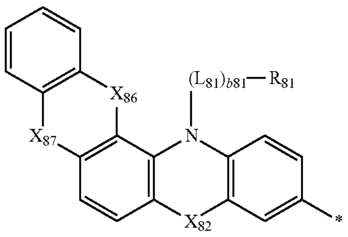
CY71-4(19)
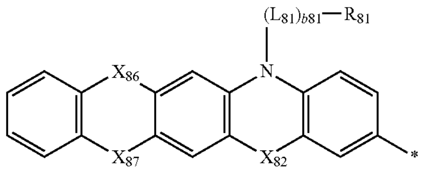

-continued
CY71-4(20)
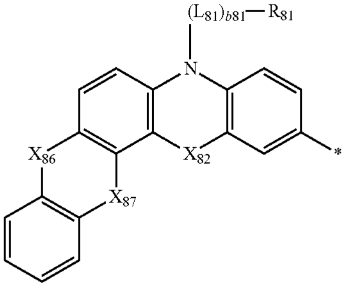
CY71-4(21)
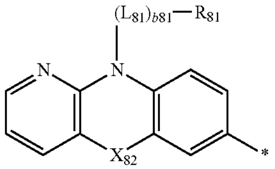
CY71-4(22)
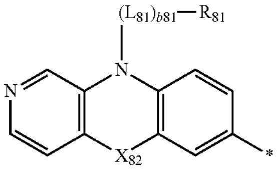
CY71-4(23)
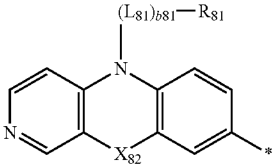
CY71-4(24)
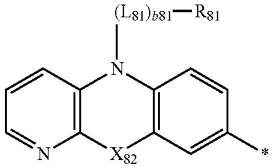
CY71-4(25)
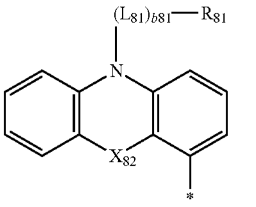
CY71-4(26)
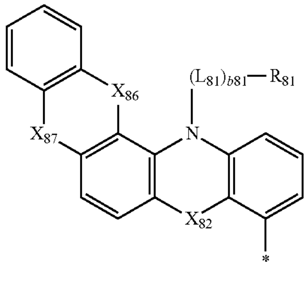
-continued
CY71-4(27)
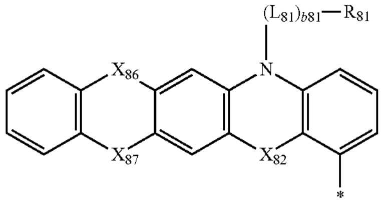
CY71-4(28)
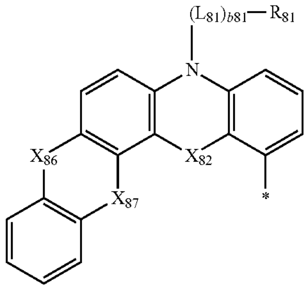
CY71-4(29)
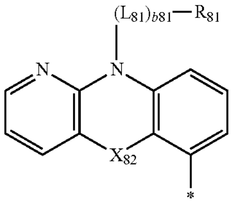
CY71-4(30)
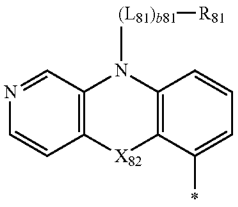
CY71-4(31)
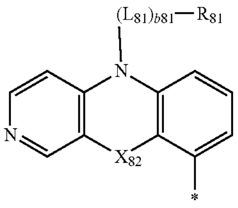
CY71-4(32)
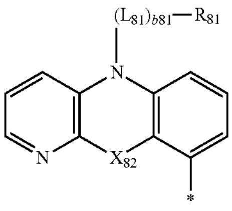
CY71-5(1)
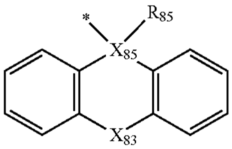

-continued

CY71-5(2)

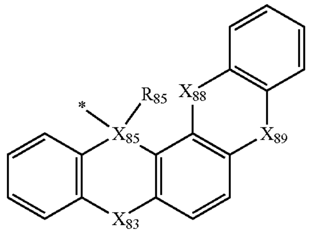

CY71-5(3)

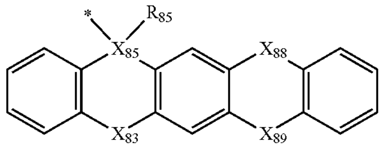

CY71-5(4)

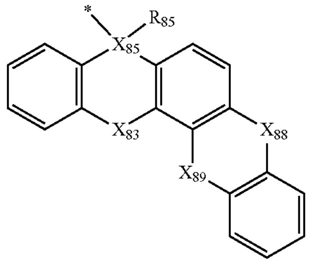

CY71-5(5)

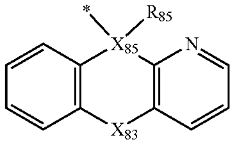

CY71-5(6)

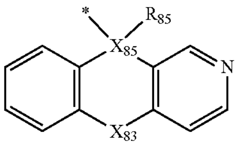

CY71-5(7)

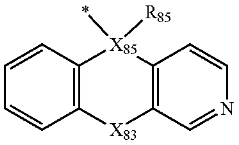

CY71-5(8)

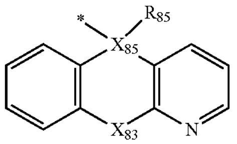

wherein in Formulae CY71-1(1) to CY71-1(8), CY71-2(1) to CY71-2(8), CY71-3(1) to CY71-3(32), CY71-4(1) to CY71-4(32), and CY71-5(1) to CY71-5(8), $X_{81}$ to $X_{85}$, $L_{81}$, b81, $R_{81}$, and $R_{85}$ are respectively the same as described in the specification, $X_{86}$ may be a single bond, O, S, $N(R_{86})$, $B(R_{86})$, $C(R_{86a})(R_{86b})$, or $Si(R_{86a})(R_{86b})$, $X_{87}$ may be a single bond, O, S, $N(R_{87})$, $B(R_{87})$, $C(R_{87a})(R_{87b})$, or $Si(R_{87a})(R_{87b})$, $X_{86}$ and $X_{87}$ in Formulae CY71-1(1) to CY71-1(8) and CY71-4(1) to CY71-4(32) may not both simultaneously be a single bond, $X_{88}$ may be a single bond, O, S, $N(R_{88})$, $B(R_{88})$, $C(R_{88a})(R_{88b})$, or $Si(R_{88a})(R_{88b})$, $X_{89}$ may be a single bond, O, S, $N(R_{89})$, $B(R_{89})$, $C(R_{89a})(R_{89b})$, or $Si(R_{89a})(R_{89b})$, $X_{88}$ and $X_{89}$ in Formulae CY71-2(1) to CY71-2(8), CY71-3(1) to CY71-3(32), and CY71-5(1) to CY71-5(8) may not both simultaneously be a single bond, and $R_{86}$ to $R_{89}$, $R_{86a}$, $R_{86b}$, $R_{87a}$, $R_{87b}$, $R_{88a}$, $R_{88b}$, $R_{89a}$, and $R_{89b}$ are each independently the same as described in connection with $R_{81}$ in the specification.

In an embodiment, the light-emitting device may include a capping layer located outside the first electrode or outside the second electrode.

For example, the light-emitting device may further include at least one of a first capping layer located outside the first electrode and a second capping layer located outside the second electrode, and at least one of the first capping layer and the second capping layer may include the organometallic compound represented by Formula 1. The first capping layer and/or the second capping layer are respectively the same as those described in the specification.

In an embodiment, the light-emitting device may include:

a first capping layer arranged outside the first electrode and including the organometallic compound represented by Formula 1;

a second capping layer arranged outside the second electrode and including the organometallic compound represented by Formula 1; or the first capping layer and the second capping layer.

The wording "(interlayer and/or capping layer) includes an organometallic compound" as used herein may be understood as "(interlayer and/or capping layer) may include one kind of organometallic compound represented by Formula 1 or two different kinds of organometallic compounds, each represented by Formula 1".

In an embodiment, the interlayer and/or the capping layer may include Compound 1 only as the organometallic compound. In this regard, Compound 1 may be present in the emission layer of the light-emitting device. In an embodiment, the interlayer may include, as the organometallic compound, Compound 1 and Compound 2. In this regard, Compound 1 and Compound 2 may be present in the same layer (for example, both Compound 1 and Compound 2 may be present in an emission layer), or may be present in different layers (for example, Compound 1 may be present in an emission layer, and Compound 2 may be present in an electron transport region).

The term "interlayer" as used herein refers to a single layer and/or all layers located between the first electrode and the second electrode of the light-emitting device.

According to embodiments, provided is an electronic apparatus which may include the light-emitting device. The electronic apparatus may further include a thin-film transistor. For example, in an embodiment, the electronic apparatus may include the light-emitting device and a thin-film transistor, wherein the thin-film transistor may include a source electrode and a drain electrode, and the first electrode of the light-emitting device may be electrically connected to at least one of the source electrode or the drain electrode.

In an embodiment, the electronic apparatus may further include a color filter, a color conversion layer, a touch screen layer, a polarizing layer, or any combination thereof. More details for the electronic apparatus are as described herein.

[Description of FIG. 1]

FIG. 1 is a schematic cross-sectional view of a light-emitting device 10 according to an embodiment. The light-emitting device 10 includes a first electrode 110, an interlayer 130, and a second electrode 150.

Hereinafter, a structure of the light-emitting device 10 according to an embodiment and a method of manufacturing the light-emitting device 10 will be described in connection with FIG. 1.

[First Electrode 110]

In FIG. 1, a substrate may be further included under the first electrode 110 or above the second electrode 150. The substrate may be a glass substrate or a plastic substrate. In an embodiment, the substrate may be a flexible substrate, and may include plastics with excellent heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide ($SnO_2$), zinc oxide (ZnO), or any combinations thereof. In embodiments, when the first electrode 110 is a semi-transmissive electrode or a reflective electrode, a material for forming a first electrode may include magnesium (Mg), silver (Ag), aluminum (Al), aluminum-lithium (Al—Li), calcium (Ca), magnesium-indium (Mg—In), magnesium-silver (Mg—Ag), or any combinations thereof.

The first electrode 110 may have a structure consisting of a single layer or a structure including multiple layers. For example, the first electrode 110 may have a three-layered structure of ITO/Ag/ITO.

[Interlayer 130]

The interlayer 130 may be located on the first electrode 110. The interlayer 130 may include an emission layer.

The interlayer 130 may further include a hole transport region between the first electrode 110 and the emission layer and an electron transport region between the emission layer and the second electrode 150.

The interlayer 130 may further include metal-containing compounds such as organometallic compounds, inorganic materials such as quantum dots, and the like, in addition to various organic materials.

In embodiments, the interlayer 130 may include two or more emitting units sequentially stacked between the first electrode 110 and the second electrode 150, and at least one charge generation layer between the two emitting units. When the interlayer 130 includes the emitting units and the at least one charge generation layer as described above, the light-emitting device 10 may be a tandem light-emitting device.

[Hole Transport Region in Interlayer 130]

The hole transport region may have a structure consisting of a layer consisting of a single material, a structure consisting of a layer consisting of different materials, or a structure including multiple layers including different materials.

The hole transport region may include a hole injection layer, a hole transport layer, an emission auxiliary layer, an electron blocking layer, or any combination thereof.

In an embodiment, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein the layers of each structure are stacked from the first electrode 110 in its respective stated order, but the structure of the hole transport region is not limited thereto.

The hole transport region may include a compound represented by Formula 201, a compound represented by Formula 202, or any combination thereof:

[Formula 201]

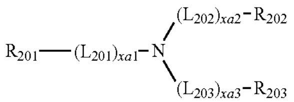

[Formula 202]

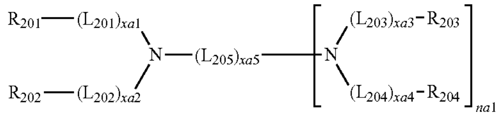

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of groups represented by Formulae CY201 to CY217:

CY201

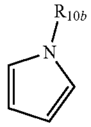

-continued

CY202

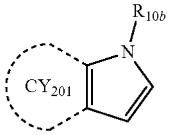

CY203

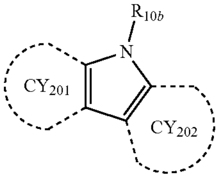

CY204

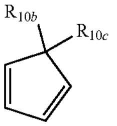

CY205

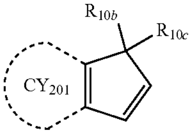

CY206

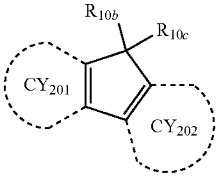

CY207

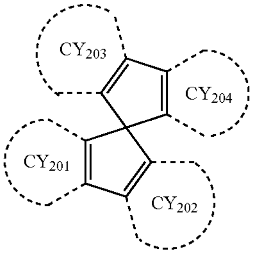

CY208

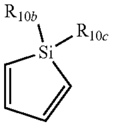

CY209

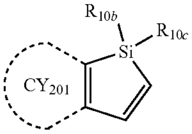

CY210

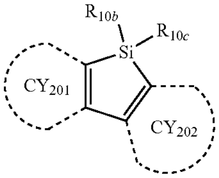

-continued

CY211

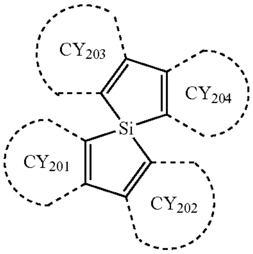

CY212

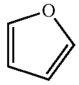

CY213

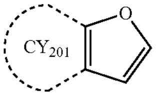

CY214

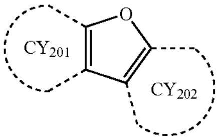

CY215

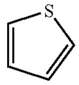

CY216

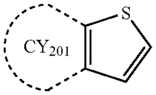

CY217

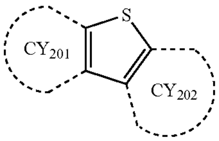

In Formulae CY201 to CY217, $R_{10b}$ and $R_{10c}$ may each independently be the same as described in connection with $R_{10a}$ in the specification, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$ as described in the specification.

In an embodiment, ring CY201 to ring CY204 in Formulae CY201 to CY217 may each independently be a benzene group, a naphthalene group, a phenanthrene group, or an anthracene group.

In an embodiment, each of Formulae 201 and 202 may include at least one of groups represented by Formulae CY201 to CY203.

In an embodiment, Formula 201 may include at least one of groups represented by Formulae CY201 to CY203 and at least one of groups represented by Formulae CY204 to CY217.

In an embodiment, xa1 in Formula 201 may be 1, $R_{201}$ may be a group represented by one of Formulae CY201 to CY203, xa2 may be 0, and $R_{202}$ may be a group represented by one of Formulae CY204 to CY207.

In an embodiment, each of Formulae 201 and 202 may not include groups represented by Formulae CY201 to CY203.

In an embodiment, each of Formulae 201 and 202 may not include groups represented by Formulae CY201 to CY203, and may include at least one of groups represented by Formulae CY204 to CY217.

In an embodiment, each of Formulae 201 and 202 may not include groups represented by Formulae CY201 to CY217.

For example, the hole transport region may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

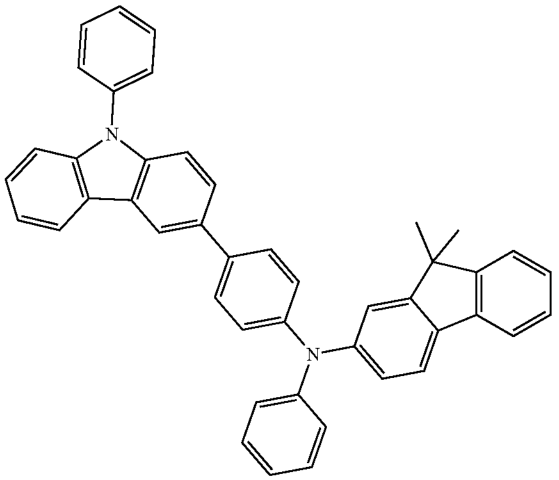

HT2

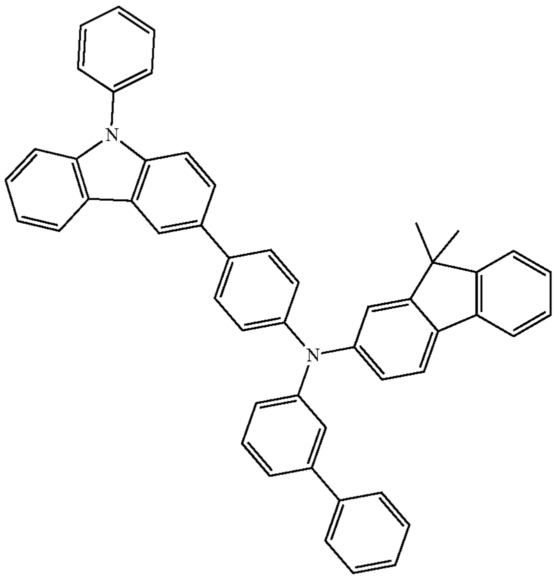

-continued

HT3

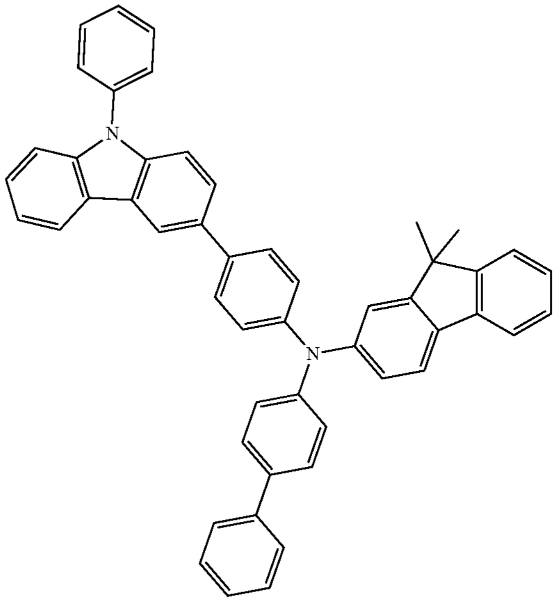

HT4

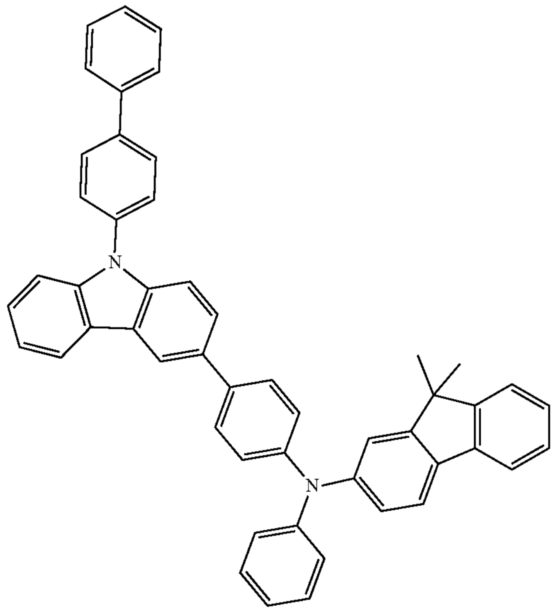

HT5
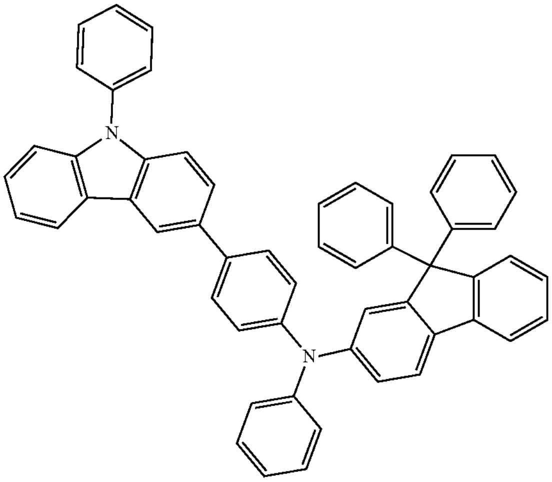
HT6
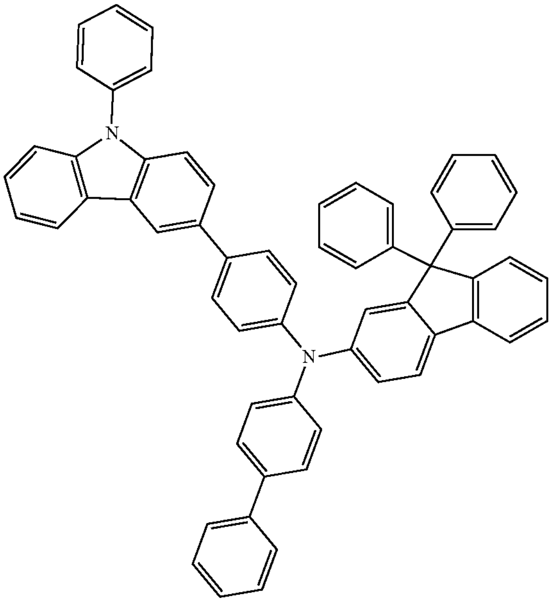
HT7
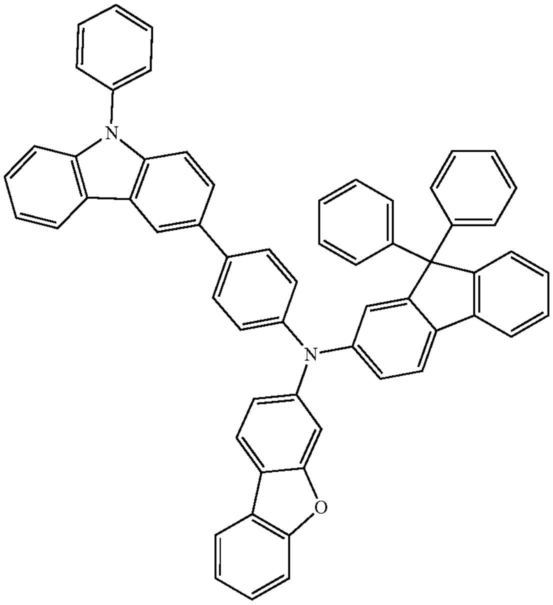
HT8
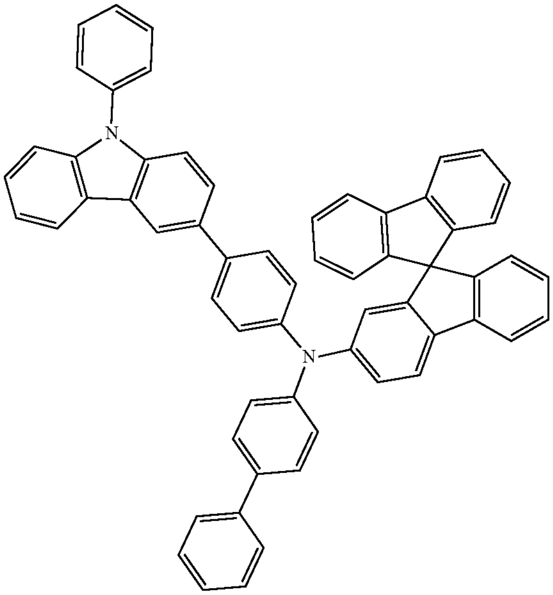

-continued
HT9
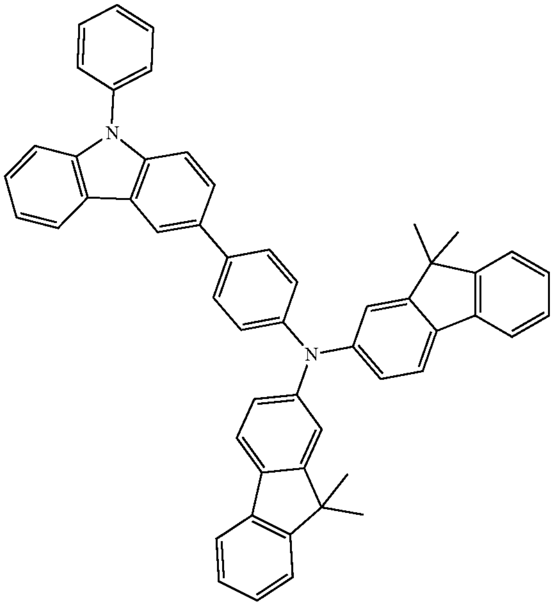
HT10
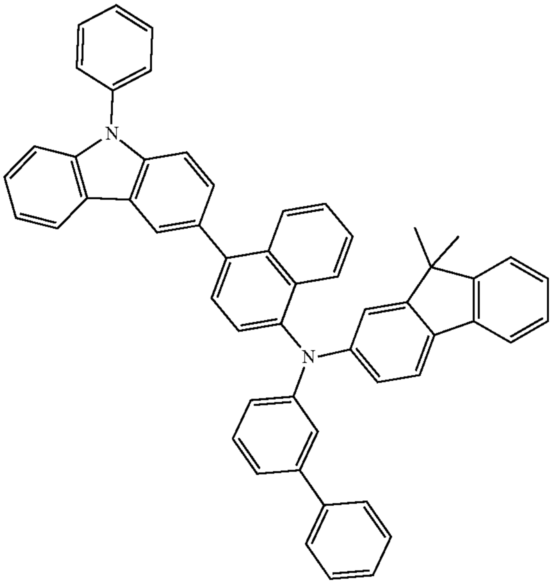
-continued
HT11
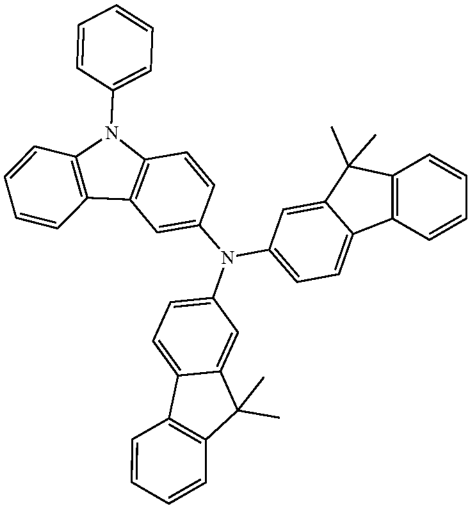
H12
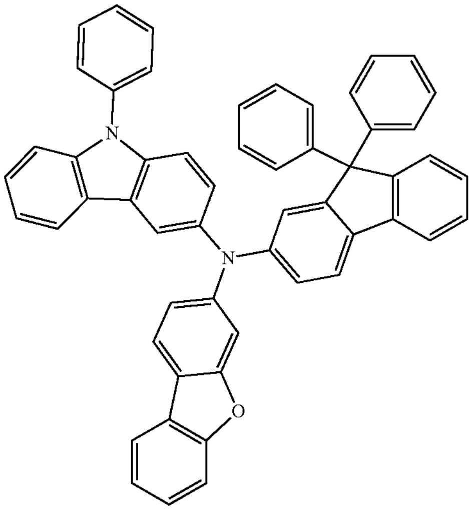
H13
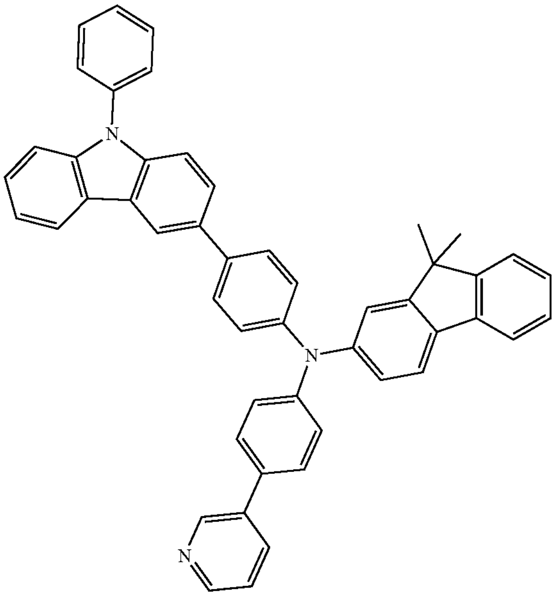

-continued
H14
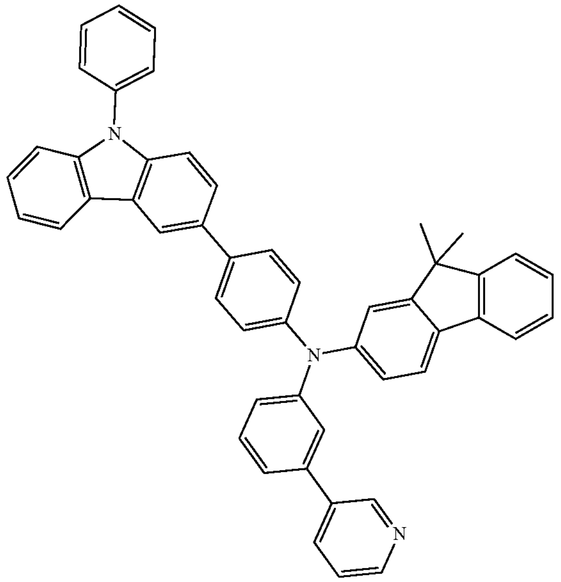
HT15
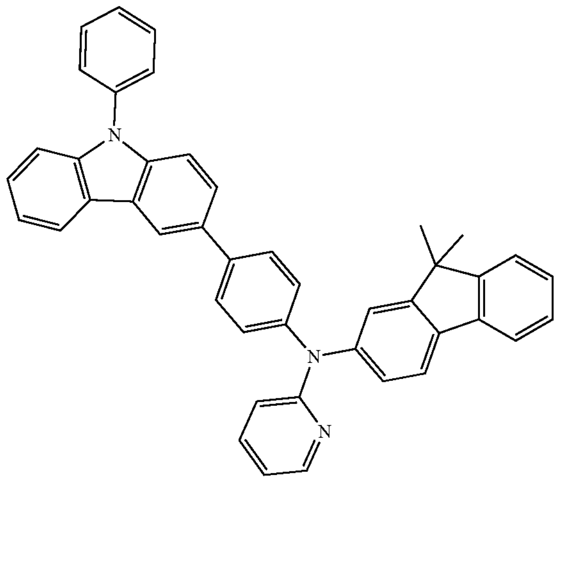
HT16
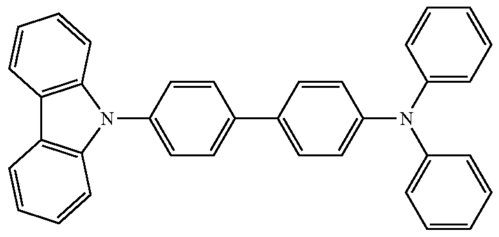
-continued
HT17
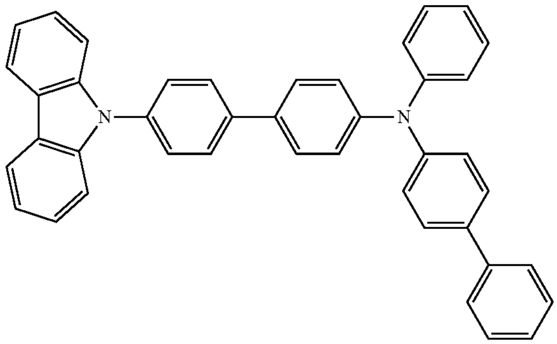
HT18
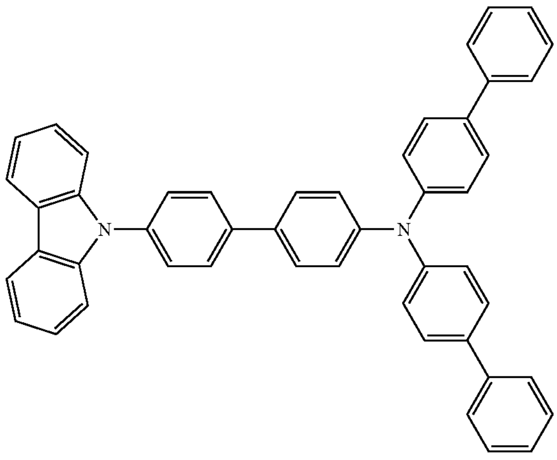
HT19
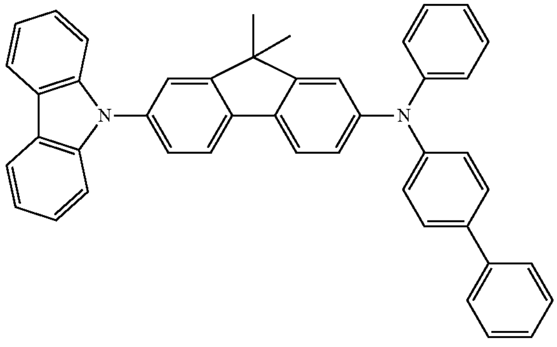

-continued
HT20
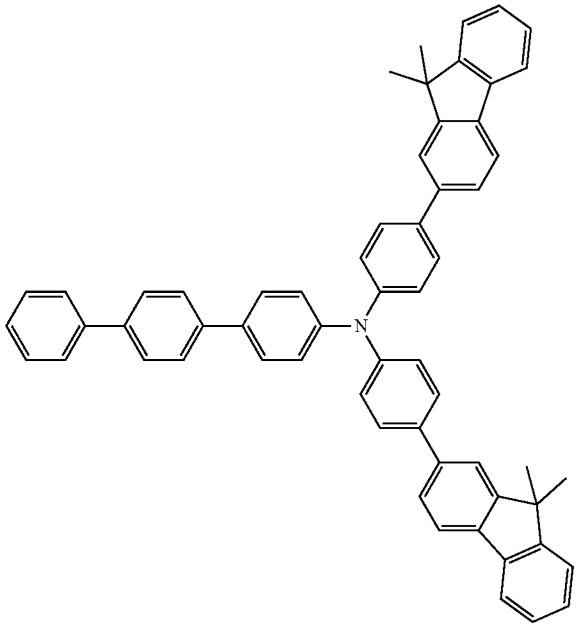
HT21
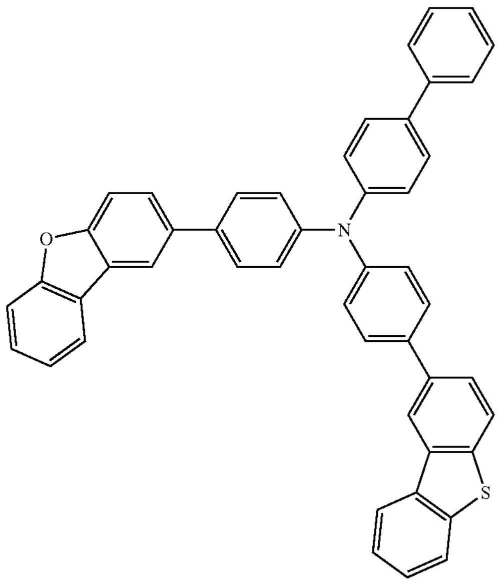
HT22
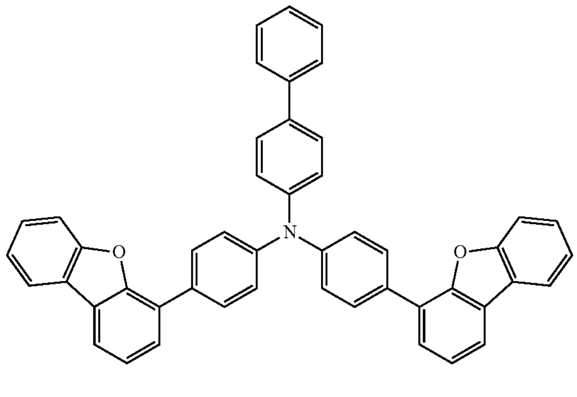
-continued
HT23
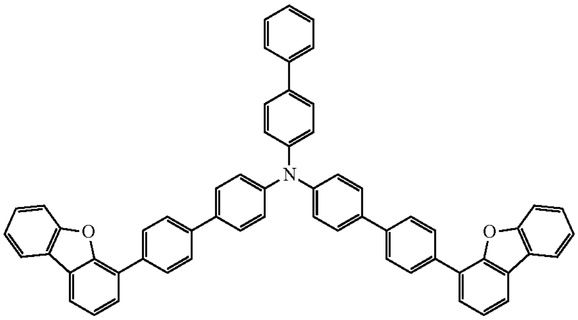
HT24
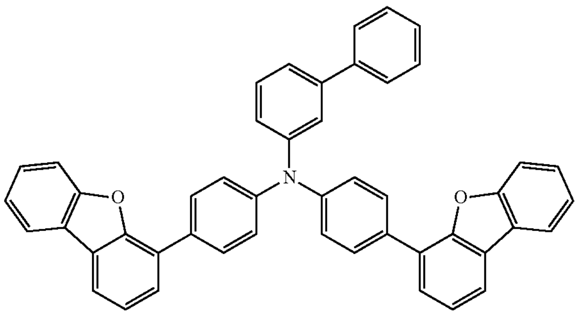
HT25
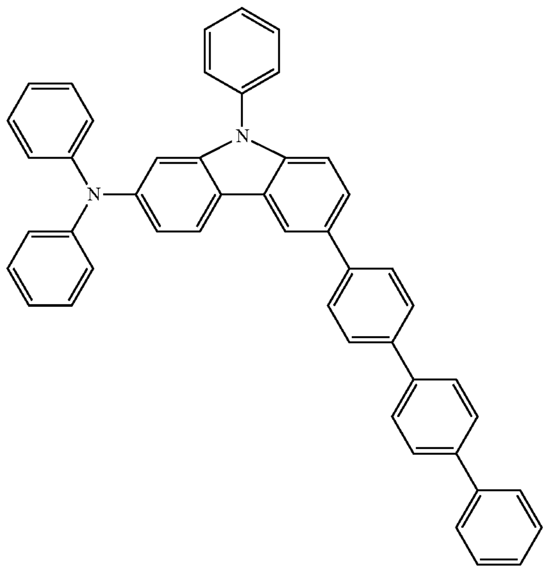

-continued
HT26
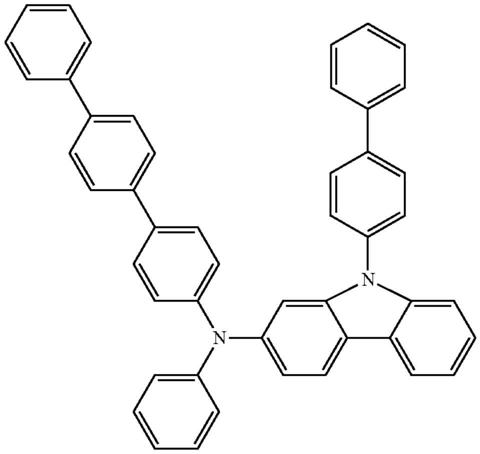
HT27
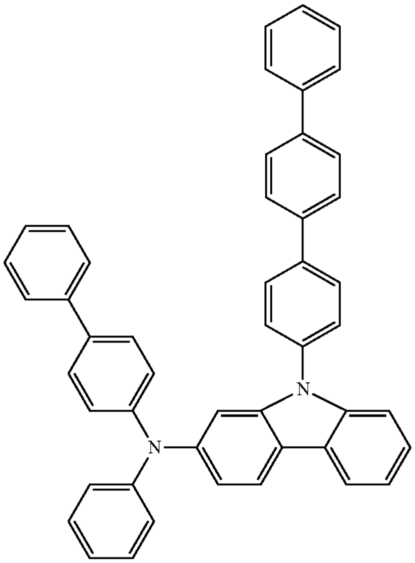
HT28
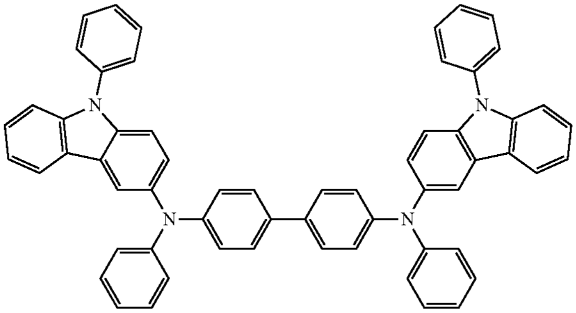
-continued
HT29
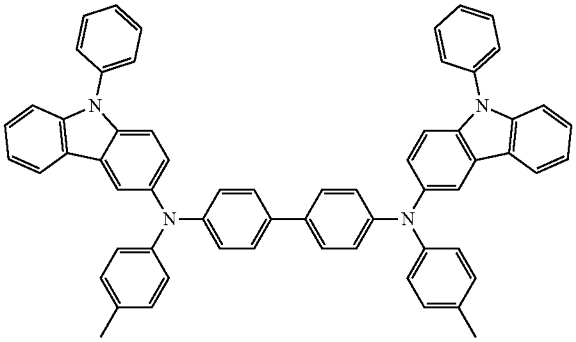
HT30
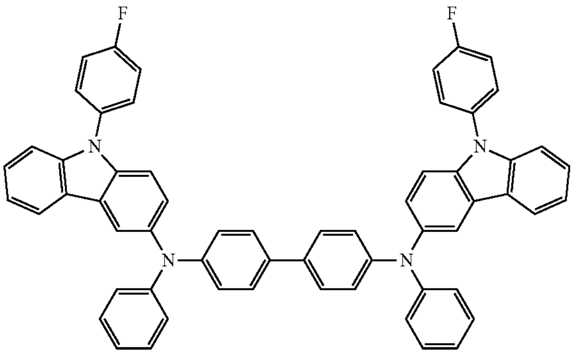
HT31
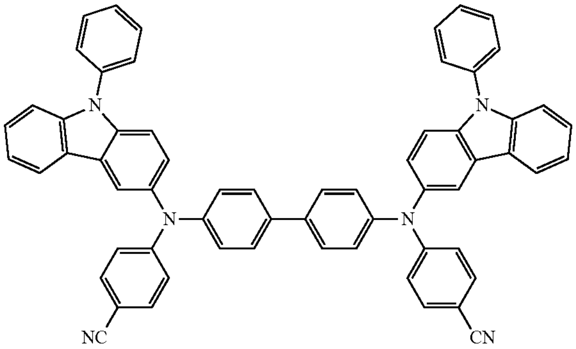
HT32
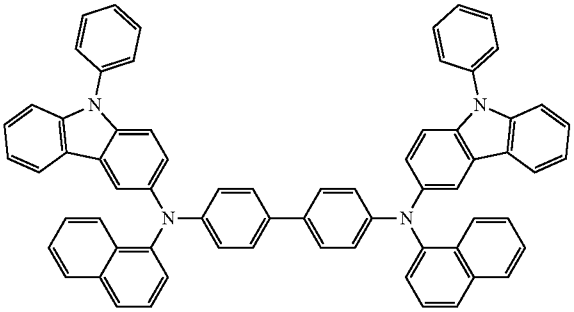

-continued
HT33
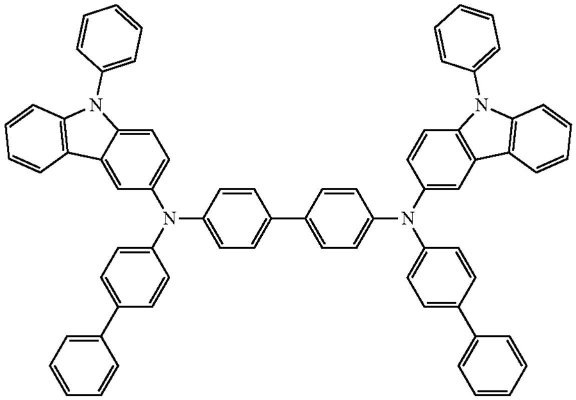
HT34
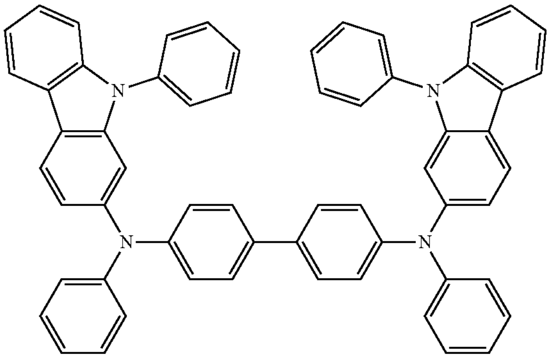
HT35
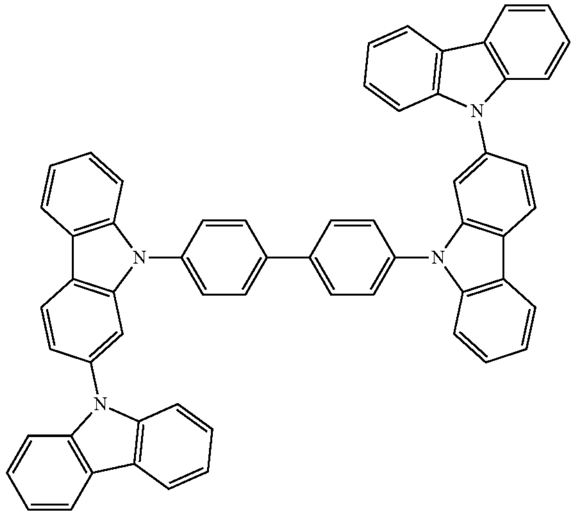
-continued
HT36
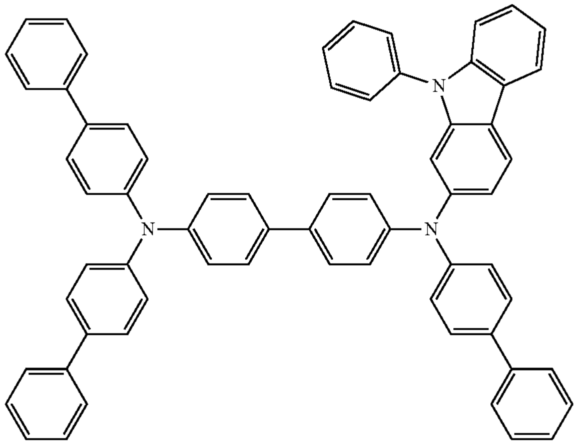
HT37
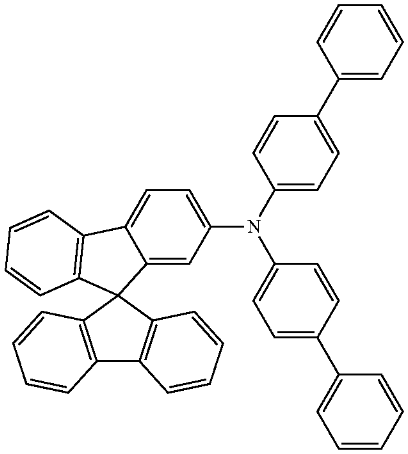
HT38
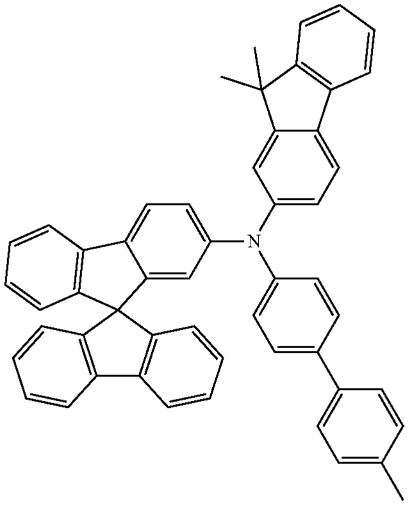

-continued
HT39
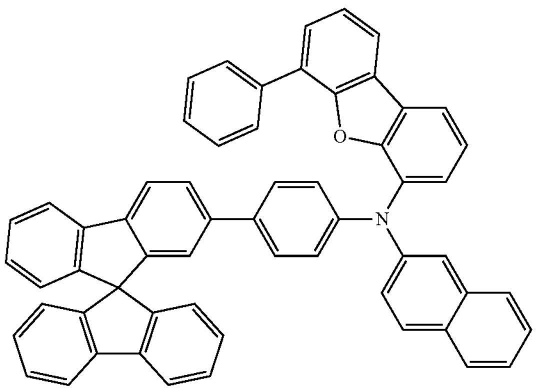
HT40
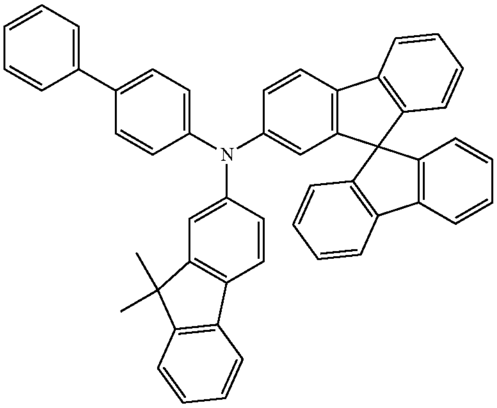
HT41
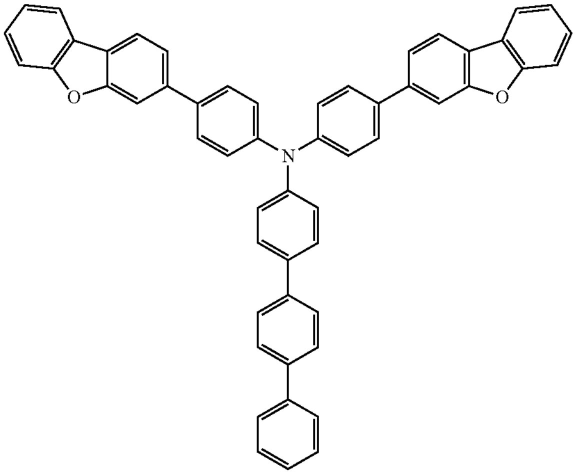
HT42
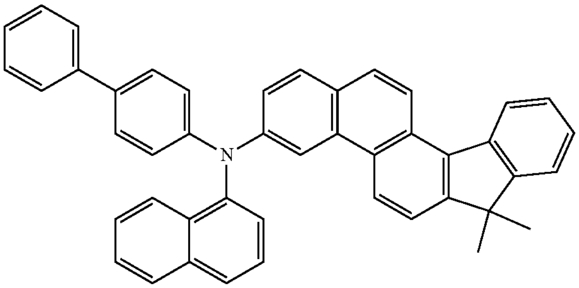
-continued
HT43
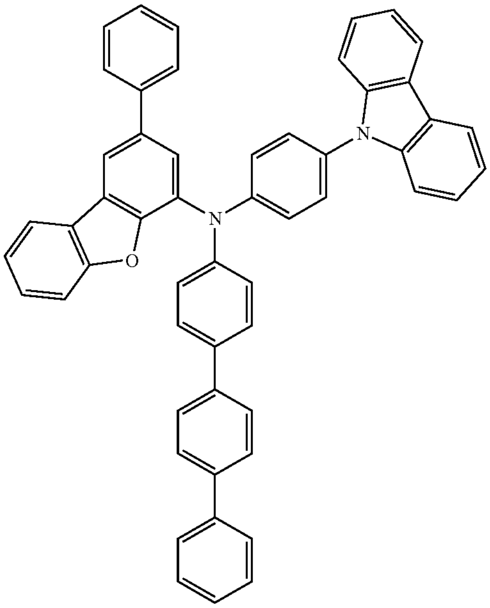
HT44
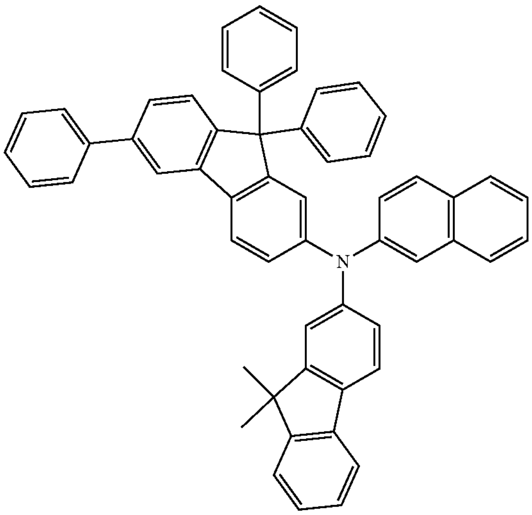
HT45
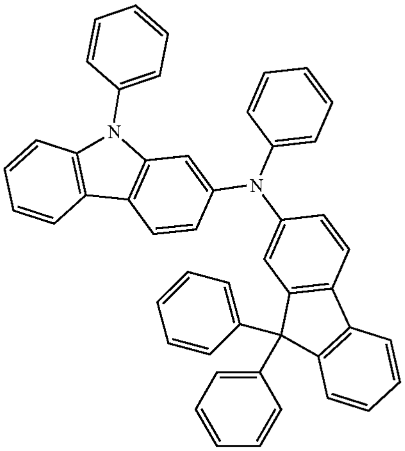

-continued
HT46
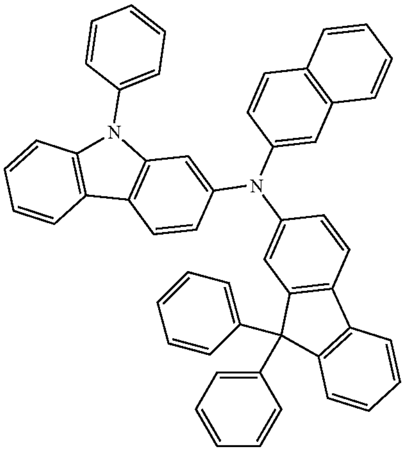
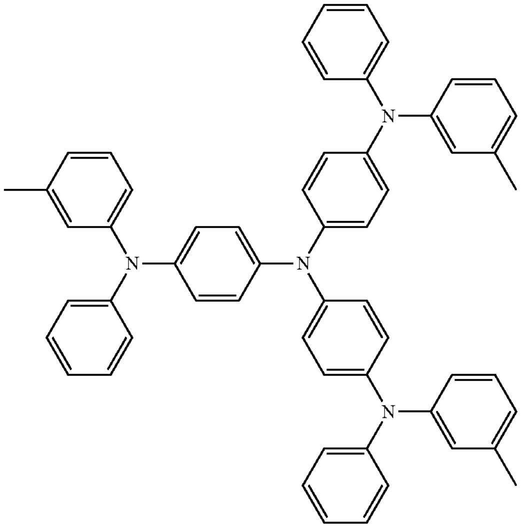
m-MTDATA
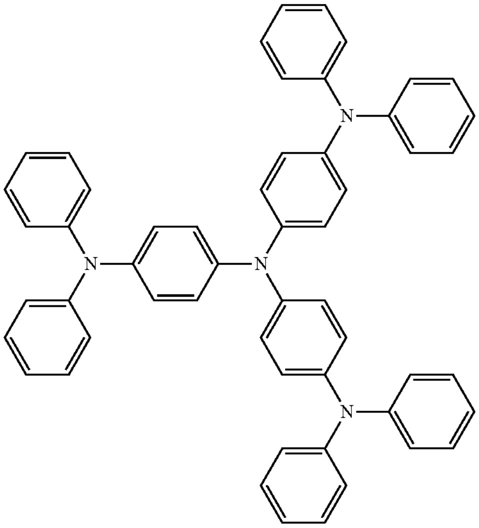
TDATA
-continued
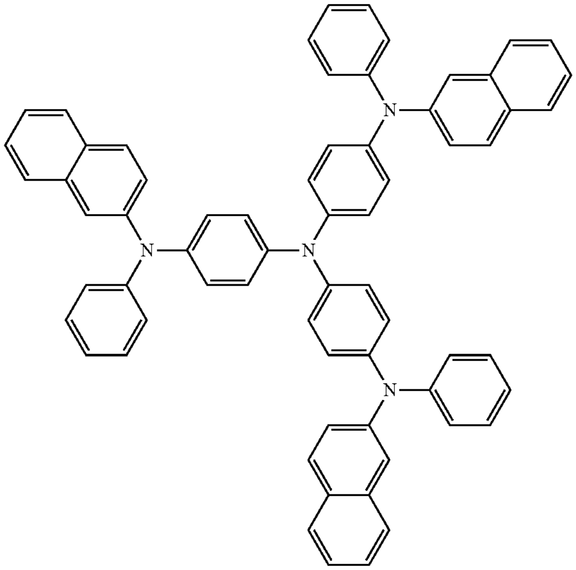
2-TNATA
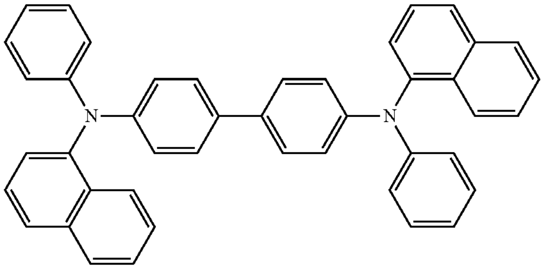
NPB
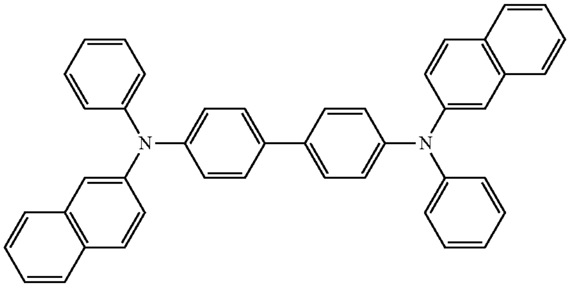
β-NPB
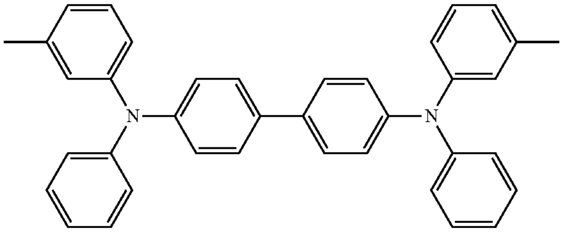
TPD -continued

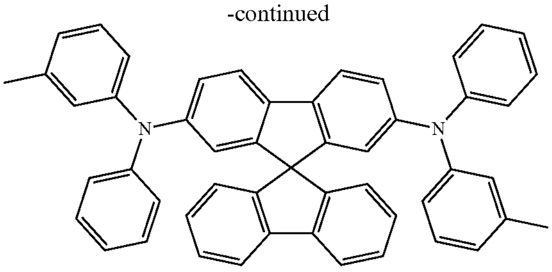

Spiro-TPD

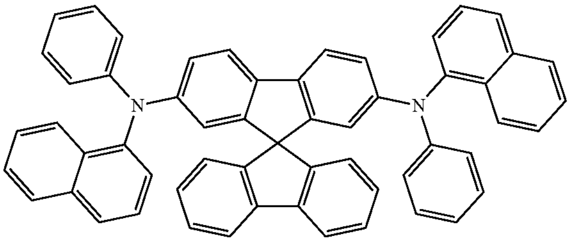

Spiro-NPB

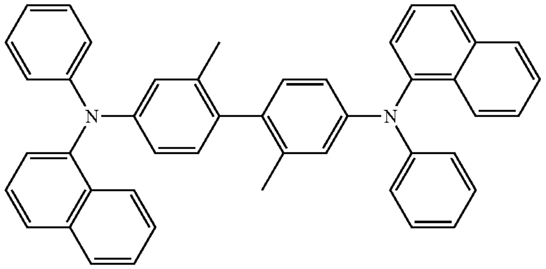

methylated-NPB

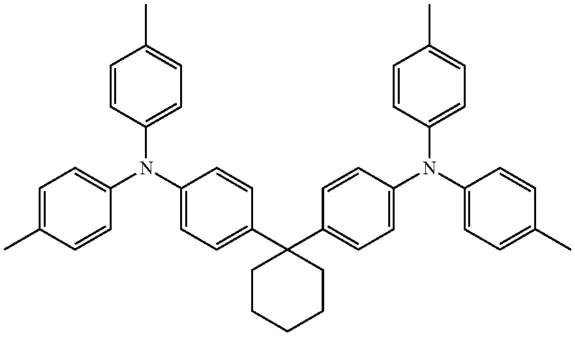

TAPC

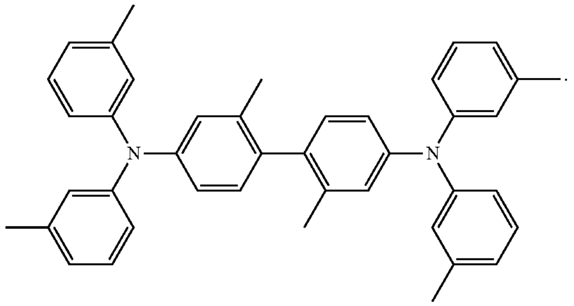

HMTPD

A thickness of the hole transport region may be in a range of about 50 Å to about 10,000 Å. For example, the thickness of the hole transport region may be in a range of about 100 Å to about 4,000 Å. When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of about 100 Å to about 1,000 Å. For example, the thickness of the hole transport layer may be in a range of about 100 Å to about 1,500 Å. When the thicknesses of the hole transport region, the hole injection layer, and the hole transport layer are within these ranges, satisfactory hole-transporting characteristics may be obtained without a substantial increase in driving voltage.

The emission auxiliary layer may increase light-emission efficiency by compensating for an optical resonance distance according to a wavelength of light emitted by an emission layer, and the electron blocking layer may block the leakage of electrons from an emission layer to a hole transport region. Materials that may be included in the hole transport region may be included in the emission auxiliary layer and the electron blocking layer.

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

In an embodiment, a lowest unoccupied molecular orbital (LUMO) energy level of the p-dopant may be equal to or less than about −3.5 eV.

In an embodiment, the p-dopant may include a quinone derivative, a cyano group-containing compound, a compound containing element EL1 and element EL2, or any combination thereof.

Examples of the quinone derivative may include TCNQ, F4-TCNQ, and the like.

Examples of the cyano group-containing compound may include HAT-CN, a compound represented by Formula 221, and the like.

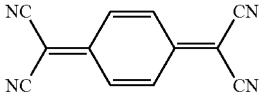

TCNQ

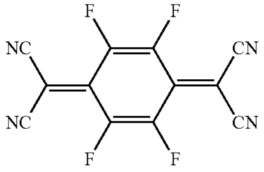

F4-TCNQ

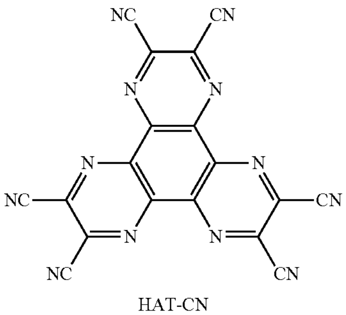

HAT-CN

-continued

[Formula 221]

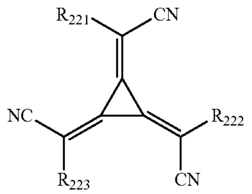

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or a combination thereof, and element EL2 may be a non-metal, a metalloid, or a combination thereof.

Examples of the metal may include an alkali metal (for example, lithium (Li), sodium (Na), potassium (K), rubidium (Rb), cesium (Cs), and the like.); an alkaline earth metal (for example, beryllium (Be), magnesium (Mg), calcium (Ca), strontium (Sr), barium (Ba), and the like); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), and the like); a post-transition metal (for example, zinc (Zn), indium (In), tin (Sn), and the like); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), and the like).

Examples of the metalloid may include silicon (Si), antimony (Sb), and tellurium (Te).

Examples of the non-metal may include oxygen (O) and a halogen (for example, F, Cl, Br, I, etc.).

In an embodiment, examples of the compound containing element EL1 and element EL2 may include a metal oxide, a metal halide (for example, a metal fluoride, a metal chloride, a metal bromide, or a metal iodide), a metalloid halide (for example, a metalloid fluoride, a metalloid chloride, a metalloid bromide, or a metalloid iodide), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_{203}$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide may include an alkali metal halide, an alkaline earth metal halide, a transition metal halide, a post-transition metal halide, and a lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhI_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), and a gold halide (for example, AuF, AuCl, AuBr, AuI, etc.).

Examples of the post-transition metal halide may include a zinc halide (for example, $ZnF_2$, $ZnCl_2$, $ZnBr_2$, $ZnI_2$, etc.), an indium halide (for example, $InI_3$, etc.), and a tin halide (for example, $SnI_2$, etc.).

Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$, $SmBr_3$, YbI, $YbI_2$, $YbI_3$, and $SmI_3$.

Examples of the metalloid halide may include an antimony halide (for example, $SbCl_5$, etc.).

Examples of the metal telluride may include an alkali metal telluride (for example, $Li_2Te$, $Na_2Te$, $K_2Te$, $Rb_2Te$, $Cs_2Te$, etc.), an alkaline earth metal telluride (for example, BeTe, MgTe, CaTe, SrTe, BaTe, etc.), a transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), a post-transition metal telluride (for example, ZnTe, etc.), and a lanthanide metal telluride (for example, LaTe, CeTe, PrTe, NdTe, PmTe, EuTe, GdTe, TbTe, DyTe, HoTe, ErTe, TmTe, YbTe, LuTe, etc.).

[Emission Layer in Interlayer 130]

When the light-emitting device 10 is a full-color light-emitting device, the emission layer may be patterned into a red emission layer, a green emission layer, and/or a blue emission layer, according to a subpixel. In an embodiment, the emission layer may have a stacked structure of two or more layers of a red emission layer, a green emission layer, and a blue emission layer, in which the two or more layers may contact each other or may be separated from each other. In embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

An amount of the dopant in the emission layer may be in a range of about 0.01 parts by weight to about 15 parts by weight, based on 100 parts by weight of the host.

In an embodiment, the emission layer may include a quantum dot.

In an embodiment, the emission layer may include a delayed fluorescence material. The delayed fluorescence material may function as a host or as a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within the range, excellent light-emission characteristics may be obtained without a substantial increase in driving voltage.

[Host]

The host may be at least one of the second compound to the fourth compound.

The host may further include a compound represented by Formula 301:

$$[Ar_{301}]_{xb11}\text{-}[(L_{301})_{xb1}\text{-}R_{301}]_{xb21} \qquad \text{[Formula 301]}$$

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, or —$P(=O)(Q_{301})(Q_{302})$, xb21 may be an integer from 1 to 5, and $Q_{301}$ to $Q_{303}$ may each independently be the same as described in connection with $Q_1$ in the specification.

In an embodiment, when xb11 in Formula 301 is 2 or more, two or more of $Ar_{301}$(s) may be linked to each other via a single bond.

In an embodiment, the host may include a compound represented by Formula 301-1, a compound represented by Formula 301-2, or any combination thereof:

[Formula 301-1]

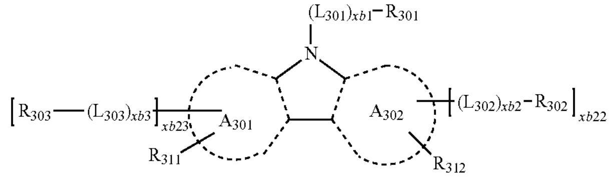

[Formula 301-2]

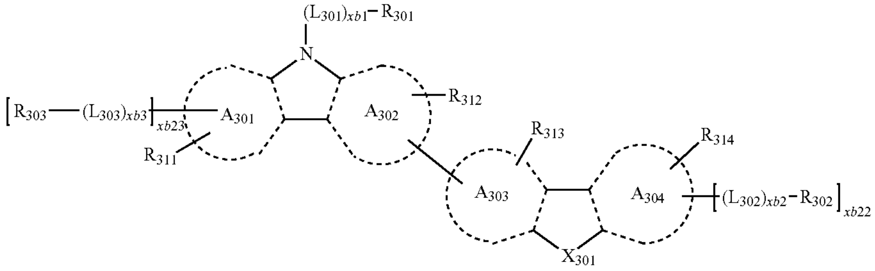

In Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-$[(L_{304})_{xb4}$-$R_{304}]$, $C(R_{304})(R_{305})$, or $Si(R_{304})(R_{305})$, xb22 and xb23 may each independently be 0, 1, or 2, $L_{301}$, xb1, and $R_{301}$ are respectively the same as those described in the specification, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each independently be the same as described in connection with $R_{301}$.

In an embodiment, the host may include an alkali earth metal complex, a post-transition metal complex, or a combination thereof. In an embodiment, the host may include a Be complex (for example, Compound H55), an Mg complex, a Zn complex, or a combination thereof.

In an embodiment, the host may include one of Compounds H1 to H124, 9,10-Di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolyl-benzene (mCP), 1,3,5-tri(carbazol-9-yl)benzene (TCP), or any combination thereof:

-continued
H1
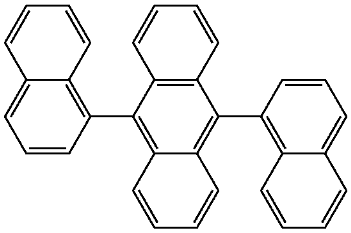
H2
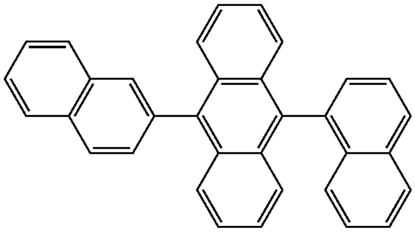
H3
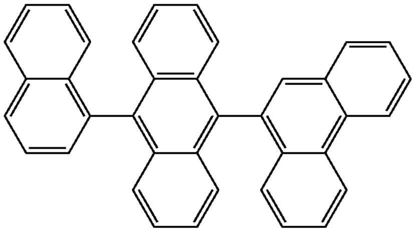
H4
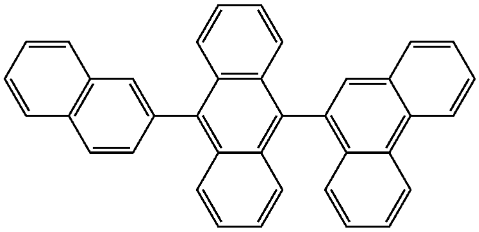
H5
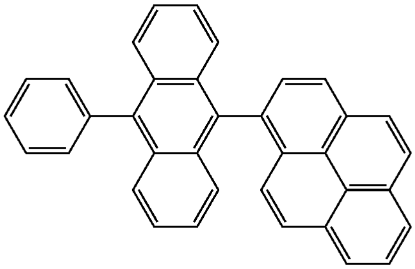
H6
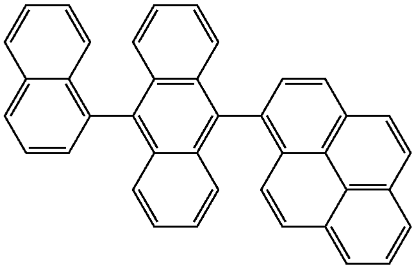
H7
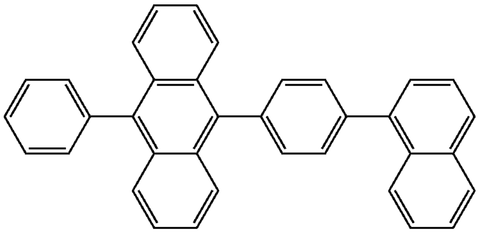
H8
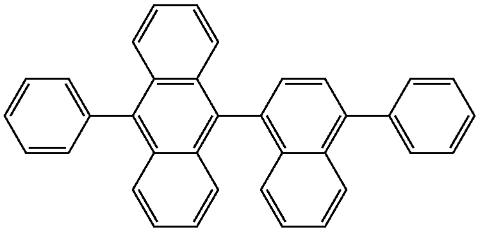
H9
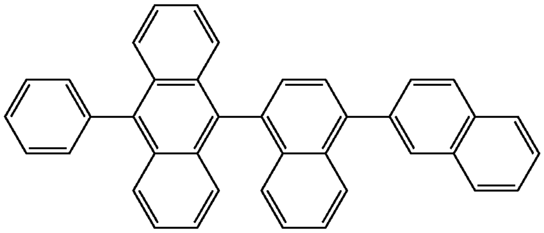
H10
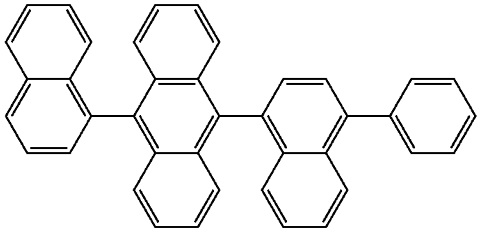
H11
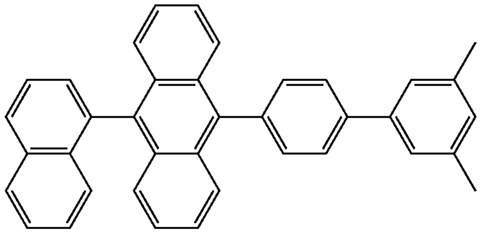
H12
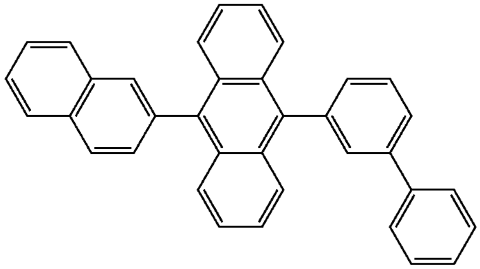

-continued
H13
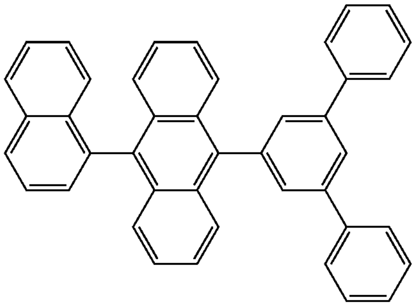
H14
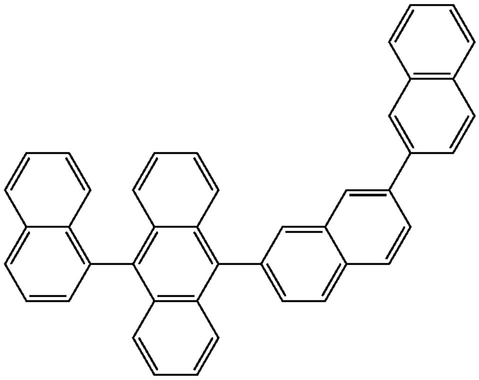
H15
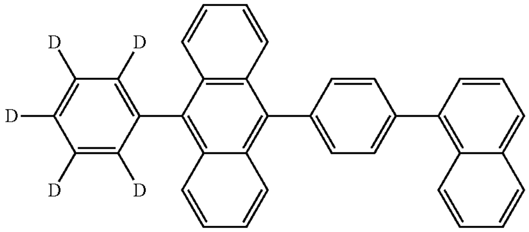
H16
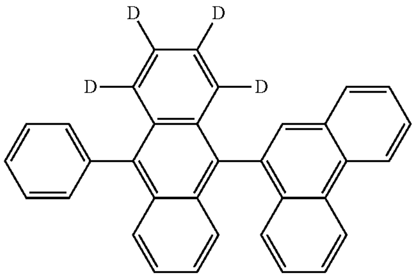
H17
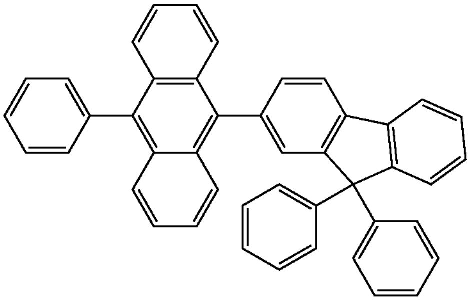
-continued
H18
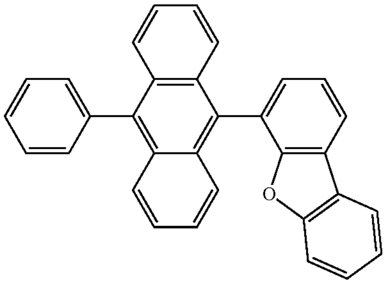
H19
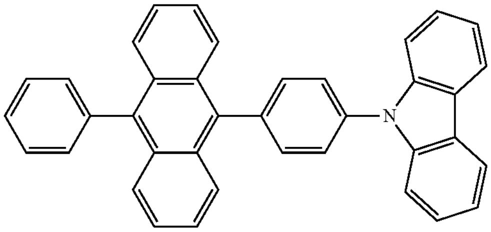
H20
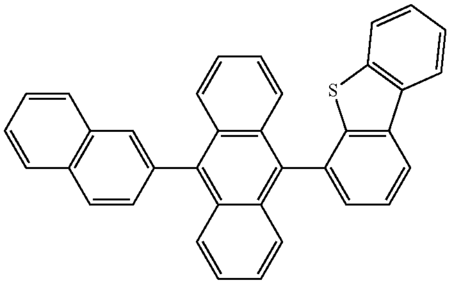
H21
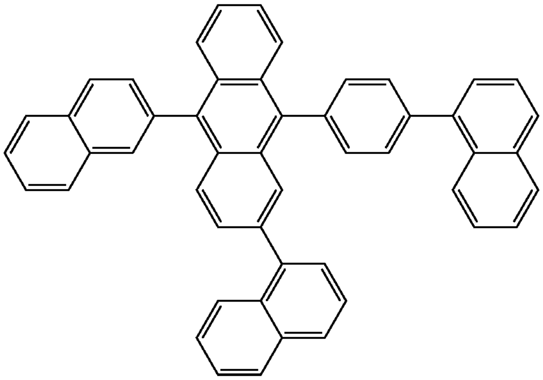
H22
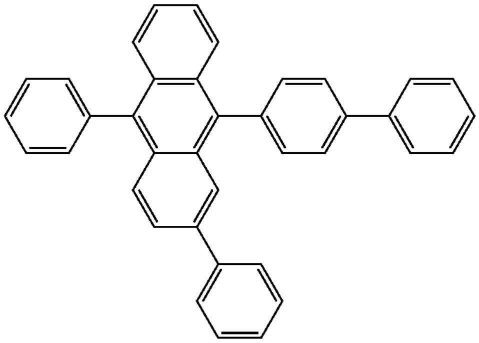

-continued
H23
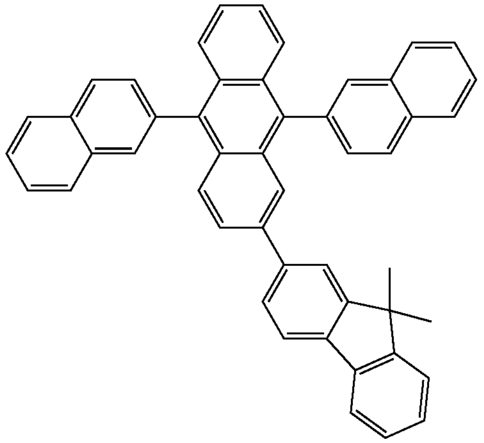
H24
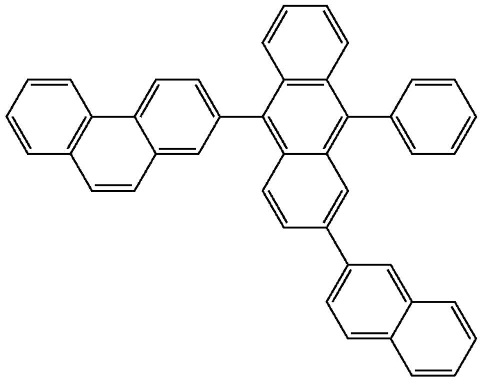
H25
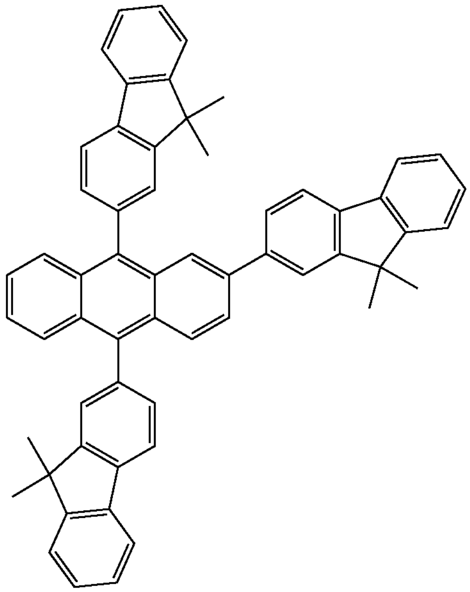
-continued
H26
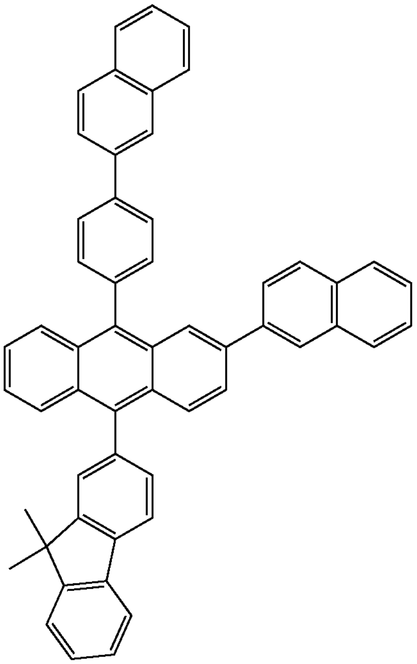
H27
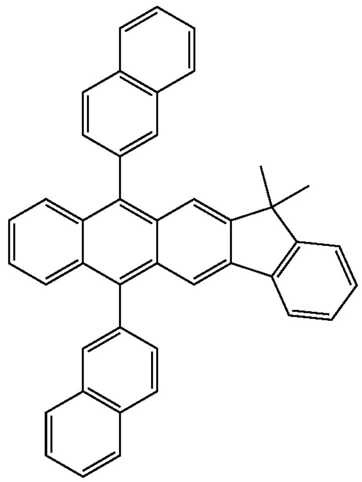
H28
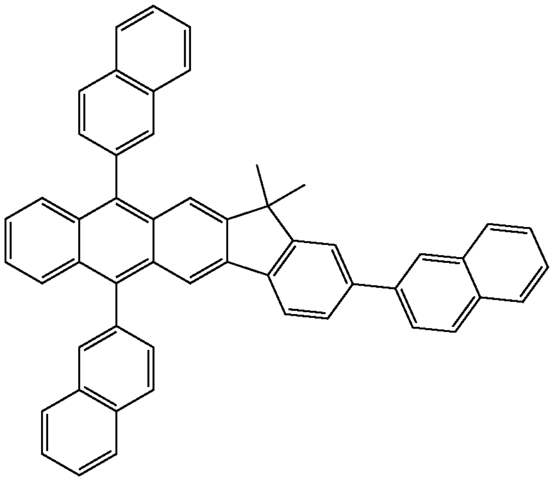

H29
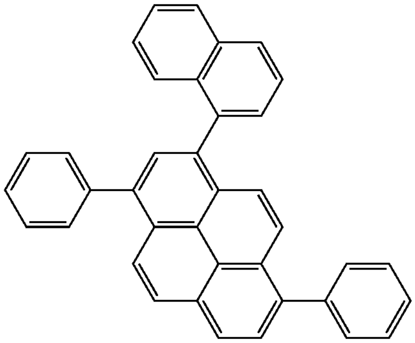
H30
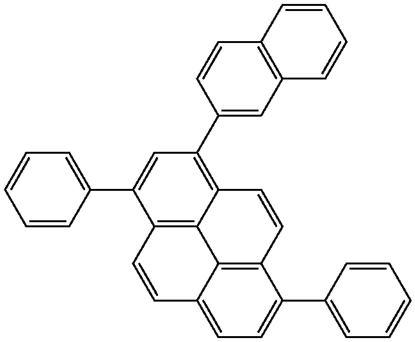
H31
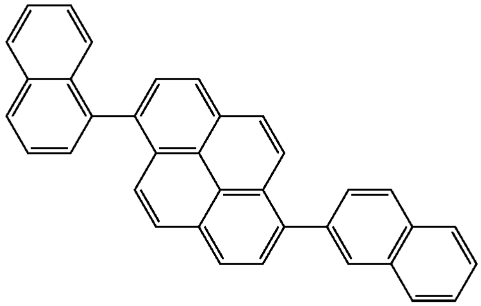
H32
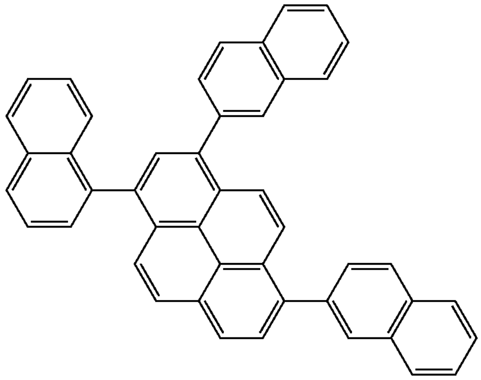
H33
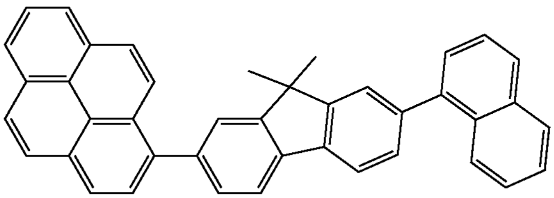
H34
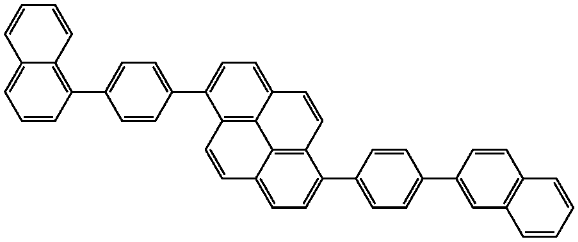
H35
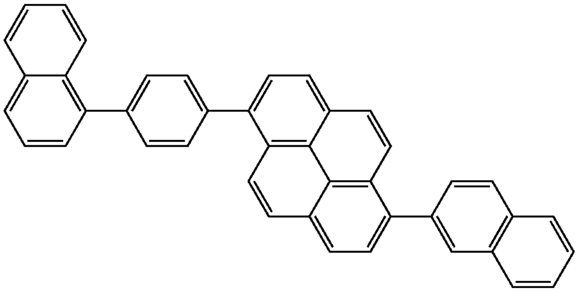
H36
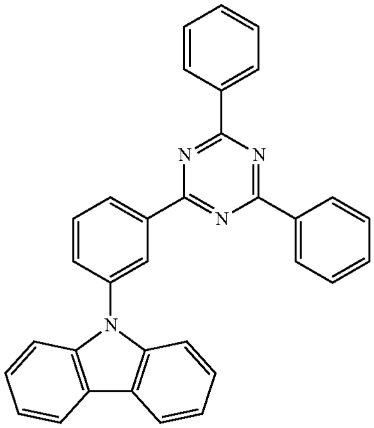
H37
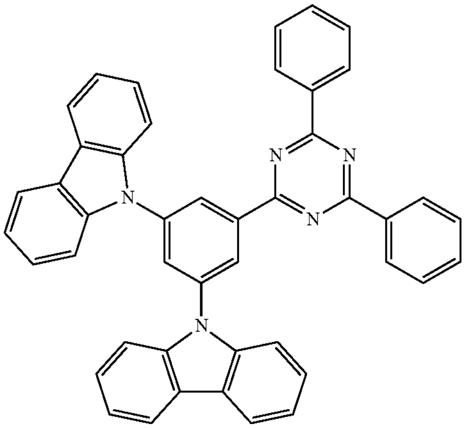

-continued
H38
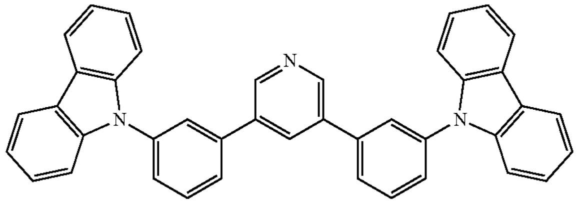
H39
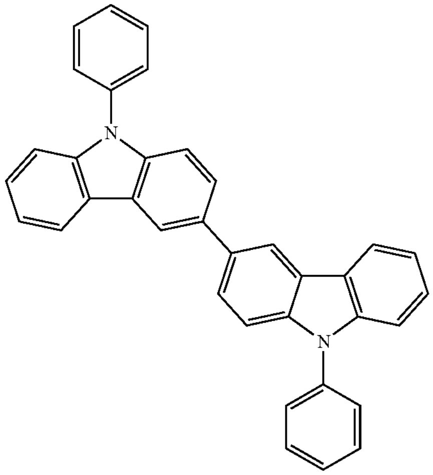
H40
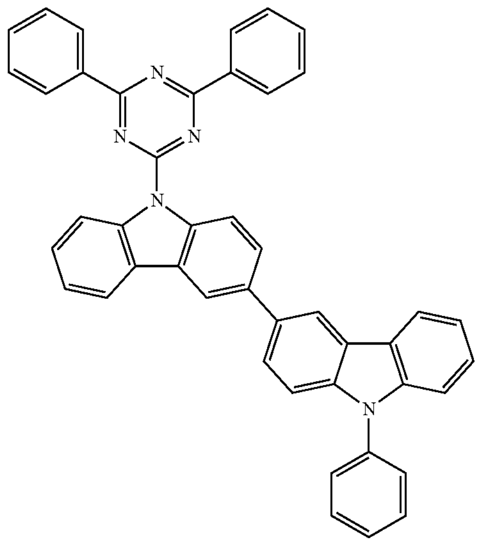
-continued
H41
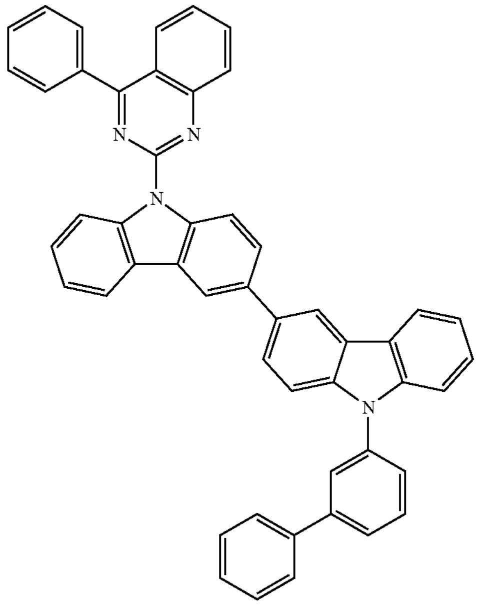
H42
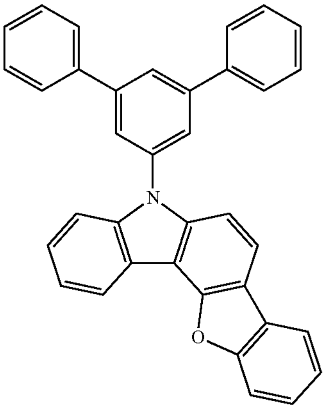
H43
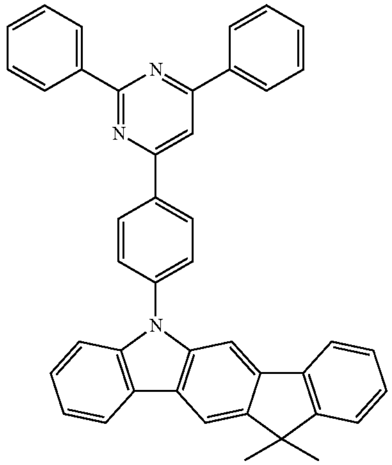

-continued
H44
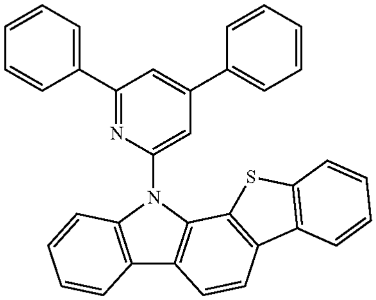
H45
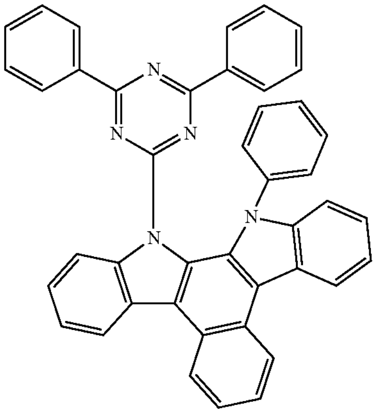
H46
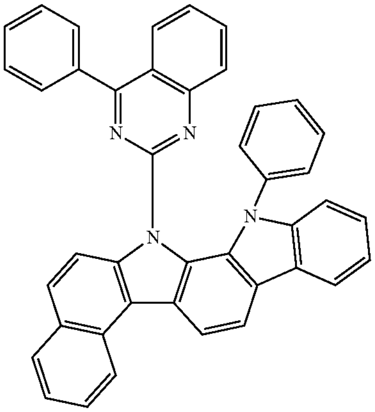
H47
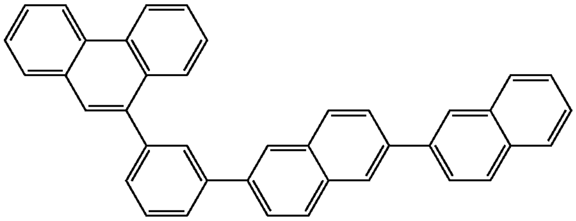
H48
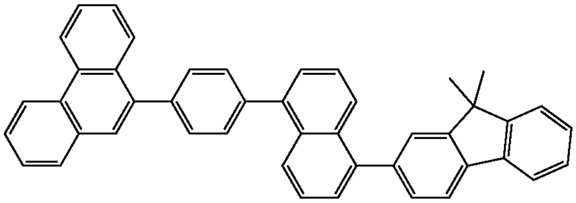
-continued
H49
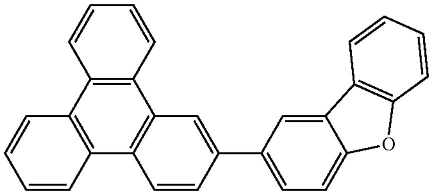
H50
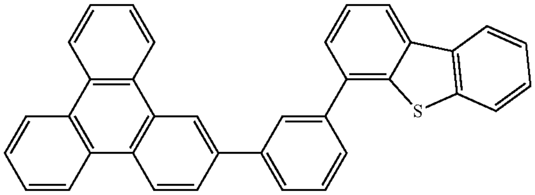
H51
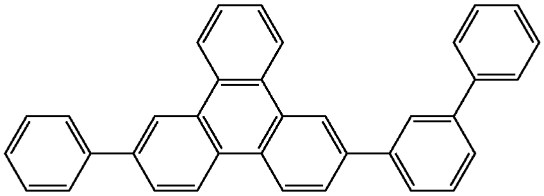
H52
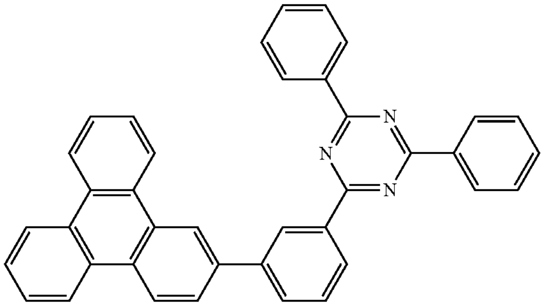
H53
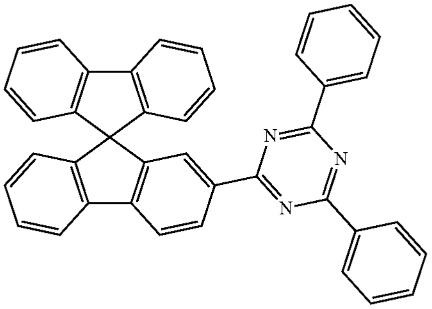

H54
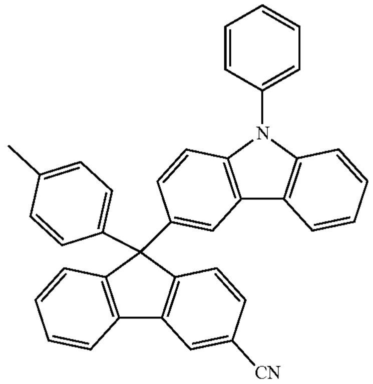
H55
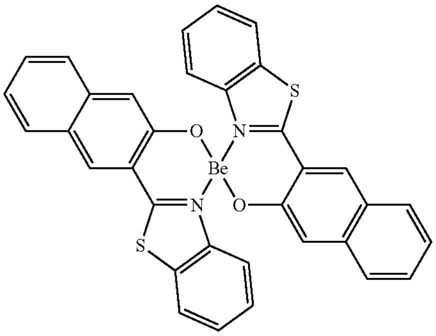
H56
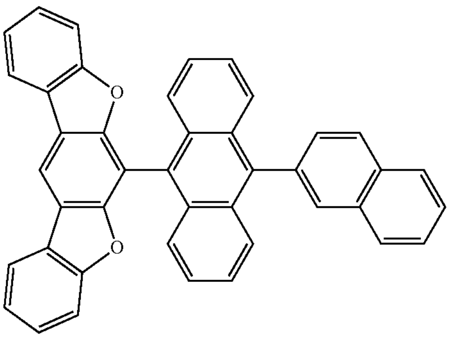
H57
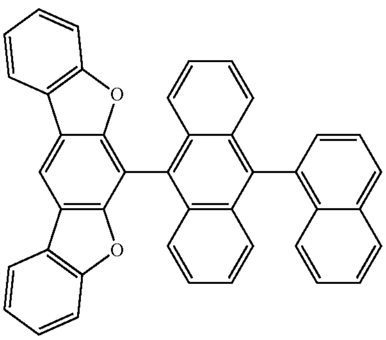
H58
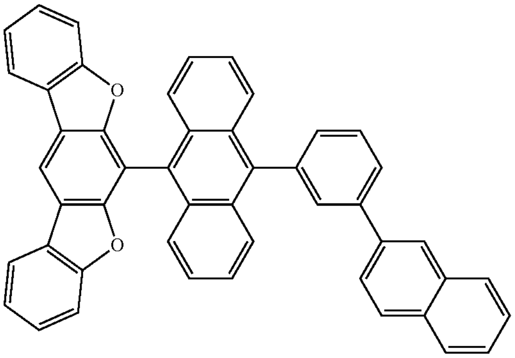
H59
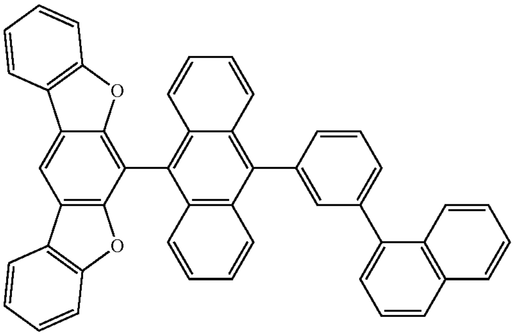
H60
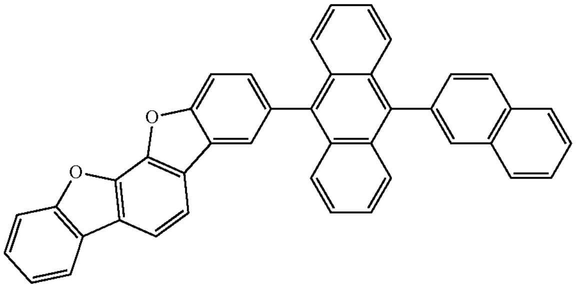
H61
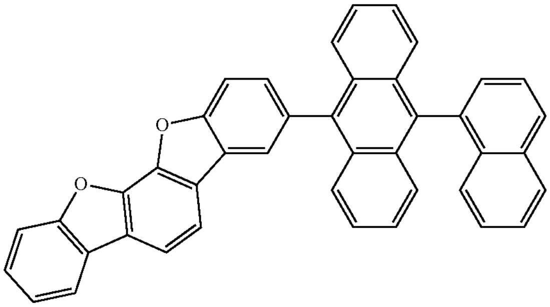

-continued
H62
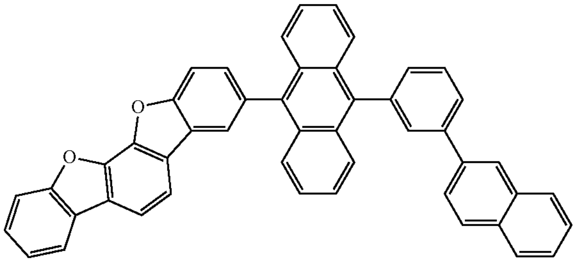
H63
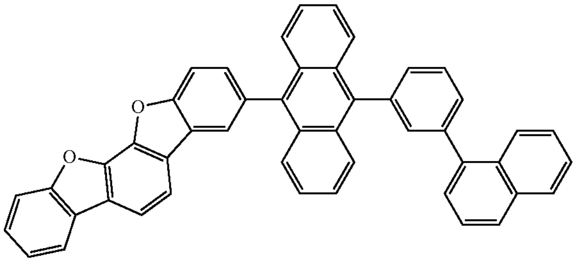
H64
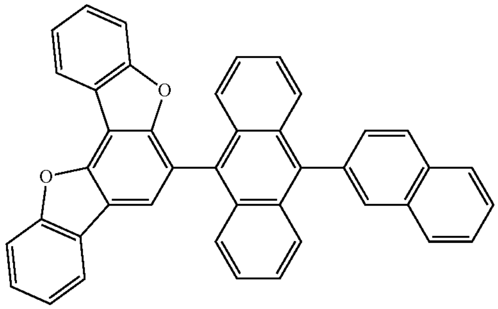
H65
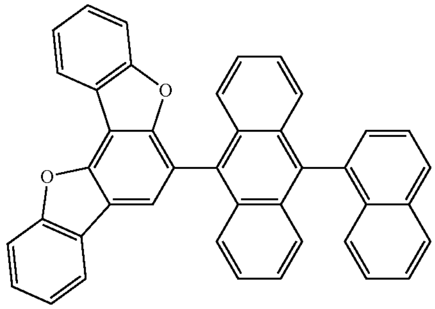
H66
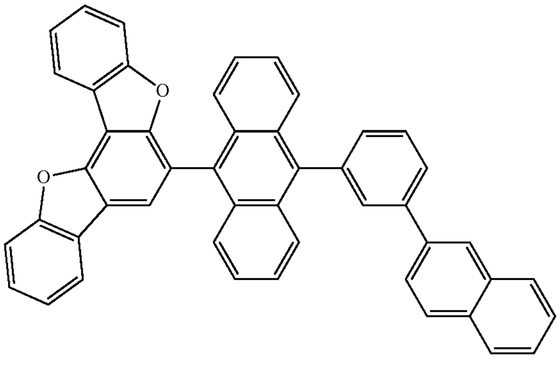
-continued
H67
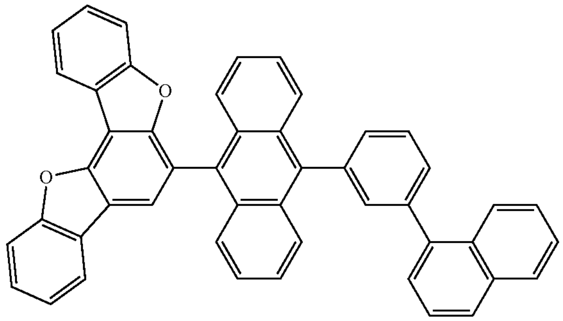
H68
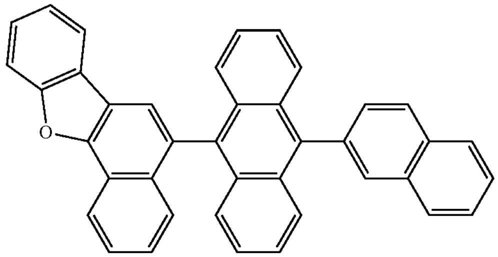
H69
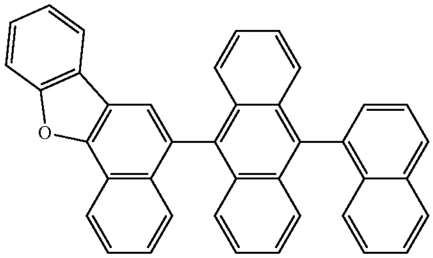
H70
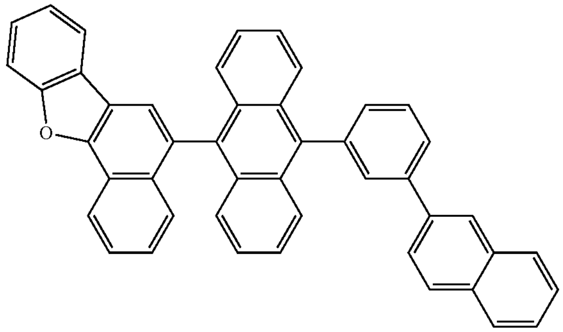
H71
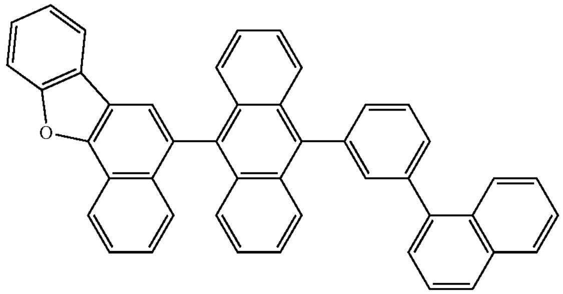

-continued
H72
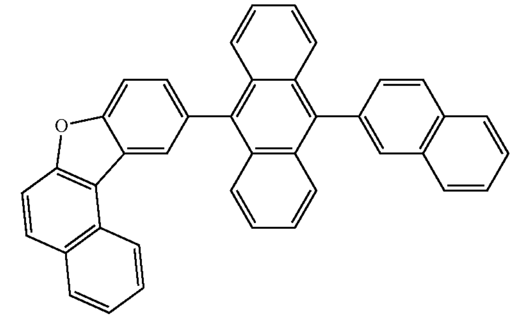
H73
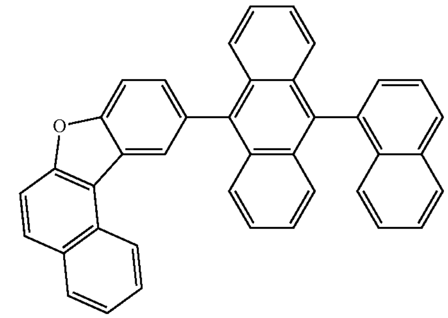
H74
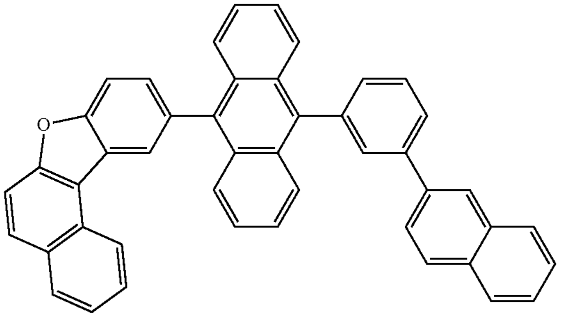
H75
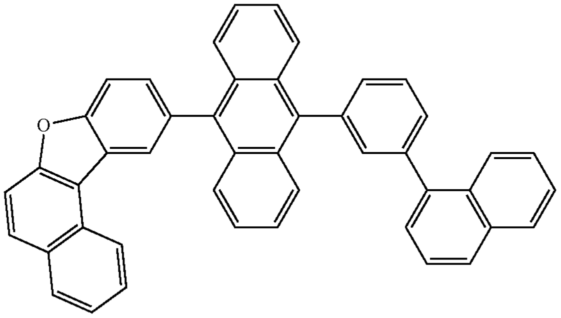
H76
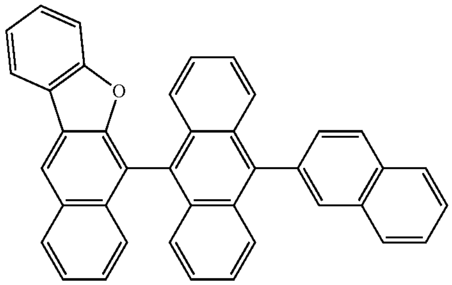
-continued
H77
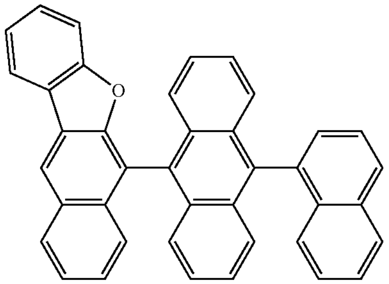
H78
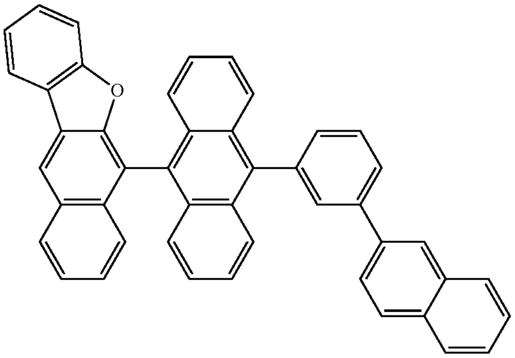
H79
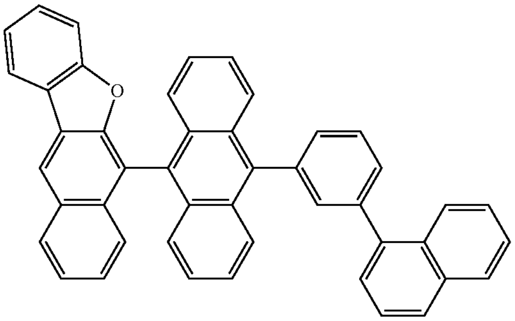
H80
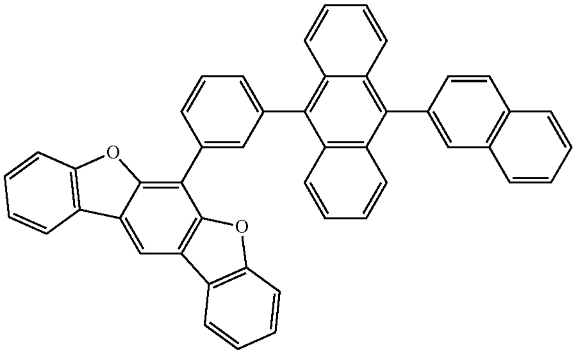

-continued
H81
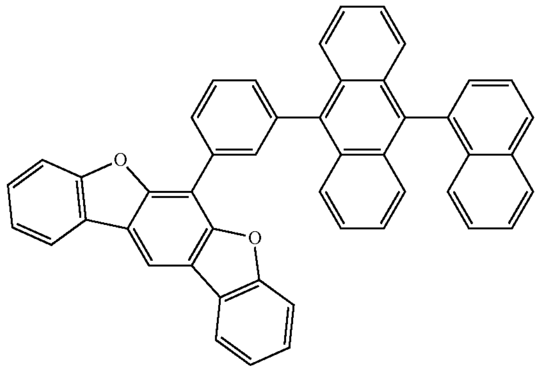
H82
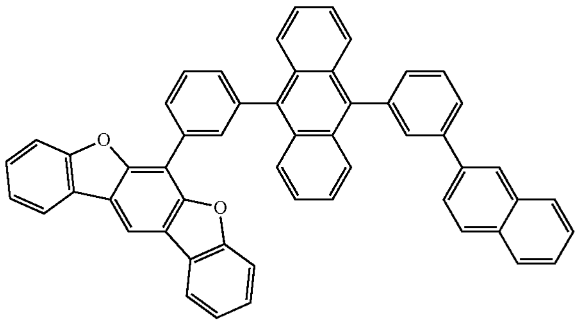
H83
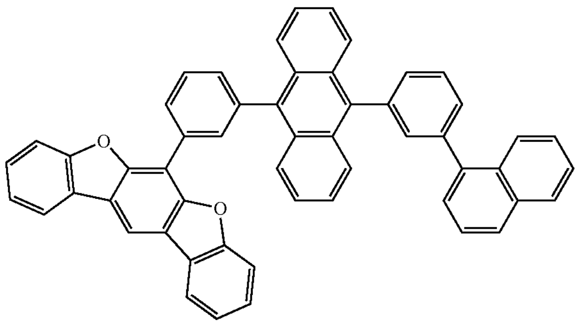
H84
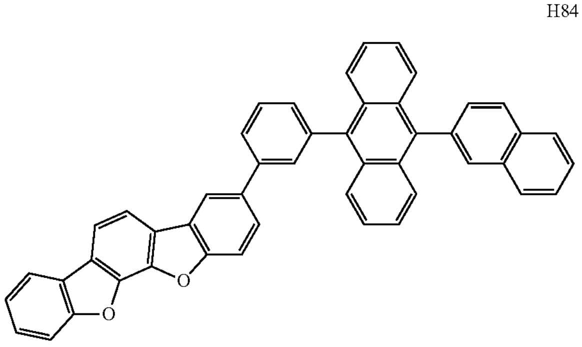
-continued
H85
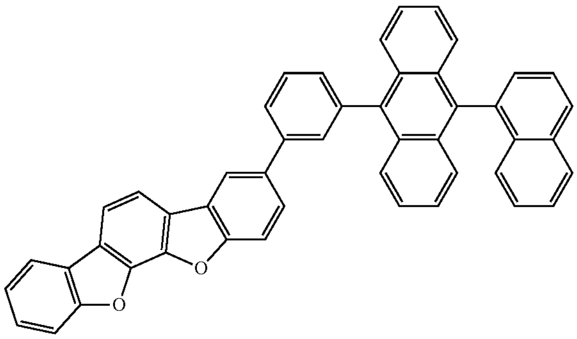
H86
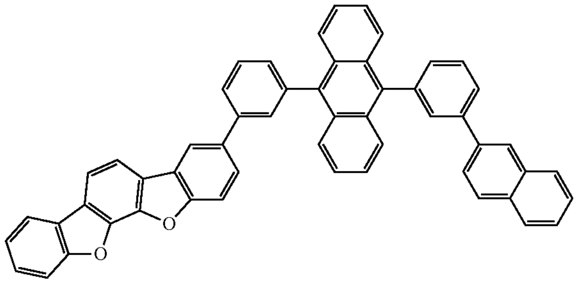
H87
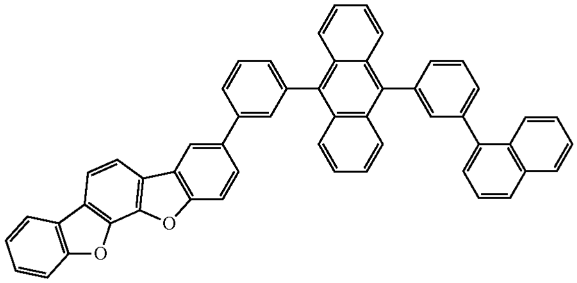
H88
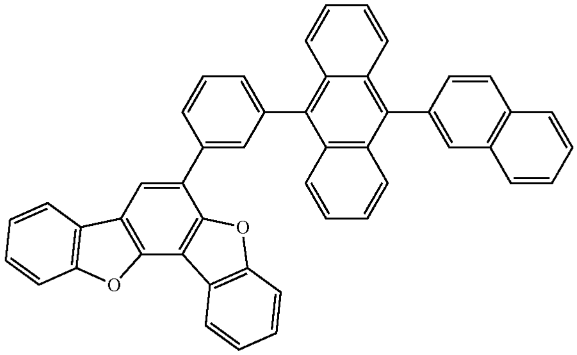

H89
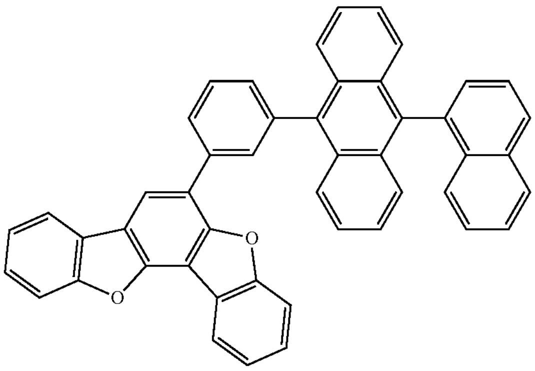
H90
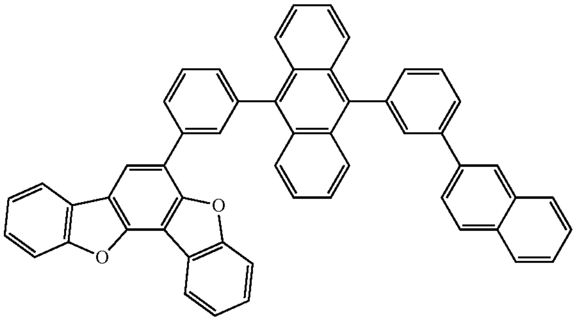
H91
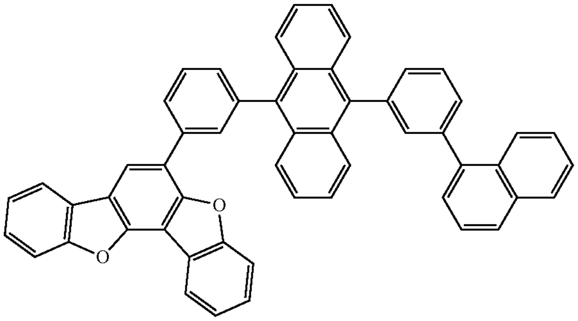
H92
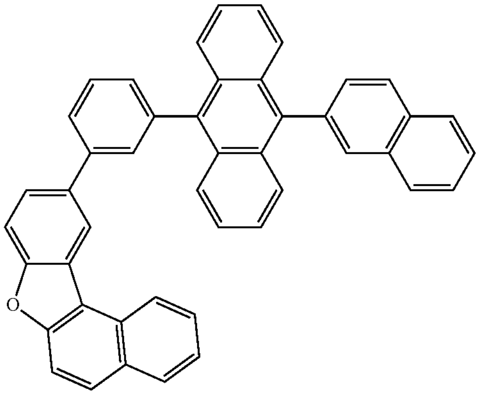
H93
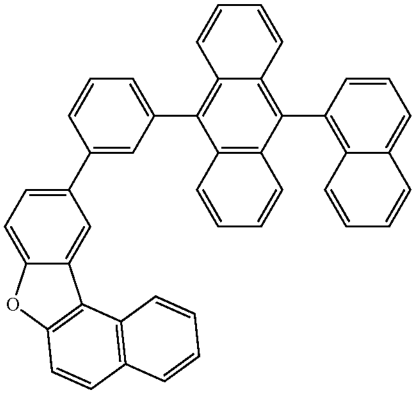
H94
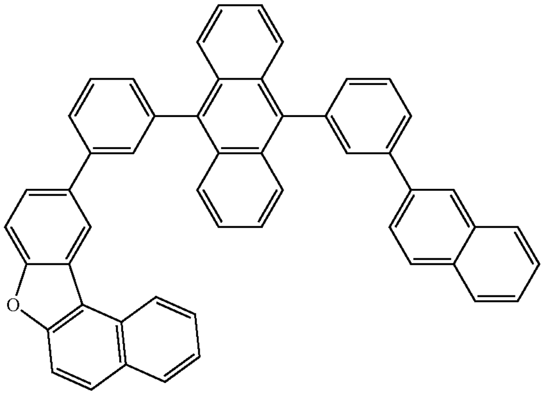
H95
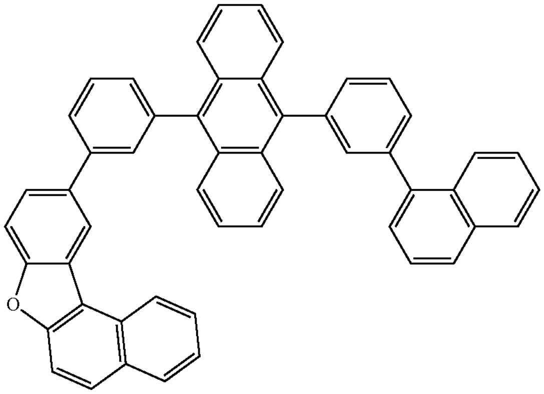
H96
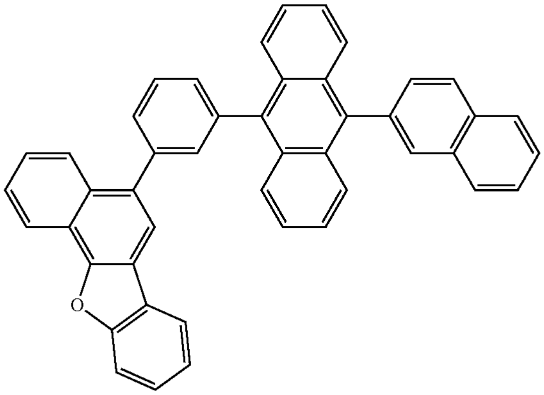

-continued
H97
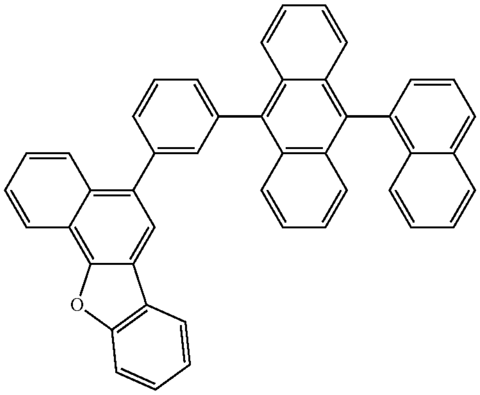
H98
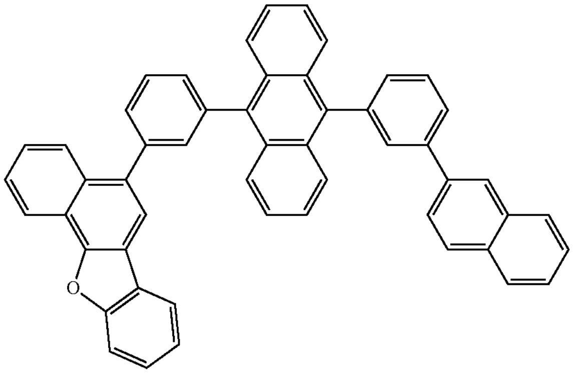
H99
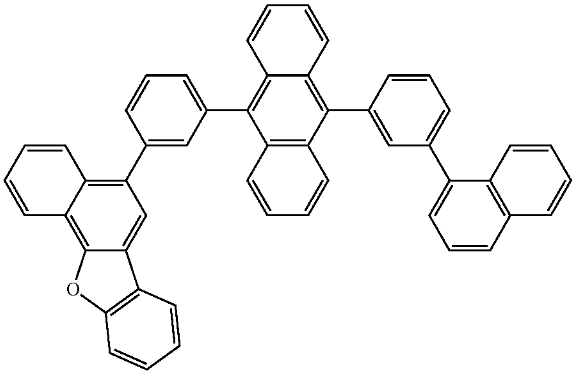
H100
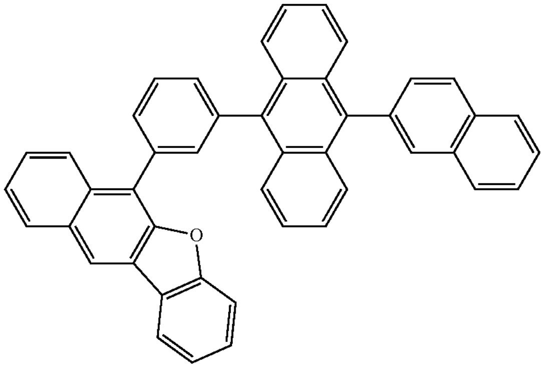
-continued
H101
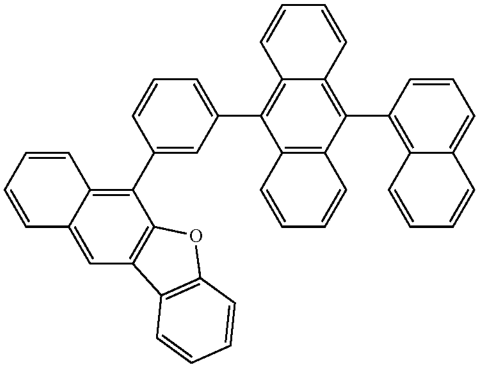
H102
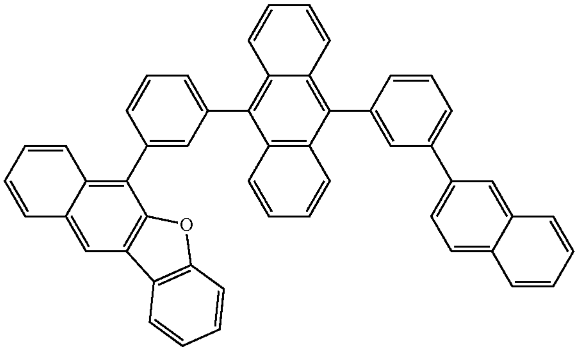
H103
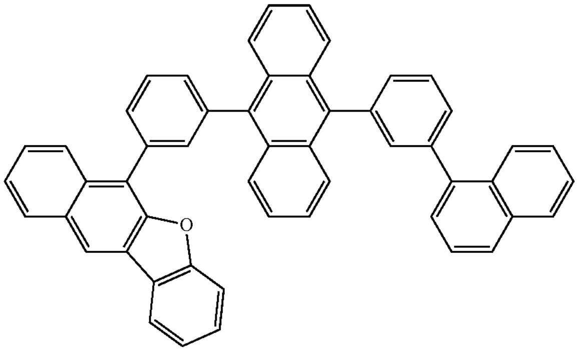
H104
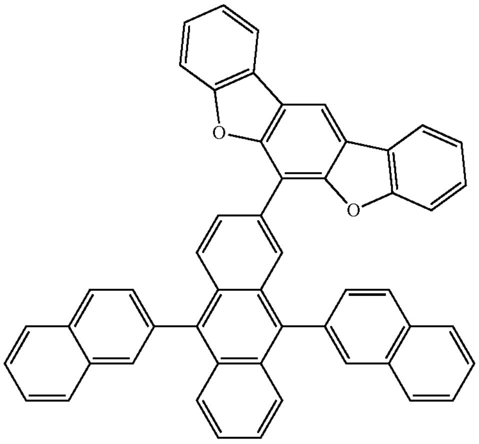

-continued
H105
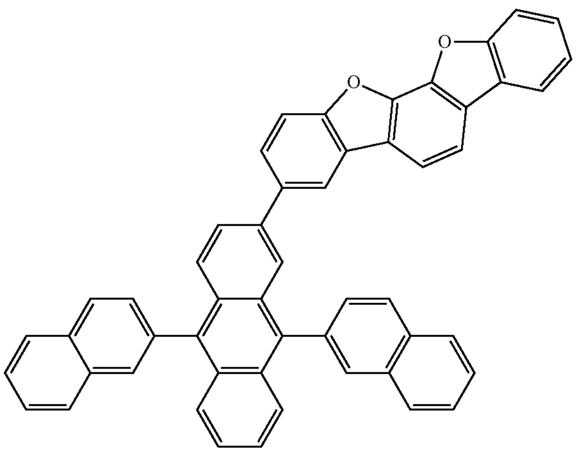
H106
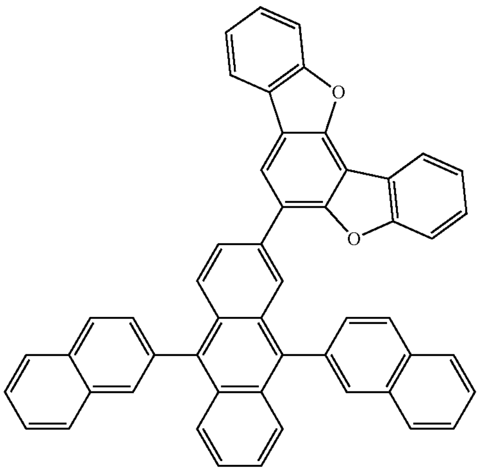
H107
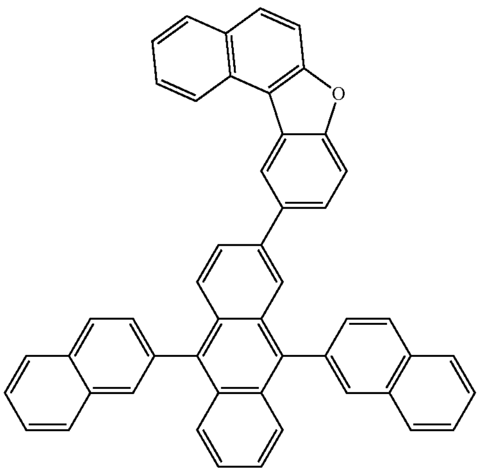
-continued
H108
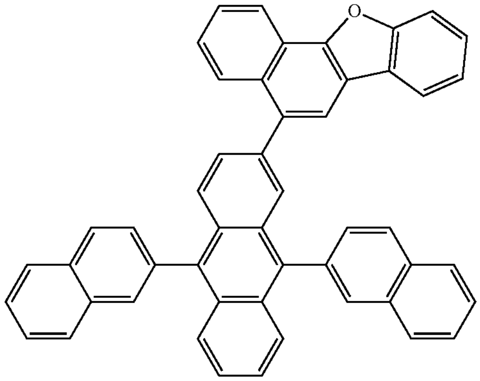
H109
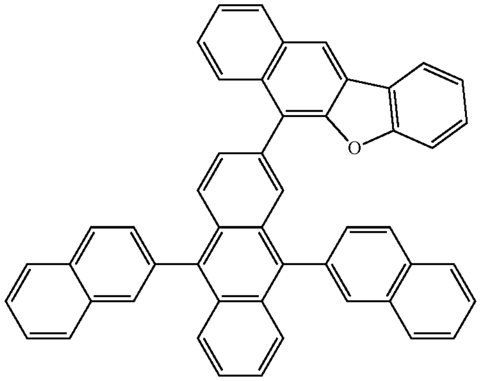
H110
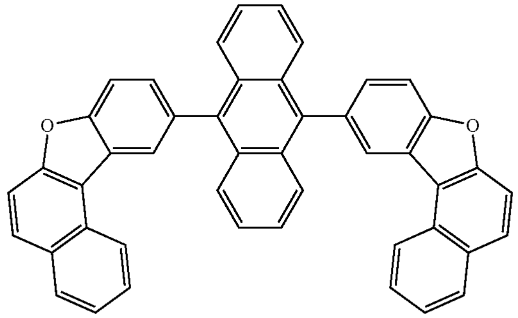
H111
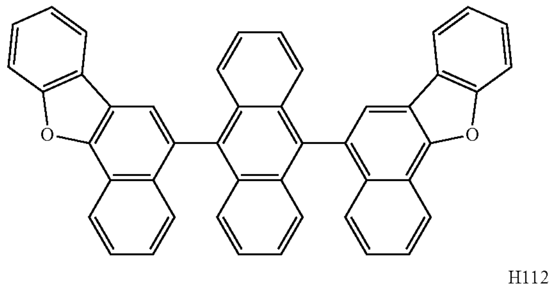
H112
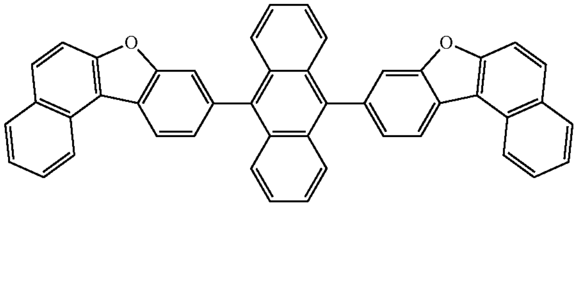

-continued
H113
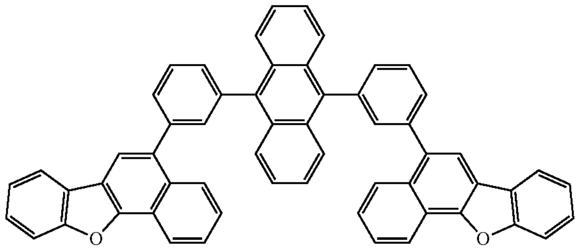
H114
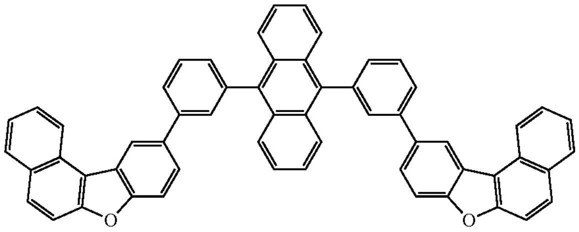
H115
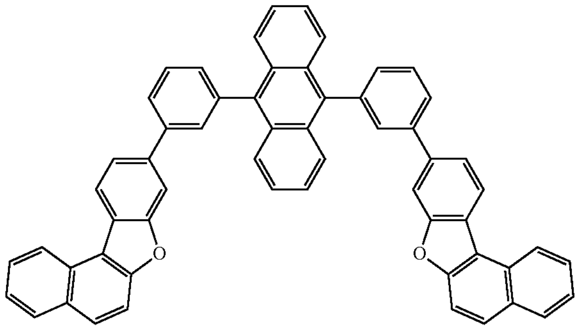
H116
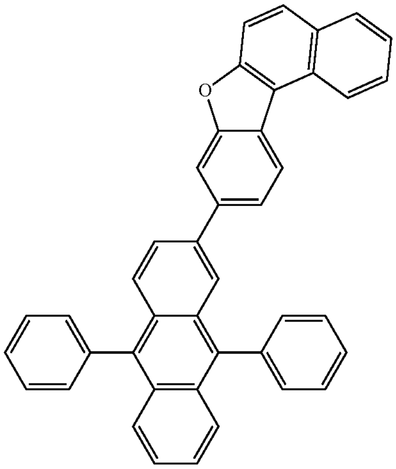
-continued
H117
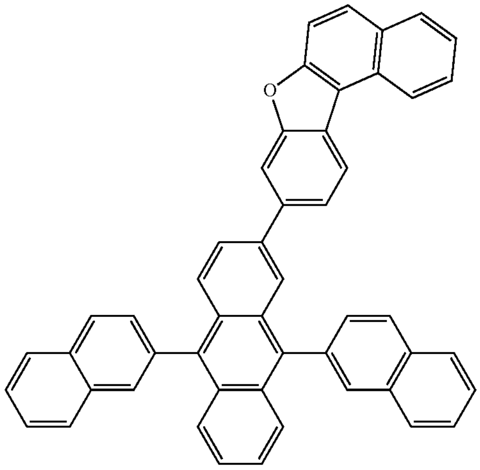
H118
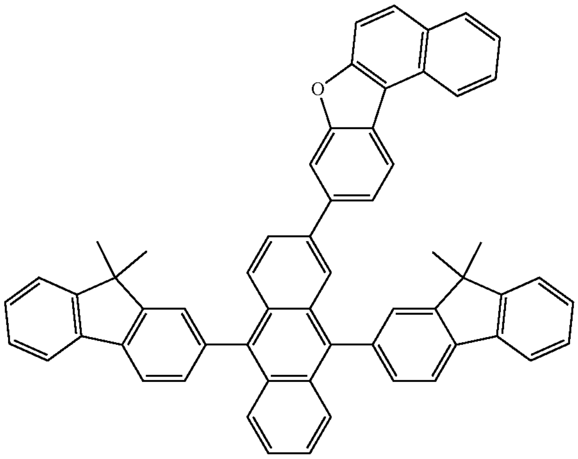
H119
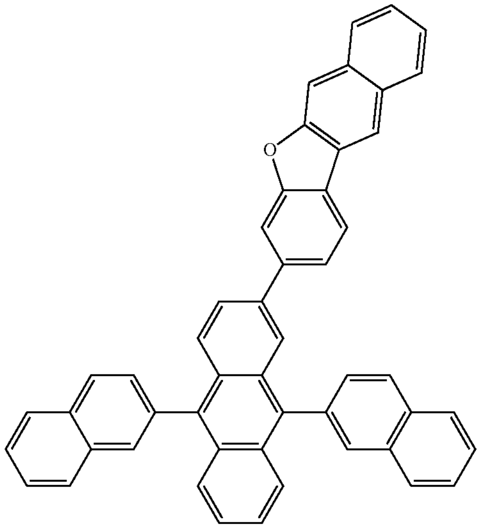

-continued

H120

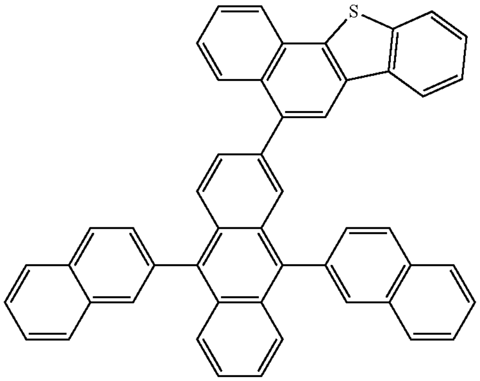

H121

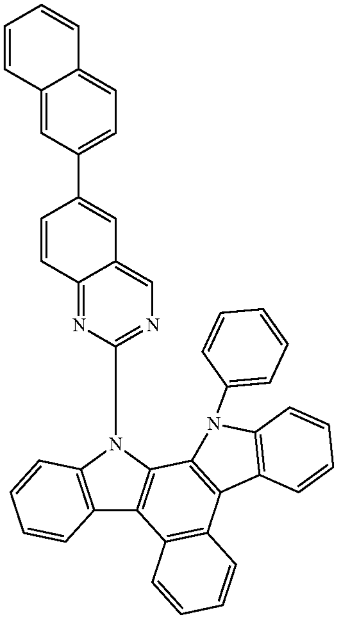

H122

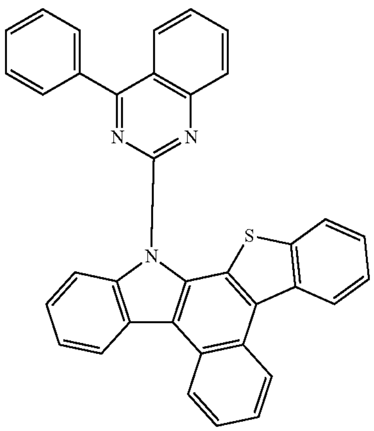

-continued

H123

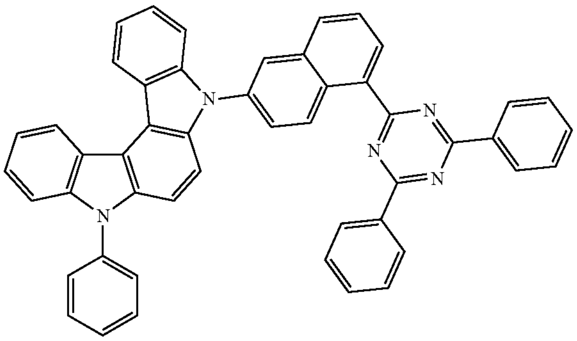

H124

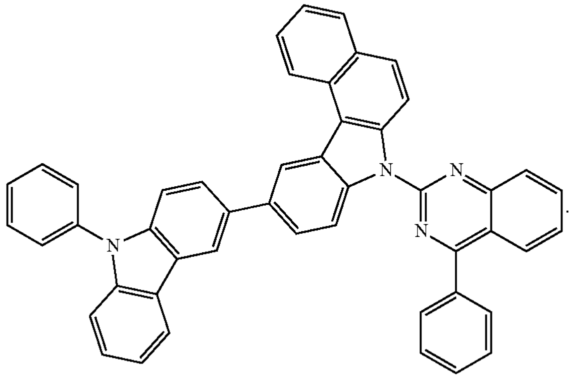

[Phosphorescent Dopant]

The phosphorescent dopant may include the organometallic compound represented by Formula 1.

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

[Formula 401]

$$M(L_{401})_{xc1}(L_{402})_{xc2}$$

[Formula 402]

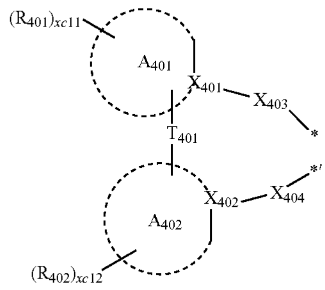

In Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is 2 or more, two or more of $L_{401}$(s) may be identical to or different from each other, $L_{402}$ may be an organic ligand, and xc2 may be 0, 1, 2, 3, or 4, wherein, when xc2 is 2 or more, two or more of $L_{402}$(s) may be identical to or different from each other, $X_{401}$ and $X_{402}$ may each independently be nitrogen (N) or carbon (C), ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S*', *—C(═O)—*', *—N($Q_{411}$)-*', *—C($Q_{411}$)($Q_{412}$)-*', *—C($Q_{411}$)═C($Q_{412}$)-*', *—C($Q_{411}$)═*', or *═C═*', $X_{403}$ and $X_{404}$ may each independently be a chemical bond (for example, a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(═O)($Q_{401}$), —S(═O)$_2$($Q_{401}$), or —P(═O)($Q_{401}$)($Q_{402}$), $Q_{401}$ to $Q_{403}$ may each independently be the same as described in connection with $Q_1$, xc11 and xc12 may each independently be an integer from 0 to 10, and

* and *' in Formula 402 each indicate a binding site to M in Formula 401.

In an embodiment, in Formula 402, $X_{401}$ may be nitrogen and $X_{402}$ may be carbon, or each of $X_{401}$ and $X_{402}$ may be nitrogen.

In an embodiment, when xc1 in Formula 402 is 2 or more, two ring $A_{401}$ in two or more of $L_{401}$(s) may be optionally linked to each other via $T_{402}$, which is a linking group, and two ring $A_{402}$ may optionally be linked to each other via $T_{403}$, which is a linking group (see Compounds PD1 to PD4 and PD7). $T_{402}$ and $T_{403}$ may each independently be the same as described in connection with $T_{401}$.

In Formula 401, $L_{402}$ may be an organic ligand. In an embodiment, $L_{402}$ may include a halogen group, a diketone group (for example, an acetylacetonate group), a carboxylic acid group (for example, a picolinate group), —C(═O), an isonitrile group, —CN group, a phosphorus group (for example, a phosphine group, a phosphite group, etc.), or any combination thereof.

The phosphorescent dopant may include, for example, one of Compounds PD1 to PD39, or any combination thereof:

PD1

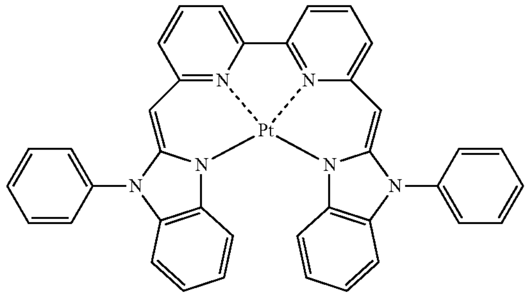

PD2

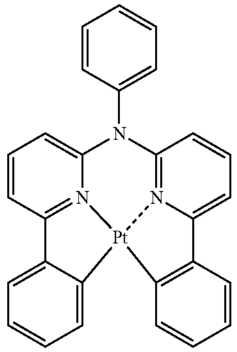

PD3

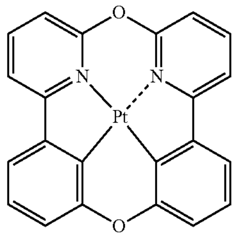

PD4

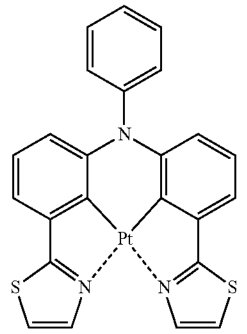

PD5

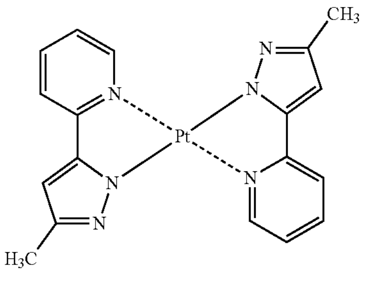

-continued
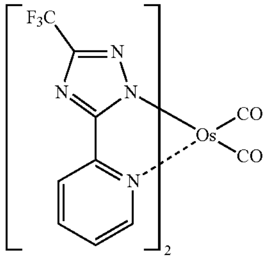
PD6
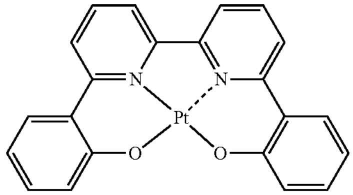
PD7
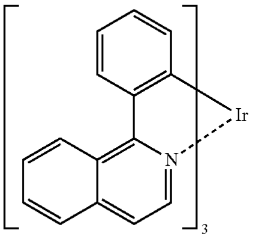
PD8
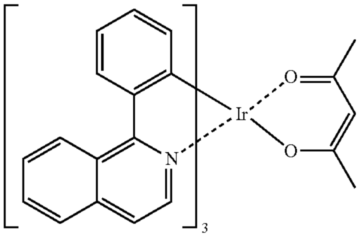
PD9
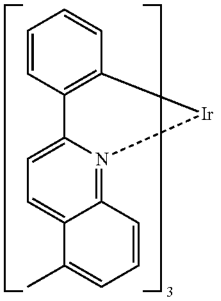
PD10
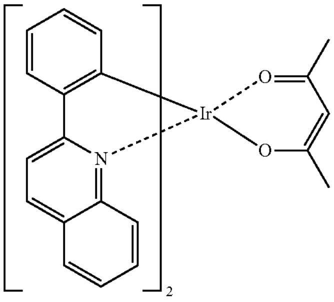
PD11
-continued
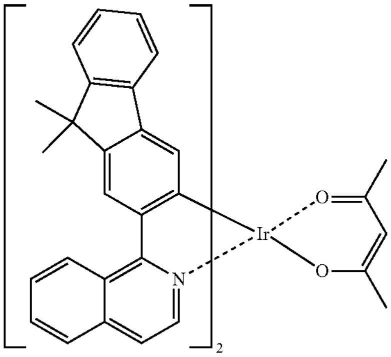
PD12
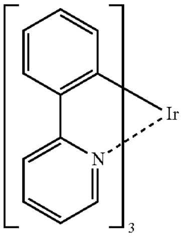
PD13
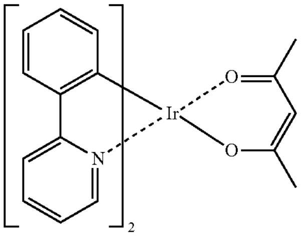
PD14
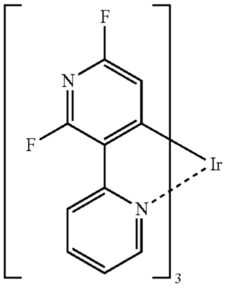
PD15
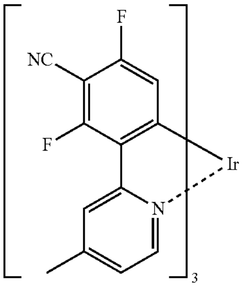
PD16

-continued
PD17
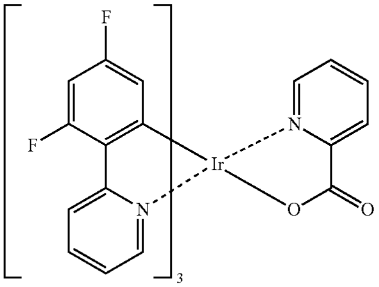
PD18
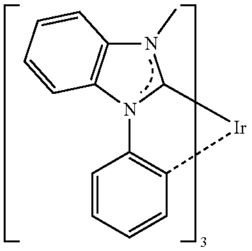
PD19
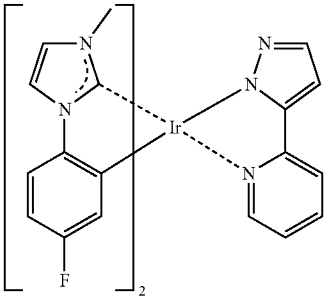
PD20
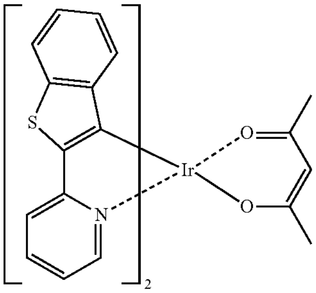
PD21
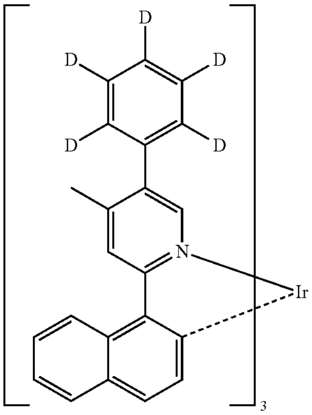
-continued
PD22
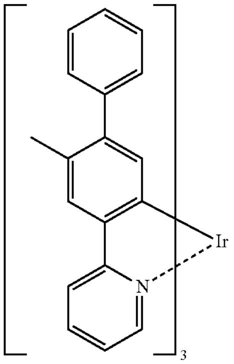
PD23
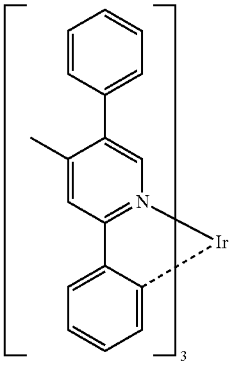
PD24
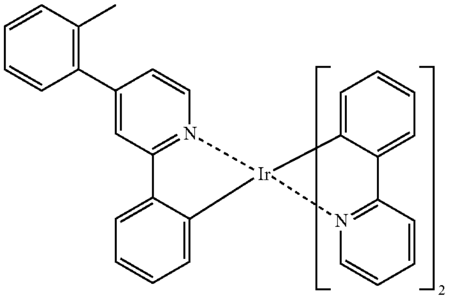
PD25
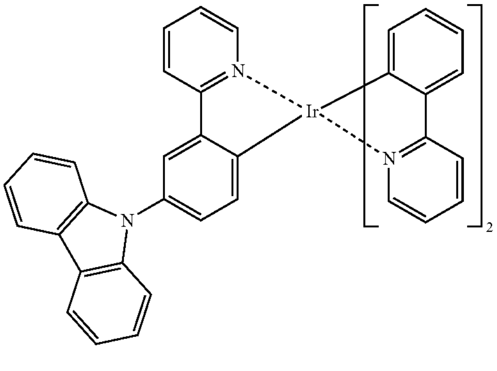

-continued
PD26
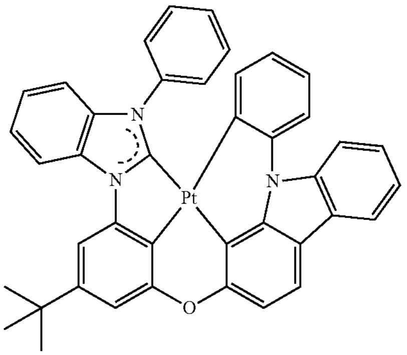
PD27
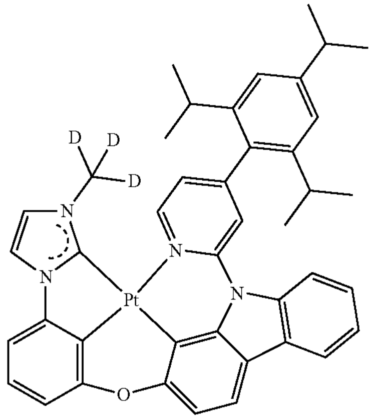
PD28
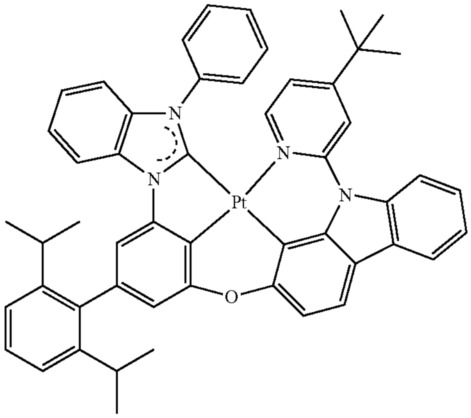
PD29
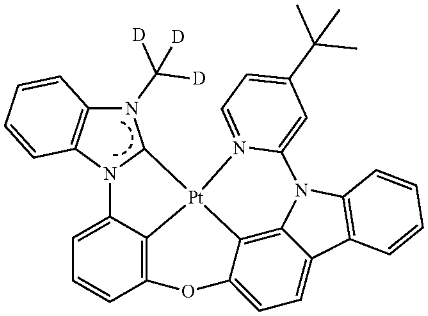
-continued
PD30
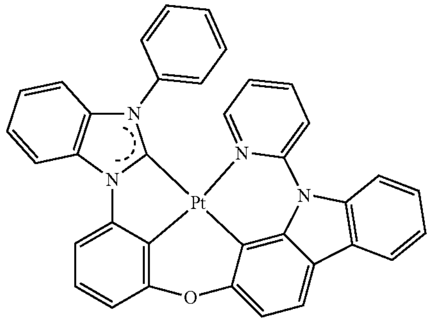
PD31
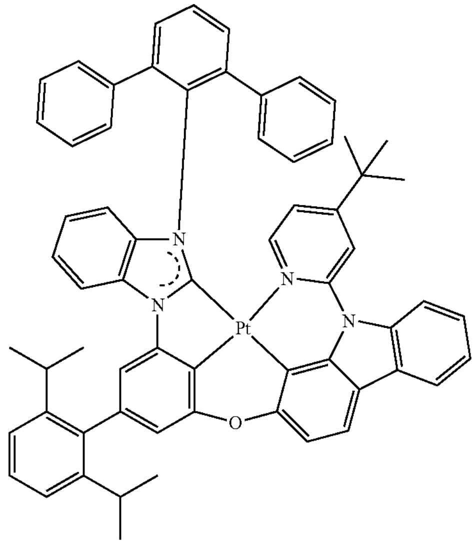
PD32
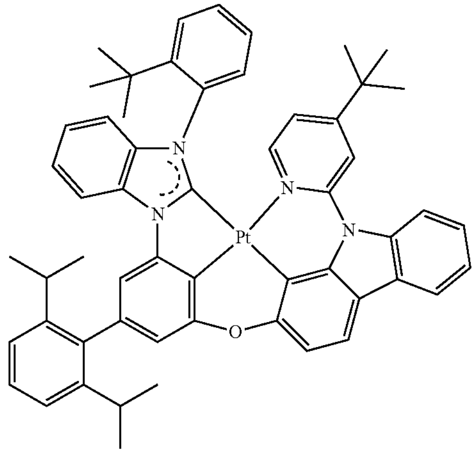

-continued
PD33
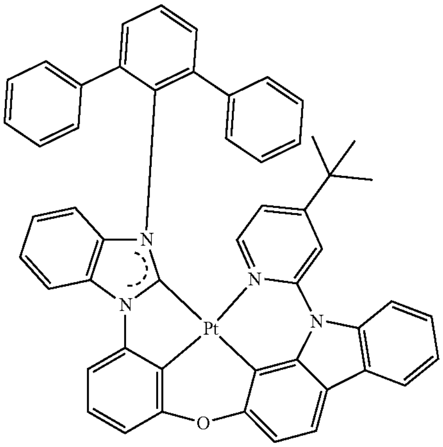
PD34
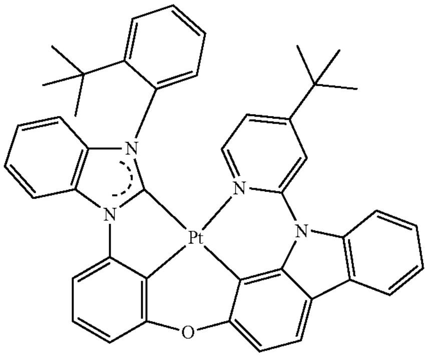
PD35
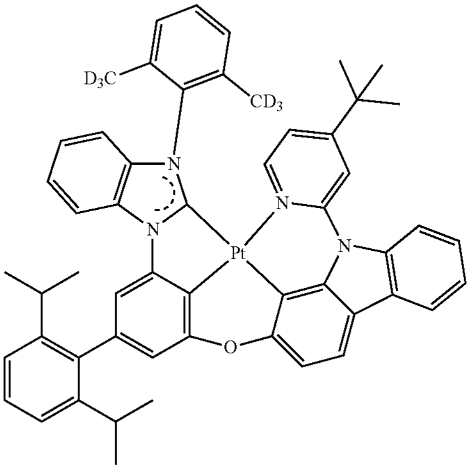
-continued
PD36
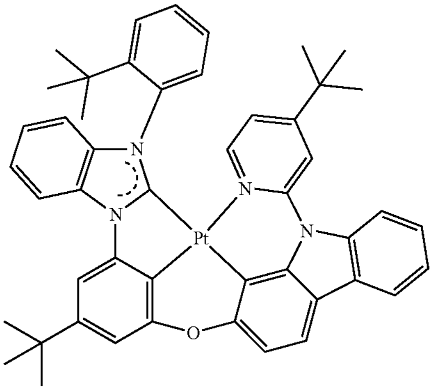
PD37
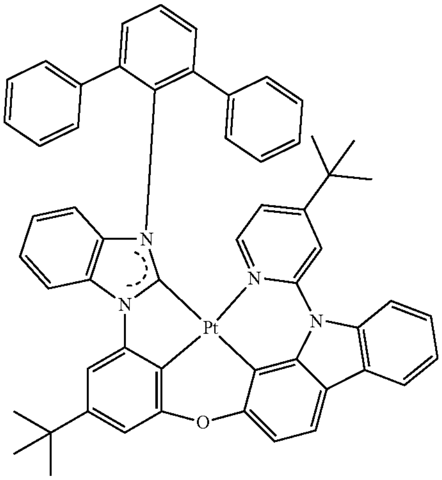
PD38
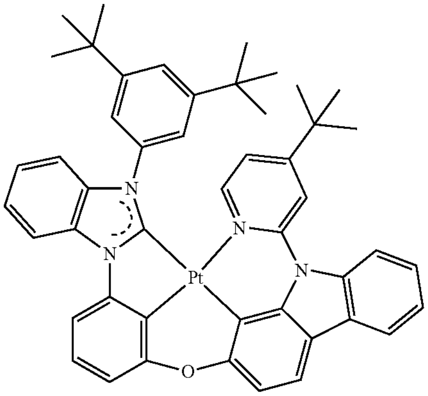

-continued

PD39

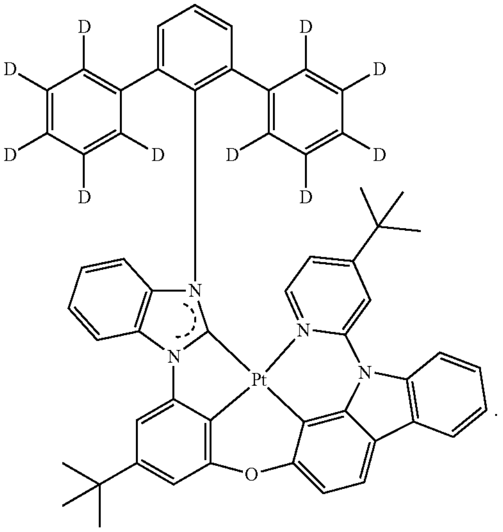

[Fluorescent Dopant]

The fluorescent dopant may include an amine group-containing compound, a styryl group-containing compound, or any combination thereof.

In an embodiment, the fluorescent dopant may include a compound represented by Formula 501:

[Formula 501]

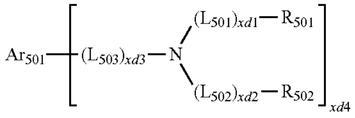

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may include a condensed cyclic group (for example, an anthracene group, a chrysene group, or a pyrene group) in which three or more monocyclic groups are condensed together.

In an embodiment, xd4 in Formula 501 may be 2.

In an embodiment, the fluorescent dopant may include one of Compounds FD1 to FD36, DPVBi, DPAVBi, or any combination thereof:

FD1

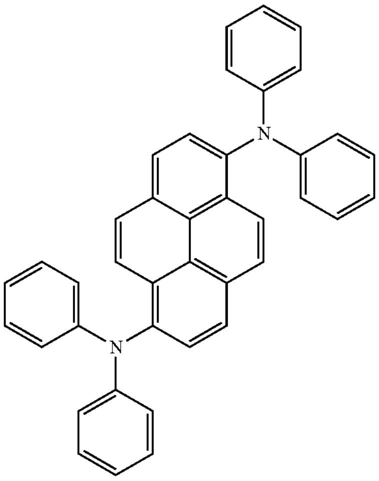

FD2

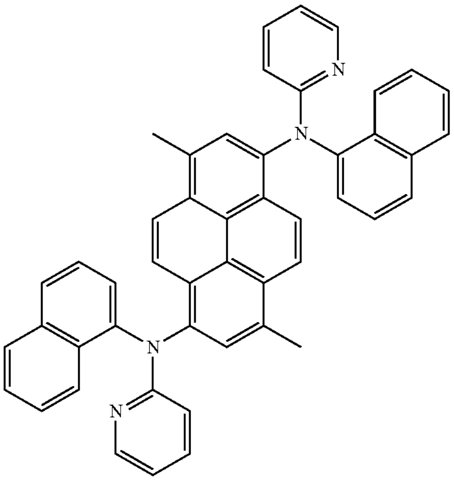

-continued
FD3
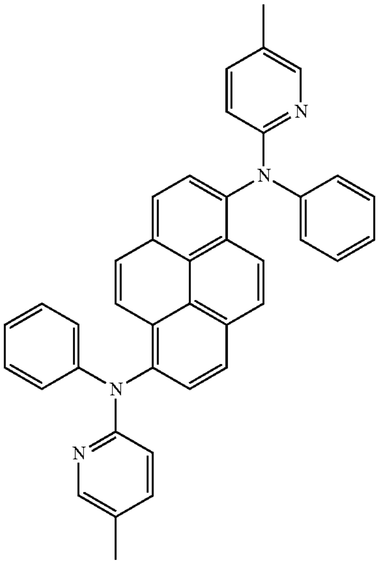
FD4
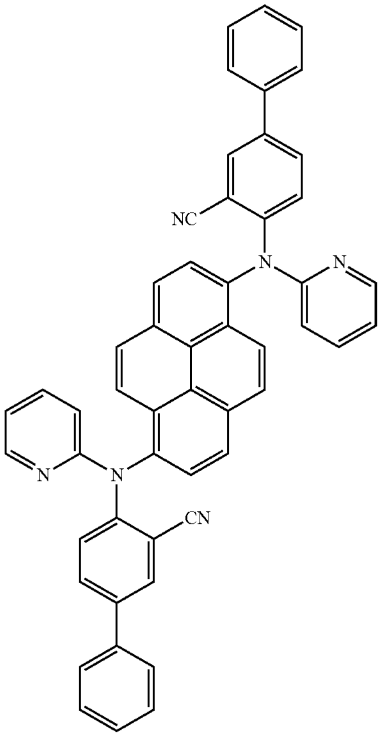
FD5
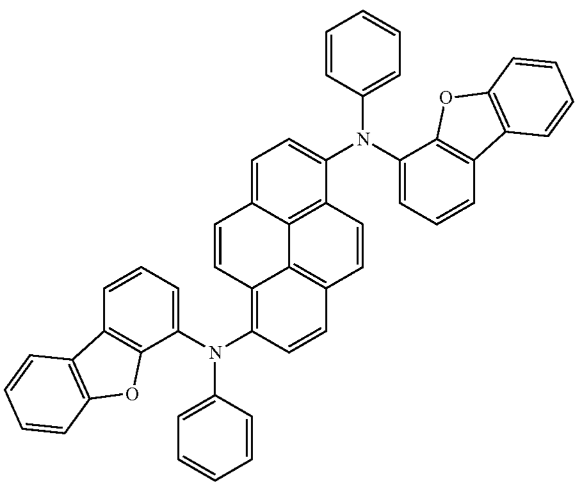
FD6
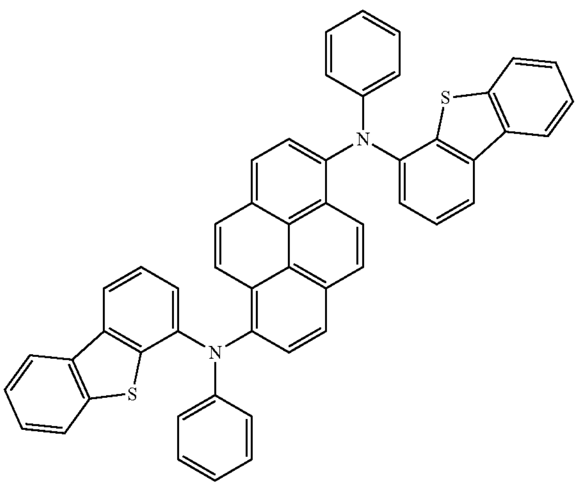

-continued
FD7
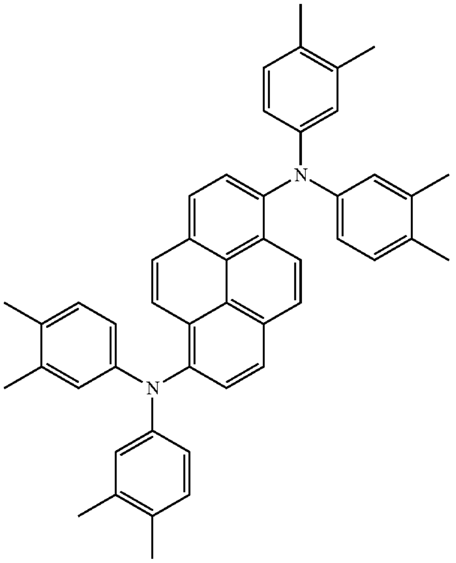
FD8
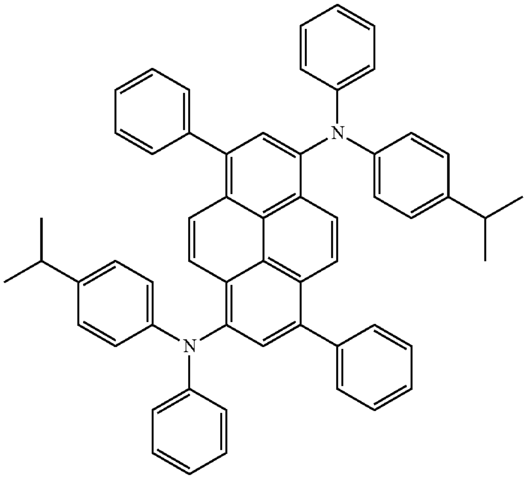
FD9
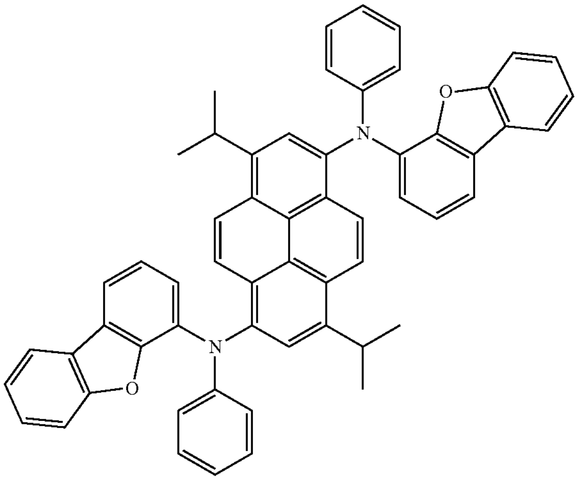
FD10
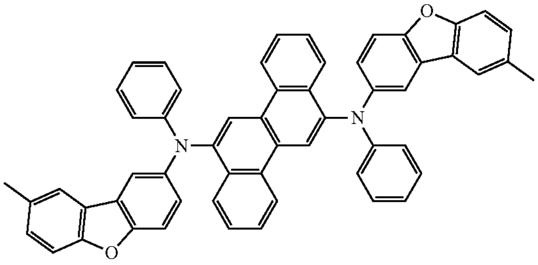
FD11
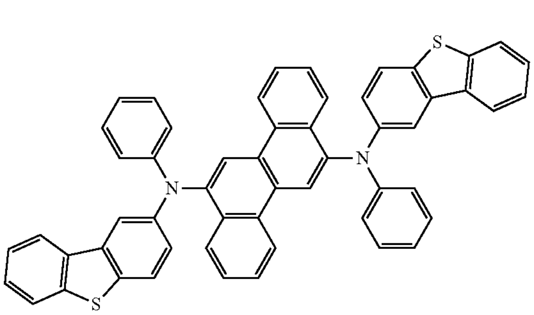
FD12
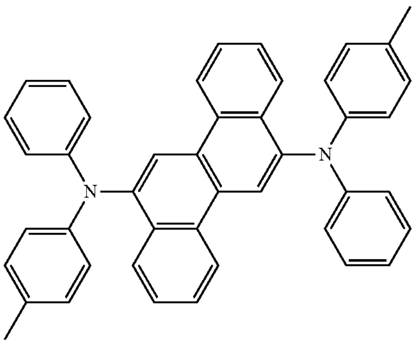

-continued
FD13
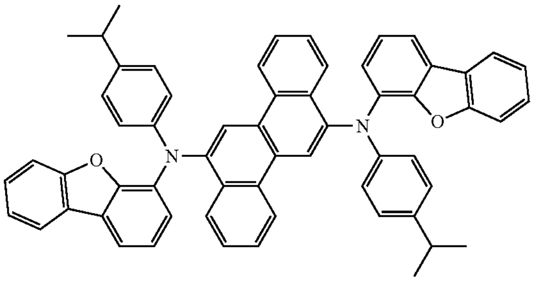
FD14
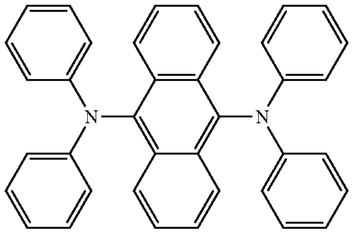
FD15
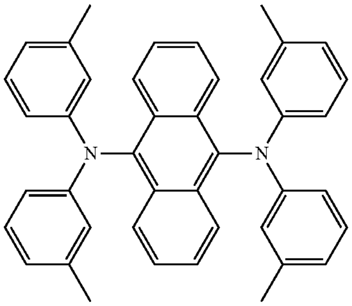
FD16
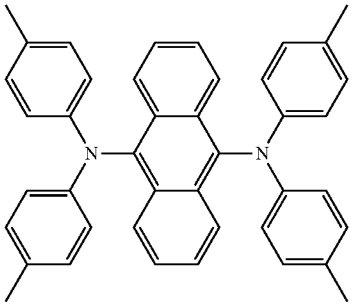
FD17
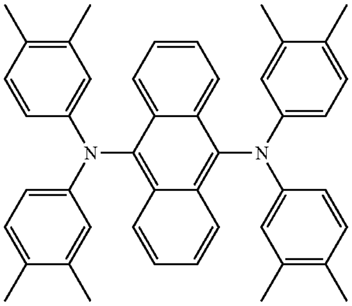
FD18
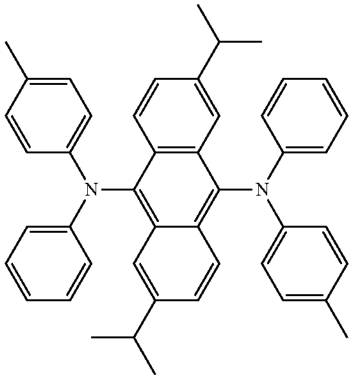
FD19
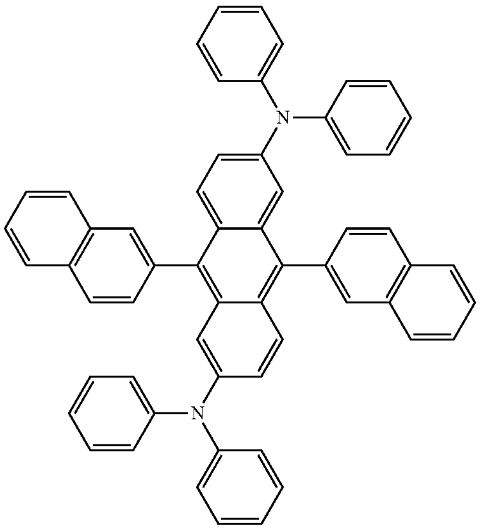
FD20
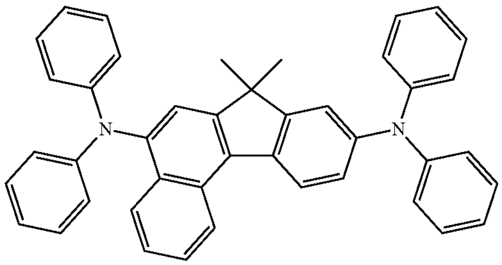

-continued
FD21
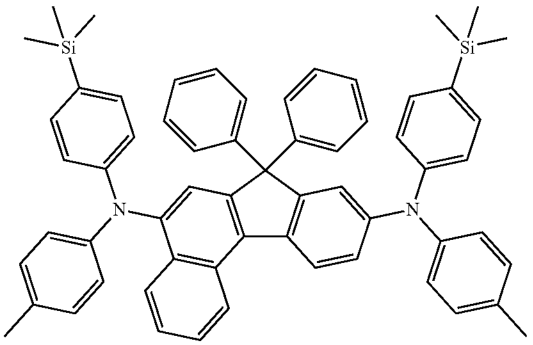
FD22
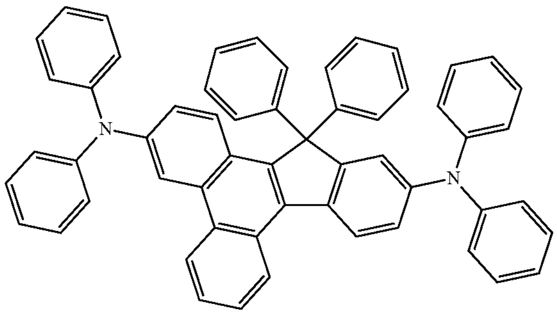
FD23
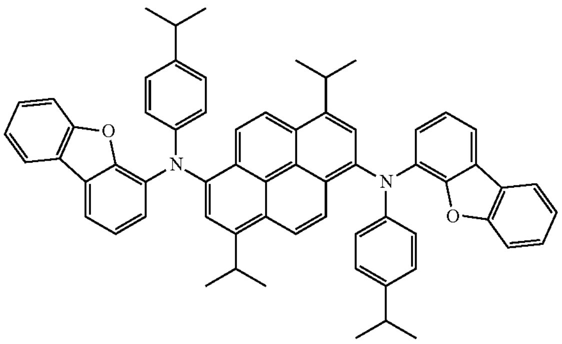
FD24
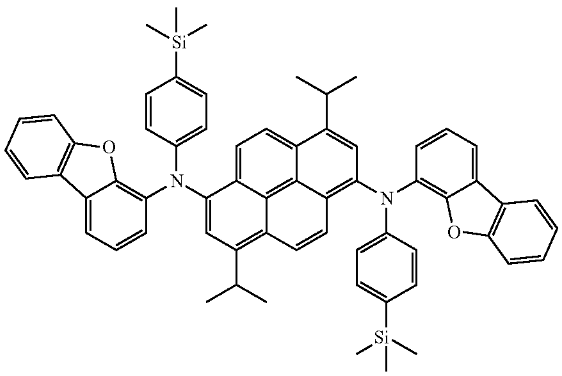
FD25
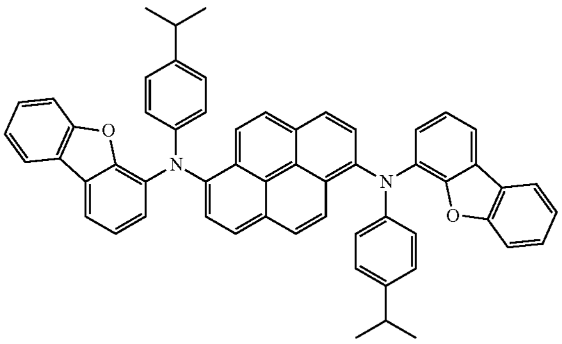
FD26
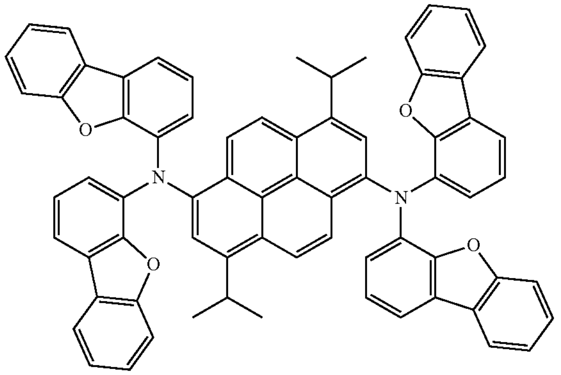
FD27
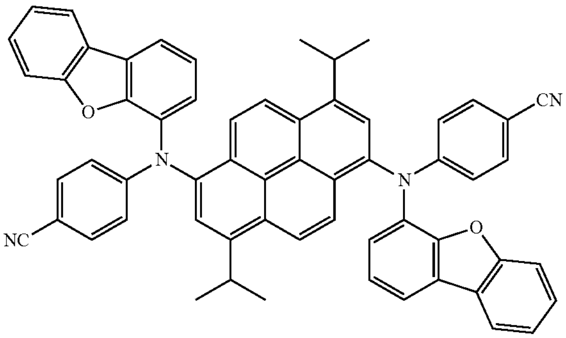
FD28
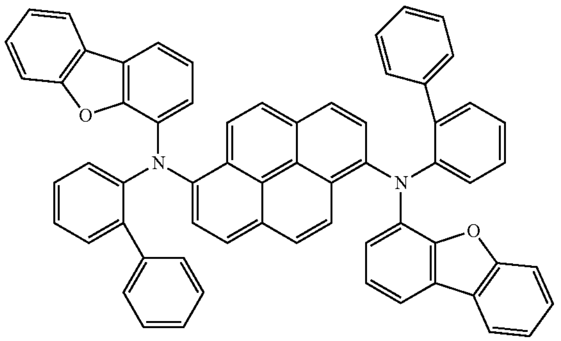

-continued
FD29
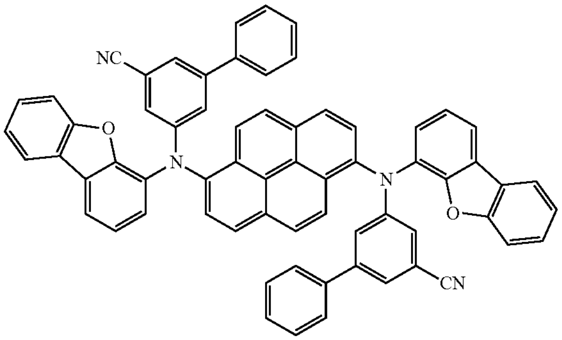
FD30
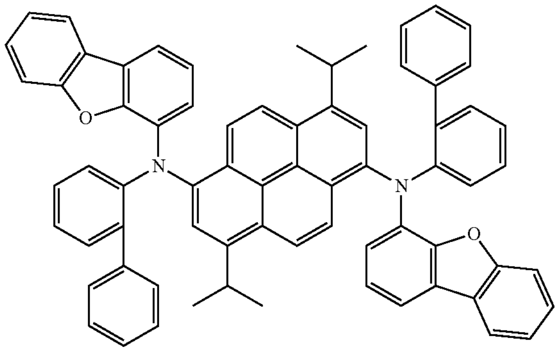
FD31
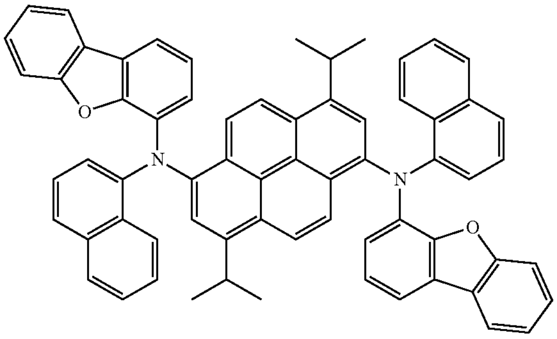
FD32
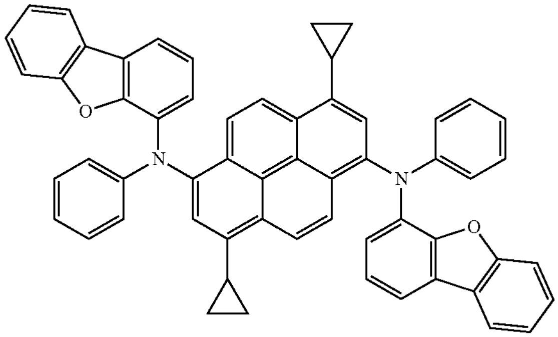
FD33
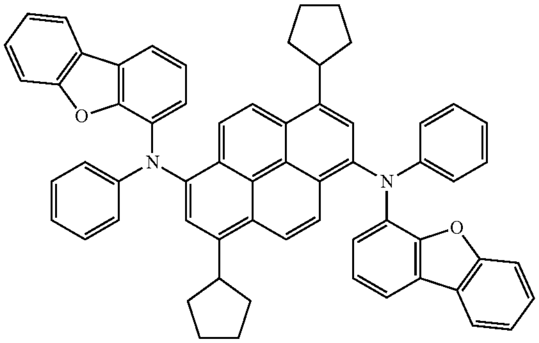
FD34
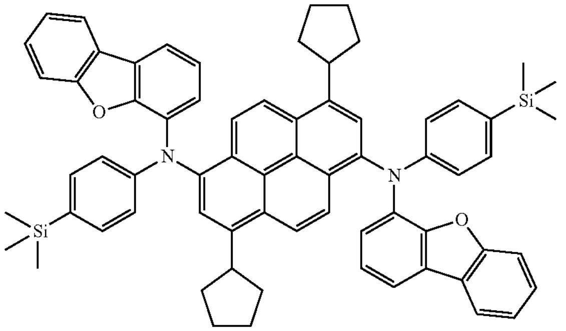
FD35
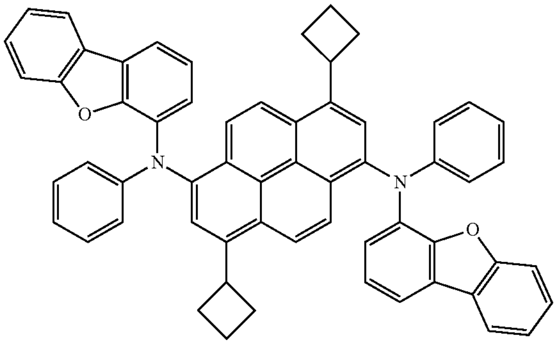
FD36
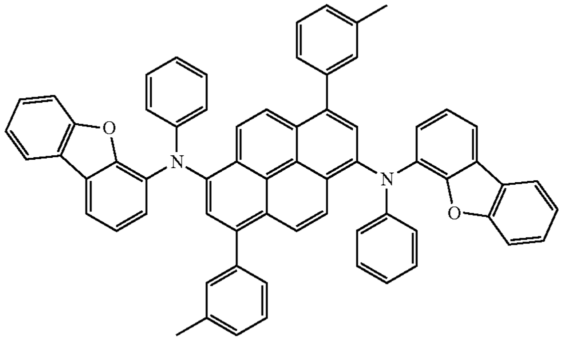

-continued

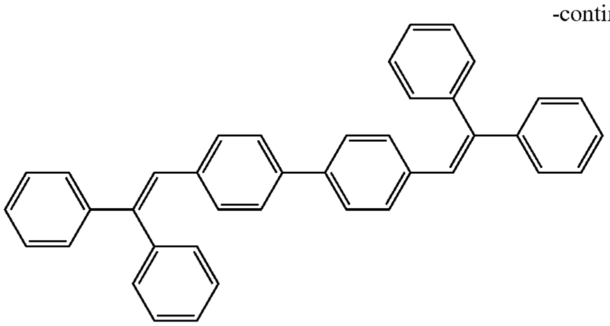

DPVBi

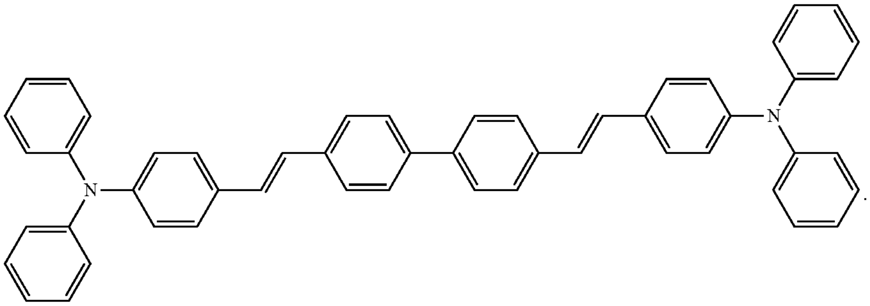

DPAVBi

[Delayed Fluorescence Material]

The emission layer may include a delayed fluorescence material.

In the specification, the delayed fluorescence material may be selected from compounds capable of emitting delayed fluorescence based on a delayed fluorescence emission mechanism.

The delayed fluorescence material included in the emission layer may function as a host or as a dopant, depending on the type of other materials included in the emission layer.

In an embodiment, a difference between a triplet energy level (eV) of the delayed fluorescence material and a singlet energy level (eV) of the delayed fluorescence material may be in a range of about 0 eV to about 0.5 eV. When the difference between the triplet energy level (eV) of the delayed fluorescence material and the singlet energy level (eV) of the delayed fluorescence material satisfies the above-described range, up-conversion from the triplet state to the singlet state of the delayed fluorescence materials may effectively occur, and thus, the luminescence efficiency of the light-emitting device 10 may be improved.

In an embodiment, the delayed fluorescence material may include a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group); or a material including a $C_8$-$C_{60}$ polycyclic group in which two or more cyclic groups are condensed while sharing boron (B).

Examples of the delayed fluorescence material may include at least one of Compounds DF1 to DF9:

DF1(DMAC-DPS)

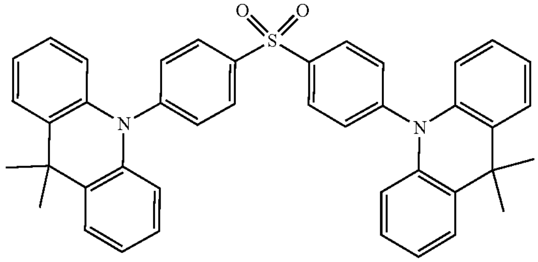

DF2(ACRFLCN)

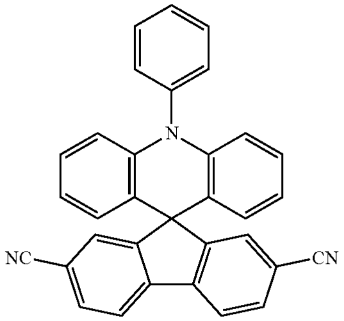

-continued

DF3(ACRSA)

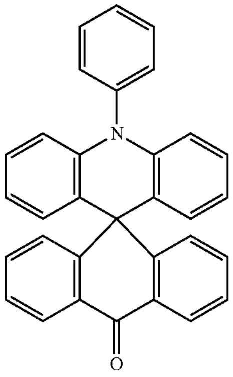

DF4(CC2TA)

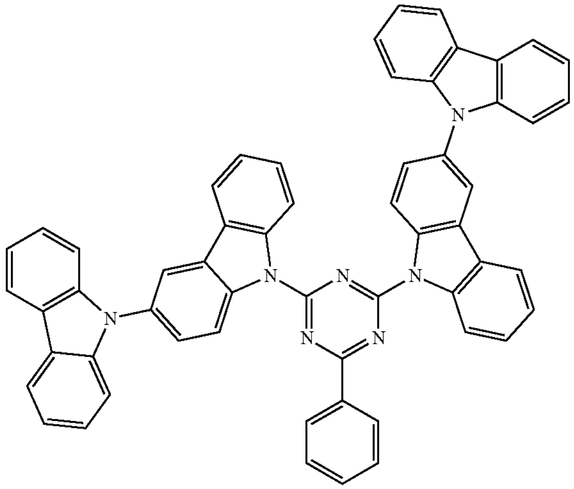

DF5(PIC-TRZ)

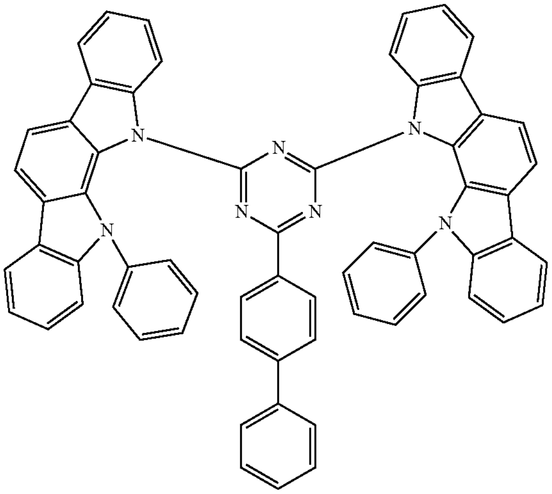

-continued

DF6(PIC-TRZ2)

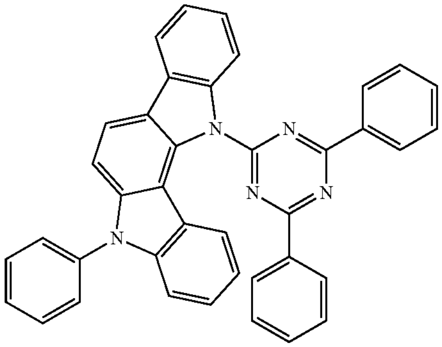

DF7(PXZ-TRZ)

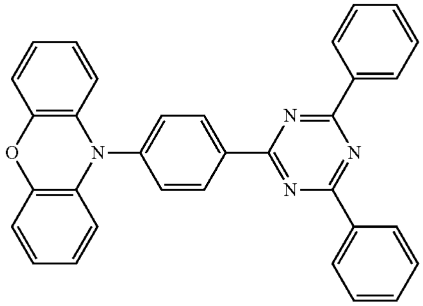

DF8(DABNA-1)

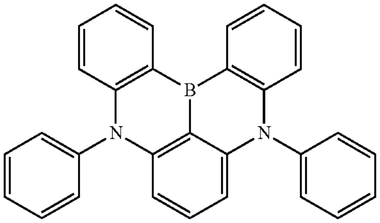

DF9(DABNA-2)

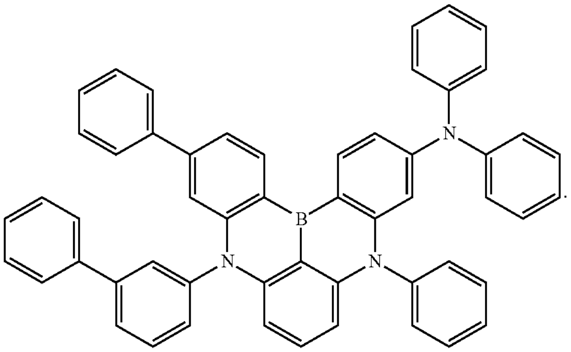

[Quantum Dot]

The emission layer may include a quantum dot.

In the specification, a quantum dot may be a crystal of a semiconductor compound, and may include any material capable of emitting light of various emission wavelengths according to a size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more readily performed than vapor deposition methods, such as metal organic chemical vapor deposition (MOCVD) or molecular beam epitaxy (MBE), and which requires low costs.

The quantum dot may include a Group II-VI semiconductor compound, a Group III-V semiconductor compound, a Group III-VI semiconductor compound, a Group I-III-VI semiconductor compound, a Group IV-VI semiconductor compound, a Group IV element or compound, or any combination thereof.

Examples of the Group II-VI semiconductor compound may include: a binary compound, such as CdSe, CdTe, ZnS, ZnSe, ZnTe, ZnO, HgS, HgSe, HgTe, MgSe, or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, or MgZnS; a quaternary compound, such as CdZnSeS, CdZnSeTe, CdZnSTe, CdHgSeS, CdHgSeTe, CdHgSTe, HgZnSeS, HgZnSeTe, or HgZnSTe; or any combination thereof.

Examples of the Group III-V semiconductor compound may include: a binary compound, such as GaN, GaP, GaAs, GaSb, AlN, AlP, AlAs, AlSb, InN, InP, InAs, InSb, and the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and the like; a quaternary compound, such as GaAlNP, GaAlNAs, GaAlNSb, GaAlPAs, GaAlPSb, GaInNP, GaInNAs, GalnNSb, GaInPAs, GalnPSb, InAlNP, InAlNAs, InAlNSb, InAlPAs, InAlPSb, and the like; or any combination thereof. In an embodiment, the Group III-V semiconductor compound may further include Group II elements. Examples of the Group III-V semiconductor compound further including Group II elements may include InZnP, InGaZnP, InAlZnP, and the like.

Examples of the Group III-VI semiconductor compound may include: a binary compound, such as GaS, GaSe, $Ga_2Se_3$, GaTe, InS, InSe, $In_2S_3$, $In_2Se_3$, InTe, and the like; a ternary compound, such as $InGaS_3$, $InGaSe_3$, and the like; or any combination thereof.

Examples of the Group I-III-VI semiconductor compound may include: a ternary compound, such as AgInS, $AgInS_2$, CulnS, $CulnS_2$, $CuGaO_2$, AgGaO2, or $AgAlO_2$; or any combination thereof.

Examples of the Group IV-VI semiconductor compound may include: a binary compound, such as SnS, SnSe, SnTe, PbS, PbSe, PbTe, or the like; a ternary compound, such as SnSeS, SnSeTe, SnSTe, PbSeS, PbSeTe, PbSTe, SnPbS, SnPbSe, SnPbTe, or the like; a quaternary compound, such as SnPbSSe, SnPbSeTe, SnPbSTe, or the like; or any combination thereof.

The Group IV element or compound may include: a single element such as Si or Ge; a binary compound, such as SiC or SiGe; or any combination thereof.

Each element included in a multi-element compound such as a binary compound, a ternary compound, or a quaternary compound, may exist in a particle at a uniform concentration or at a non-uniform concentration.

In an embodiment, the quantum dot may have a single structure or a core-shell structure. When the quantum dot has a single structure, the concentration of each element included in the corresponding quantum dot may be uniform. When the quantum dot has a core-shell structure, a material contained in the core and a material contained in the shell may be different from each other.

The shell of the quantum dot may function as a protective layer to prevent chemical degeneration of the core to maintain semiconductor characteristics and/or may function as a charging layer to impart electrophoretic characteristics to the quantum dot. The shell may be a single layer or a multilayer. An element present in an interface between the core and the shell of the quantum dot may have a concentration gradient that decreases toward the center of the quantum dot.

Examples of the shell of the quantum dot may include a metal oxide, a metalloid oxide, a non-metal oxide, a semiconductor compound, or a combination thereof. Examples of the metal oxide, the metalloid oxide, or the non-metal oxide may include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, or NiO; a ternary compound, such as $MgAl_2O_4$, $CoFe_2O_4$, $NiFe_2O_4$, or $CoMn_2O_4$; or any combination thereof. Examples of the semiconductor compound may include, as described herein, a Group II-VI semiconductor compound, a Group III-V semiconductor compound, a Group III-VI semiconductor compound, a Group I-III-VI semiconductor compound, a Group IV-VI semiconductor compound, or any combination thereof. Examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be equal to or less than about 45 nm. For example, a FWHM of an emission wavelength spectrum of the quantum dot may be equal to or less than about 40 nm. For example, a FWHM of an emission wavelength spectrum of the quantum dot may be equal to or less than about 30 nm. Within these ranges, color purity or color reproducibility may be increased. Light emitted through the quantum dot may be emitted in all directions, and thus, a wide viewing angle can be improved.

The quantum dot may be a spherical particle, a pyramidal particle, a multi-arm particle, a cubic nanoparticle, a nanotube particle, a nanowire particle, a nanofiber particle, or a nanoplate particle.

Since the energy band gap can be adjusted by controlling the size of the quantum dot, light having various wavelength bands can be obtained from the quantum dot emission layer. Therefore, by using quantum dots of different sizes, a light-emitting device that emits light of various wavelengths may be implemented. In an embodiment, the size of the quantum dot may be selected such that the quantum dot may emit red, green and/or blue light. The size of the quantum dot may be configured so that the quantum dot may emit white light by combining light of various colors.

[Electron Transport Region in Interlayer 130]

The electron transport region may have a structure consisting of a layer consisting of a single material, a structure consisting of a layer consisting of different materials, or a structure including multiple layers including different materials.

The electron transport region may include a buffer layer, a hole blocking layer, an electron control layer, an electron transport layer, an electron injection layer, or a combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein the layers of each structure are stacked from the emission layer in its respective stated order, but the structure of the electron transport region is not limited thereto.

The electron transport region (for example, a buffer layer, a hole blocking layer, an electron control layer, or an electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$$[Ar_{601}]_{xe11}\text{-}[(L_{601})_{xe1}\text{-}R_{601}]_{xe21} \qquad \text{[Formula 601]}$$

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ may each independently be the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked via a single bond.

In an embodiment, $Ar_{601}$ in Formula 601 may be a substituted or unsubstituted anthracene group.

In an embodiment, the electron transport region may include a compound represented by Formula 601-1:

[Formula 601-1]

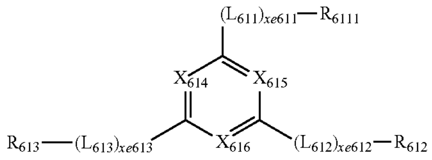

In Formula 601-1, $X_{614}$ may be N or $C(R_{614})$, $X_{615}$ may be N or $C(R_{615})$, $X_{616}$ may be N or $C(R_{616})$, at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, or any combination thereof:

ET1

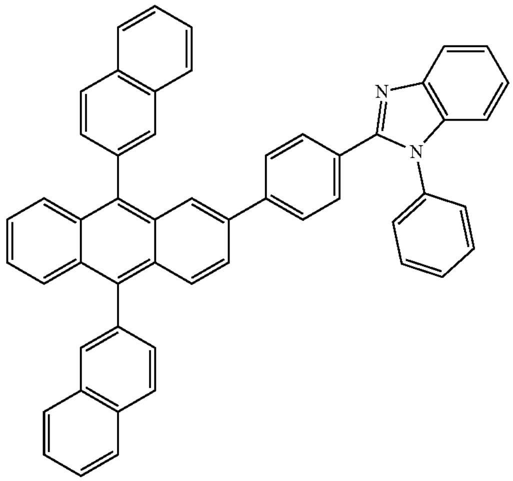

ET2

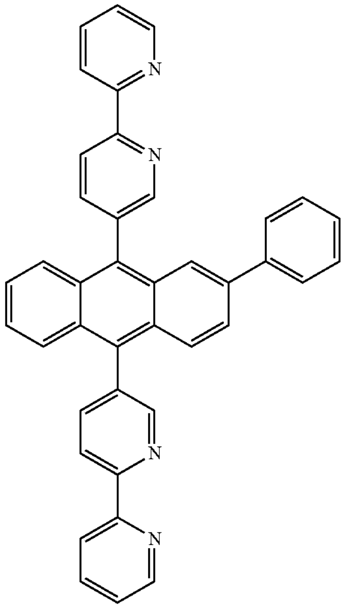

-continued
ET3
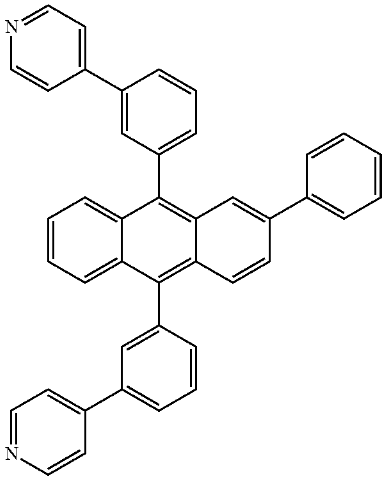
ET-4
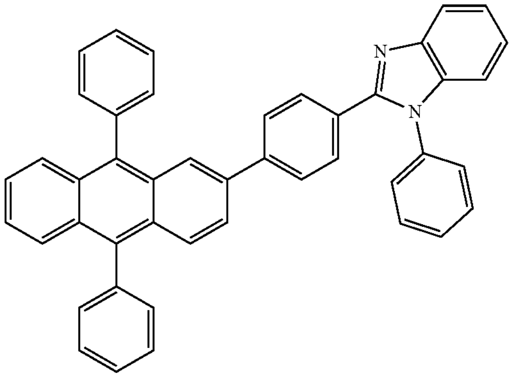
ET-5
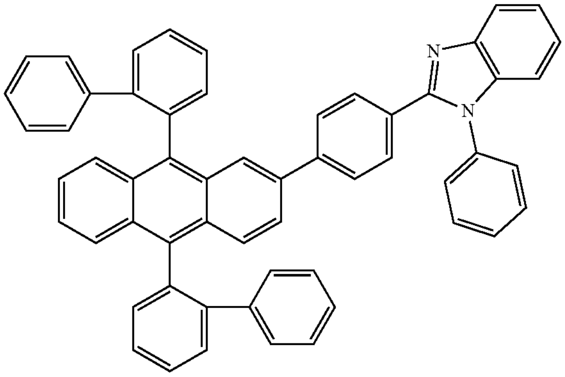
-continued
ET-6
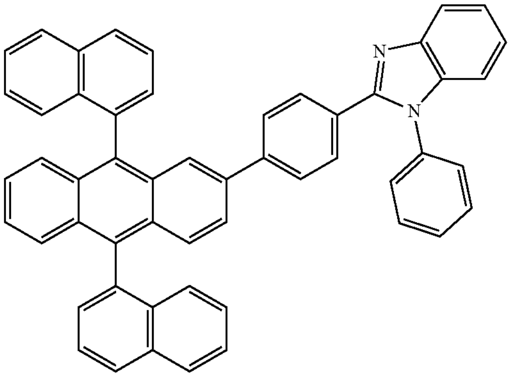
ET-7
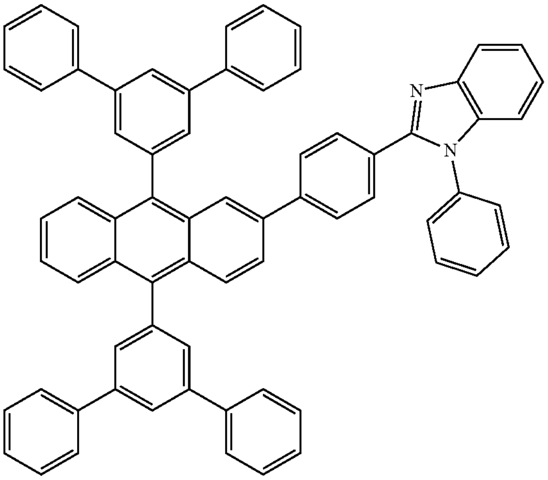
ET8
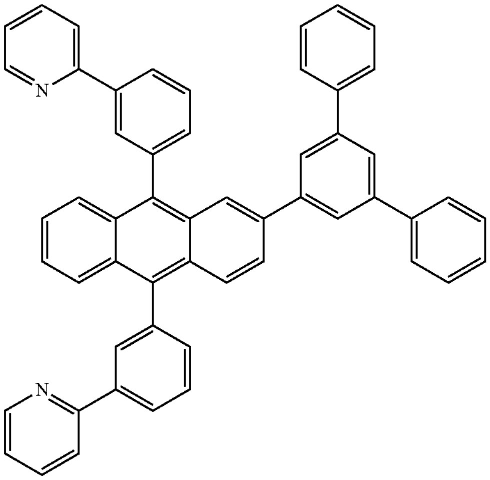

-continued
ET9
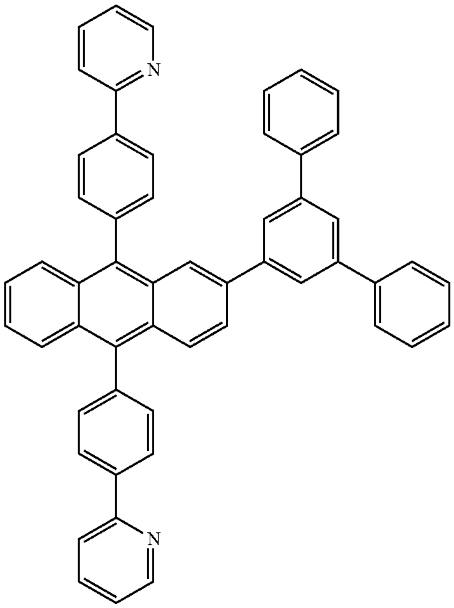
ET10
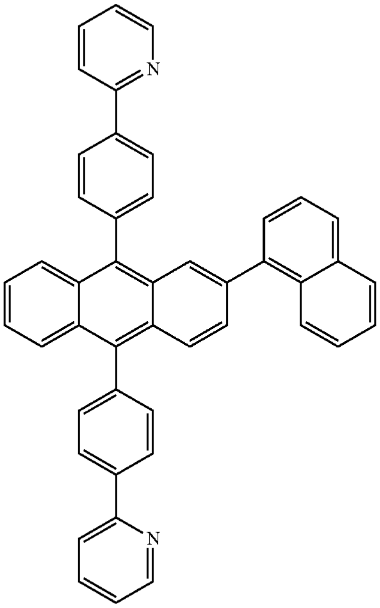
-continued
ET11
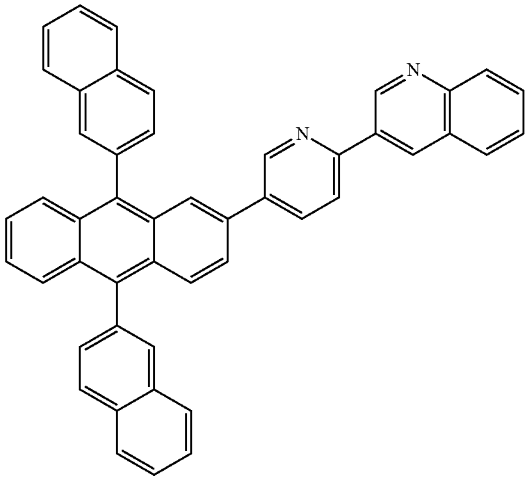
ET12
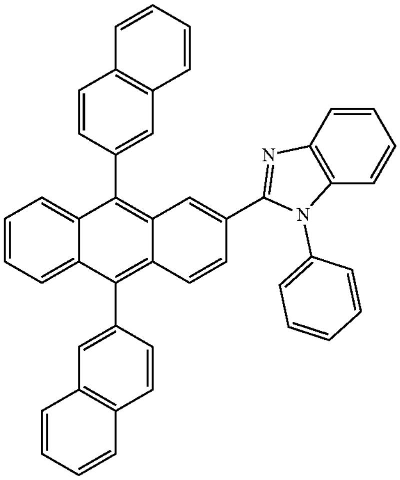
ET13
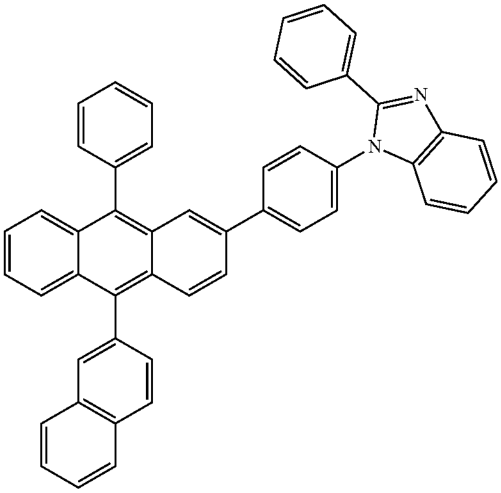

-continued
ET14
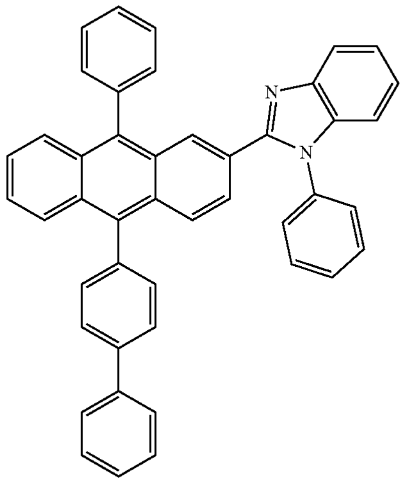
ET15
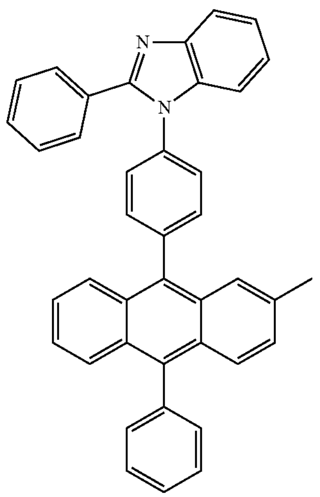
ET16
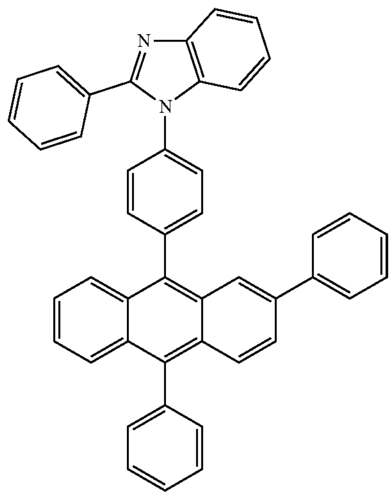
-continued
ET17
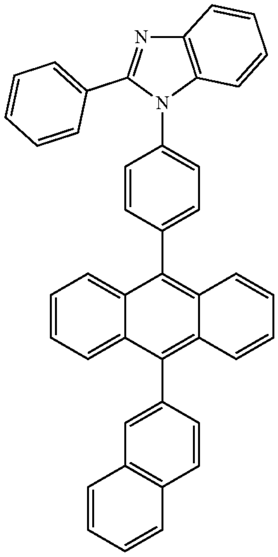
ET18
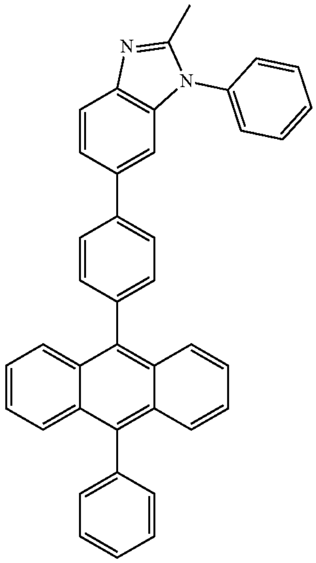
ET19
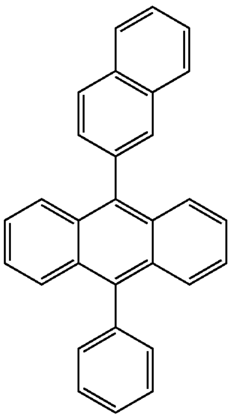

-continued
ET20
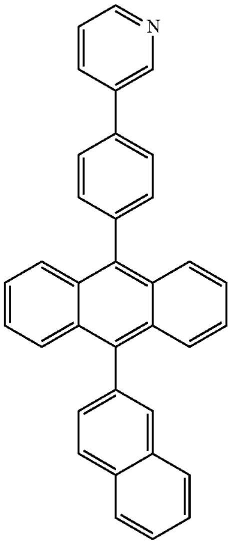
ET21
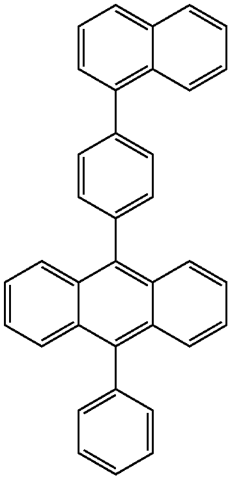
ET22
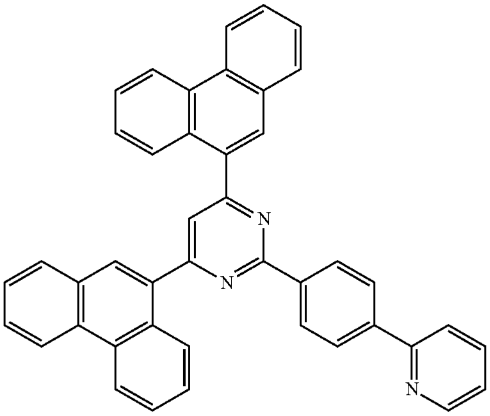
-continued
ET23
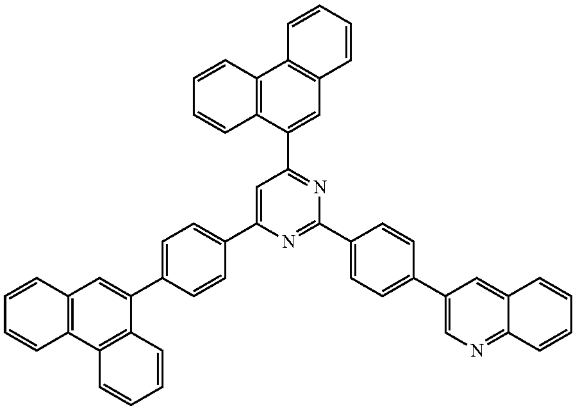
ET24
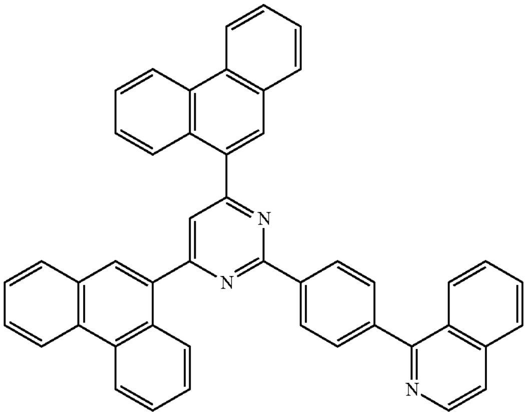
ET25
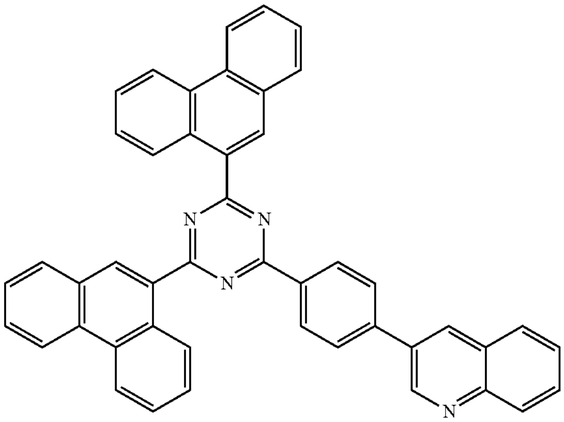

-continued
ET26
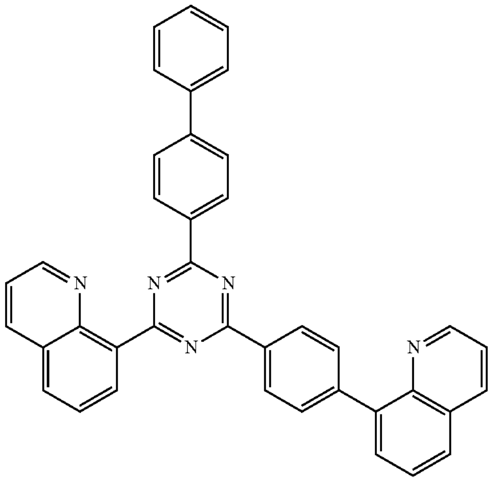
ET27
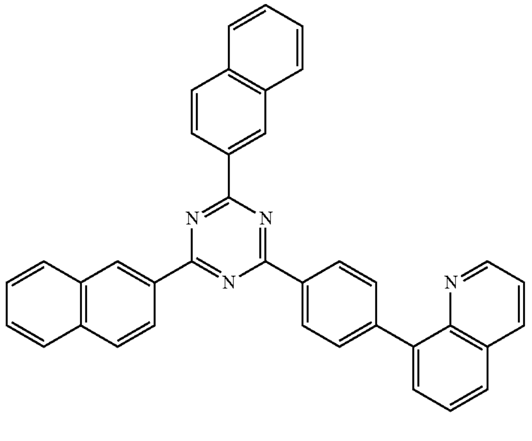
ET28
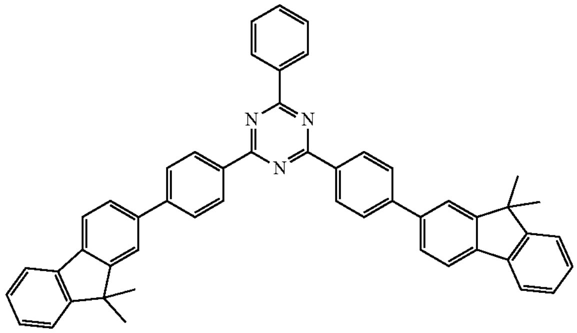
-continued
ET29
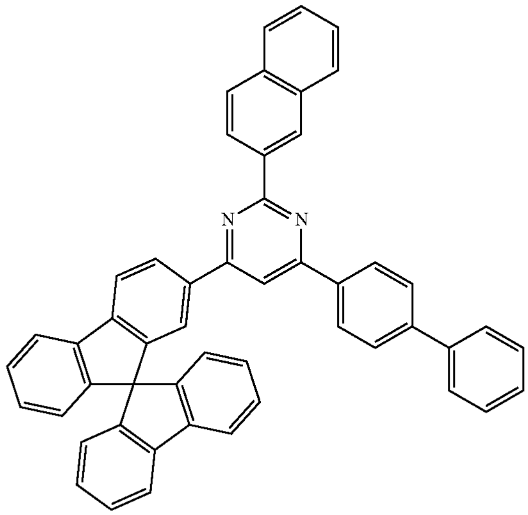
ET30
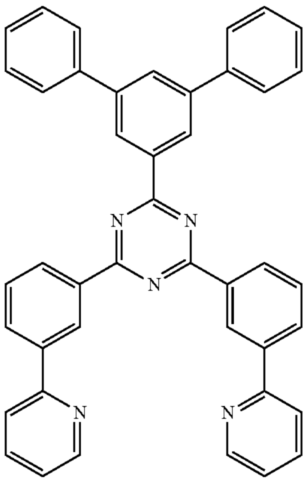
ET31
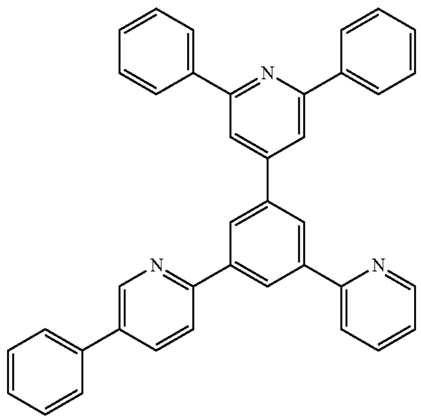

-continued
ET32
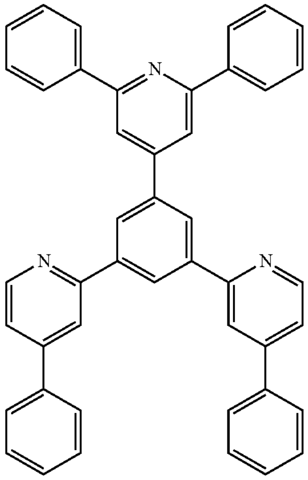
ET33
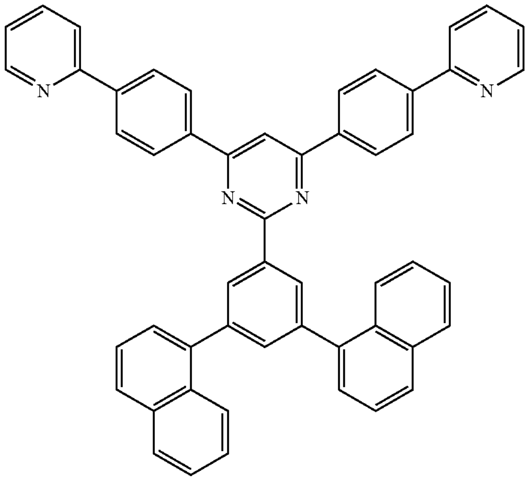
ET34
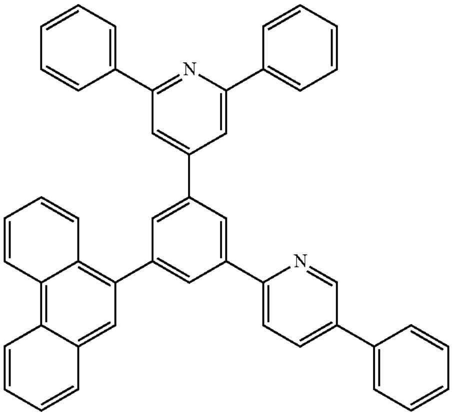
-continued
ET35
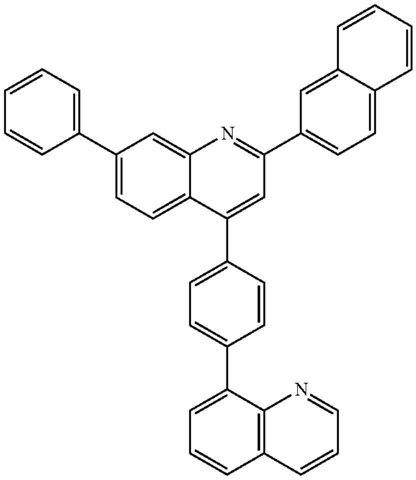
ET36
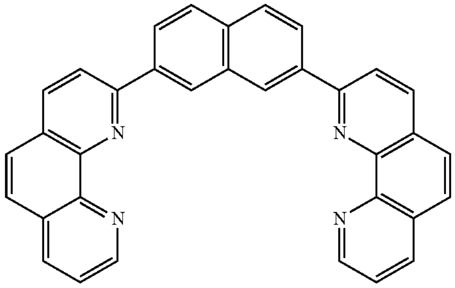
ET37
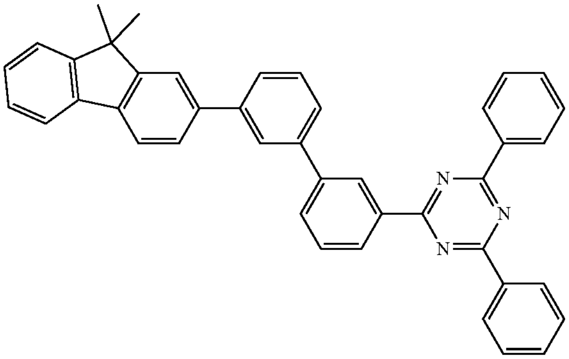
ET38
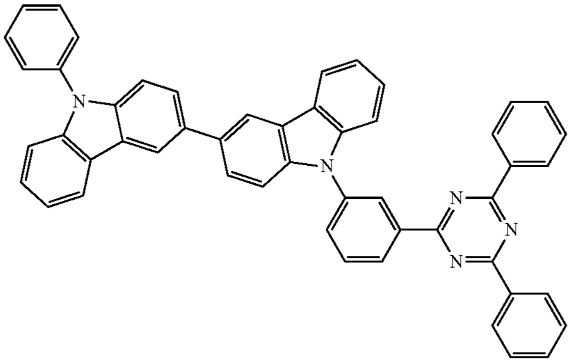

ET39
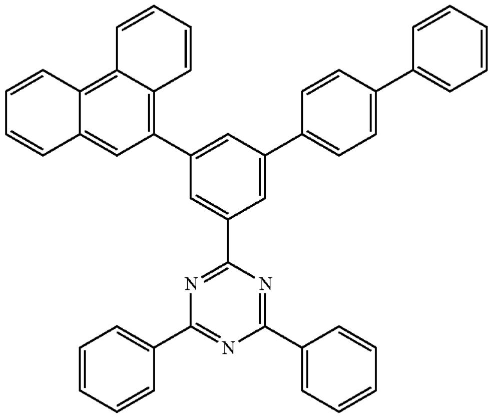
ET40
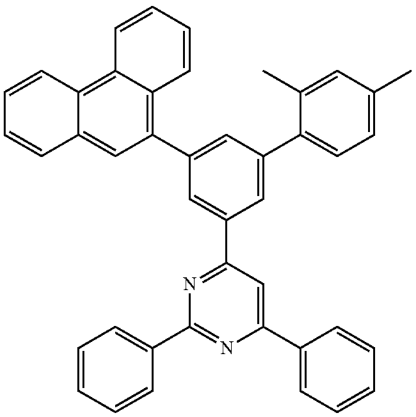
ET41
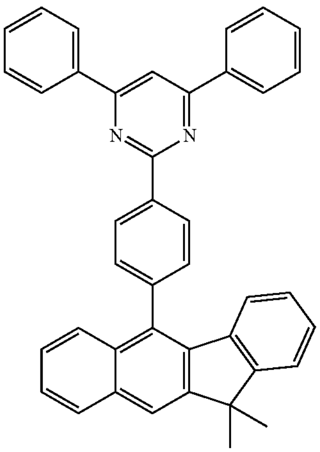
ET42
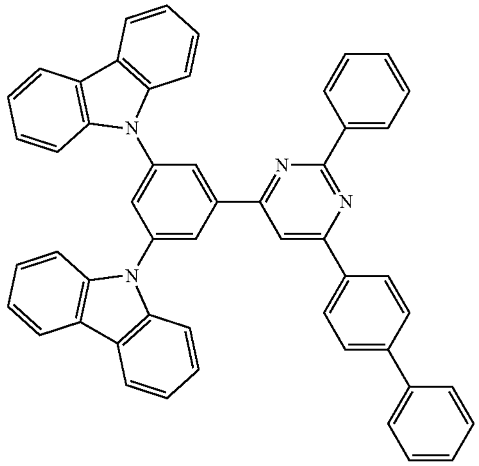
ET43
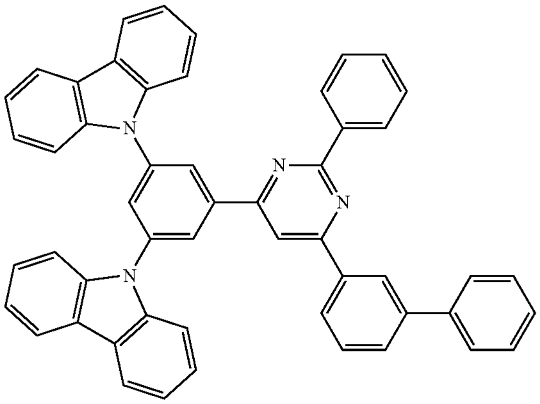
ET44
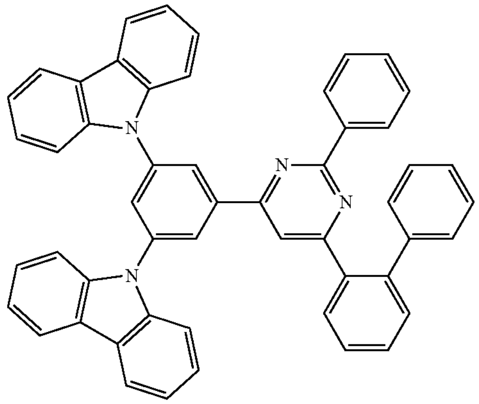
ET45
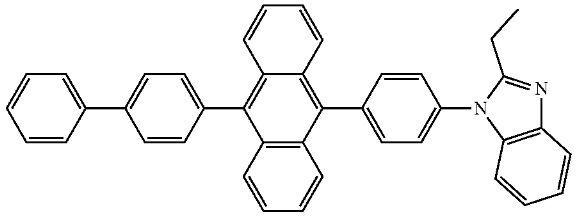

-continued

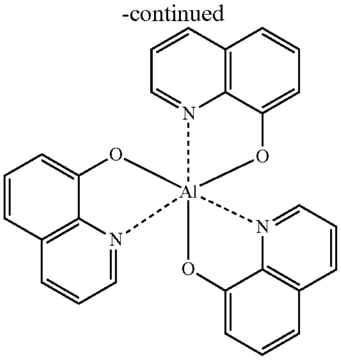

Alq3

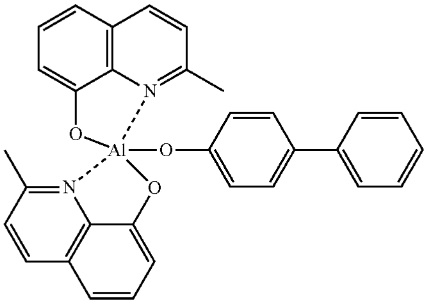

Balq

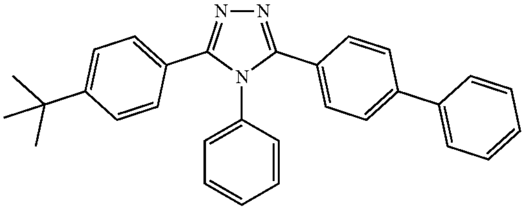

TAZ

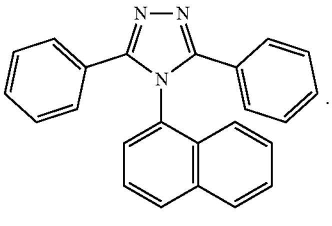

NTAZ

A thickness of the electron transport region may be in a range of about 100 Å to about 5,000 Å. For example, the thickness of the electron transport region may be in a range of about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, and a thickness of the electron transport layer may be from about 100 Å to about 1,000 Å. For example, the thickness of the buffer layer, the hole blocking layer, or the electron control layer may each independently be in a range of about 30 Å to about 300 Å. For example, the thickness of the electron transport layer may be in a range of about 150 Å to about 500 Å. When the thicknesses of the buffer layer, the hole blocking layer, the electron control layer, the electron transport layer, and/or the electron transport region are within these ranges, satisfactory electron transporting characteristics may be obtained without a substantial increase in driving voltage.

The electron transport region (for example, an electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. A ligand coordinated with the metal ion of the alkali metal complex or the metal ion of the alkaline earth-metal complex may each independently include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

In an embodiment, the metal-containing material may include a Li complex. The Li complex may include, for example, Compound ET-D1 (LiQ) or Compound ET-D2:

ET-D1

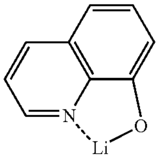

ET-D2

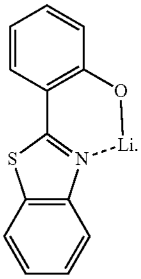

The electron transport region may include an electron injection layer that facilitates the injection of electrons from the second electrode 150. The electron injection layer may directly contact the second electrode 150.

The electron injection layer may have a structure consisting of a layer consisting of a single material, a structure consisting of a layer consisting of different materials, or a structure including multiple layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may respectively include oxides, halides (for example, fluorides, chlorides, bromides, or iodides), or tellurides of the alkali metal, the alkaline earth metal, and the rare earth metal, or any combination thereof.

The alkali metal-containing compound may include: alkali metal oxides, such as $Li_2O$, $Cs_2O$, or $K_2O$; alkali metal halides, such as LiF, NaF, CsF, KF, LiI, NaI, CsI, or KI; or any combination thereof. The alkaline earth metal-containing compound may include an alkaline earth metal compound, such as BaO, SrO, CaO, $Ba_xSr_{1-x}O$ (x is a real number satisfying the condition of $0<x<1$), $Ba_xCa_{1-x}O$ (x is a real number satisfying the condition of $0<x<1$), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include one of the ions of the alkali metal, ions of the alkaline earth metal, and ions of the rare earth metal, and a ligand bonded to the metal ion, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenyl benzimidazole, a hydroxyphenylbenzothiazole, a bipyridine, a phenanthroline, a cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In an embodiment, the electron injection layer may further include an organic material (for example, a compound represented by Formula 601).

In an embodiment, the electron injection layer may consist of an alkali metal-containing compound (for example, an alkali metal halide); or the electron injection layer may consist of an alkali metal-containing compound (for example, an alkali metal halide), and an alkali metal, an alkaline earth metal, a rare earth metal, or any combination thereof. For example, the electron injection layer may be a KI:Yb co-deposited layer, an RbI:Yb co-deposited layer, a LiF:Yb co-deposited layer, or the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be homogeneously or non-homogeneously dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within the range described above, satisfactory electron injection characteristics may be obtained without a substantial increase in driving voltage.

[Second Electrode 150]

The second electrode 150 may be on the interlayer 130 having such a structure as described above. The second electrode 150 may be a cathode, which is an electron injection electrode. The second electrode 150 may include a material having a low work function, for example, a metal, an alloy, an electrically conductive compound, or any combination thereof.

In an embodiment, the second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or a combination thereof. The second electrode 150 may be a transmissive electrode, a semi-transmissive electrode, or a reflective electrode.

The second electrode 150 may have a single-layered structure or a multi-layered structure including two or more layers.

[Capping Layer]

A first capping layer may be located outside the first electrode 110, and/or a second capping layer may be located outside the second electrode 150. For example, the light-emitting device 10 may have a structure in which the first capping layer, the first electrode 110, the interlayer 130, and the second electrode 150 are stacked in this stated order, a structure in which the first electrode 110, the interlayer 130, the second electrode 150, and the second capping layer are stacked in this stated order, or a structure in which the first capping layer, the first electrode 110, the interlayer 130, the second electrode 150, and the second capping layer are stacked in this stated order.

Light generated in an emission layer of the interlayer 130 of the light-emitting device 10 may be extracted toward the outside through the first electrode 110, which may be a semi-transmissive electrode or a transmissive electrode, and through the first capping layer. Light generated in an emission layer of the interlayer 130 of the light-emitting device 10 may be extracted toward the outside through the second electrode 150, which may be a semi-transmissive electrode or a transmissive electrode, and through the second capping layer.

The first capping layer and the second capping layer may each increase external emission efficiency according to the principle of constructive interference. Accordingly, the light extraction efficiency of the light-emitting device 10 may be increased, so that the luminescence efficiency of the light-emitting device 10 may be improved.

The first capping layer and the second capping layer may each include a material having a refractive index greater than or equal to about 1.6 (at a wavelength of about 589 nm).

The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may each be optionally substituted with a substituent containing O, N, S, Se, Si, F, Cl, Br, I, or any combination thereof.

In an embodiment, at least one of the first capping layer and the second capping layer may each independently include an amine group-containing compound.

In an embodiment, at least one of the first capping layer and the second capping layer may each independently include a compound represented by Formula 201, a compound represented by Formula 202, or any combination thereof.

In an embodiment, at least one of the first capping layer and the second capping layer may each independently include one of Compounds HT28 to HT33, one of Compounds CP1 to CP6, β-NPB, or any combination thereof:

CP1

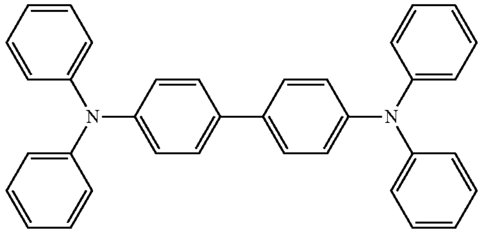

CP2

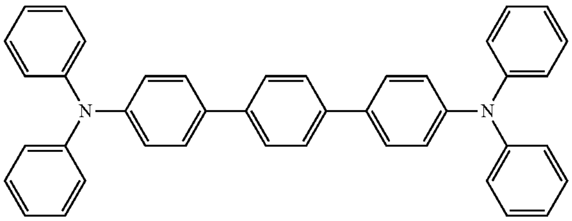

CP3

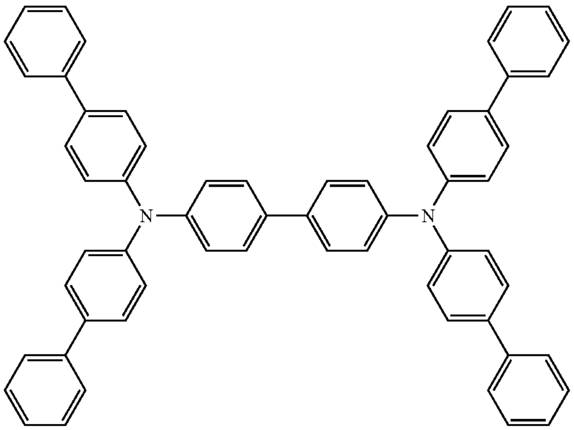

-continued

CP4

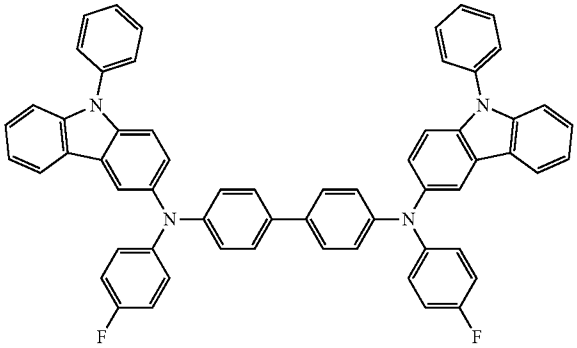

CP5

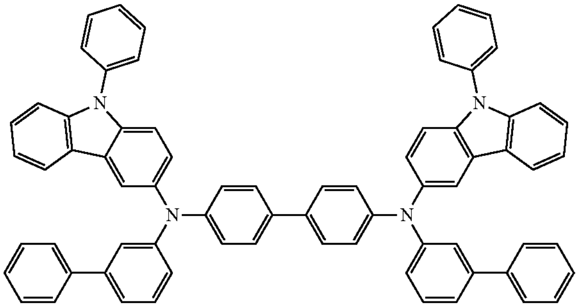

CP6

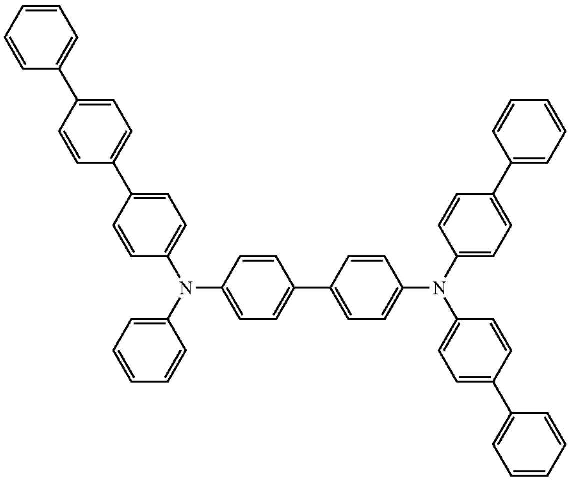

β-NPB

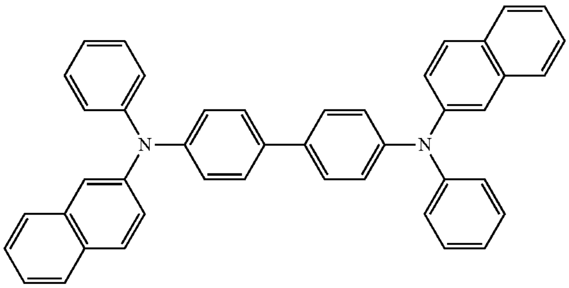

[Film]

An organometallic compound represented by Formula 1 may be included in various films. Thus, according to an embodiment, provided is a film including an organometallic compound represented by Formula 1. The film may be, for example, an optical member (or, a light-controlling member) (e.g., a color filter, a color-conversion member, a capping layer, a light extraction efficiency improvement layer, a selective light-absorbing layer, a polarizing layer, a quantum dot-containing layer, or the like), a light-blocking member (e.g., a light reflection layer or a light-absorbing layer), or a protection member (e.g., an insulating layer or a dielectric material layer).

[Electronic Apparatus]

The light-emitting device may be included in various electronic apparatuses. In an embodiment, the electronic apparatus including the light-emitting device may be a light-emitting apparatus, an authentication apparatus, or the like.

The electronic apparatus (for example, light-emitting apparatus) may further include, in addition to the light-emitting device, a color filter, a color conversion layer, or a color filter and a color conversion layer. The color filter and/or the color conversion layer may be located in at least one traveling direction of light emitted from the light-emitting device. In an embodiment, light emitted from the light-emitting device may be blue light or white light. The light-emitting device may be the same as described above. In an embodiment, the color conversion layer may include quantum dots. The quantum dot may be, for example, a quantum dot as described herein.

The electronic apparatus may include a first substrate. The first substrate may include subpixels, the color filter may include color filter areas respectively corresponding to the subpixels, and the color conversion layer may include color conversion areas respectively corresponding to the subpixels.

A pixel-defining film may be located between the subpixels to define each subpixel.

The color filter may further include color filter areas and light-shielding patterns located between the color filter areas, and the color conversion layer may include color conversion areas and light-shielding patterns located between the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In an embodiment, the first color light may be red light, the second color light may be green light, and the third color light may be blue light. In an embodiment, the color filter areas (or the color conversion areas) may include quantum dots. For example, the first area may include a red quantum dot, the second area may include a green quantum dot, and the third area may not include a quantum dot. The quantum dot may be the same as described in the specification. The first area, the second area, and/or the third area may each further include a scatterer.

In an embodiment, the light-emitting device may emit first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths. For example, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an active layer, wherein any one of the source electrode or the drain electrode may be electrically connected to any one of the first electrode or the second electrode of the light-emitting device.

The thin-film transistor may further include a gate electrode, a gate insulating film, etc.

The active layer may include crystalline silicon, amorphous silicon, organic semiconductor, oxide semiconductor, or the like.

The electronic apparatus may further include a sealing portion for sealing the light-emitting device. The sealing portion may be located between the color filter and/or color conversion layer and the light-emitting device. The sealing portion may allow light from the light-emitting device to be extracted to the outside, and may simultaneously prevent ambient air and/or moisture from penetrating into the light-emitting device. The sealing portion may be a sealing substrate including a transparent glass substrate or a plastic substrate. The sealing portion may be a thin-film encapsulation layer including an organic layer and/or an inorganic layer. When the sealing portion is a thin film encapsulation layer, the electronic apparatus may be flexible.

Various functional layers may be further included on the sealing portion, in addition to the color filter and/or the color conversion layer, according to a use of the electronic apparatus. The functional layers may include a touch screen layer, a polarizing layer, an authentication apparatus, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device, a biometric information collector.

The electronic apparatus may be applied to various displays, such as light sources, lighting, personal computers (for example, a mobile personal computer), mobile phones, digital cameras, electronic diaries, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
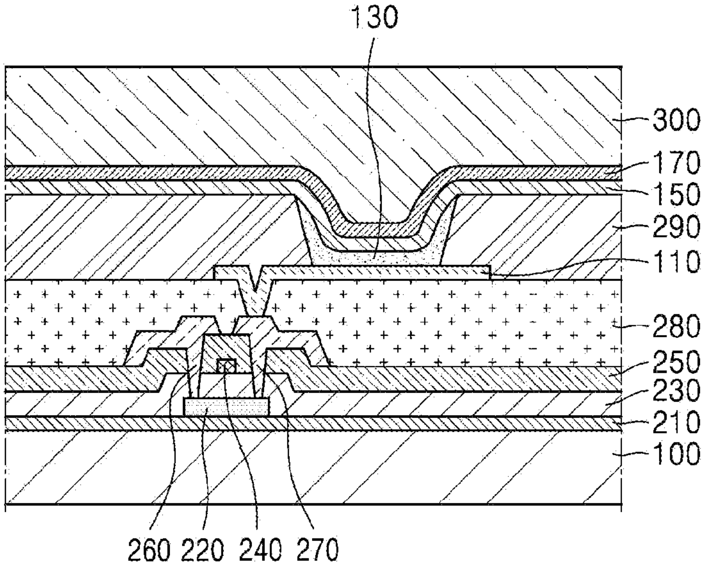
FIG. 2 is a schematic cross-sectional view of an electronic apparatus according to an embodiment.
Figure 3:
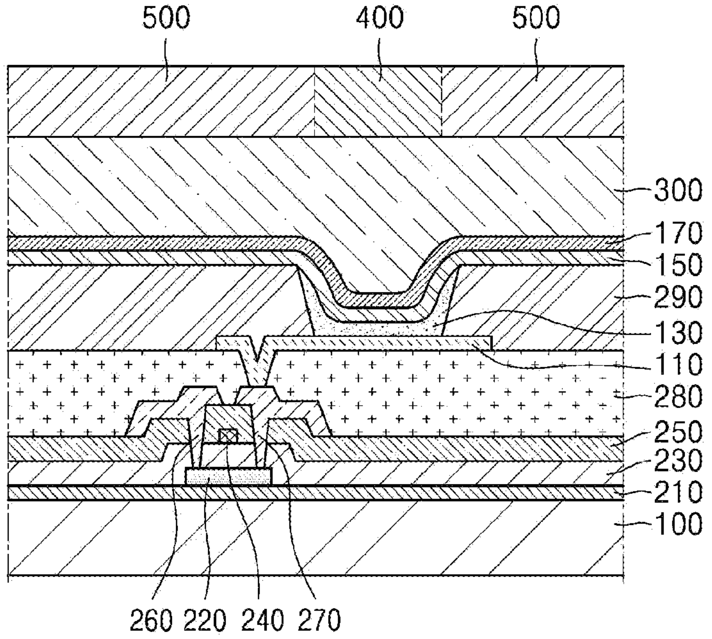
FIG. 3 is schematic cross-sectional view of an electronic apparatus according to another embodiment.

[Description of FIGS. 2 and 3]

FIG. 2 is a schematic cross-sectional view of an electronic apparatus according to an embodiment.

The electronic apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be formed on the substrate 100. The buffer layer 210 may prevent penetration of impurities through the substrate 100 and may provide a flat surface on the substrate 100.

A TFT may be located on the buffer layer 210. The TFT may include an active layer 220, a gate electrode 240, a source electrode 260, and a drain electrode 270.

The active layer 220 may include an inorganic semiconductor such as silicon or polysilicon, an organic semiconductor, or an oxide semiconductor, and may include a source region, a drain region, and a channel region.

A gate insulating film 230 for insulating the active layer 220 from the gate electrode 240 may be located on the active layer 220, and the gate electrode 240 may be located on the gate insulating film 230.

An interlayer insulating film 250 is located on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the active layer 220, and the source electrode 260 and the drain electrode 270 may respectively contact the exposed portions of the source region and the drain region of the active layer 220.

The TFT may be electrically connected to a light-emitting device to drive the light-emitting device, and may be covered by a passivation layer 280. The passivation layer 280 may include an inorganic insulating film, an organic insulating film, or a combination thereof. A light-emitting device is provided on the passivation layer 280.

The light-emitting device may include a first electrode 110, an interlayer 130, and a second electrode 150.

The first electrode 110 may be formed on the passivation layer 280. The passivation layer 280 does not completely cover the drain electrode 270 and may expose a portion of the drain electrode 270, and the first electrode 110 may be electrically connected to the exposed portion of the drain electrode 270.

A pixel-defining layer 290 containing an insulating material may be located on the first electrode 110. The pixel-defining layer 290 exposes a region of the first electrode 110, and an interlayer 130 may be formed in the exposed region of the first electrode 110. The pixel-defining layer 290 may be a polyimide or polyacrylic organic film. Although not shown in FIG. 2, at least one layer of the interlayer 130 may extend beyond the upper portion of the pixel-defining layer 290 to be provided in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, or the like), an epoxy-based resin (for example, aliphatic glycidyl ether (AGE), or the like), or a combination thereof; or a combination of the inorganic film and the organic film.

FIG. 3 is a schematic cross-sectional view of an electronic apparatus according to another embodiment.

The electronic apparatus of FIG. 3 differs from the electronic apparatus of FIG. 2, at least in that a light-shielding pattern 500 and a functional region 400 are further included on the encapsulation portion 300. The functional region 400 may be a color filter area, a color conversion area, or a combination of the color filter area and the color conversion area. In an embodiment, the light-emitting device included in the electronic apparatus of FIG. 3 may be a tandem light-emitting device.

[Manufacture Method]

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definitions of Terms

The term "$C_3$-$C_{60}$ carbocyclic group" as used herein may be a cyclic group consisting of carbon as the only ring-forming atoms and having three to sixty carbon atoms, and the term "$C_1$-$C_{60}$ heterocyclic group" as used herein may be a cyclic group that has one to sixty carbon atoms and further has, in addition to carbon, at least one heteroatom as ring-forming atoms. The $C_3$-$C_{60}$ carbocyclic group and the $C_1$-$C_{60}$ heterocyclic group may each be a monocyclic group consisting of one ring or a polycyclic group in which two or more rings are condensed with each other. In an embodiment, the $C_1$-$C_{60}$ heterocyclic group may have 3 to 61 ring-forming atoms.

The term "cyclic group" as used herein may include the $C_3$-$C_{60}$ carbocyclic group or the $C_1$-$C_{60}$ heterocyclic group.

The term "π electron-rich $C_3$-$C_{60}$ cyclic group" as used herein may be a cyclic group that has three to sixty carbon atoms and may not include *—N═*' as a ring-forming moiety, and the term "π electron-deficient nitrogen-containing $C_1$-$C_{60}$ cyclic group" as used herein may be a heterocyclic group that has one to sixty carbon atoms and may include *—N═*' as a ring-forming moiety.

In embodiments, the $C_3$-$C_{60}$ carbocyclic group may be a T1 group or a group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be a T2 group, a group in which two or more T2 groups are condensed with each other, or a group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be a T1 group, a group in which two or more T1 groups are condensed with each other, a T3 group, a group in which two or more T3 groups are condensed with each other, or a group in which at least one T3 group and at least one T1 group are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be a T4 group, a group in which two or more T4 groups are condensed with each other, a group in which at least one T4 group and at least one T1 group are condensed with each other, a group in which at least one T4 group and at least one T3 group are condensed with each other, or a group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), wherein the group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein may each be a group condensed to any cyclic group, a monovalent group, or a polyvalent group (for example, a divalent group, a trivalent group, a tetravalent group, etc.), depending on the structure of a formula in connection with which the terms are used. For example, a "benzene group" may be a benzo group, a phenyl group, a phenylene group, or the like, which may be readily understood by one of ordinary skill in the art according to the structure of a formula including the "benzene group."

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein may be a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein may be a divalent group having a same structure as the $C_1$-$C_{60}$ alkyl group.

The term "$C_2$-$C_{60}$ alkenyl group" as used herein may be a monovalent hydrocarbon group having at least one carbon-carbon double bond in the middle or at a terminus of a $C_2$-$C_{60}$ alkyl group, and examples thereof may include an ethenyl group, a propenyl group, and a butenyl group. The term "$C_2$-$C_{60}$ alkenylene group" as used herein may be a divalent group having a same structure as the $C_2$-$C_{60}$ alkenyl group.

The term "$C_2$-$C_{60}$ alkynyl group" as used herein may be a monovalent hydrocarbon group having at least one carbon-carbon triple bond in the middle or at a terminus of a $C_2$-$C_{60}$ alkyl group, and examples thereof may include an ethynyl group and a propynyl group. The term "$C_2$-$C_{60}$ alkynylene group" as used herein may be a divalent group having a same structure as the $C_2$-$C_{60}$ alkynyl group.

The term "$C_1$-$C_{60}$ alkoxy group" as used herein may be a monovalent group represented by —O($A_{101}$) (wherein $A_{101}$ may be a $C_1$-$C_{60}$ alkyl group), and examples thereof may include a methoxy group, an ethoxy group, and an isopropyloxy group.

The term "$C_3$-$C_{10}$ cycloalkyl group" as used herein may be a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or a bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein may be a divalent group having a same structure as the $C_3$-$C_{10}$ cycloalkyl group.

The term "$C_1$-$C_{10}$ heterocycloalkyl group" as used herein may be a monovalent cyclic group that further includes, in addition to a carbon atom, at least one heteroatom as a ring-forming atom and has 1 to 10 carbon atoms, and examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein may be a divalent group having a same structure as the $C_1$-$C_{10}$ heterocycloalkyl group.

The term "$C_3$-$C_{10}$ cycloalkenyl group" as used herein may be a monovalent cyclic group that has three to ten carbon atoms and at least one carbon-carbon double bond in the ring thereof and no aromaticity, and examples thereof may include a cyclopentenyl group, a cyclohexenyl group, and a cycloheptenyl group. The term "$C_3$-$C_{10}$ cycloalkenylene group" as used herein may be a divalent group having a same structure as the $C_3$-$C_{10}$ cycloalkenyl group.

The term "$C_1$-$C_{10}$ heterocycloalkenyl group" as used herein may be a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein may be a divalent group having a same structure as the $C_1$-$C_{10}$ heterocycloalkenyl group.

The term "$C_6$-$C_{60}$ aryl group" as used herein may be a monovalent group having a carbocyclic aromatic system having six to sixty carbon atoms, and the term "$C_6$-$C_{60}$ arylene group" as used herein may be a divalent group having a carbocyclic aromatic system having six to sixty carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the respective rings may be condensed with each other.

The term "$C_1$-$C_{60}$ heteroaryl group" as used herein may be a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein may be a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the respective rings may be condensed with each other.

The term "monovalent non-aromatic condensed polycyclic group" as used herein may be a monovalent group having two or more rings condensed to each other, only carbon atoms (for example, having 8 to 60 carbon atoms) as ring-forming atoms, and non-aromaticity in its molecular structure when considered as a whole. Examples of the monovalent non-aromatic condensed polycyclic group may include an indenyl group, a fluorenyl group, a spiro-bifluorenyl group, a benzofluorenyl group, an indenophenanthrenyl group, and an indeno anthracenyl group. The term "divalent non-aromatic condensed polycyclic group" as used herein may be a divalent group having a same structure as a monovalent non-aromatic condensed polycyclic group.

The term "monovalent non-aromatic condensed heteropolycyclic group" as used herein may be a monovalent group having two or more rings condensed to each other, at least one heteroatom other than carbon atoms (for example, having 1 to 60 carbon atoms) as a ring-forming atom, and non-aromaticity in its molecular structure when considered as a whole. Examples of the monovalent non-aromatic condensed heteropolycyclic group may include a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein may be a divalent group having a same structure as a monovalent non-aromatic condensed heteropolycyclic group.

The term "$C_6$-$C_{60}$ aryloxy group" as used herein may be represented by —O($A_{102}$) (wherein $A_{102}$ may be a $C_6$-$C_{60}$ aryl group), and the term "$C_6$-$C_{60}$ arylthio group" as used herein may be represented by —S($A_{103}$) (wherein $A_{103}$ may be a $C_6$-$C_{60}$ aryl group).

The term "$C_7$-$C_{60}$ aryl alkyl group" as used herein may be represented by -($A_{104}$)($A_{105}$) (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" as used herein may be represented by -($A_{106}$)($A_{107}$) (where $A_{106}$ may be a $C_1$-$C_{59}$ alkylene group, and $A_{107}$ may be a $C_1$-$C_{59}$ heteroaryl group).

The group $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$).

The groups $Q_1$ to $Q_3$, $Q_{11}$ to $Q_{13}$, $Q_{21}$ to $Q_{23}$, and $Q_{31}$ to $Q_{33}$ as used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein may be any atom other than a carbon atom or a hydrogen atom. Examples of the heteroatom may include O, S, N, P, Si, B, Ge, Se, or any combination thereof.

The term "Ph" as used herein refers to a phenyl group, the term "Me" as used herein refers to a methyl group, the term "Et" as used herein refers to an ethyl group, the terms "tert-Bu" or "$Bu^t$" as used herein refers to a tert-butyl group, and the term "OMe" as used herein refers to a methoxy group.

The term "biphenyl group" as used herein may be a phenyl group substituted with a phenyl group. For example, the "biphenyl group" may be a substituted phenyl group having a $C_6$-$C_{60}$ aryl group as a substituent.

The term "terphenyl group" as used herein may be a phenyl group substituted with a biphenyl group. The "terphenyl group" may be a substituted phenyl group having, as a substituent, a $C_6$-$C_{60}$ aryl group substituted with a $C_6$-$C_{60}$ aryl group.

The symbols * and *' as used herein, unless defined otherwise, each refer to a binding site to a neighboring atom in a corresponding formula or moiety.

Hereinafter, compounds according to embodiments and light-emitting devices according to embodiments will be described in detail with reference to the Synthesis Examples and the Examples. The wording "B was used instead of A" used in describing Synthesis Examples means that an identical molar equivalent of B was used in place of A.

EXAMPLE
Synthesis Example 1: Synthesis of Compound 1
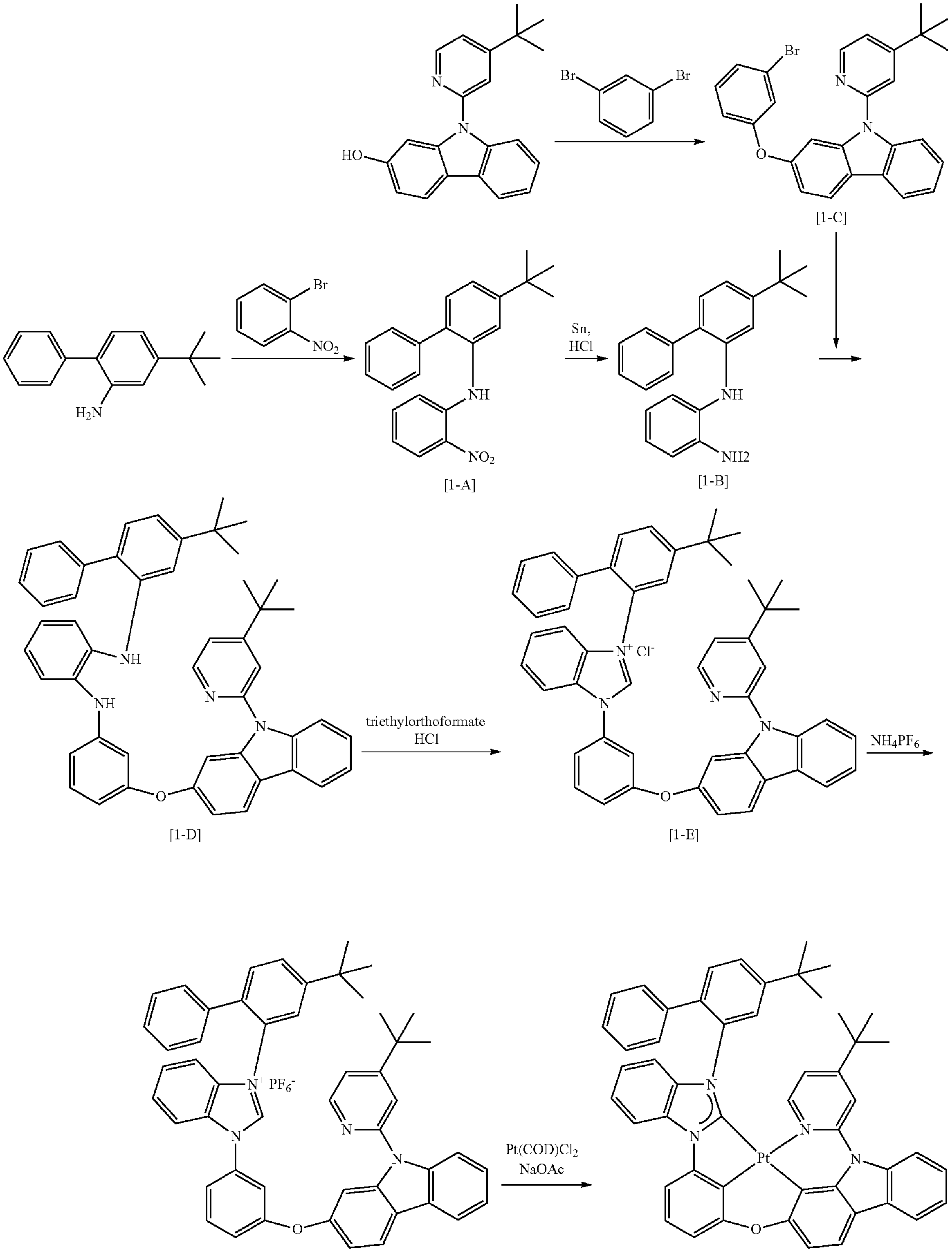
[1-C]
[1-A]
[1-B]
[1-D]
[1-E]
[1-F]
1

Synthesis of Intermediate [1-A]

6.8 g (30 mmol) of 4-(tert-butyl)-[1,1'-biphenyl]-2-amine, 9.1 g (45 mmol) of 1-bromo-2-nitrobenzene, 1.4 g (1.5 mmol) of tris(dibenzylideneacetone)dipalladium, 1.4 g (3.0 mmol) of X-phos, and 6.8 g (90 mmol) of sodium tert-butoxide were added to a reaction vessel and suspended in 300 mL of toluene. The reaction temperature was raised to 110° C., and the reaction mixture was stirred for 3 hours. After completion of the reaction, the reaction mixture was cooled to room temperature and an organic layer was extracted with ethyl acetate. The extracted organic layer was washed with a saturated aqueous sodium chloride solution and dried by using sodium sulfate. A residue obtained by removing the solvent therefrom was separated by column chromatography to obtain 8.7 g (25 mmol) of Intermediate 1-A.

Synthesis of Intermediate [1-B]

8.7 g (25 mmol) of Intermediate [1-A], 10.4 g (88 mmol) of tin, and 12.0 mL (138 mmol) of a HCl 35 wt % solution were added to a reaction vessel and suspended in 250 mL of ethanol. The reaction temperature was raised to 80° C., and the reaction mixture was stirred for 12 hours. After completion of the reaction, the reaction mixture was cooled at room temperature, and a saturated aqueous sodium bicarbonate solution was used for neutralization. An organic layer was extracted with ethyl acetate, and the extracted organic layer was washed with a saturated aqueous sodium chloride solution and dried by using sodium sulfate. A residue obtained by removing the solvent therefrom was separated by column chromatography to obtain 7.0 g (22 mmol) of Intermediate 1-B.

Synthesis of Intermediate [1-C]

9.5 g (30 mmol) of 9-(4-(tert-butyl)pyridin-2-yl)-9H-carbazol-2-ol, 14.2 g (60 mmol) of 1,3-dibromo benzene, 12.7 g (60 mmol) of potassium phosphate tribasic, 570 mg (3.0 mmol) of iodo copper, and 360 mg (3.0 mmol) of picolinic acid were added to a reaction vessel and suspended in 300 mL of dimethylsulfoxide. The reaction mixture was heated to a temperature of 160° C. and stirred for 12 hours. After completion of the reaction, the reaction mixture was cooled to room temperature and an organic layer was extracted with ethyl acetate. The extracted organic layer was washed with a saturated aqueous sodium chloride solution and dried by using sodium sulfate. A residue obtained by removing the solvent therefrom was separated by column chromatography to obtain 11.3 g (24 mmol) of Intermediate 1-C.

Synthesis of Intermediate [1-D]

7.0 g (22 mmol) of Intermediate [1-B], 11.3 g (24 mmol) of Intermediate [1-C], 1.0 g (1.1 mmol) of tris(dibenzylideneacetone)dipalladium(0), 520 mg (1.1 mmol) of X-phos, and 4.2 g (44 mmol) of sodium tert-butoxide were added to a reaction vessel and suspended in 220 mL of toluene. The reaction mixture was heated to a temperature of 110° C. and stirred for 3 hours. After completion of the reaction, the reaction mixture was cooled to room temperature and an organic layer was extracted with ethyl acetate. The extracted organic layer was washed with a saturated aqueous sodium chloride solution and dried by using sodium sulfate. A residue obtained by removing the solvent therefrom was separated by column chromatography to obtain 8.5 g (12 mmol) of Intermediate 1-D.

Synthesis of Intermediate [1-E]

8.5 g (12 mmol) of Intermediate [1-D], 80 mL (600 mmol) of triethylorthoformate, and 5.7 mL (66 mmol) of a HCl 35 wt % solution were added to a reaction vessel, heated, and stirred at 80° C. for 12 hours. After completion of the reaction, the reaction mixture was cooled to room temperature, and a residue obtained by removing the solvent therefrom was separated by column chromatography to obtain 6.9 g (9.2 mmol) of Intermediate [1-E].

Synthesis of Intermediate [1-F]

6.9 g (9.2 mmol) of Intermediate [1-E] and 2.9 g (18 mmol) of ammonium hexafluorophosphate were added to a reaction vessel and suspended in a solution containing methanol and water in a ratio of 2:1. The reaction mixture was stirred at room temperature for 12 hours. The resulting solid was filtered and separated by column chromatography to obtain 7.0 g (8.1 mmol) of Intermediate [1-F].

Synthesis of Compound [1]

7.0 g (8.1 mmol) of Intermediate [1-F], 3.3 g (8.9 mmol) of dichloro(1,5-cyclooctadiene)platinum, and 1.3 g (16 mmol) of sodium acetate were suspended in 160 mL of dioxane. The reaction mixture was heated, and stirred at 110° C. for 72 hours. After completion of the reaction, the reaction mixture was cooled to room temperature and an organic layer was extracted with ethyl acetate. The extracted organic layer was washed with a saturated aqueous sodium chloride solution and dried by using sodium sulfate. A residue obtained by removing the solvent therefrom was separated by column chromatography to obtain 1.6 g (1.8 mmol) of Compound [1].

Synthesis Example 2: Synthesis of Compound 2
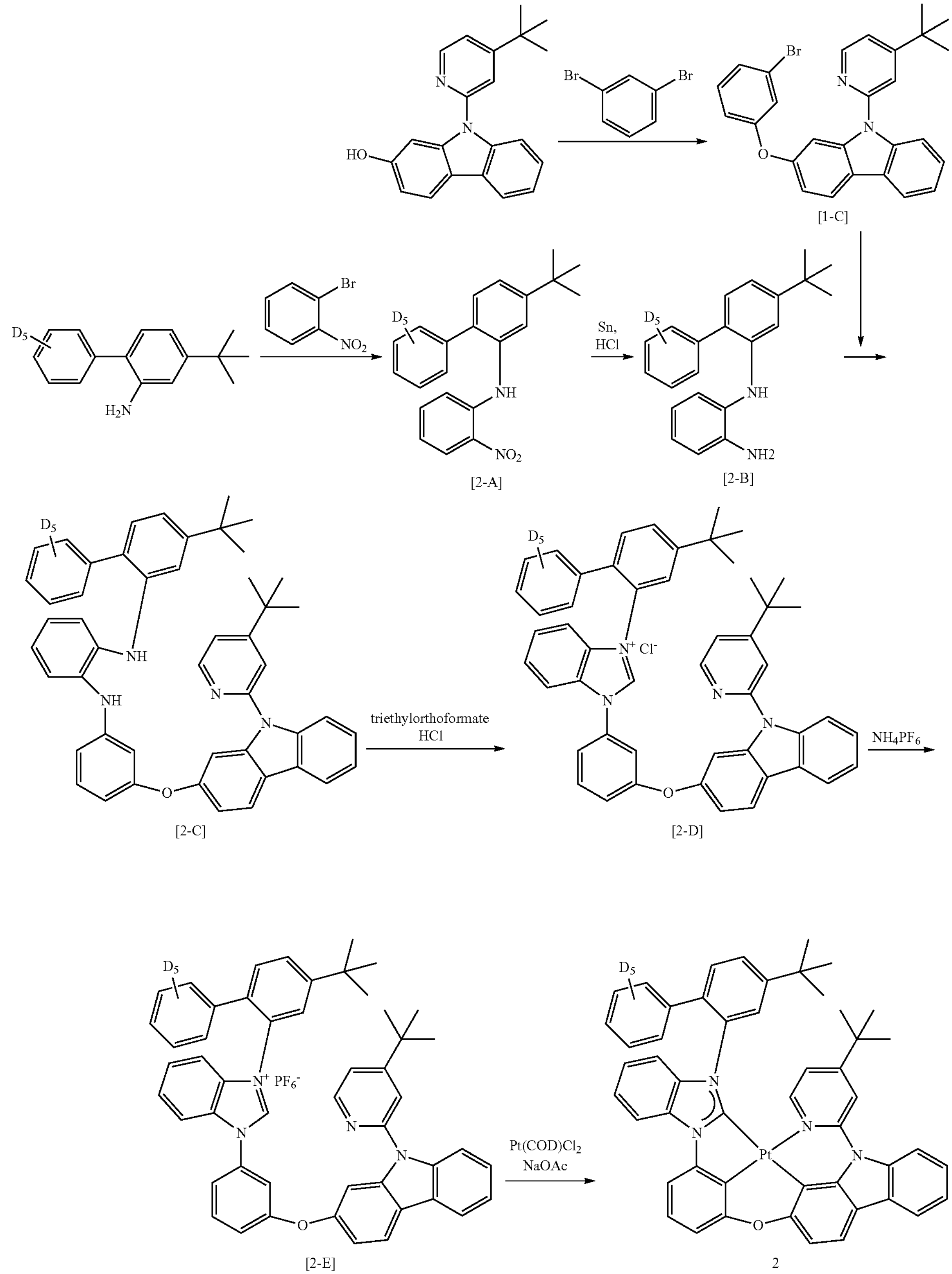
[1-C]
[2-A]
[2-B]
[2-C]
[2-D]
[2-E]
2

1.7 g (1.9 mmol) of Compound 2 was obtained in the same manner as in Synthesis Example 1, except that 4-(tert-butyl)-[1,1'-biphenyl]-2',3',4',5',6'-d5-2-amine was used instead of 4-(tert-butyl)-[1,1'-biphenyl]-2-amine in a process of the synthesis of Intermediate [1-A] of Synthesis Example 1.
Synthesis Example 3: Synthesis of Compound 41
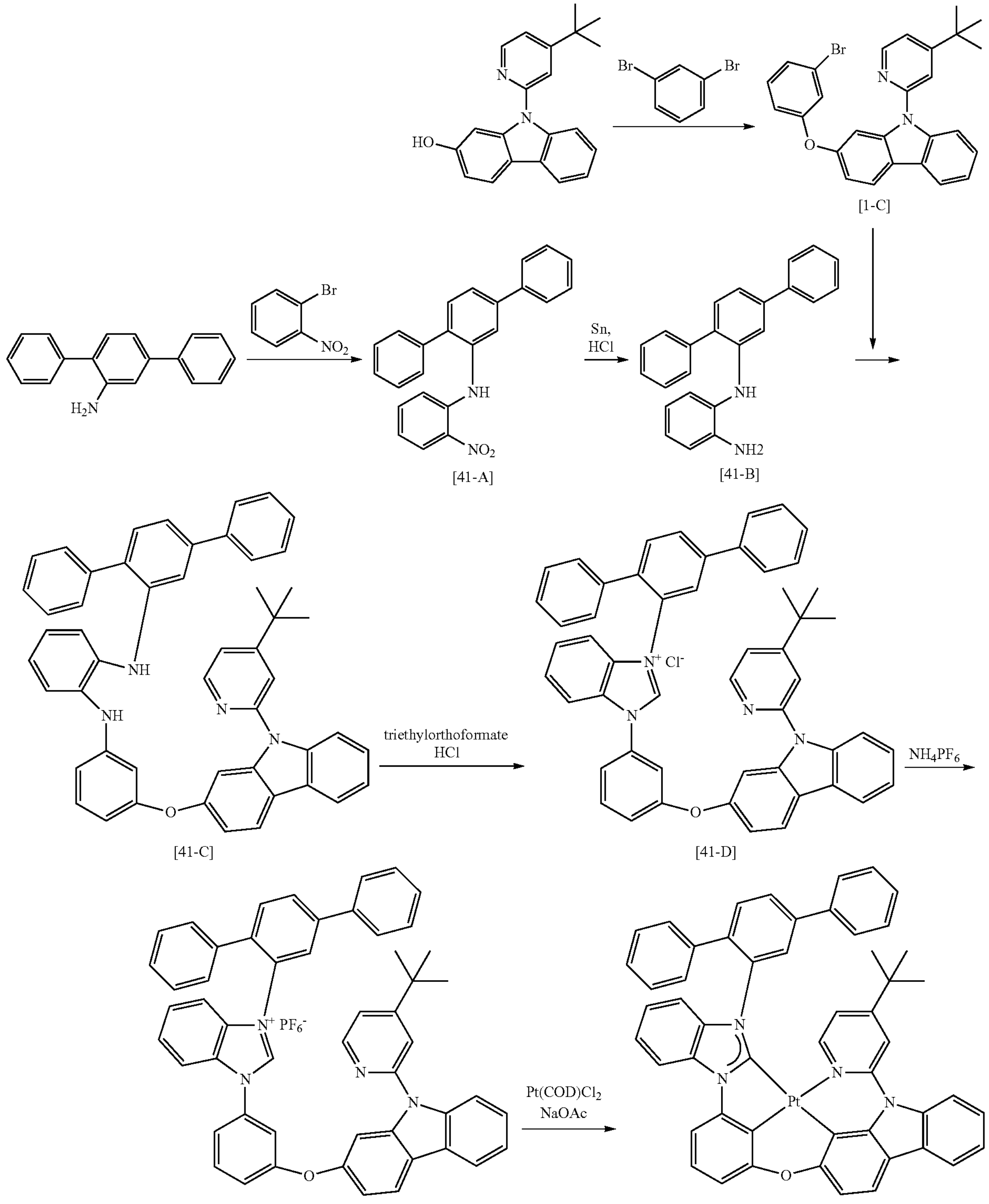
41

2.0 g (2.2 mmol) of Compound 41 was obtained in the same manner as in Synthesis Example 1, except that [1,1':4',1"-terphenyl]-2'-amine was used instead of 4-(tert-butyl)-[1,1'-biphenyl]-2-amine in a process of the synthesis of Intermediate [1-A] of Synthesis Example 1.
Synthesis Example 4: Synthesis of Compound 51
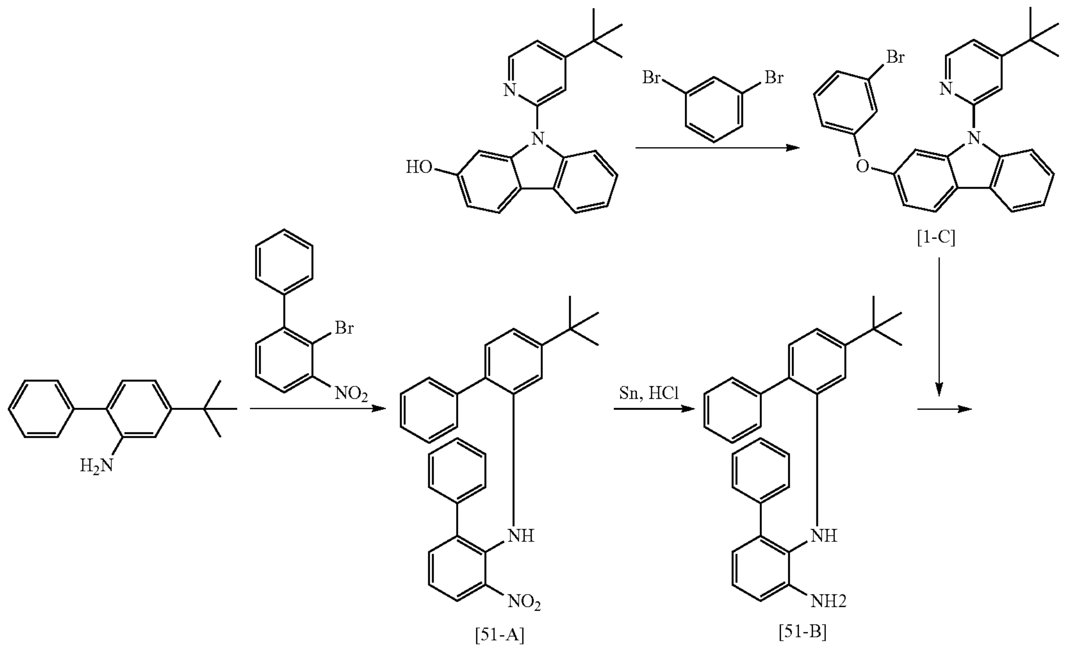
[1-C]
[51-A]
[51-B]
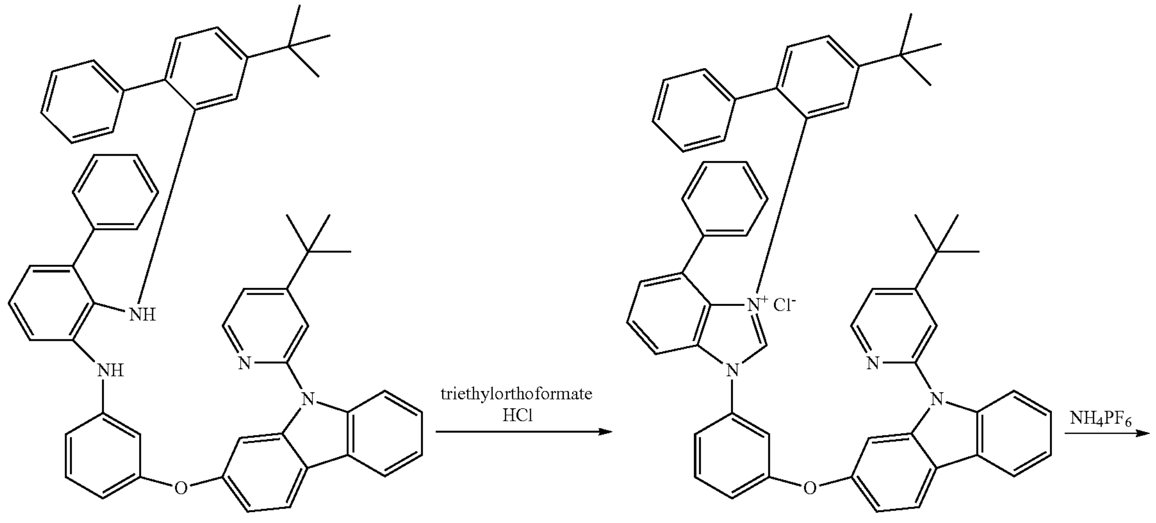
[51-C]
[51-D]

-continued
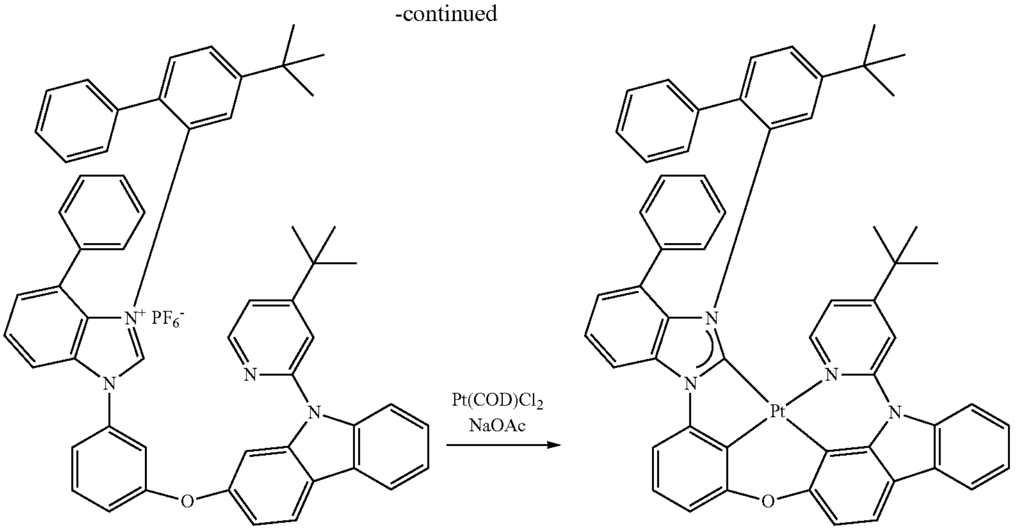
[51-E] 51
690 mg (0.7 mmol) of Compound 51 was obtained in the same manner as in Synthesis Example 1, except that 2-bromo-3-nitro-1,1'-biphenyl was used instead of 1-bromo-2-nitrobenzene in a process of the synthesis of Intermediate [1-A] of Synthesis Example 1.
Synthesis Example 5: Synthesis of Compound 84
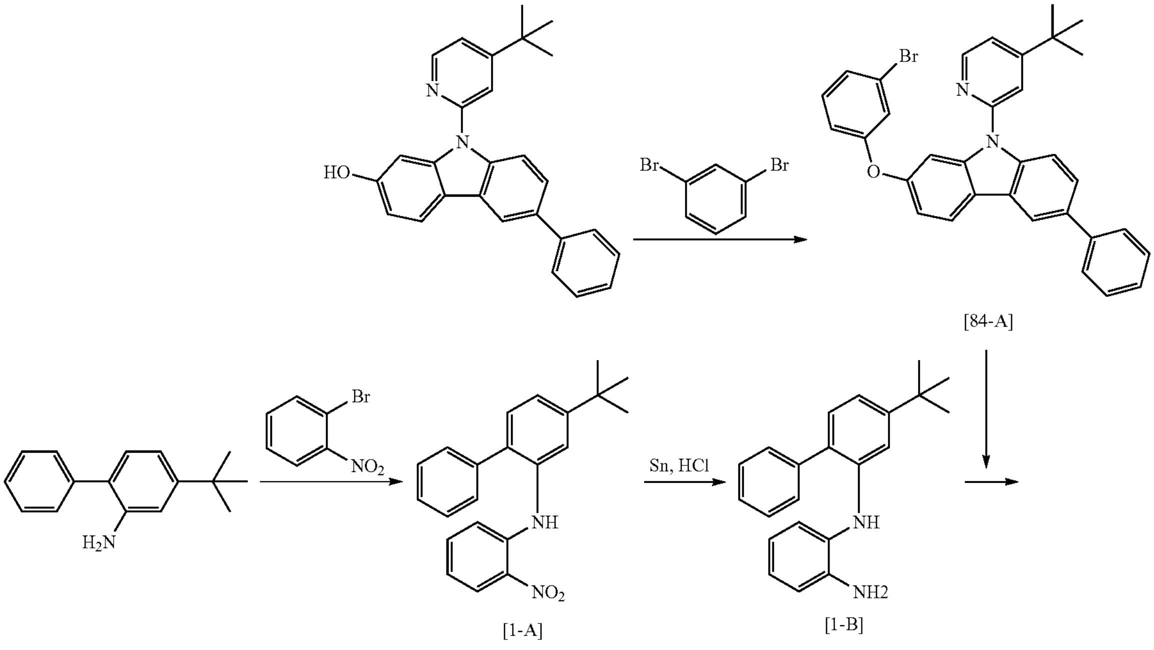
[84-A]
[1-A] [1-B]

-continued
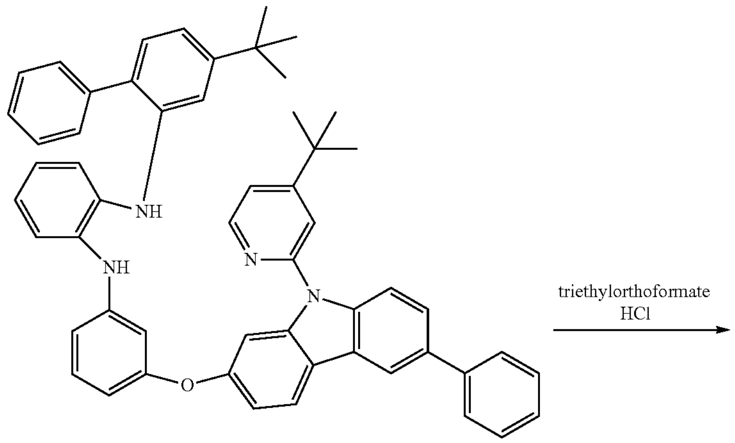
[84-B]
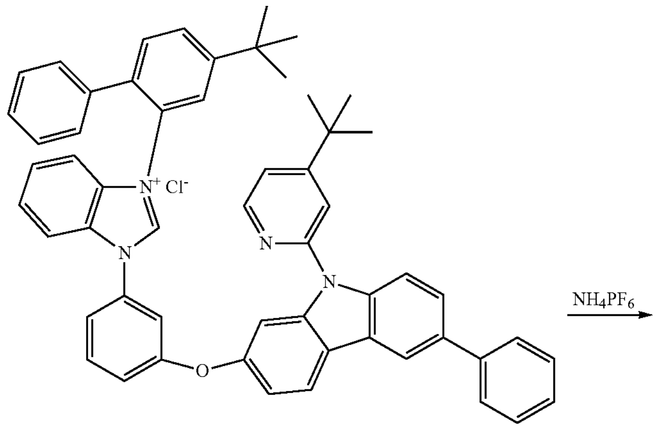
[84-C]
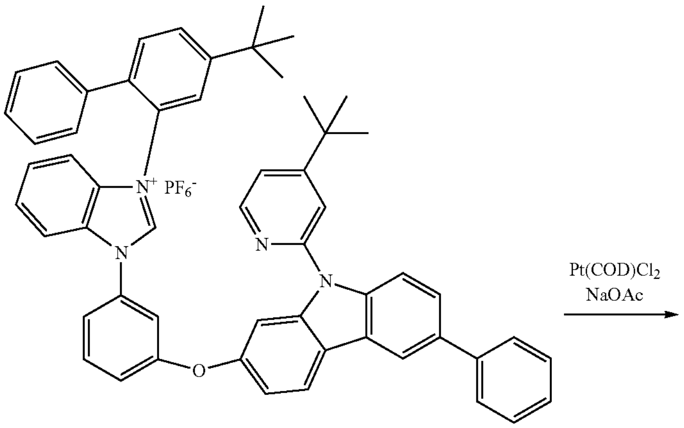
[84-D]

-continued

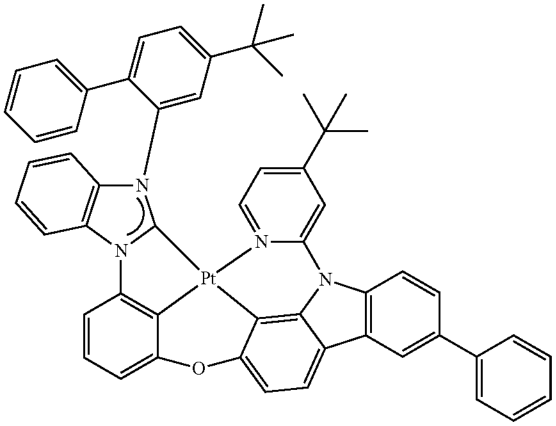

84

1.5 g (1.5 mmol) of Compound 84 was obtained in the same manner as in Synthesis Example 1, except that 9-(4-(tert-butyl)pyridin-2-yl)-6-phenyl-9H-carbazol-2-ol was used instead of 9-(4-(tert-butyl)pyridin-2-yl)-9H-carbazol-2-ol in a process of the synthesis of Intermediate [1-C] of Synthesis Example 1.

$^1$H NMR and MS/FAB of the compounds synthesized according to Synthesis Examples 1 to 5 are shown in Table 1 below. Synthesis methods of other compounds in addition to the compounds synthesized in Synthesis Examples 1 to 5 may be readily recognized by those skilled in the art by referring to the synthesis paths and source materials.

TABLE 1

| Compound | $^1$H NMR ($CDCl_3$, 400 MHz) | MS/FAB found | MS/FAB calc. |
|---|---|---|---|
| 1 | 8.76 (m, 1H), 8.41 (m, 1H), 8.20 (m, 1H), 7.66 (m, 1H), 7.59-7.56 (m, 2H), 7.51 (m, 1H), 7.44-7.39 (m, 5H), 7.21-7.15 (m, 4H), 7.08-7.05 (m, 3H), 6.96-6.95 (m, 3H), 6.67-6.65 (m, 2H), 1.33 (s, 9H), 1.22 (s, 9H) | 909.3003 | 909.3006 |
| 2 | 8.74 (m, 1 H), 8.40 (m, 1H), 8.21 (m, 1H), 7.63 (m, 1H), 7.61-7.55 (m, 2H), 7.49-7.45 (m, 3H), 7.22-7.17 (m, 4H), 7.03-6.94 (m, 4H), 6.70-6.67 (m, 2H), 1.34 (s, 9H), 1.25 (s, 9H) | 914.3315 | 914.3320 |
| 41 | 8.81 (m, 1H), 8.44 (m, 1H), 8.15 (m, 1H), 7.85-7.80 (m, 3H), 7.53-7.45 (5H), 7.42-7.38 (m, 6H), 7.19-7.15 (m, 4H), 7.07-7.06 (m, 2H), 6.94-6.88 (m, 4H), 6.68-6.64 (m, 2H), 1.30 (s, 9H) | 929.2690 | 929.2693 |
| 51 | 8.80 (m, 1H), 8.45 (m, 1H), 8.11 (m, 1H), 7.85 (m, 1H), 7.66-7.57 (m, 4H), 7.45-7.39 (m, 8H), 7.23-7.16 (m, 4H), 7.05-7.03 (m, 5H), 6.91 (m, 1H), 6.81-6.75 (m, 2H), 1.37 (s, 9H), 1.23 (s, 9H) | 985.33158 | 985.3319 |
| 84 | 8.77 (m, 1H), 8.42 (m, 1H), 7.95-7.93 (m, 2H), 7.76-7.74 (m, 3H), 7.64-7.61 (m, 2H), 7.48-7.41 (m, 8H), 7.15-7.11 (m, 3H), 7.05-7.04 (m, 3H), 6.99-6.97 (m, 3H), 6.66-6.63 (m, 2H), 1.33 (s, 9H), 1.24 (s, 9H) | 985.3321 | 985.3319 |

TABLE 1-continued

| Compound | $^1$H NMR ($CDCl_3$, 400 MHz) | MS/FAB found | MS/FAB calc. |
|---|---|---|---|

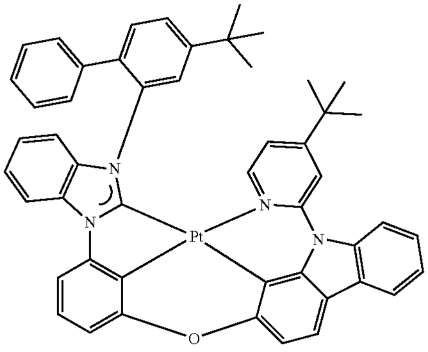

1

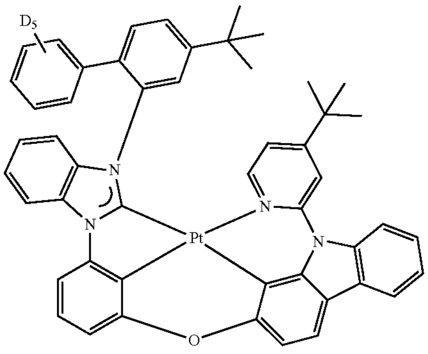

2

TABLE 1-continued

| Compound | $^1H$ NMR ($CDCl_3$, 400 MHz) | MS/FAB found | MS/FAB calc. |
|---|---|---|---|
| 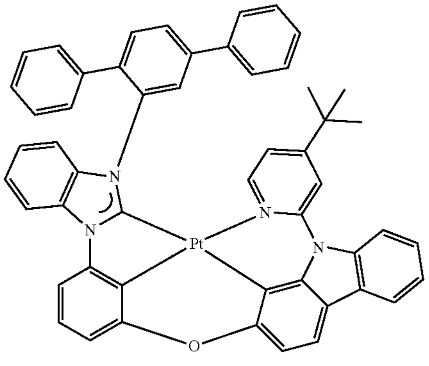 41 | | | |
| 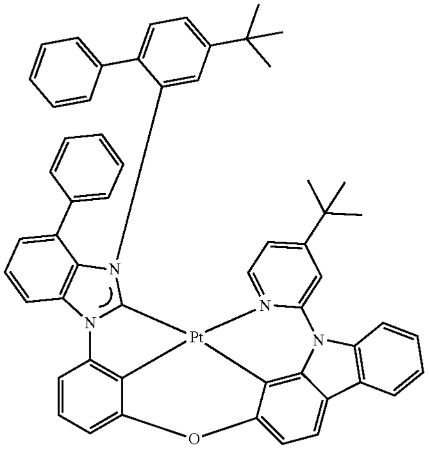 51 | | | |
| 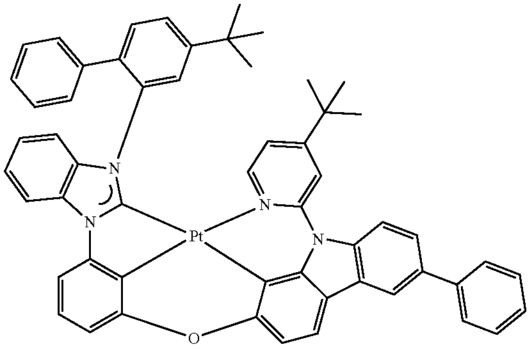 84 | | | |

Example 1

As an anode, a glass substrate (product of Corning Inc.) with a 15 $\Omega/cm^2$ (1,200 Å) ITO formed thereon was cut to a size of 50 mm×50 mm×0.7 mm, sonicated using isopropyl alcohol and pure water each for 5 minutes, washed by irradiation of ultraviolet rays and exposure of ozone thereto for 30 minutes, and mounted on a vacuum deposition apparatus.

2-TNATA was vacuum-deposited on the anode to form a hole injection layer having a thickness of 600 Å, and 4,4'-bis[N-(1-naphthyl)-N-phenylamino]biphenyl (hereinafter, referred as "NPB") was vacuum-deposited on the hole injection layer to form a hole transport layer having a thickness of 300 Å.

Compound 1, Compound H1-4, and Compound E1 were vacuum-deposited on the hole transport layer to form an emission layer having a thickness of 300 Å. In this regard, an amount of Compound 1 is 10 wt % based on a total weight (100 wt %) of the emission layer, and a weight ratio of Compound H2 to Compound E2 was adjusted to 5:5.

Compound E1 was vacuum-deposited on the emission layer to form a hole blocking layer having a thickness of 50 Å, $Alq_3$ was vacuum-deposited on the hole blocking layer to form an electron transport layer having a thickness of 300 Å, LiF was vacuum-deposited on the electron transport layer to form an electron injection layer having a thickness of 10 Å, and Al was vacuum-deposited thereon to form a cathode having a thickness of 3,000 Å, thereby completing manufacture of an organic light-emitting device.

2-TNATA

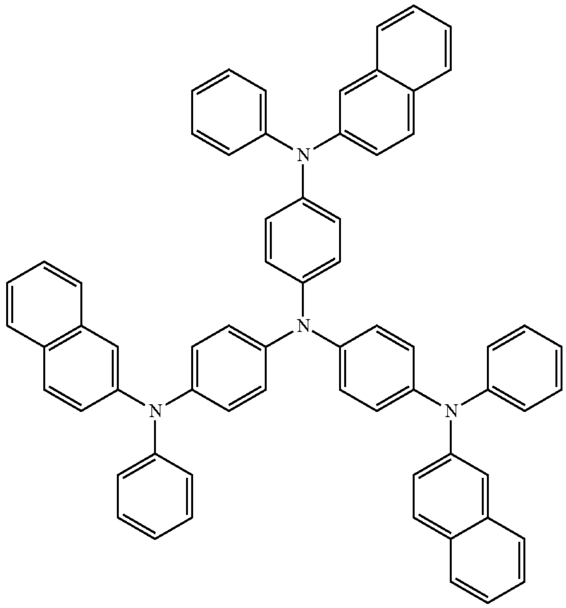

NPB

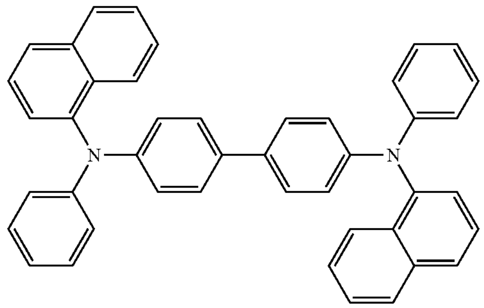

Examples 2 to 13

Organic light-emitting devices were manufactured in the same manner as in Example 1, except that compounds described in Table 2 were used instead of the Compound 1, Compound H1-4, and Compound E1 in the formation of the emission layer.

Comparative Examples 1 to 3

Organic light-emitting devices were manufactured in the same manner as in Example 1, except that compounds described in Table 2 were each used instead of Compound 1 in the formation of the emission layer.

Evaluation Example 1

The driving voltage (V), luminescence efficiency (cd/A), color coordinates (CIE_y), maximum emission wavelength (nm), and lifespan ($LT_{95}$) of the organic light-emitting devices of Examples 1 to 13 and Comparative Examples 1 to 3 at 1,000 cd/$m^2$ were measured by using Keithley SMU 236 and a luminance meter PR650. The results thereof are shown in Table 2. In Table 2, the lifespan ($T_{95}$) indicates a time (hr) for the luminance to decline to 95% of its initial luminance.

TABLE 2

| No. | Dopant | Host | Luminance (cd/$m^2$) | Driving voltage (V) | Luminescence efficiency (cd/A) | CIE-y | Maximum emission wavelength (nm) | Device lifespan ($T_{95}$, h) (at 1,000 cd/$m^2$) |
|---|---|---|---|---|---|---|---|---|
| Example 1 | 1 | H1-4:E1 | 1000 | 4.5 | 160 | 0.201 | 462 | 178 |
| Example 2 | 2 | H1-4:E1 | 1000 | 4.4 | 190 | 0.202 | 462 | 195 |
| Example 3 | 41 | H1-4:E1 | 1000 | 4.6 | 225 | 0.212 | 464 | 204 |
| Example 4 | 51 | H1-4:E1 | 1000 | 4.5 | 135 | 0.193 | 461 | 150 |
| Example 5 | 84 | H1-4:E1 | 1000 | 4.3 | 207 | 0.205 | 463 | 211 |
| Example 6 | 41 | H1-4:E2 | 1000 | 4.5 | 150 | 0.200 | 463 | 125 |
| Example 7 | 41 | H1-4:E25 | 1000 | 4.4 | 201 | 0.198 | 463 | 104 |
| Example 8 | 41 | H1-8:E1 | 1000 | 4.5 | 255 | 0.211 | 464 | 255 |
| Example 9 | 41 | H1-8:E2 | 1000 | 4.4 | 234 | 0.205 | 463 | 176 |
| Example 10 | 41 | H1-8:E25 | 1000 | 4.4 | 245 | 0.199 | 463 | 135 |
| Example 11 | 41 | H1-14:E1 | 1000 | 4.5 | 260 | 0.212 | 464 | 244 |
| Example 12 | 41 | H1-14:E2 | 1000 | 4.4 | 244 | 0.207 | 463 | 170 |
| Example 13 | 41 | H1-14:E25 | 1000 | 4.3 | 220 | 0.195 | 463 | 151 |
| Comparative Example 1 | A | H1-4:E1 | 1000 | 4.8 | 100 | 0.185 | 453 | 100 |
| Comparative Example 2 | B | H1-4:E1 | 1000 | 4.9 | 88 | 0.191 | 456 | 49 |
| Comparative Example 3 | C | H1-4:E1 | 1000 | 4.8 | 110 | 0.189 | 455 | 108 |

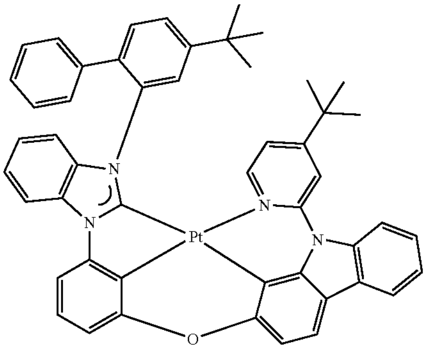

1

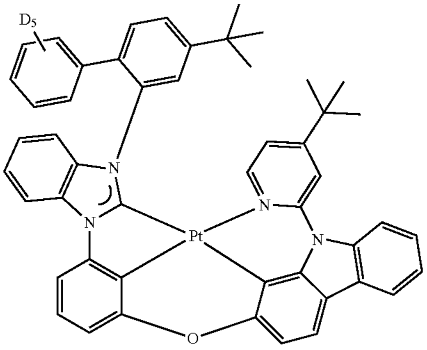

2

TABLE 2-continued
| No. | Dopant | Host | Luminance (cd/m$^2$) | Driving voltage (V) | Lumines-cence efficiency (cd/A) | CIE-y | Maximum emission wavelength (nm) | Device lifespan ($T_{95}$, h) (at 1,000 cd/m$^2$) |
|---|---|---|---|---|---|---|---|---|
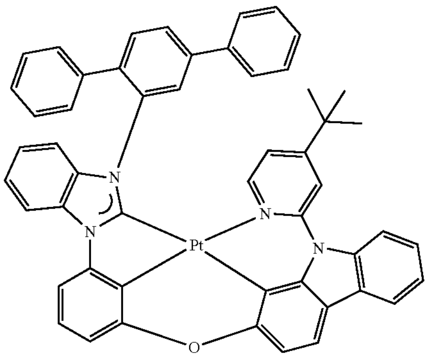
41
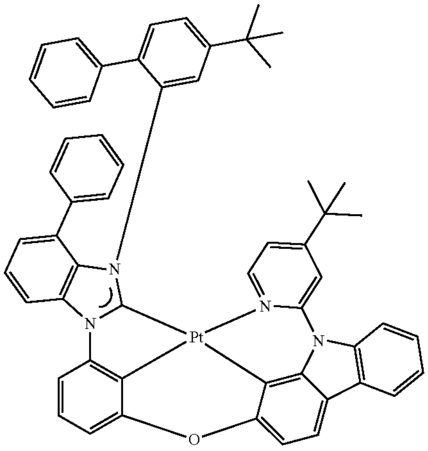
51
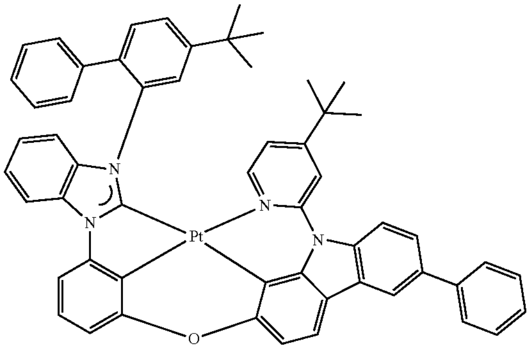
84

TABLE 2-continued
| No. | Dopant | Host | Luminance (cd/m$^2$) | Driving voltage (V) | Lumines-cence efficiency (cd/A) | CIE-y | Maximum emission wavelength (nm) | Device lifespan ($T_{95}$, h) (at 1,000 cd/m$^2$) |
|---|---|---|---|---|---|---|---|---|
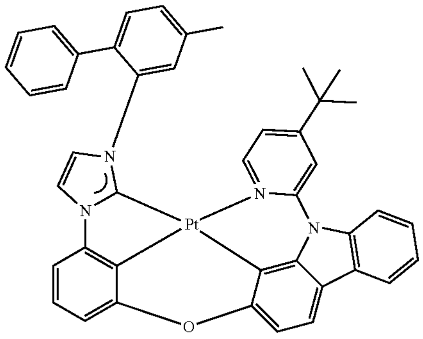
A
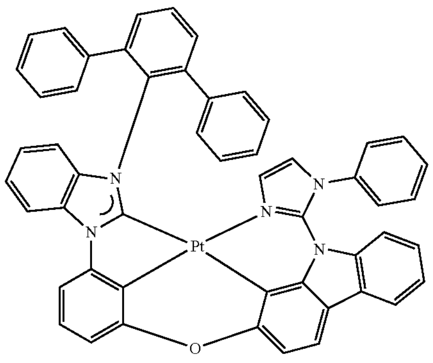
B
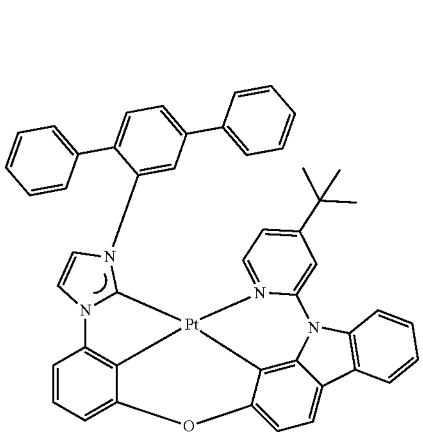
C TABLE 2-continued
| No. | Dopant | Host | Luminance ($cd/m^2$) | Driving voltage (V) | Lumines-cence efficiency (cd/A) | CIE-y | Maximum emission wavelength (nm) | Device lifespan ($T_{95}$, h) (at 1,000 $cd/m^2$) |
|---|---|---|---|---|---|---|---|---|
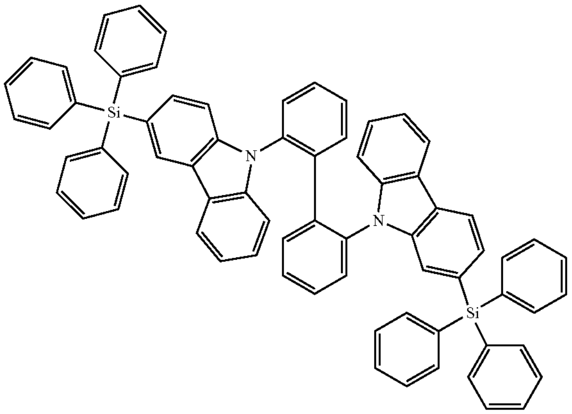
H1-4
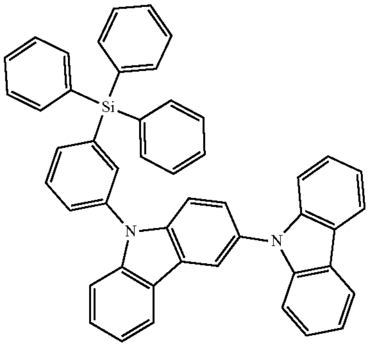
H1-8
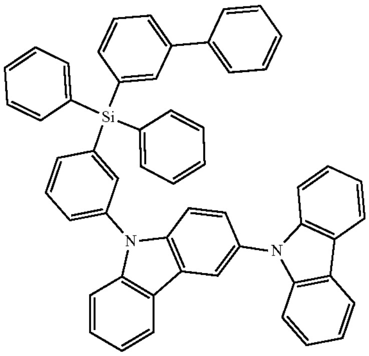
H1-14

TABLE 2-continued

| No. | Dopant | Host | Luminance (cd/m$^2$) | Driving voltage (V) | Lumines-cence efficiency (cd/A) | CIE-y | Maximum emission wavelength (nm) | Device lifespan ($T_{95}$, h) (at 1,000 cd/m$^2$) |
|---|---|---|---|---|---|---|---|---|

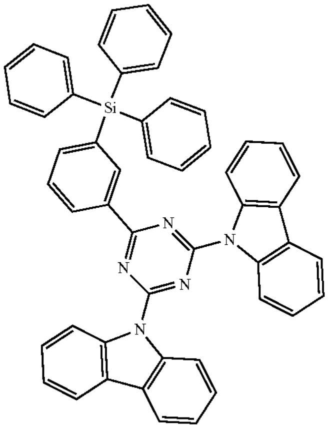

E1

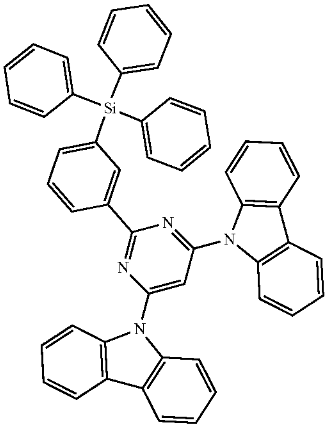

E2

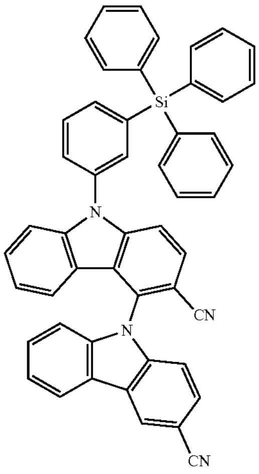

E25

From Table 2, it was confirmed that the organic light-emitting devices of Examples 1 to 13 have low driving voltage and excellent luminescence efficiency and lifespan characteristics while emitting deep blue light, compared to the organic light-emitting devices of Comparative Examples 1 to 3.

A light-emitting device including the organometallic compound may have low driving voltage, high efficiency, and long lifespan, and thus, may be used to manufacture a high-quality electronic apparatus having excellent light efficiency and long lifespan.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the claims.

What is claimed is:

1. A light-emitting device comprising:

a first electrode;

a second electrode facing the first electrode;

an interlayer between the first electrode and the second electrode and including an emission layer; and an organometallic compound represented by Formula 1:

[Formula 1]

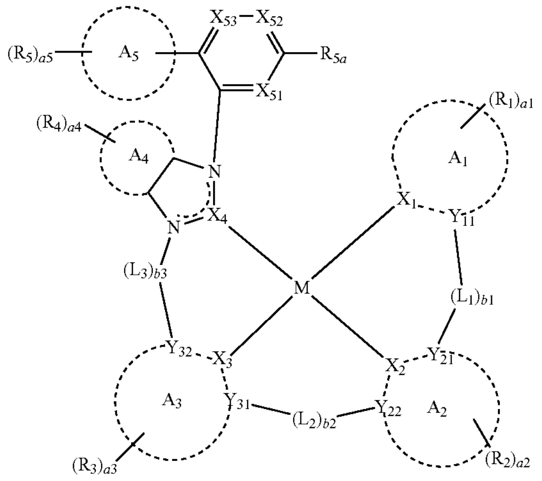

wherein in Formula 1,

M is platinum (Pt), palladium (Pd), nickel (Ni), copper (Cu), silver (Ag), gold (Au), rhodium (Rh), iridium (Ir), ruthenium (Ru), osmium (Os), titanium (Ti), zirconium (Zr), hafnium (Hf), europium (Eu), terbium (Tb), or thulium (Tm), $X_1$ is C, N, O, or S, $X_2$ to $X_4$, $Y_{11}$, $Y_{21}$, $Y_{22}$, $Y_{31}$, and $Y_{32}$ are each independently C or N, $X_{51}$ is $C(R_{51})$ or N, $X_{52}$ is $C(R_{52})$ or N, $X_{53}$ is $C(R_{53})$ or N, $A_1$ to $A_5$ are each independently a $C_3$-$C_{60}$ carbocyclic group or a $C_1$-$C_{60}$ heterocyclic group, $L_1$ to $L_3$ are each independently a single bond, a double bond, *—N($Z_{11}$)—*', *—B($Z_{11}$)—*', *—P($Z_{11}$)—*', *—C($Z_{11}$)($Z_{12}$)—*', *—Si($Z_{11}$)($Z_{12}$)—*', *—Ge($Z_{11}$)($Z_{12}$)—'*, *—S—*', *—Se—*', *—O—*', *—C(═O)—*', *—S(═O)—*', *—S(═O)$_2$—*', *—C($Z_{11}$)═*', *═C($Z_{11}$)—*', *—C($Z_{11}$)═C($Z_{12}$)—*', *—C(═S)—*', or *—C≡C—*',

* and *' each indicate a binding site to a neighboring atom, b1 to b3 are each independently an integer from 1 to 3, $R_1$ to $R_5$, $R_{51}$ to $R_{53}$, $Z_{11}$, and $Z_{12}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$),—B($Q_1$)($Q_2$), —P($Q_1$)($Q_2$), —C(═O)($Q_1$), —S(═O)($Q_1$), —S(═O)$_2$($Q_1$), —P(═O)($Q_1$)($Q_2$), or —P(═S)($Q_1$)($Q_2$), $R_{5a}$ is deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —P($Q_1$)($Q_2$), —C(═O)($Q_1$), —S(═O)($Q_1$), —S(═O)$_2$($Q_1$), —P(═O)($Q_1$)($Q_2$), or —P(═S)($Q_1$)($Q_2$), a1 to a5 are each independently an integer from 0 to 10, when a1 is 2 or more, two $R_1$ (s) of two or more $R_1$ (s) are optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a2 is 2 or more, two $R_2$ (s) of two or more $R_2$ (s) are optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(═O)($Q_{11}$), —S(═O)($Q_{11}$), —S(═O)$_2$ ($Q_{11}$), —P(═O)($Q_{11}$)($Q_{12}$), —P(═S)($Q_{11}$)($Q_{12}$), or a combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(═O)($Q_{21}$), —S(═O)($Q_{21}$), —S(═O)$_2$ ($Q_{21}$), —P(═O)($Q_{21}$)($Q_{22}$), —P(═S)($Q_{21}$)($Q_{22}$), or a combination thereof; or —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(═O)($Q_{31}$), —S(═O)($Q_{31}$), —S(═O)$_2$ ($Q_{31}$), —P(═O)($Q_{31}$)($Q_{32}$), or —P(═S)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or a combination thereof.

2. The light-emitting device of claim 1, wherein the interlayer further includes a hole transport region between the first electrode and the emission layer and an electron transport region between the emission layer and the second electrode, the hole transport region includes a hole injection layer, a hole transport layer, an emission auxiliary layer, an electron blocking layer, or a combination thereof, and the electron transport region includes a buffer layer, a hole blocking layer, an electron control layer, an electron transport layer, an electron injection layer, or a combination thereof.

3. The light-emitting device of claim 1, wherein the emission layer includes the organometallic compound represented by Formula 1.

4. The light-emitting device of claim 1, wherein the emission layer emits blue light having a maximum emission wavelength in a range of about 410 nm to about 500 nm.

5. The light-emitting device of claim 1, wherein the interlayer includes:

a first compound which is the organometallic compound represented by Formula 1; and a second compound including a group represented by Formula 2, a third compound represented by Formula 3, a fourth compound including a group represented by Formula 4, or a combination thereof, the first compound, the second compound, and the third compound are different from one another, the first compound, the second compound, and the fourth compound are different from one another, and the third compound and the fourth compound are identical to or different from each other:

[Formula 2]

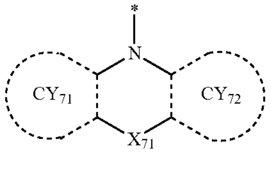

wherein in Formula 2, ring $CY_{71}$ and ring $CY_{72}$ are each independently a TT electron-rich $C_3$-$C_{60}$ cyclic group or a pyridine group, $X_{71}$ is:

a single bond; or a linking group including O, S, N, B, C, Si, or a combination thereof,

* indicates a binding site to a neighboring atom in the second compound, and CBP and mCBP are excluded from the second compound:

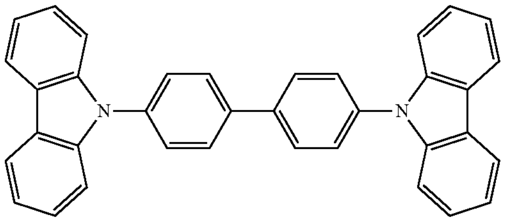

CBP

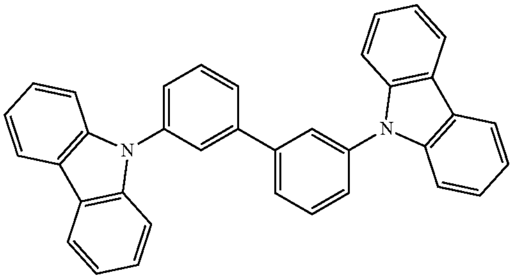

, mCBP

[Formula 3]

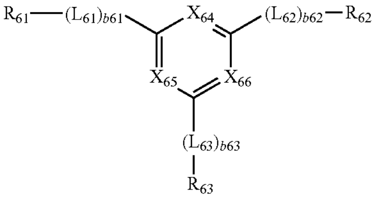

wherein in Formula 3, $L_{61}$ to $L_{63}$ are each independently a single bond, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, b61 to b63 are each independently an integer from 1 to 5, $X_{64}$ is N or C($R_{64}$), $X_{65}$ is N or C($R_{65}$), $X_{66}$ is N or C($R_{66}$), at least one of $X_{64}$ to $X_{66}$ is N, $R_{61}$ to $R_{66}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), —N($Q_1$)($Q_2$), —B($Q_1$)($Q_2$), —C(=O)($Q_1$), —S(=O) 2 ($Q_1$), or —P(=O)($Q_1$)($Q_2$), and $R_{10a}$ and $Q_1$ to $Q_3$ are respectively the same as described in connection with Formula 1,

[Formula 4]

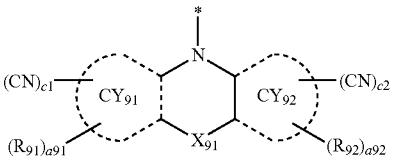

wherein in Formula 4, ring $CY_{91}$ and ring $CY_{92}$ are each independently a TT electron-rich $C_3$-$C_{60}$ cyclic group or a pyridine group, $X_{91}$ is:

a single bond; or a linking group including O, S, N, B, C, Si, or a combination thereof, $R_{91}$ and $R_{92}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —C($Q_1$)($Q_2$)($Q_3$), —Si($Q_1$)($Q_2$)($Q_3$), —N($Q_1$)($Q_2$), —B($Q_1$)($Q_2$), —C(=O)($Q_1$), —S(=O)$_2$ ($Q_1$), or —P(=O)($Q_1$)($Q_2$), a91 and a92 are each independently an integer from 0 to 5, c1 and c2 are each independently an integer from 0 to 5, the sum of c1 and c2 is 1 or more, $R_{10a}$ and $Q_1$ to $Q_3$ are respectively the same as described in connection with Formula 1, and

* indicates a binding site to a neighboring atom in the fourth compound.

6. The light-emitting device of claim 5, wherein the emission layer includes a dopant and a host, the dopant includes the first compound, and the host includes the second compound, the third compound, the fourth compound, or a combination thereof.

7. The light-emitting device of claim 5, wherein the emission layer includes a dopant and a host, the dopant includes the first compound, and the host includes:

the second compound; and at least one of the third compound and the fourth compound.

8. An electronic apparatus comprising:

the light-emitting device of claim 1; and a thin-film transistor, wherein the thin-film transistor includes a source electrode and a drain electrode, and the first electrode of the light-emitting device is electrically connected to at least one of the source electrode and the drain electrode of the thin-film transistor.

9. The electronic apparatus of claim 8, further comprising a color filter, a color conversion layer, a touch screen layer, a polarizing layer, or a combination thereof.

10. An organometallic compound represented by Formula 1:

[Formula 1]

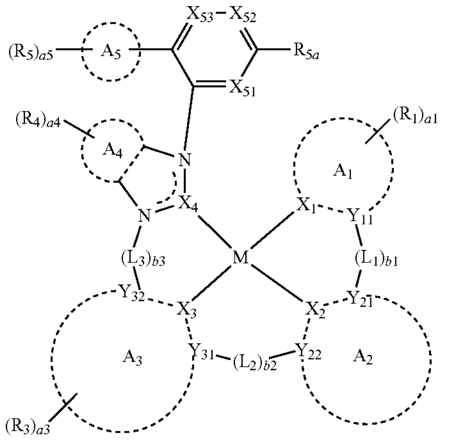

wherein in Formula 1,

M is platinum (Pt), palladium (Pd), nickel (Ni), copper (Cu), silver (Ag), gold (Au), rhodium (Rh), iridium (Ir), ruthenium (Ru), osmium (Os), titanium (Ti), zirconium (Zr), hafnium (Hf), europium (Eu), terbium (Tb), or thulium (Tm), $X_1$ is C, N, O, or S, $X_2$ to $X_4$, $Y_{11}$, $Y_{21}$, $Y_{22}$, $Y_{31}$, and $Y_{32}$ are each independently C or N, $X_{51}$ is C($R_{51}$) or N, $X_{52}$ is C($R_{52}$) or N, $X_{53}$ is C($R_{53}$) or N, $A_1$ to $A_5$ are each independently a $C_3$-$C_{60}$ carbocyclic group or a $C_1$-$C_{60}$ heterocyclic group, $L_1$ to $L_3$ are each independently a single bond, a double bond, *—N($Z_{11}$)—*', *—B($Z_{11}$)—*', *—P($Z_{11}$)—*+, *—C($Z_{11}$)($Z_{12}$)—*', *—Si($Z_{11}$)($Z_{12}$)—*', *—Ge($Z_{11}$)($Z_{12}$)—*', *—S—*', *—Se—*', *—O—*', *—C(=O)—*', *—S(=O)—*', *—S(=O)$_2$—*', *—C($Z_{11}$)=*', *=C($Z_{11}$)—*', *—C($Z_{11}$)=C($Z_{12}$)—*', *—C(=S)—*', or *—C≡C—* ', and * and *' each indicate a binding site to a neighboring atom, b1 to b3 are each independently an integer from 1 to 3, $R_1$ to $R_5$, $R_{51}$ to $R_{53}$, $Z_{11}$, and $Z_{12}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)($Q_1$), —S(=O)$_2$ ($Q_1$), —P(=O)($Q_1$)($Q_2$), or —P(=S)($Q_1$)($Q_2$), $R_{5a}$ is deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —P($Q_1$)($Q_2$), —C(═O)($Q_1$), —S(═O)($Q_1$), —S(═O)$_2$ ($Q_1$), —P(═O)($Q_1$)($Q_2$), or —P(═S)($Q_1$)($Q_2$), a1 to a5 are each independently an integer from 0 to 10, when a1 is 2 or more, two $R_1$ (s) of two or more $R_1$ (s) are optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, when a2 is 2 or more, two $R_2$ (s) of two or more $R_2$ (s) are optionally bonded together to form a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(═O)($Q_{11}$), —S(═O)($Q_{11}$), —S(═O)$_2$ ($Q_{11}$), —P(═O)($Q_{11}$)($Q_{12}$), —P(═S)($Q_{11}$)($Q_{12}$), or a combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-Coo carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(═O)($Q_{21}$), —S(═O)($Q_{21}$), —S(═O)$_2$ ($Q_{21}$), —P(═O)($Q_{21}$)($Q_{22}$), —P(═S)($Q_{21}$)($Q_{22}$), or a combination thereof; or —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(═O)($Q_{31}$), —S(═O)($Q_{31}$), —S(═O)$_2$ ($Q_{31}$), —P(═O)($Q_{31}$)($Q_{32}$), or —P(═S)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or a combination thereof.

11. The organometallic compound of claim 10, wherein $X_1$ is N, and $X_2$ to $X_4$ are each C; or $X_1$ is O or S, and $X_2$ to $X_4$ are each C; or $X_1$ to $X_4$ are each C; or $X_1$, $X_3$, and $X_4$ are each C, and $X_2$ is N.

12. The organometallic compound of claim 10, wherein a bond between $X_1$ and M is a covalent bond or a coordinate bond, a bond between $X_2$ and M is a covalent bond, a bond between $X_3$ and M is a covalent bond, and a bond between $X_4$ and M is a coordinate bond.

13. The organometallic compound of claim 10, wherein $X_{51}$ is C($R_{51}$), $X_{52}$ is C($R_{52}$), and $X_{53}$ is C($R_{53}$).

14. The organometallic compound of claim 10, wherein $A_1$ is an $X_1$-containing 6-membered ring, an $X_1$-containing 6-membered ring condensed with at least one 5-membered ring, an $X_1$-containing 5membered ring, or an $X_1$-containing 5-membered ring condensed with at least one 6-membered ring, $A_2$ is an $X_2$-containing 6-membered ring or an $X_2$-containing 6-membered ring condensed with at least one 5-membered ring, $A_3$ is an $X_3$-containing 6-membered ring, and $A_4$ is an $X_4$-containing 6-membered ring.

15. The organometallic compound of claim 10, wherein an $X_1$-containing 6-membered ring in $A_1$, an $X_1$-containing 6-membered ring condensed with at least one 5-membered ring in $A_1$, an $X_2$-containing 6-membered ring in $A_2$, an $X_2$-containing 6-membered ring condensed with at least one 5-membered ring in $A_1$, an $X_3$-containing 6-membered ring in $A_3$, and an $X_4$-containing 6-membered ring in $A_4$ are each independently a benzene group, a pyridine group, a pyrimidine group, a pyridazine group, or a pyrazine group, and an $X_1$-containing 5-membered ring in $A_1$ and an $X_1$-containing 5-membered ring condensed with at least one 6-membered ring in $A_1$ are each independently a pyrrole group, a pyrazole group, an imidazole group, a triazole group, a furan group, an oxazole group, an iso-oxazole group, a thiazole group, an isothiazole group, an oxadiazole group, or a thiadiazole group.

16. The organometallic compound of claim 10, wherein at least one of Condition 1 to Condition 4 is satisfied:

[Condition 1]

a group represented by

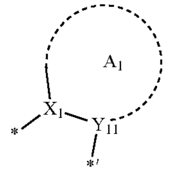

in Formula 1 is represented by one of Formulae A1(1) to A1(44):

A1(1)

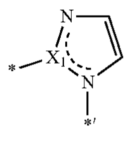

-continued
A1(2)
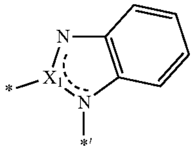
A1(3)
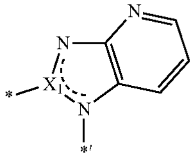
A1(4)
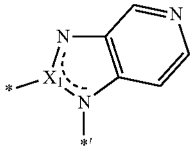
A1(5)
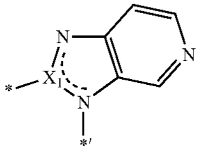
A1(6)
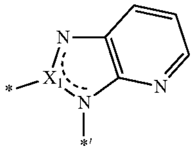
A1(7)
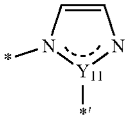
A1(8)
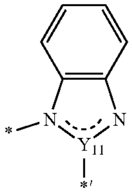
A1(9)
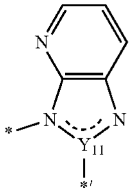
A1(10)
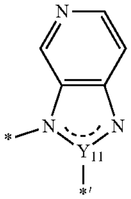
-continued
A1(11)
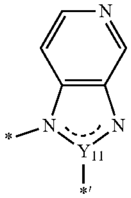
A1(12)
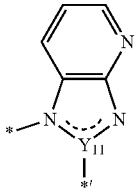
A1(13)
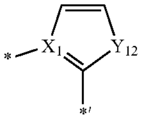
A1(14)
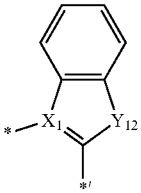
A1(15)
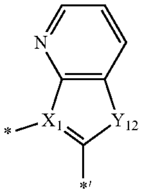
A1(16)
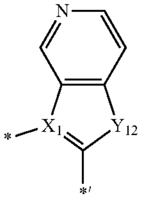
A1(17)
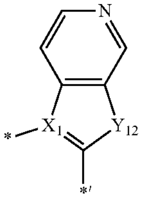
A1(18)
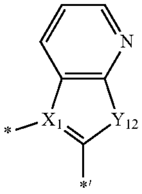

-continued
A1(19)
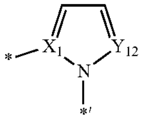
A1(20)
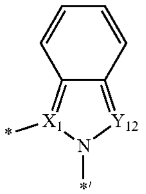
A1(21)
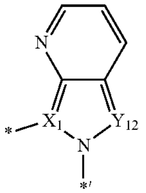
A1(22)
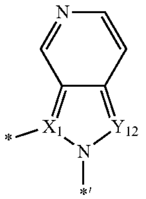
A1(23)
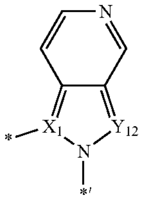
A1(24)
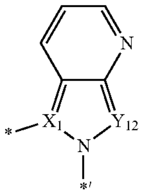
A1(25)
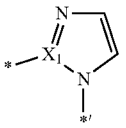
A1(26)
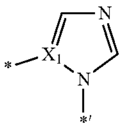
A1(27)
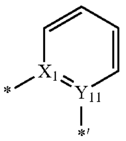
-continued
A1(28)
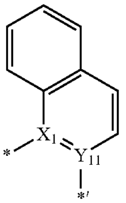
A1(29)
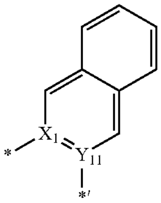
A1(30)
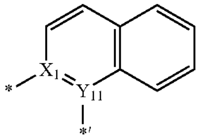
A1(31)
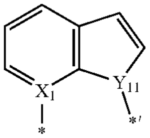
A1(32)
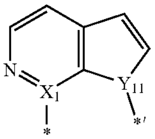
A1(33)
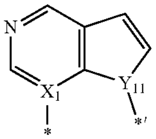
A1(34
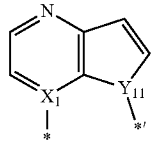
A1(35)
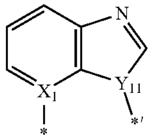
A1(36)
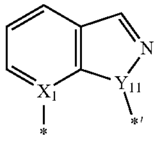

-continued
A1(37)
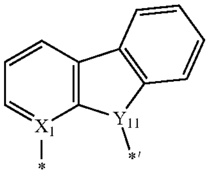
A1(38)
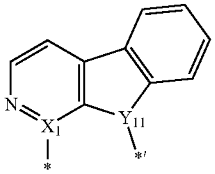
A1(39)
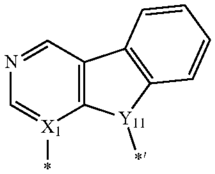
A1(40)
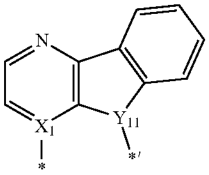
A1(41)
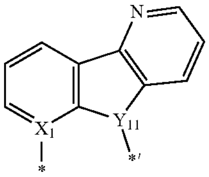
A1(42)
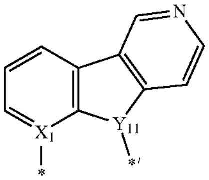
A1(43)
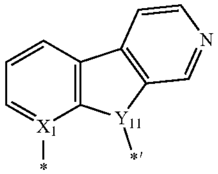
A1(44)
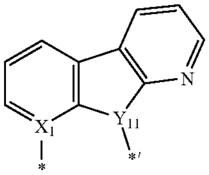
wherein in Formulae $A_1$ (1) to $A_1$ (44),
$X_1$ and $Y_{11}$ are respectively the same as described in Formula 1,
$Y_{12}$ is C, N, O, or S,
* indicates a binding site to M, and
*' indicates a binding site to $(L_1)_{b1}$;
[Condition 2]
a group represented by
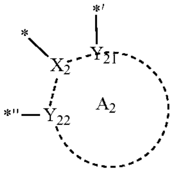
in Formula 1 is represented by one of Formulae $A_2$ (1) to $A_2$ (11):
A2(1)
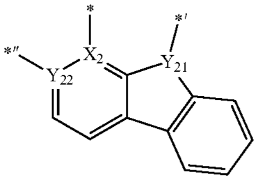
A2(2)
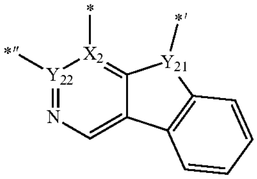
A2(3)
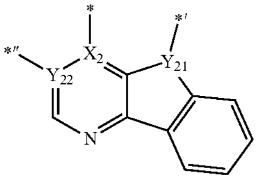
A2(4)
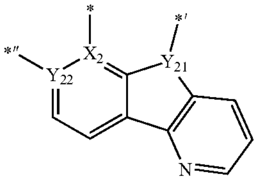
A2(5)
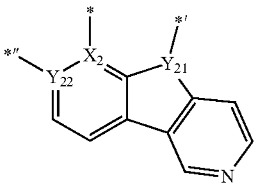
A2(6)
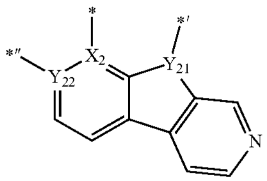

-continued

A2(7)

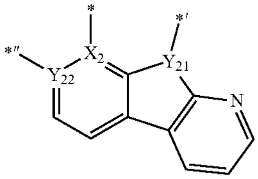

A2(8)

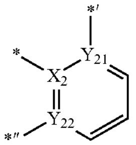

A2(9)

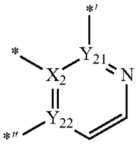

A2(10)

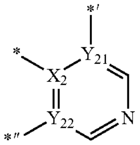

A2(11)

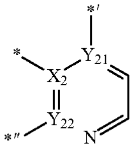

wherein in Formulae $A_2$ (1) to $A_2$ (11), $X_2$, $Y_{21}$, and $Y_{22}$ are respectively the same as described in Formula 1,

* indicates a binding site to M,

*' indicates a binding site to $(L_1)_{b1}$, and

*" indicates a binding site to $(L_2)_{b2}$;

[Condition 3]

a group represented by

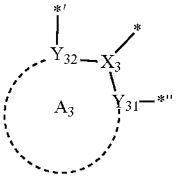

in Formula 1 is represented by one of Formulae $A_3$ (1) to $A_3$ (4):

A3(1)

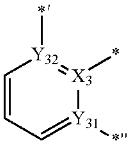

-continued

A3(2)

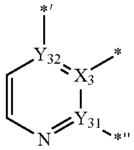

A3(3)

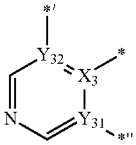

A3(4)

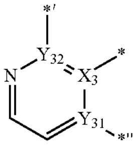

wherein in Formulae $A_3$ (1) to $A_3$ (4), $X_3$, $Y_{31}$, and $Y_{32}$ are respectively the same as described in Formula 1,

* indicates a binding site to M,

*' indicates a binding site to $(L_3)$ b3, and

*" indicates a binding site to $(L_2)$ b2;

[Condition 4]

a group represented by

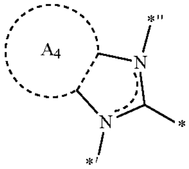

in Formula 1 is represented by one of Formulae $A_4$ (1) to $A_4$ (13):

A4(1)

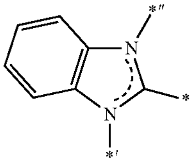

A4(2)

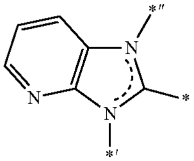

A4(3)

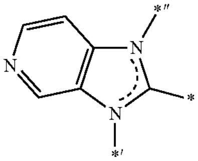

-continued

A4(4)

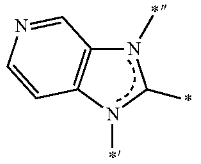

A4(5)

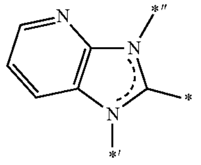

A4(6)

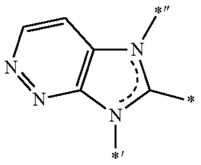

A4(7)

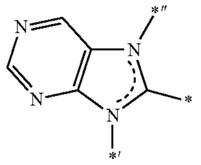

A4(8)

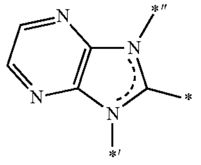

A4(9)

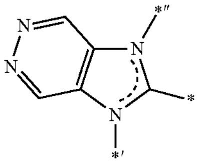

A4(10)

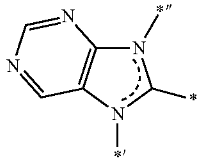

A4(11)

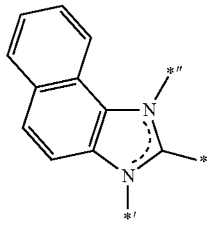

A4(12)

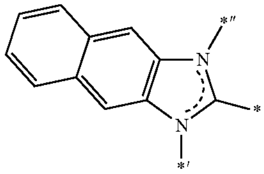

-continued

A4(13)

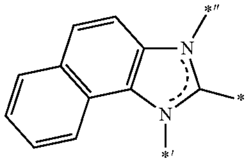

wherein in Formulae $A_4$ (1) to $A_4$ (13),

*indicates a binding site to M,

*' indicates a binding site to $(L_3)$ b3, and

*" indicates a binding site to a neighboring atom.

17. The organometallic compound of claim 10, wherein $A_5$ is a $C_6$-$C_{60}$ aryl group or a $C_1$-$C_{60}$ heteroaryl group.

18. The organometallic compound of claim 10, wherein $L_1$ is a single bond or *—N($Z_{11}$)—*';

$L_2$ is *—N($Z_{11}$)—*', *—B($Z_{11}$)—*', *—Si($Z_{11}$)($Z_{12}$)—*', *—S—*', or *—O—*';

$L_3$ is a single bond; or a combination thereof.

19. The organometallic compound of claim 10, wherein $R_{5a}$ is:

deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, an adamantanyl group, a norbornanyl group, a norbornenyl group, a cyclopentenyl group, a cyclohexenyl group, a phenyl group, a naphthyl group, a pyridinyl group, a pyrimidinyl group, or a combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, or a benzocarbazolyl group, each unsubstituted or substituted with hydrogen, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, an adamantanyl group, a norbornanyl group, a norbornenyl group, a cyclopentenyl group, a cyclohexenyl group, a phenyl group, a naphthyl group, a fluorenyl group, a phenanthrenyl group, an anthracenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a quinolinyl group, an isoquinolinyl group, a carbazolyl group, a benzoimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, or a combination thereof.

20. The organometallic compound of claim 10, wherein the organometallic compound is selected from Compounds 1 to 150:

1

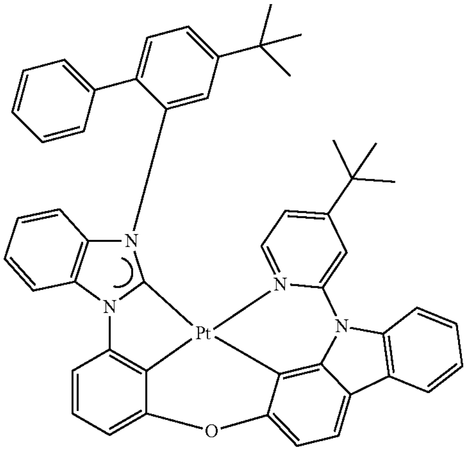

2

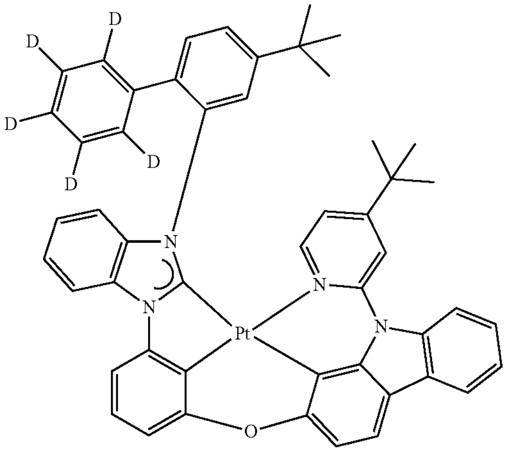

-continued

3

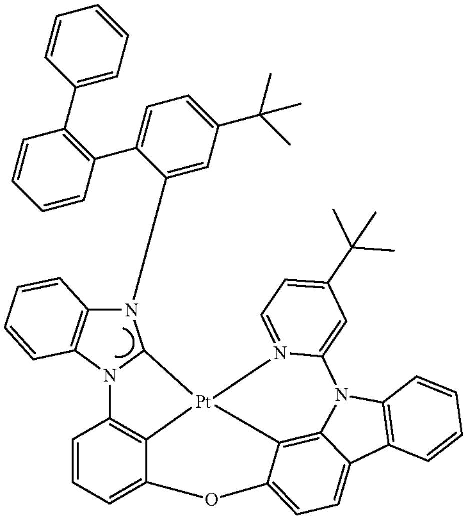

4

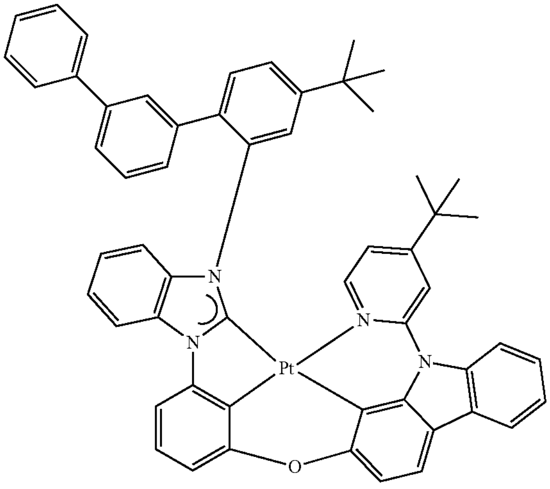

5

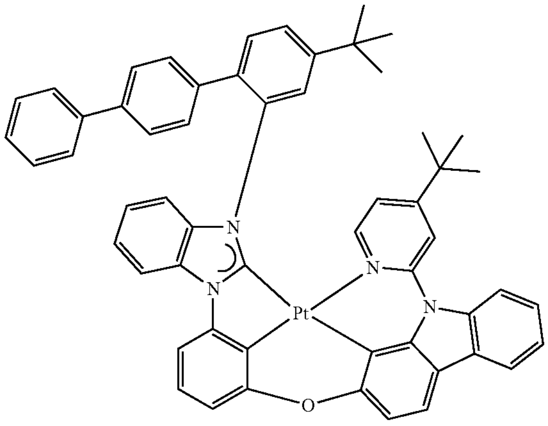

-continued
6
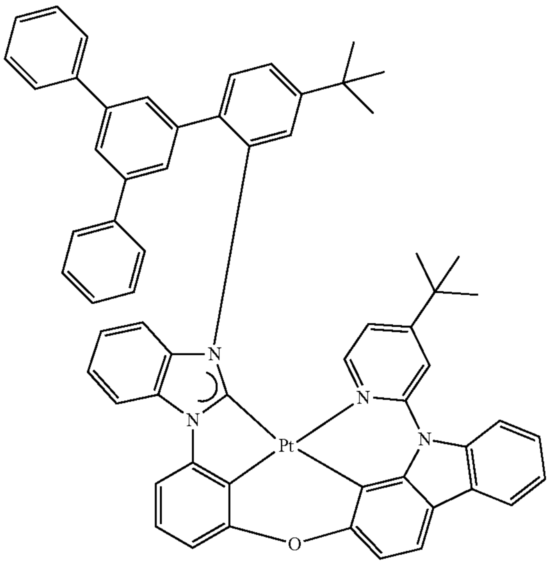
7
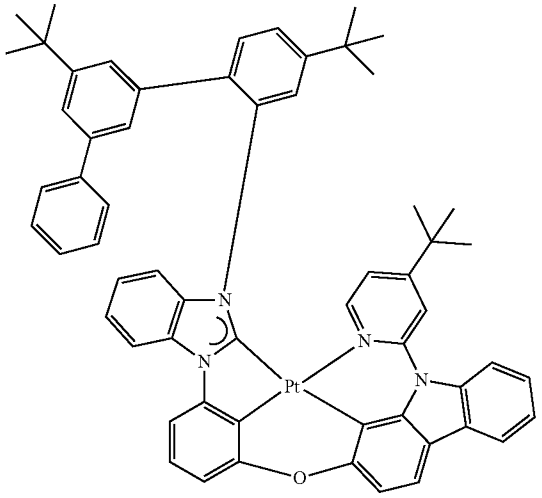
8
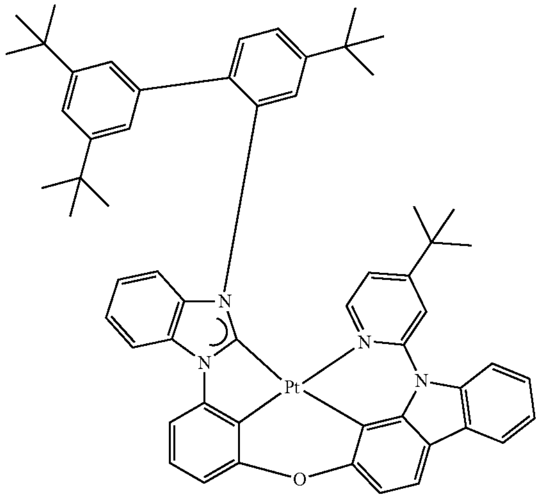
-continued
9
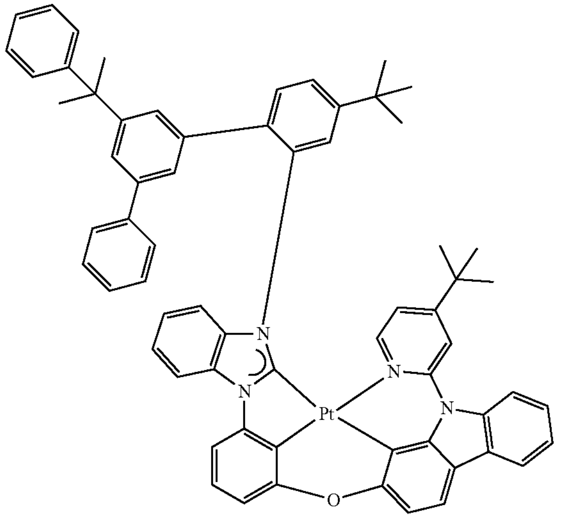
10
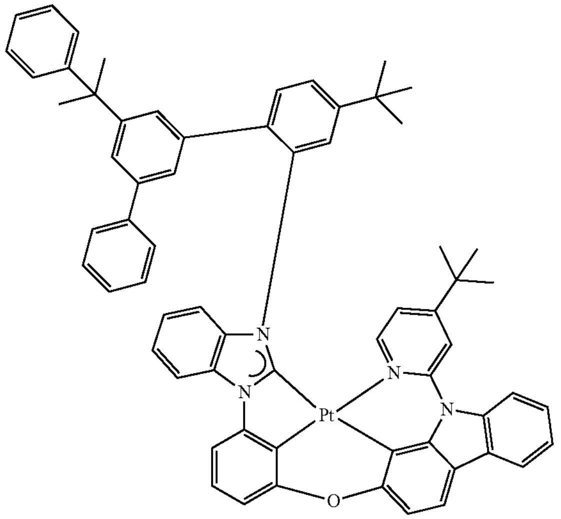
11
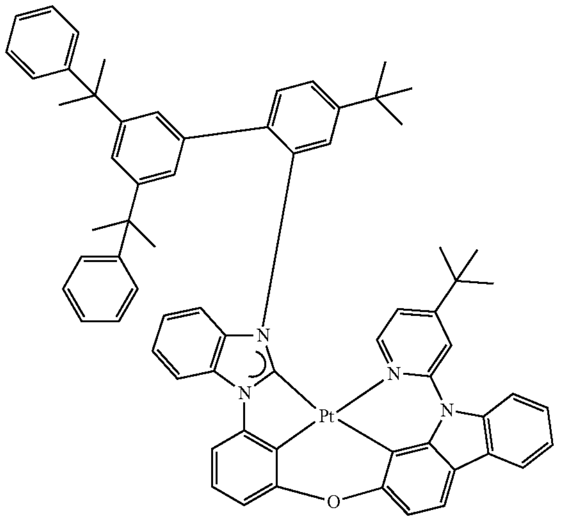

-continued
12
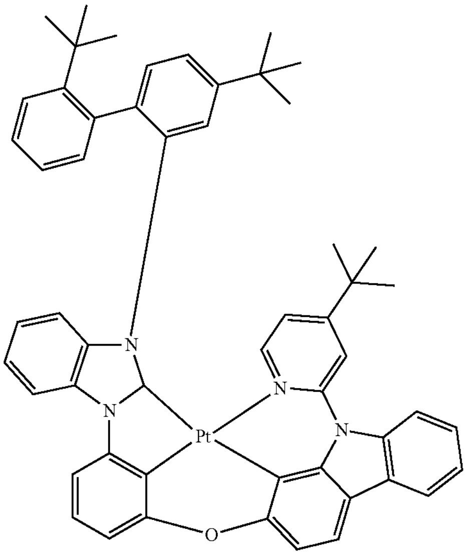
13
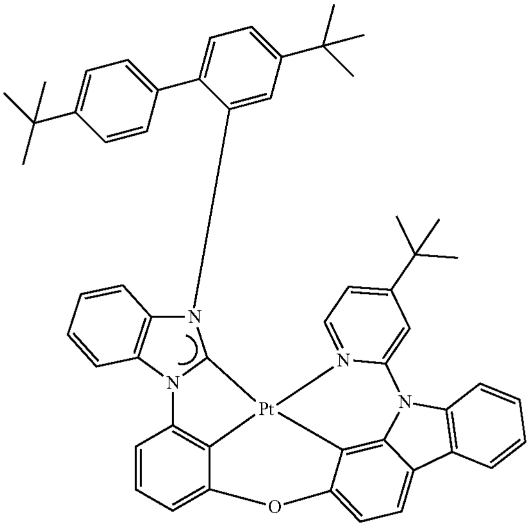
14
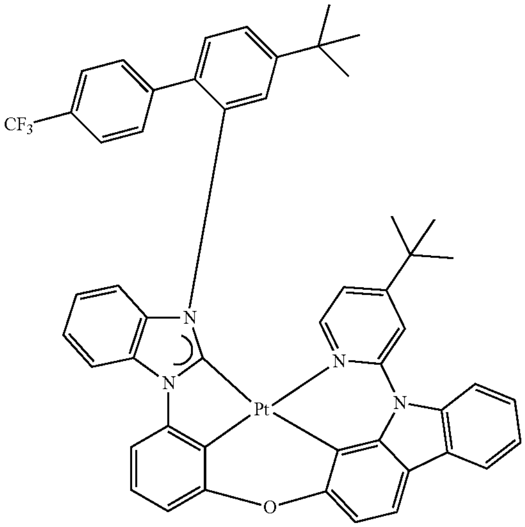
-continued
15
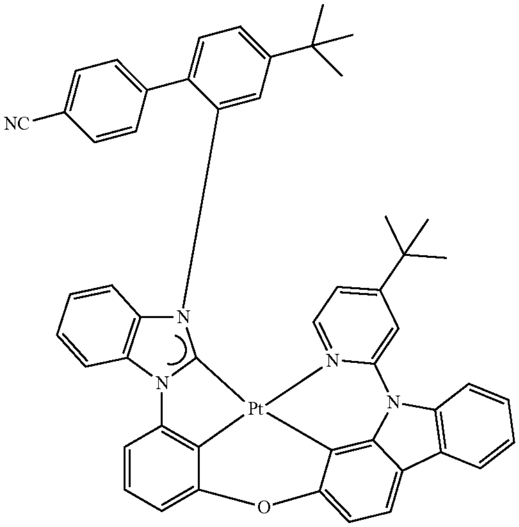
16
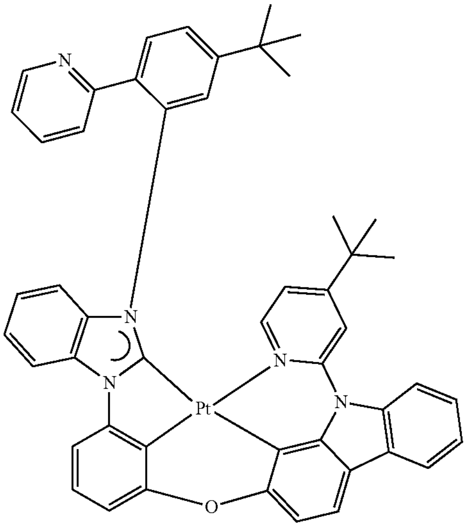
17
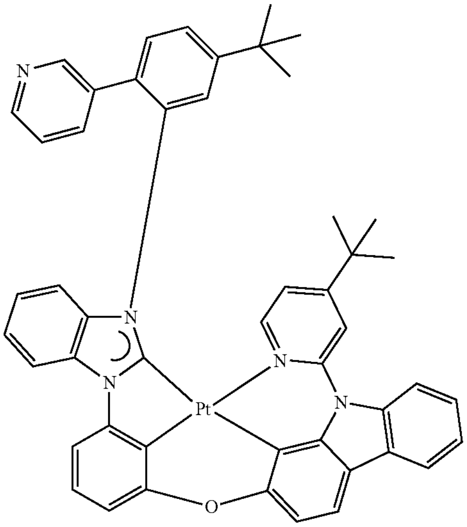

18
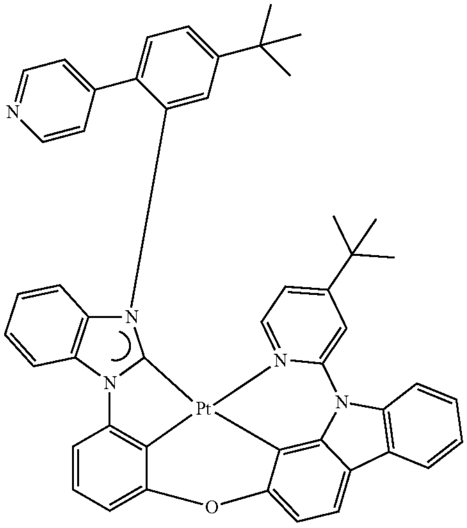
19
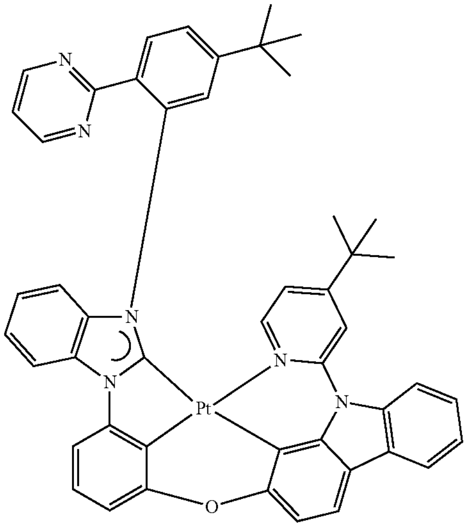
20
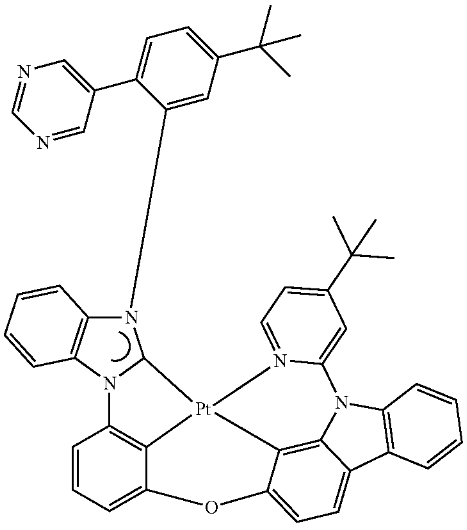
21
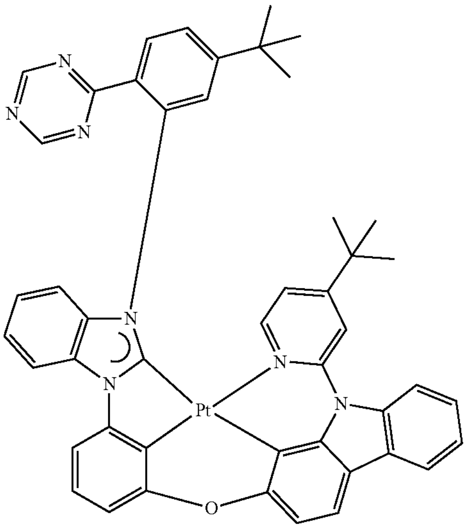
22
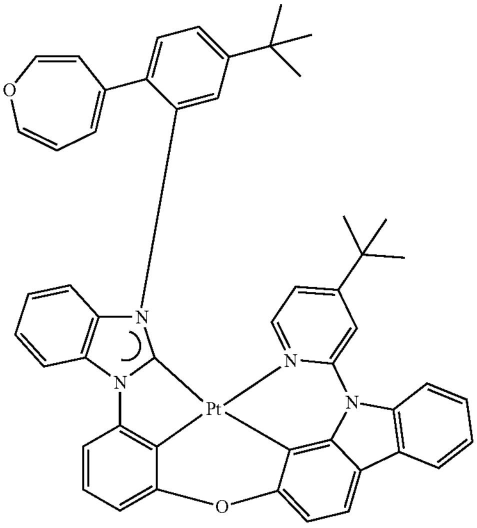
23
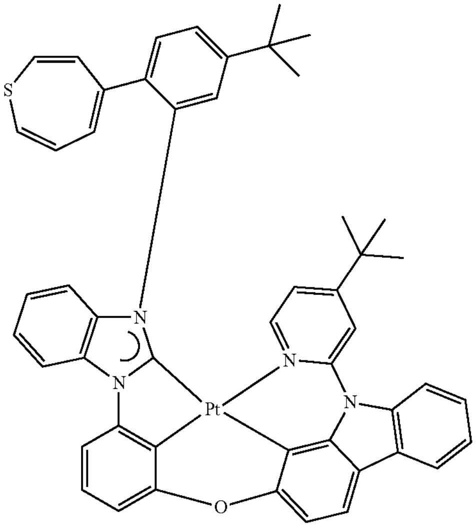

-continued
24
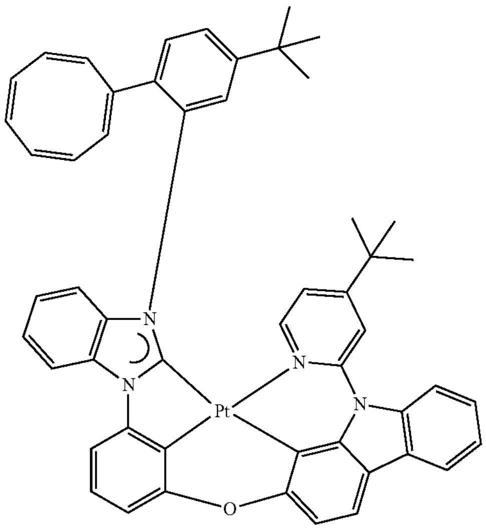
25
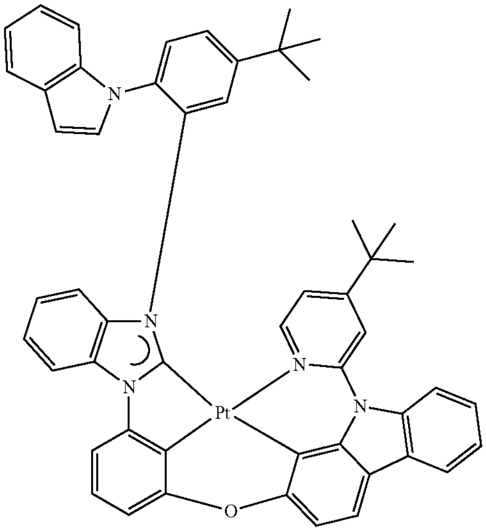
26
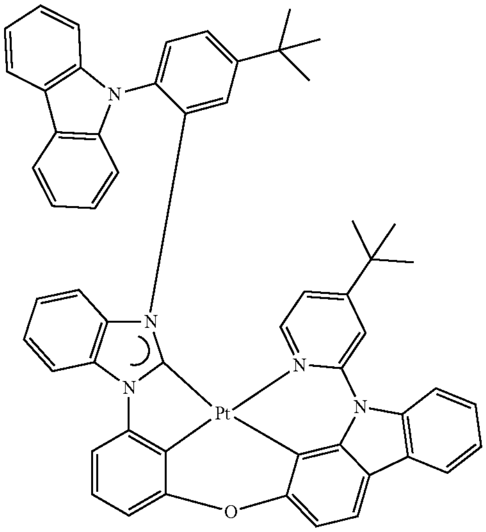
-continued
27
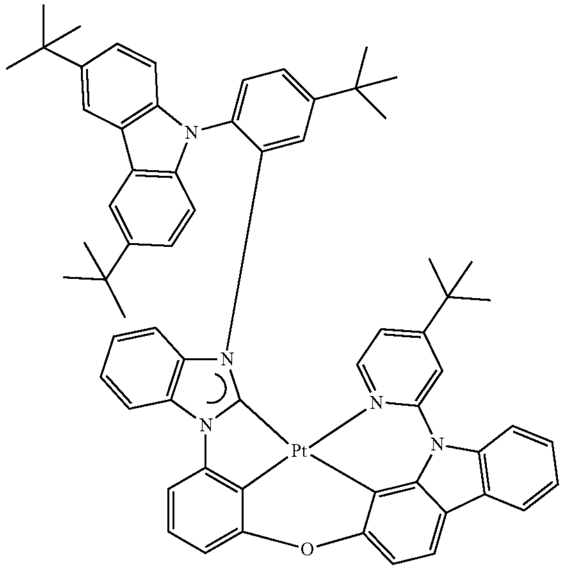
28
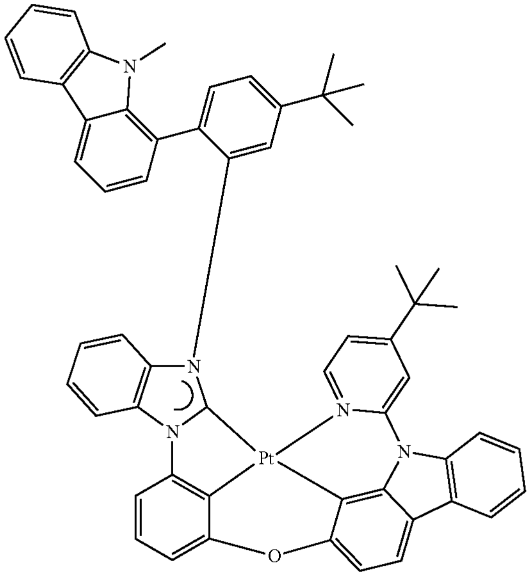

-continued
29
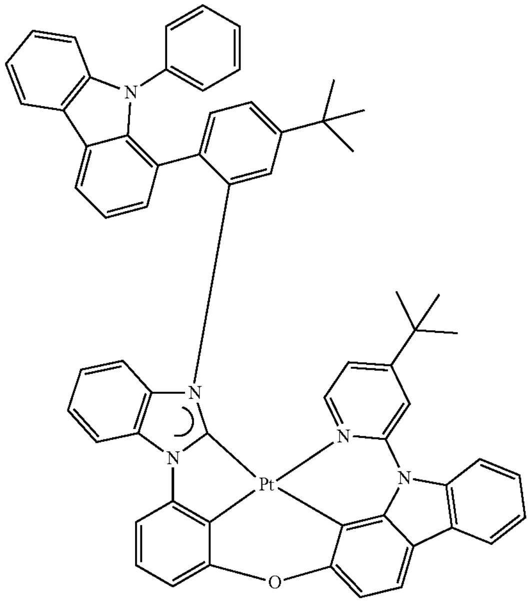
30
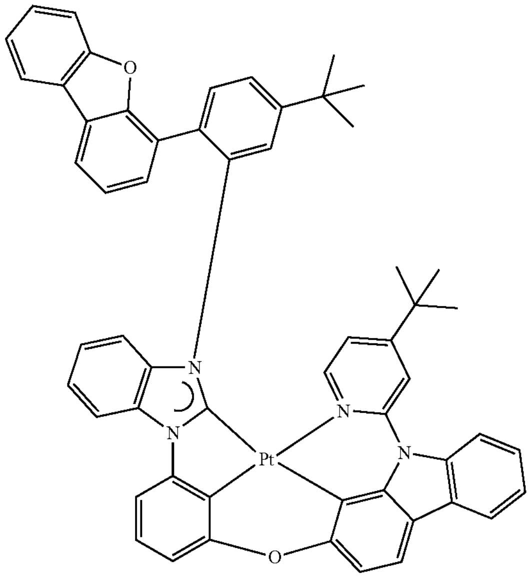
-continued
31
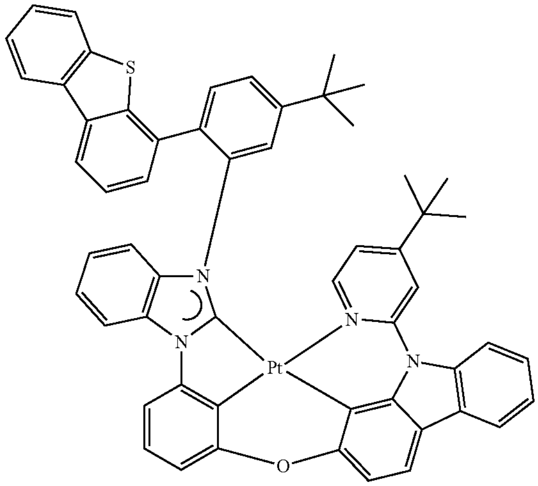
32
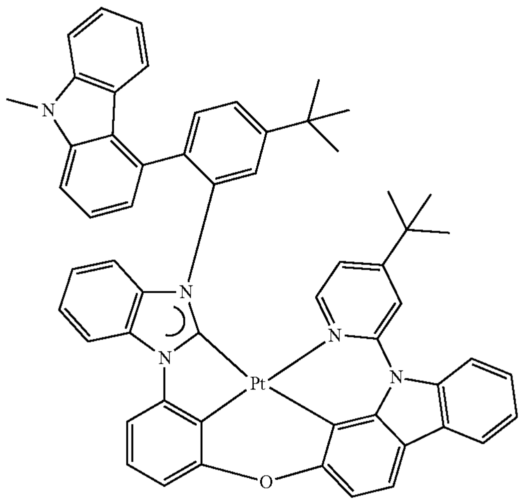
33
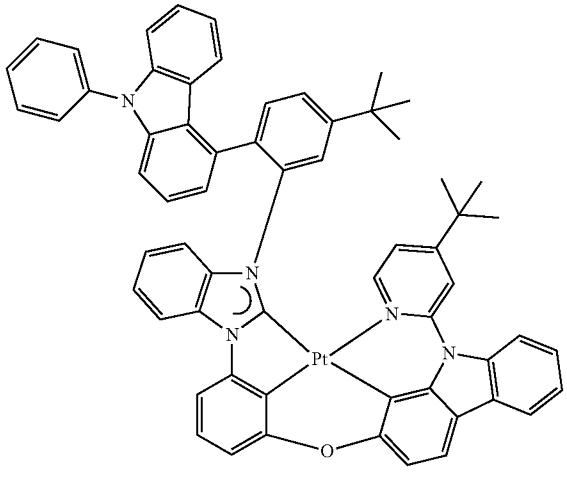

34
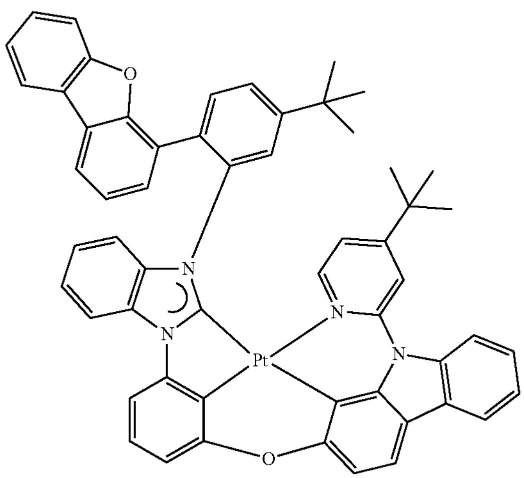
35
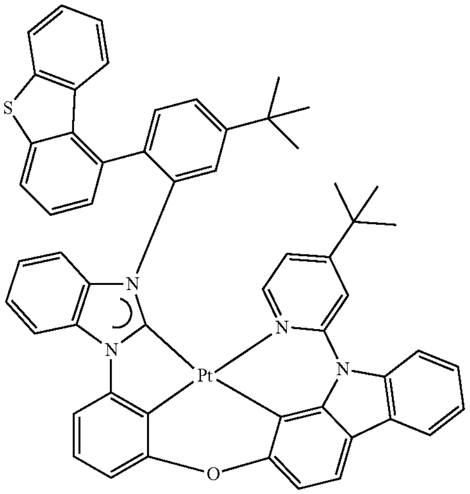
36
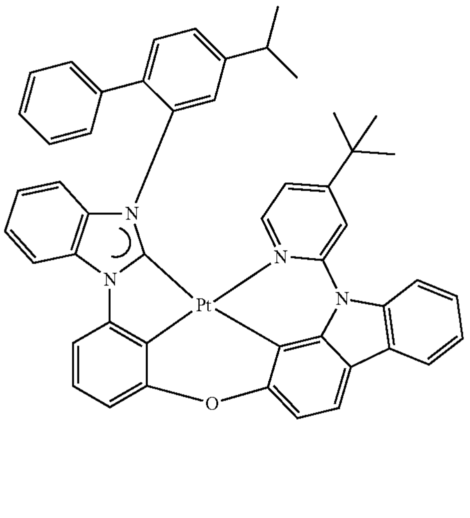
37
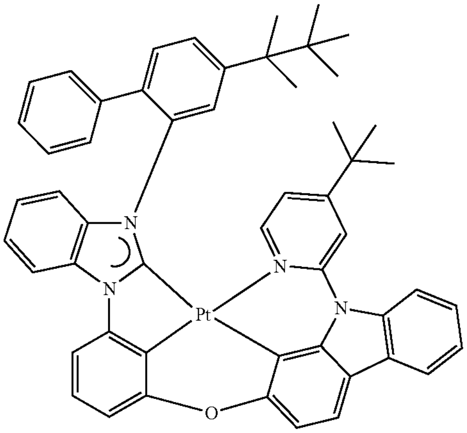
38
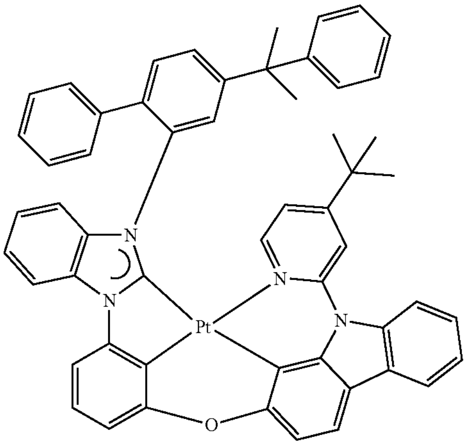
39
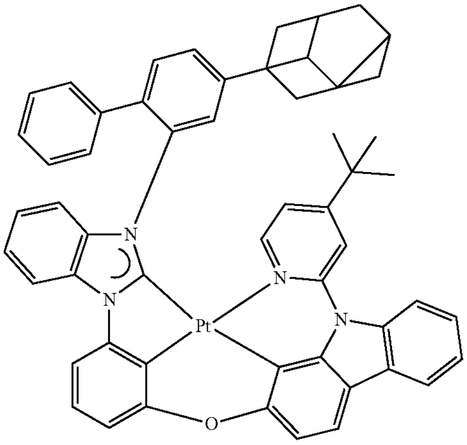

-continued
40
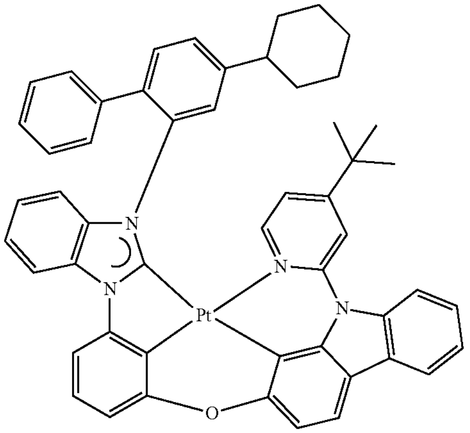
41
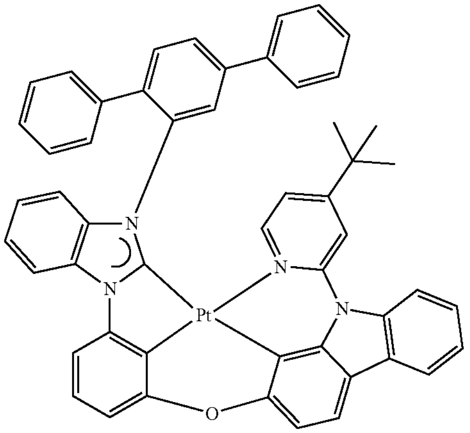
42
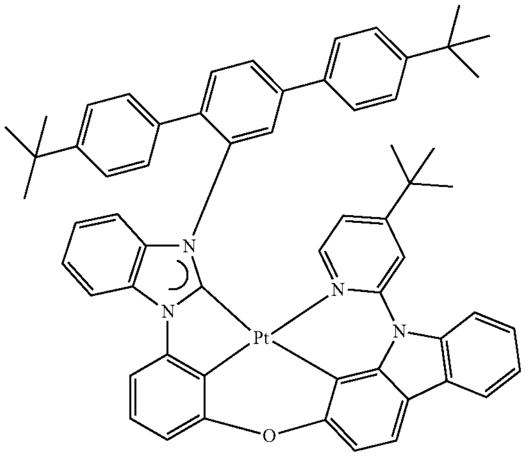
-continued
43
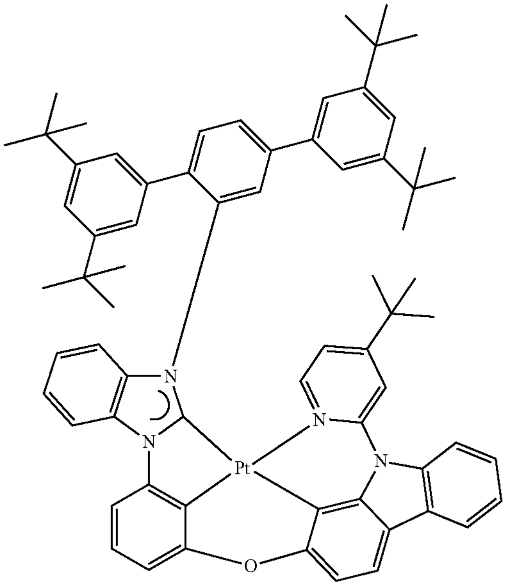
44
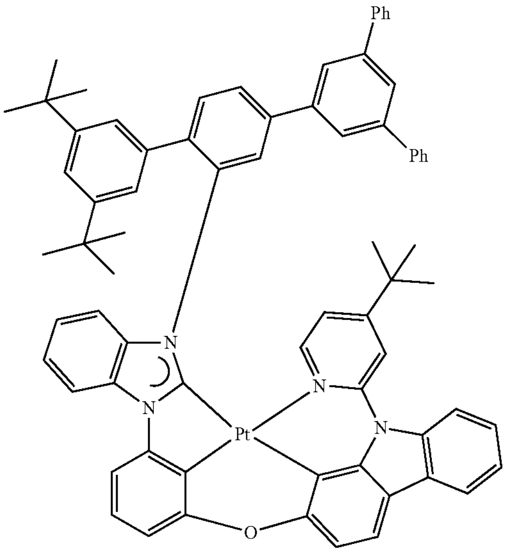

-continued
45
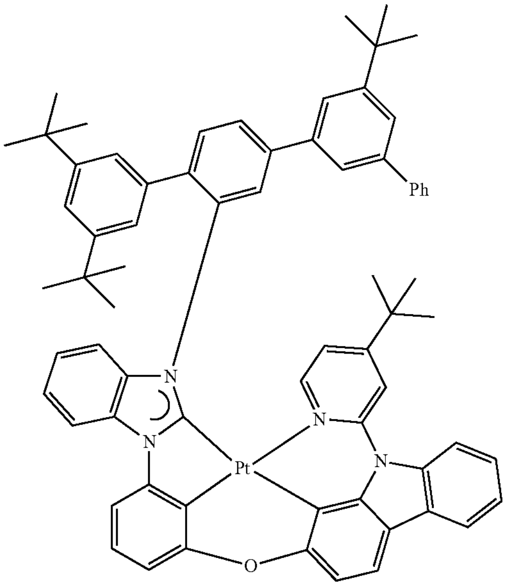
46
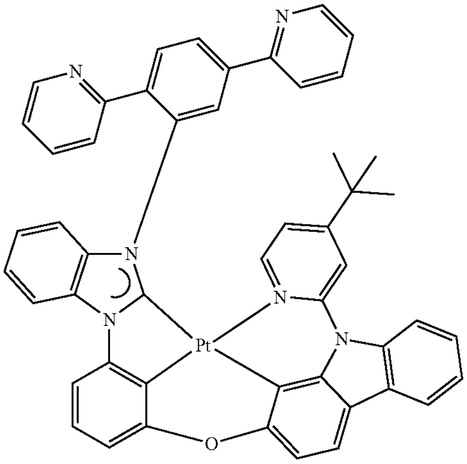
47
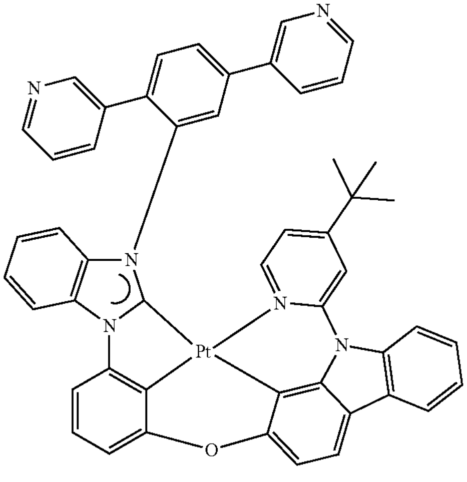
-continued
48
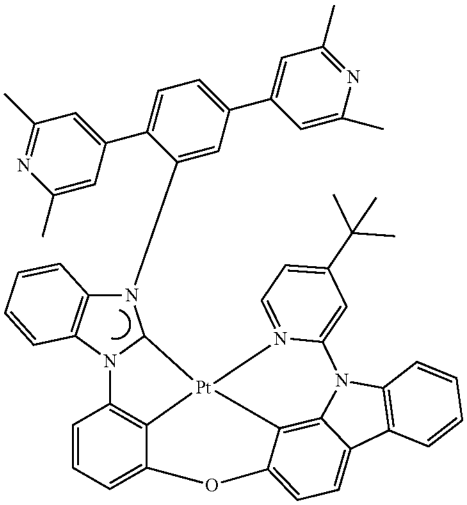
49
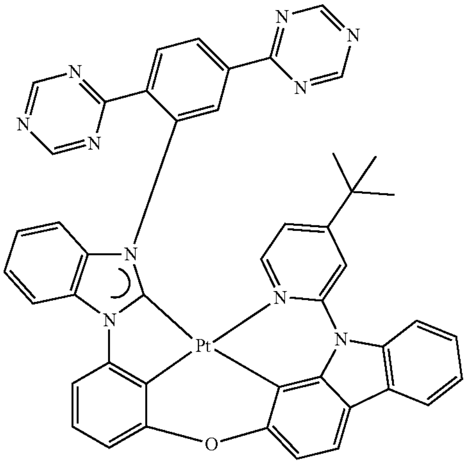
50
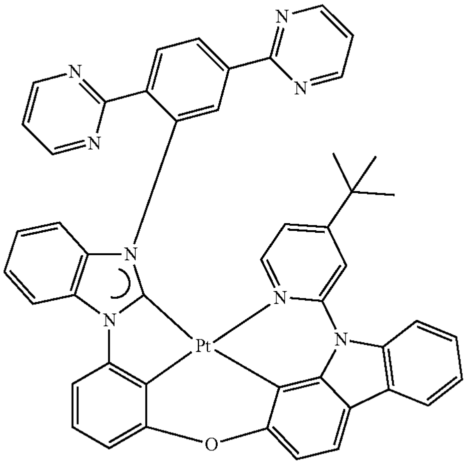

-continued
51
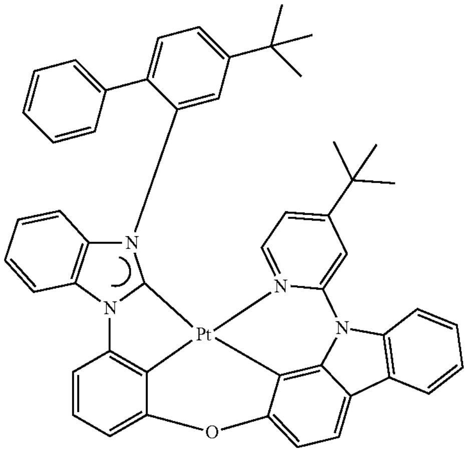
52
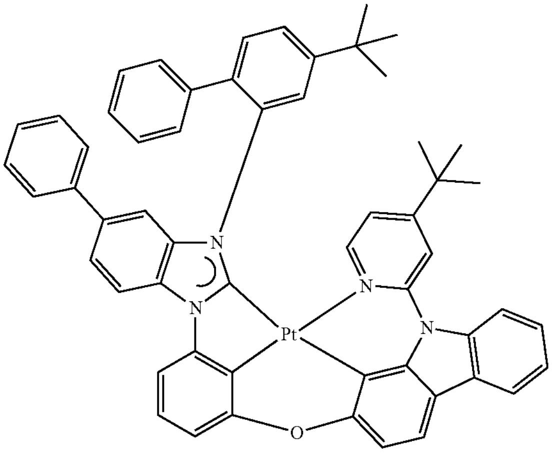
53
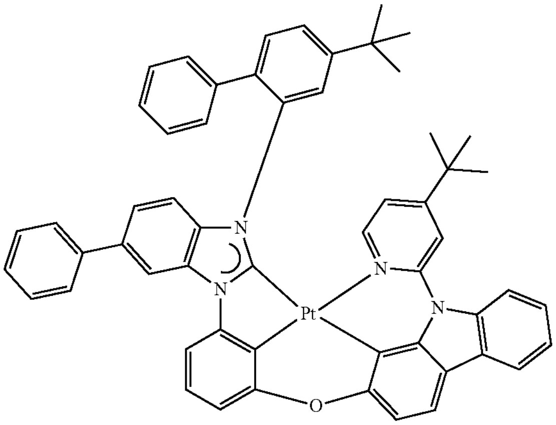
-continued
54
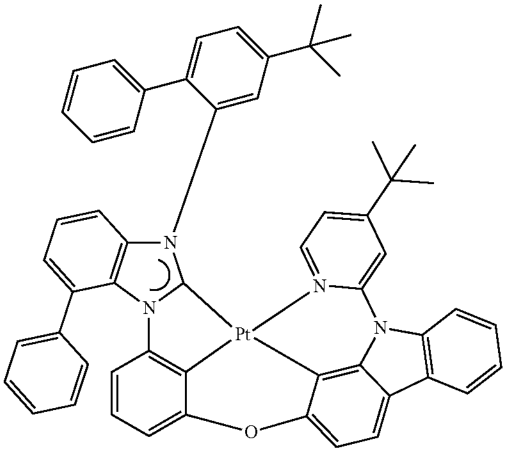
55
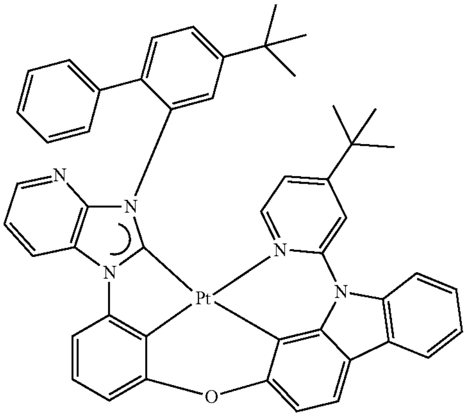
56
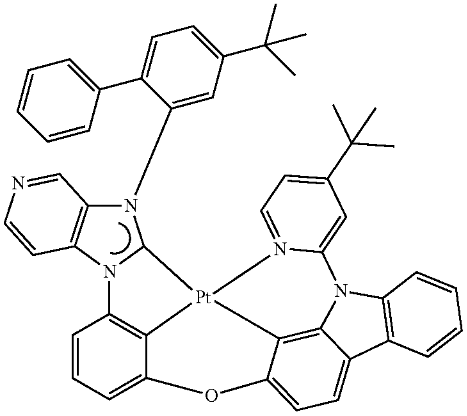

-continued
57
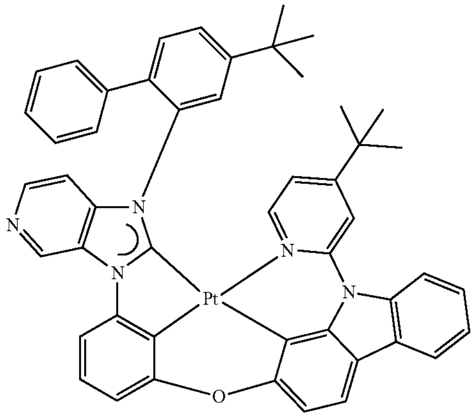
58
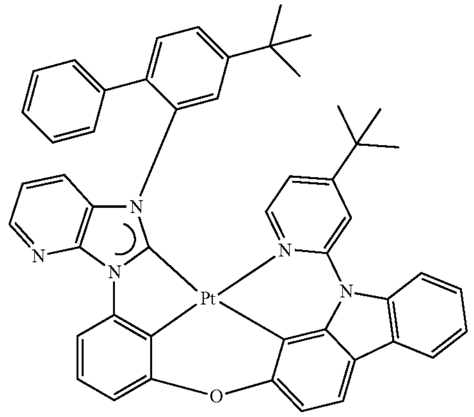
59
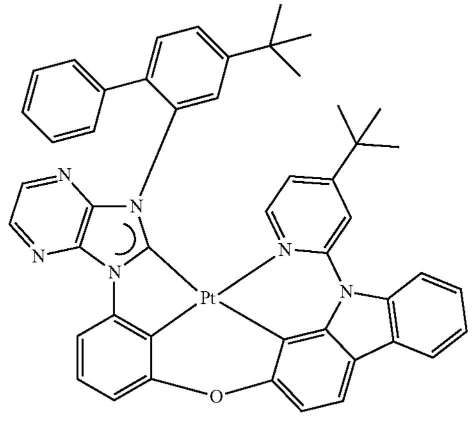
-continued
60
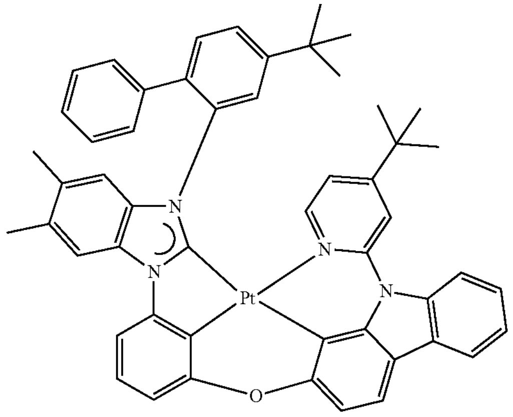
61
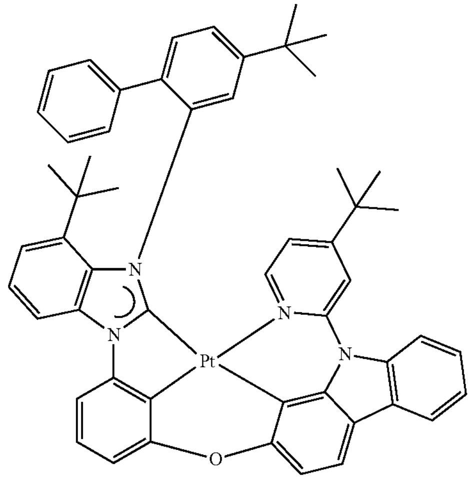
62
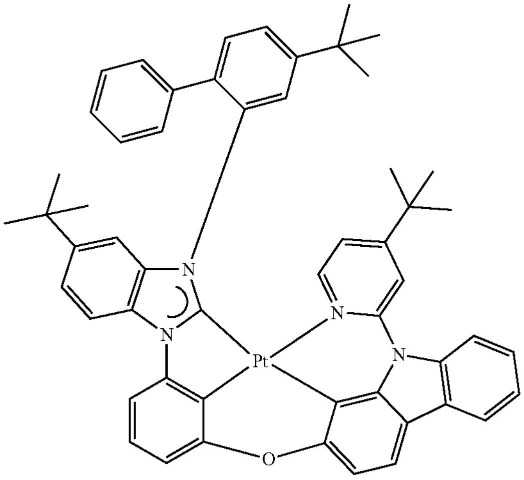

-continued
63
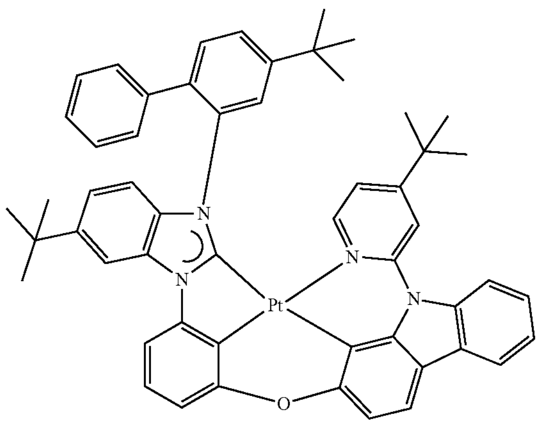
64
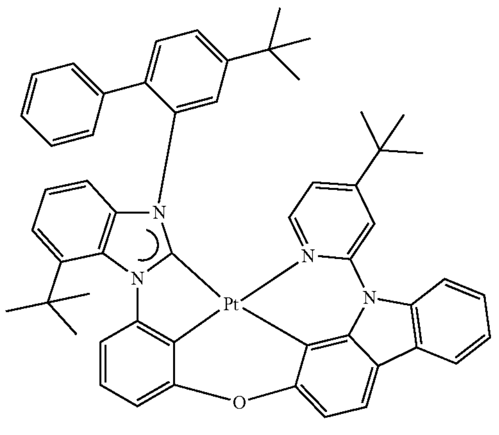
65
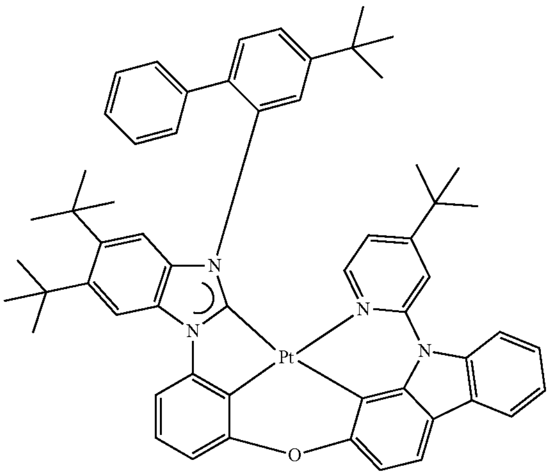
-continued
66
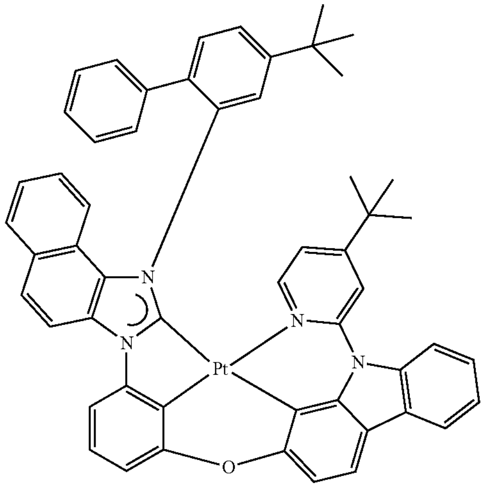
67
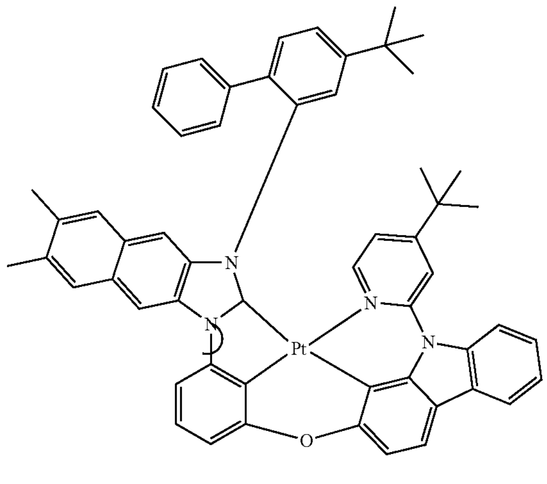
68
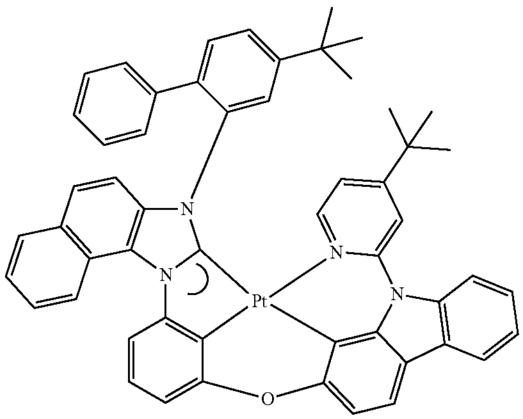

69
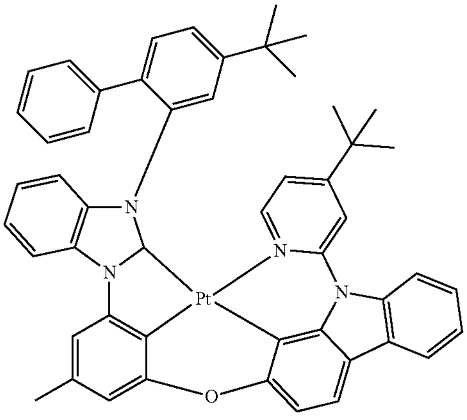
70
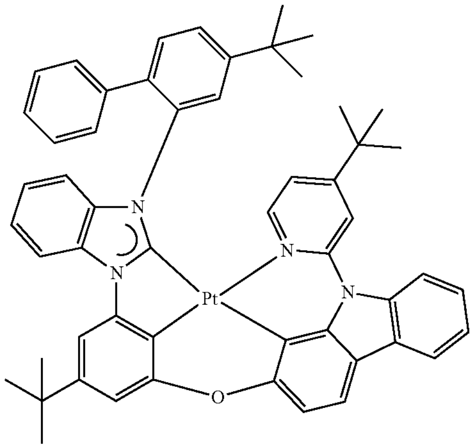
71
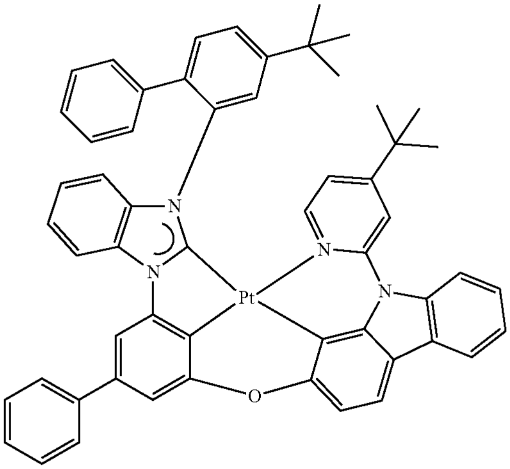
72
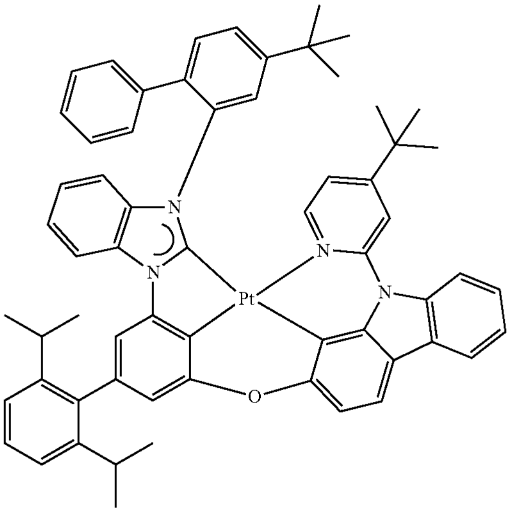
73
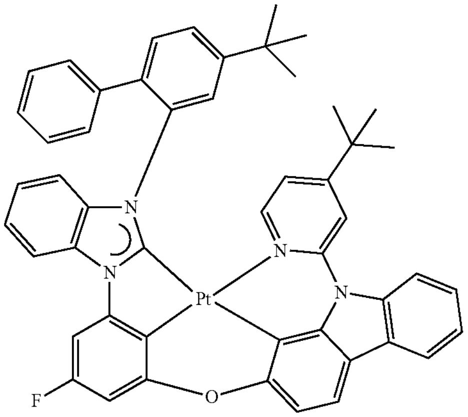
74
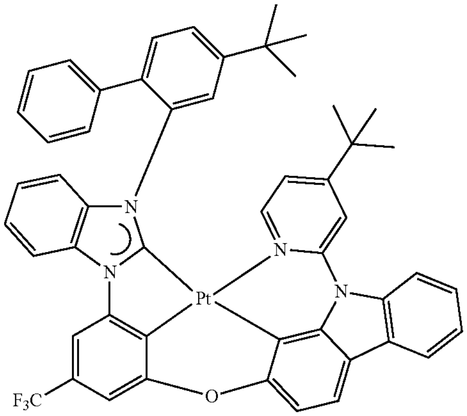

-continued
75
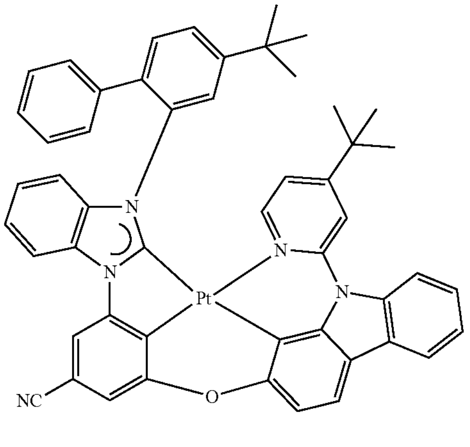
76
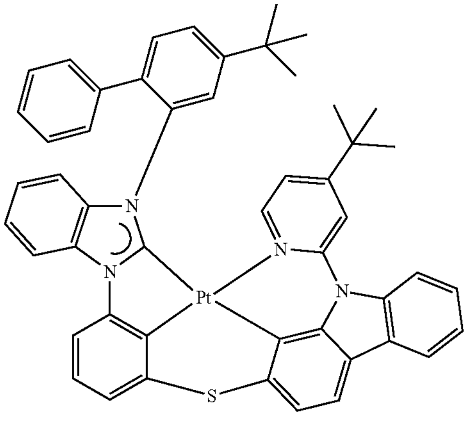
77
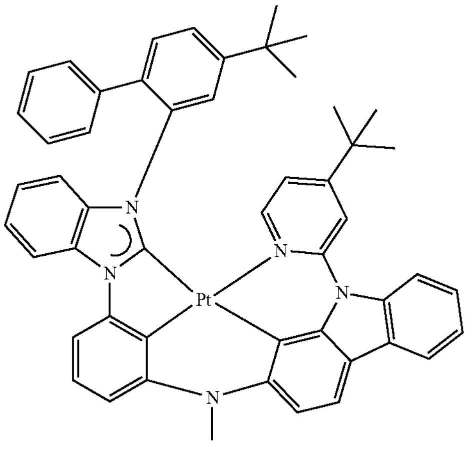
-continued
78
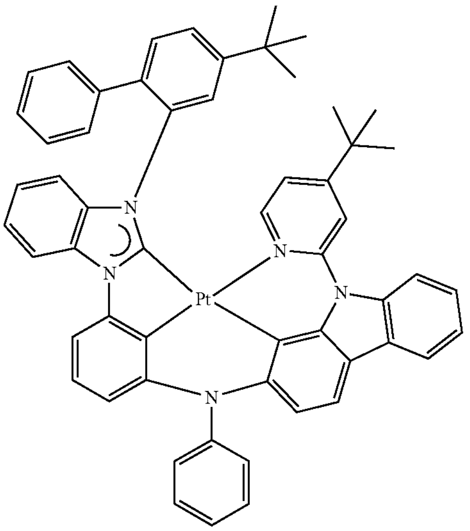
79
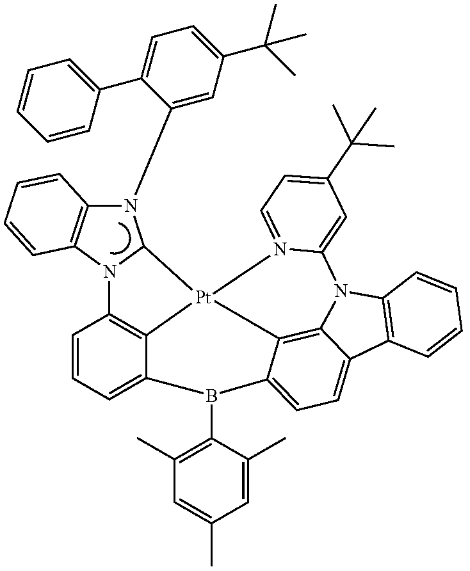
80
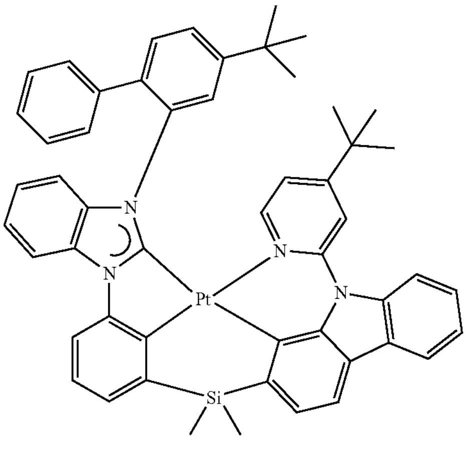

81
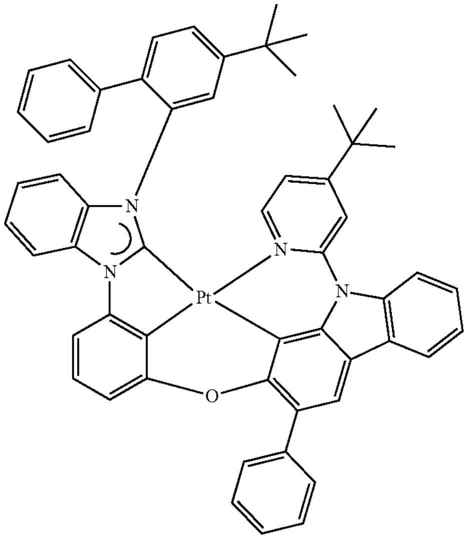
82
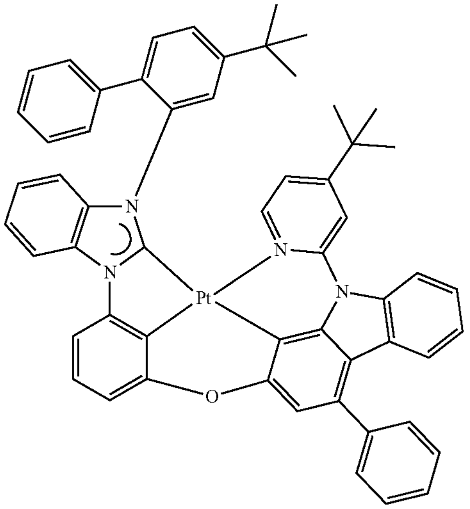
83
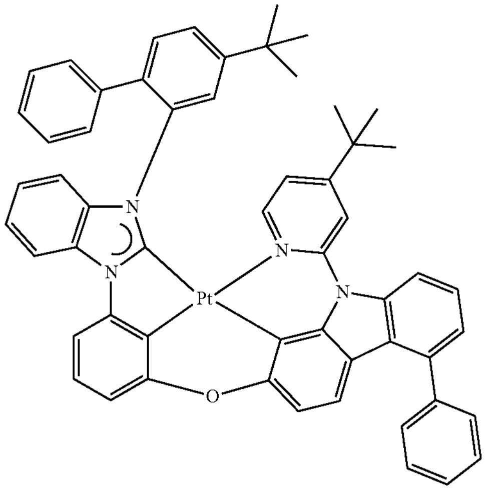
84
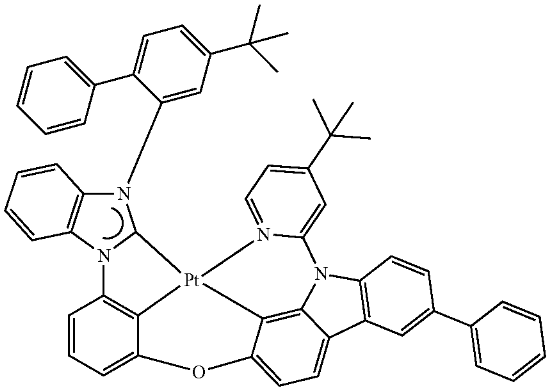
85
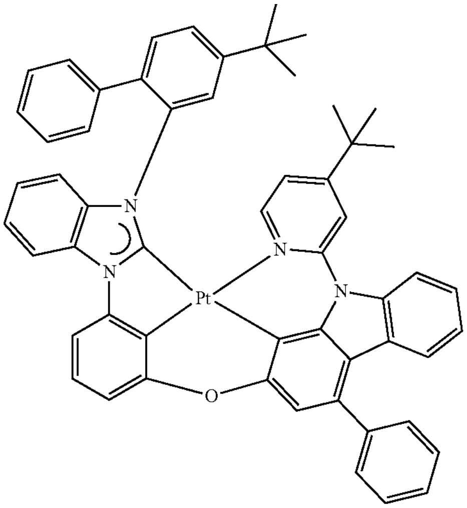
86
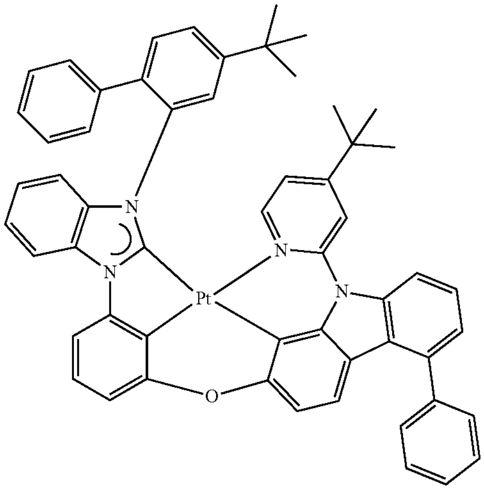

-continued
87
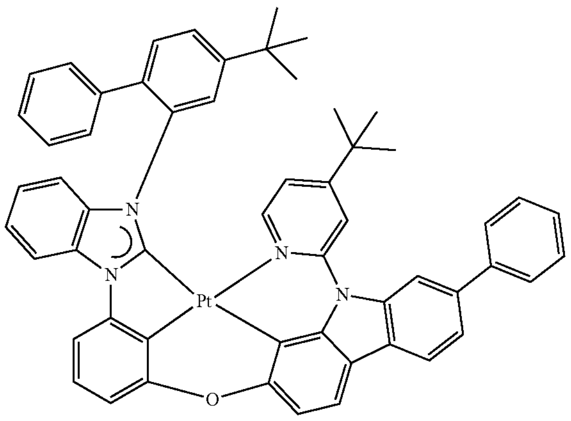
88
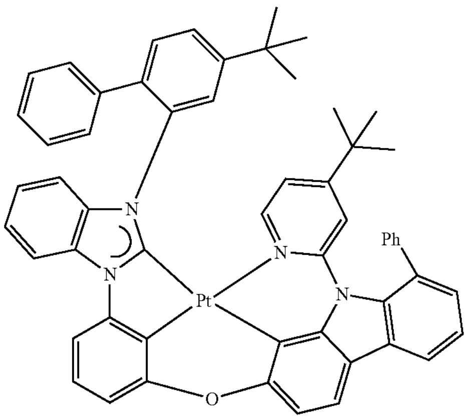
89
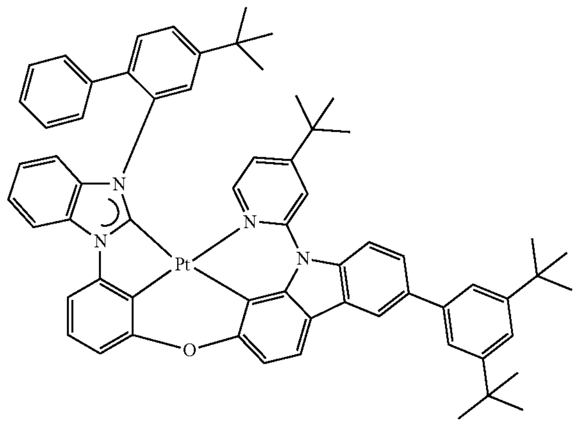
-continued
90
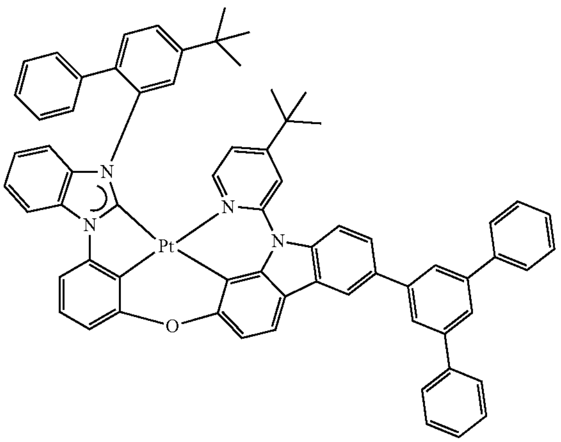
91
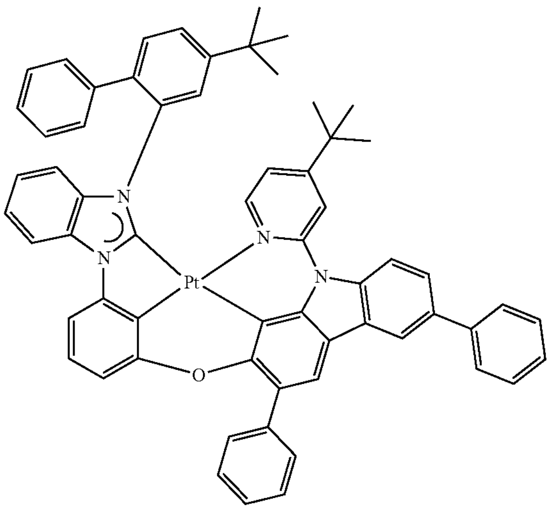
92
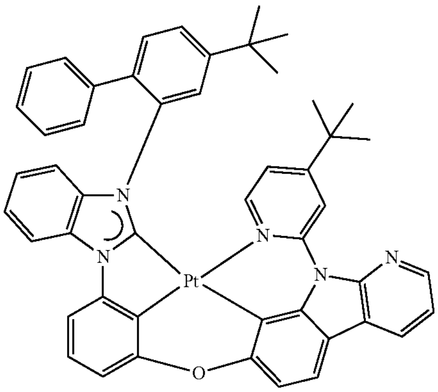

-continued
93
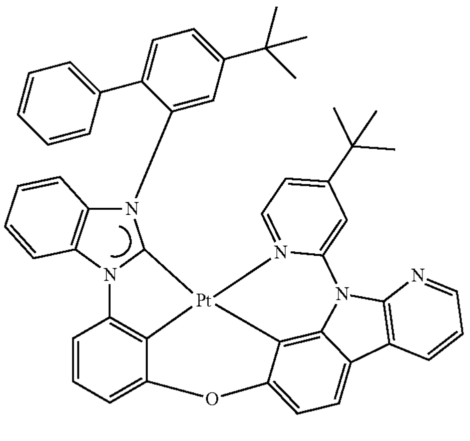
94
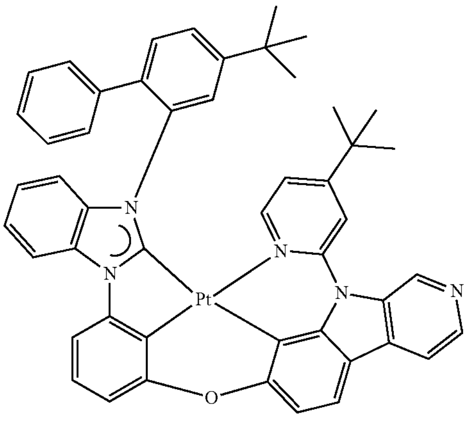
95
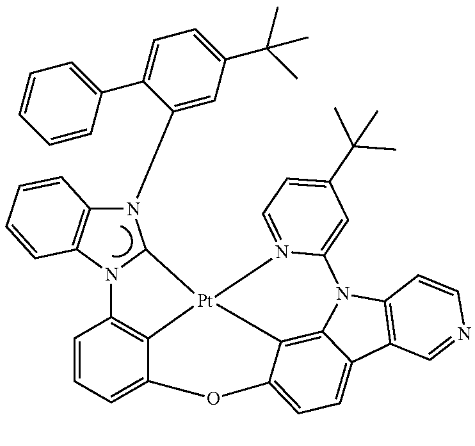
-continued
96
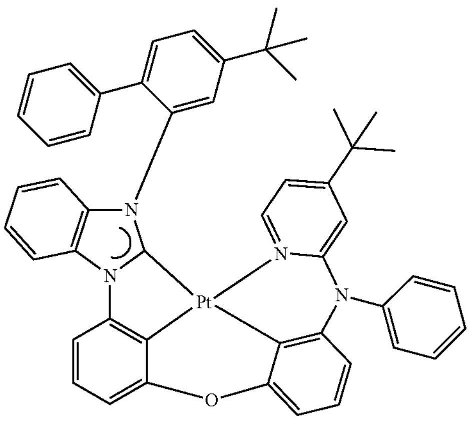
97
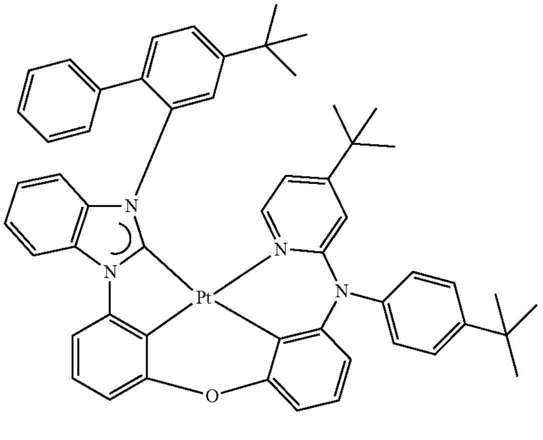
98
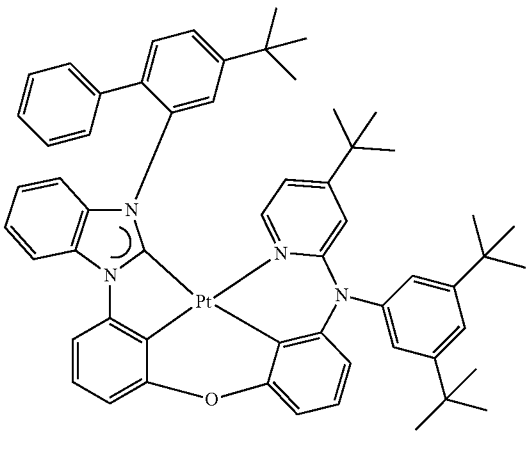

-continued
99
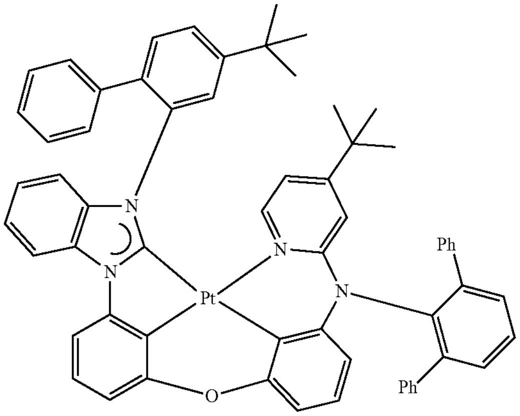
100
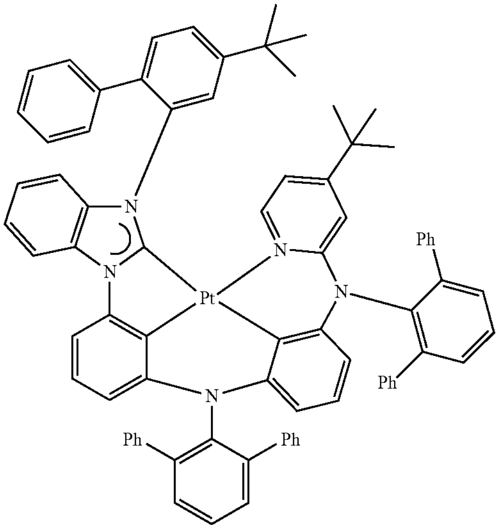
101
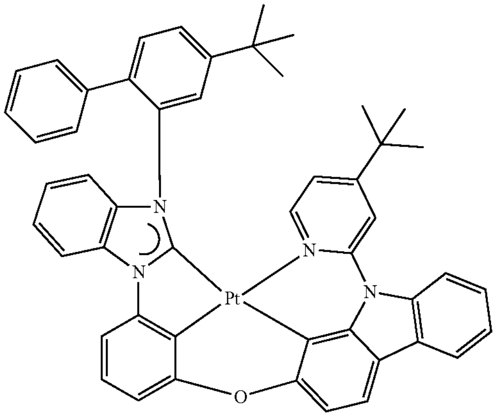
-continued
102
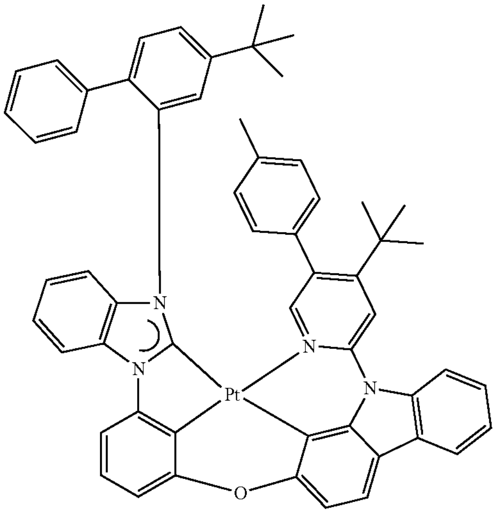
103
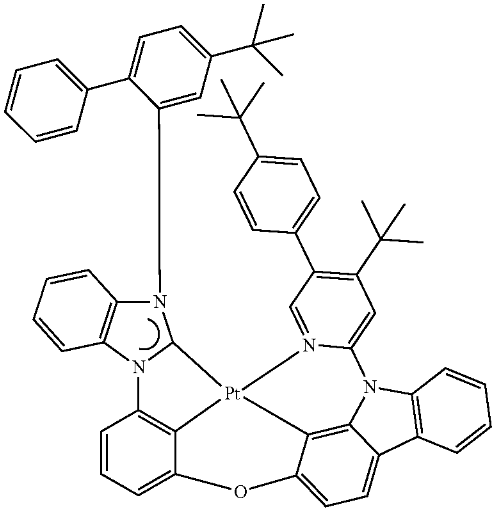
104
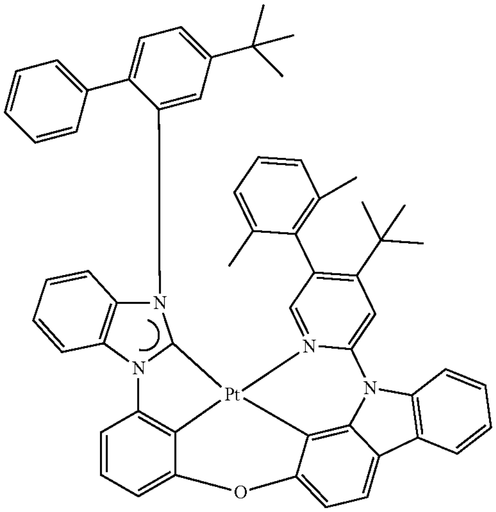

-continued
105
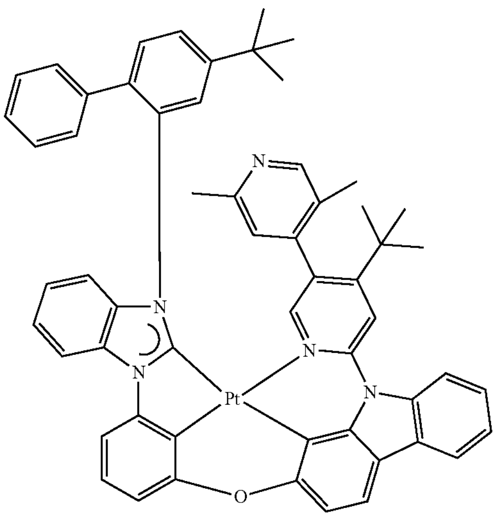
106
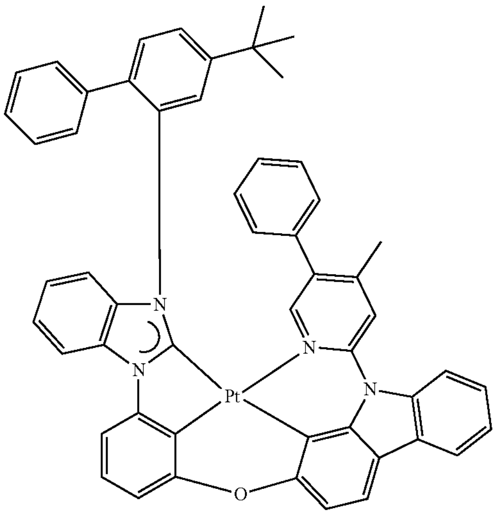
107
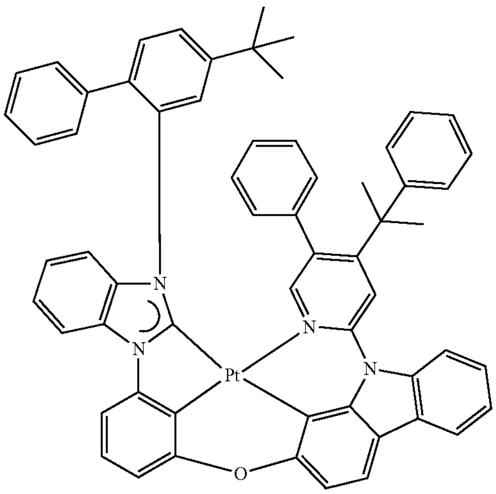
108
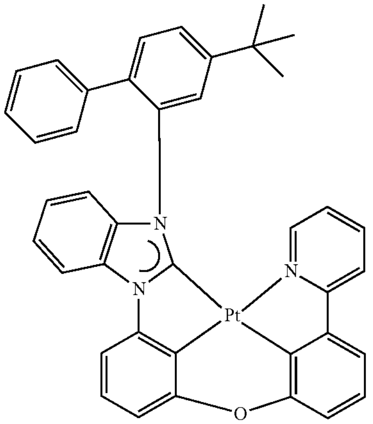
109
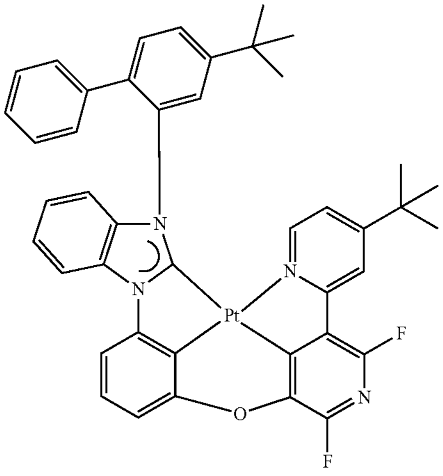
110
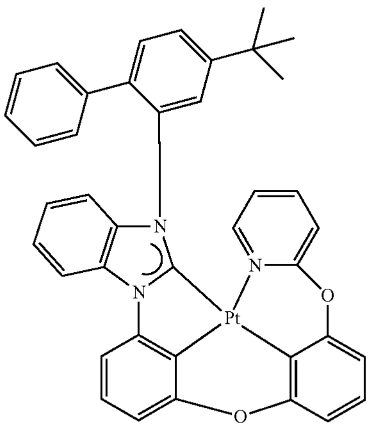

-continued
111
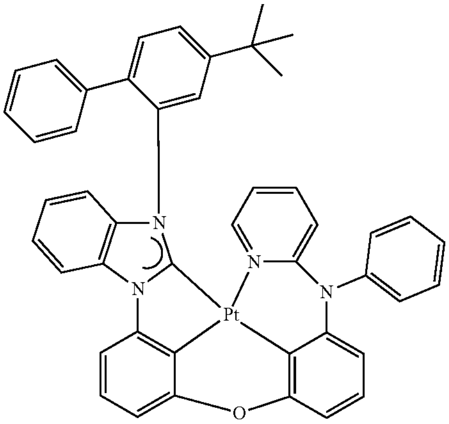
112
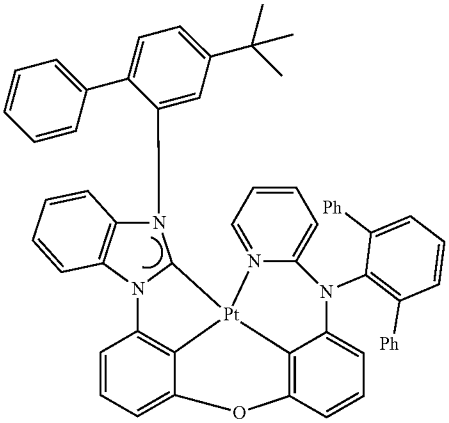
113
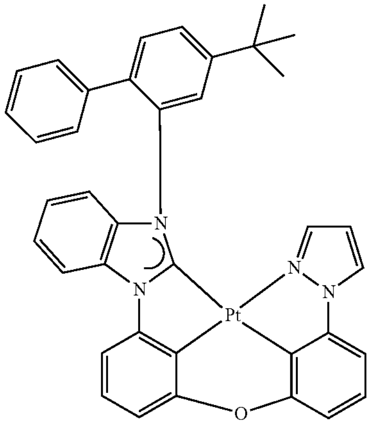
-continued
114
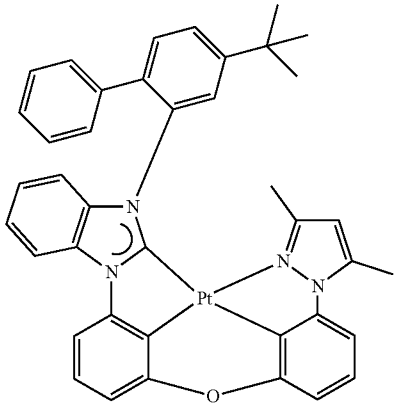
115
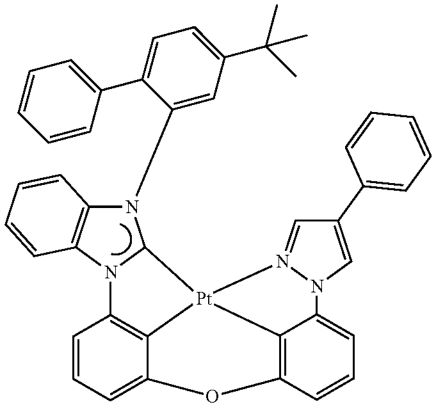
116
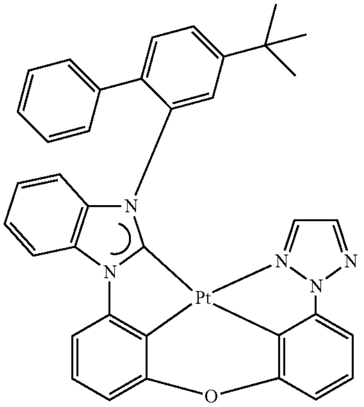
117
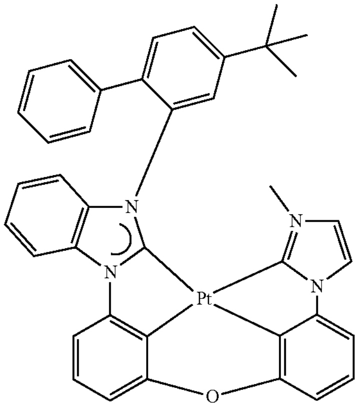

-continued
118
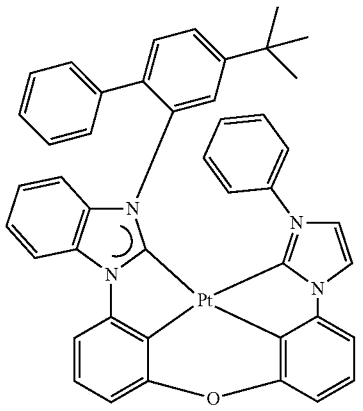
119
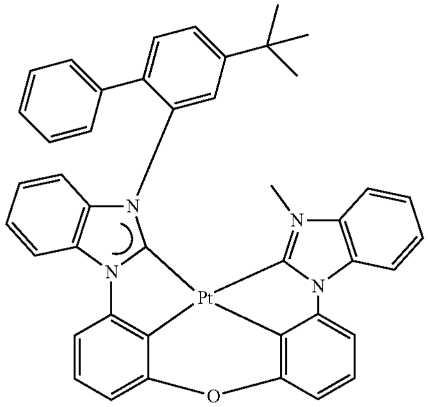
120
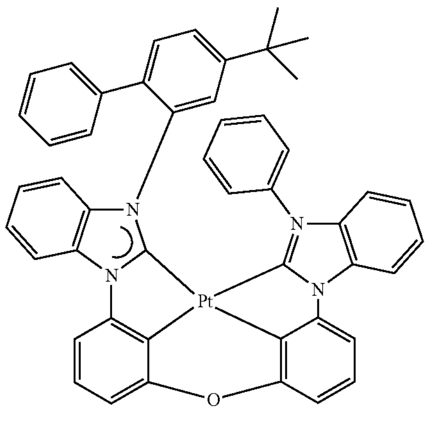
-continued
121
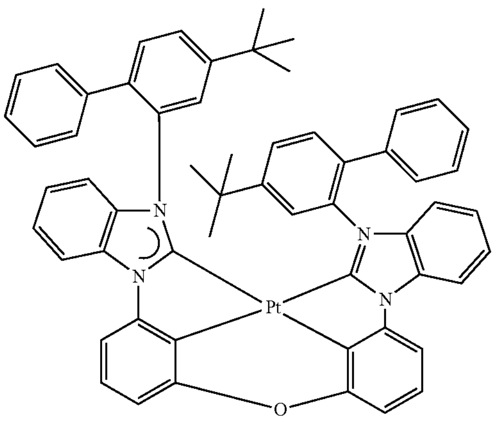
122
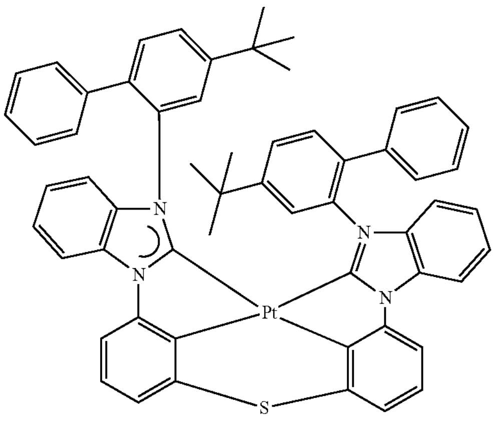
123
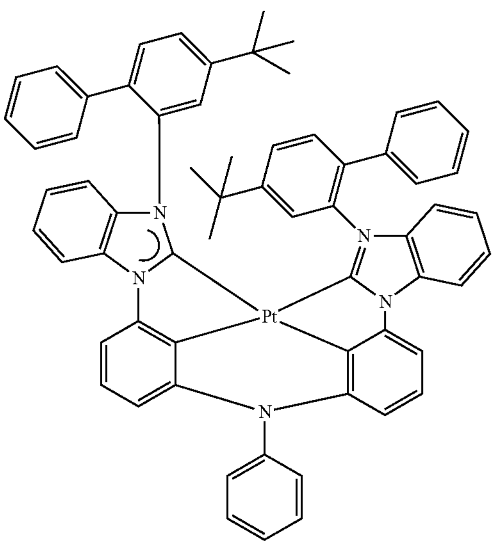

-continued
124
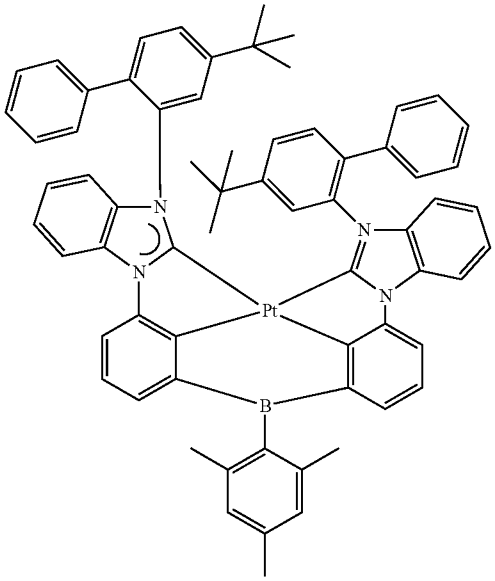
125
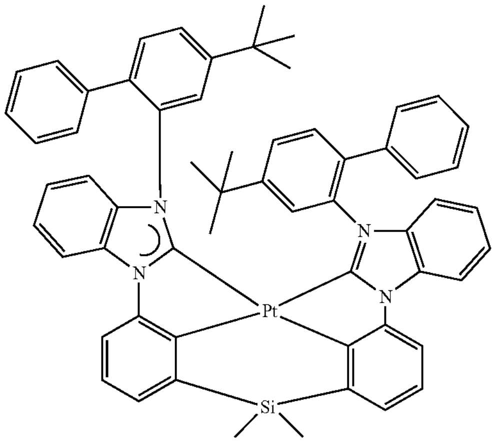
126
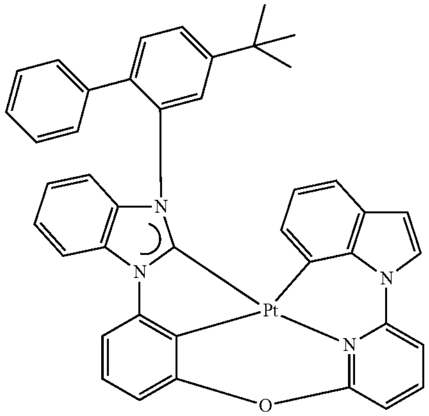
-continued
127
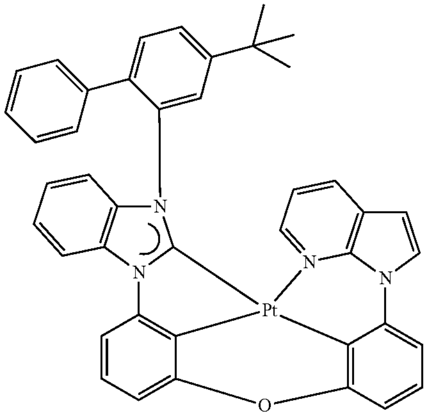
128
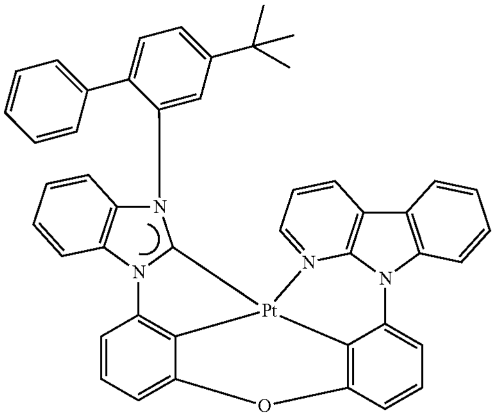
129
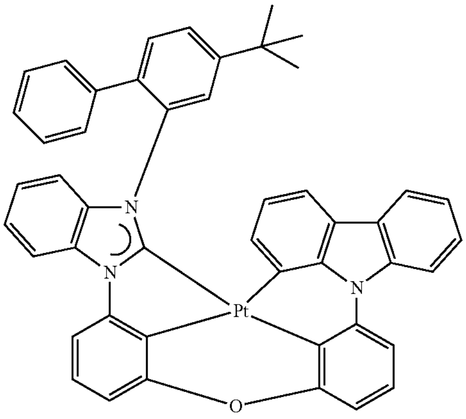

-continued
130
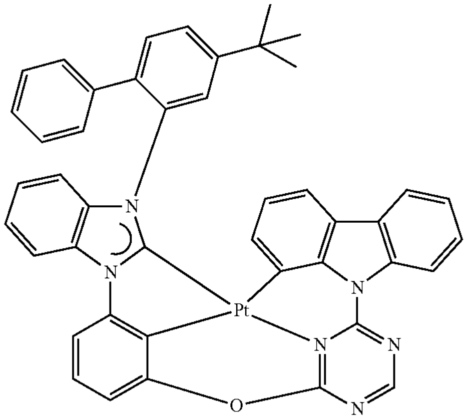
131
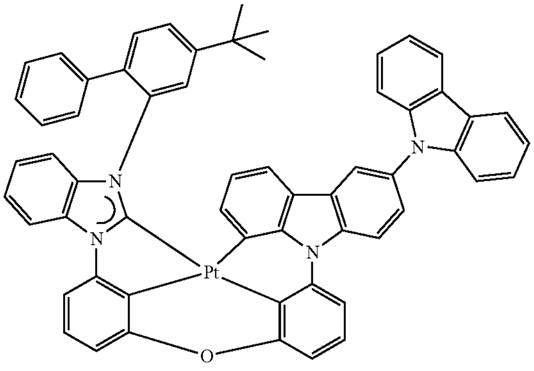
132
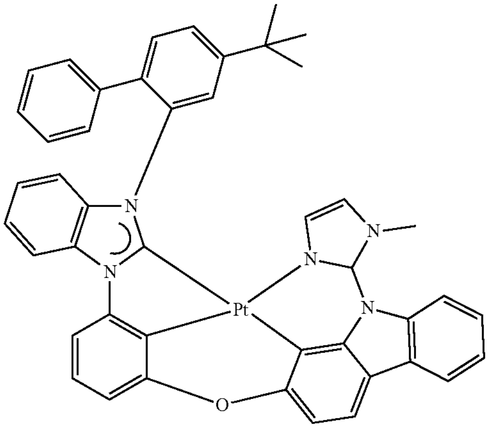
-continued
133
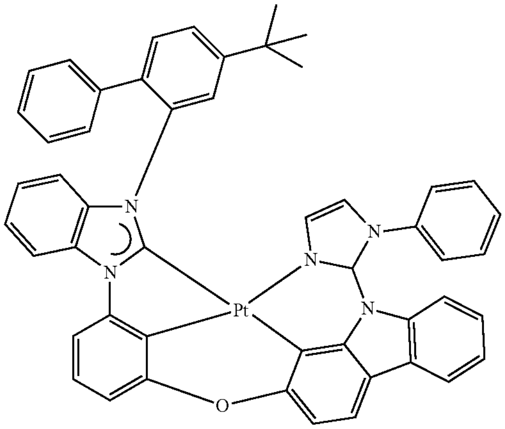
134
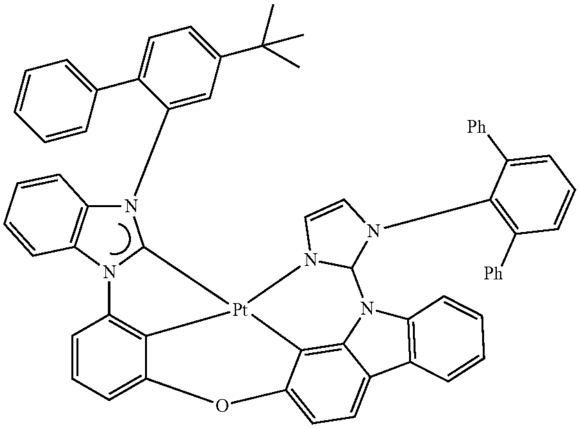
135
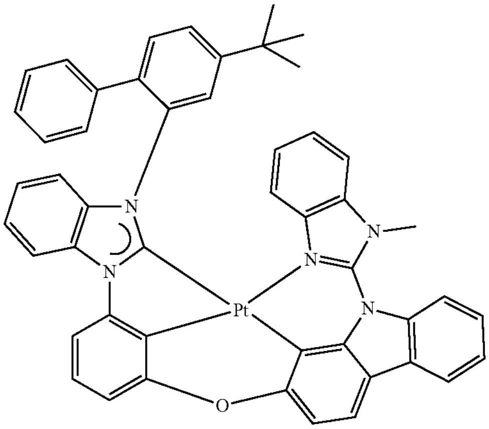

-continued
136
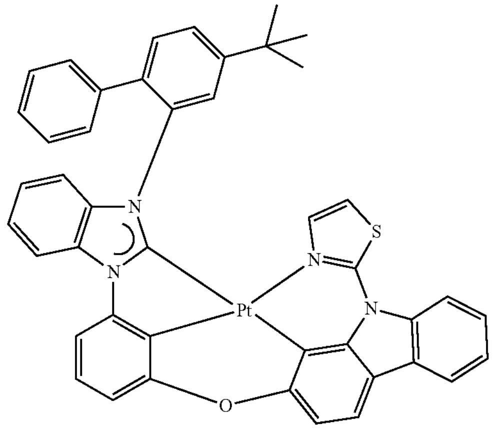
137
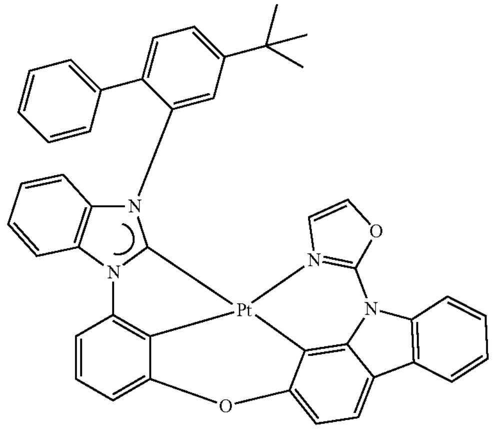
138
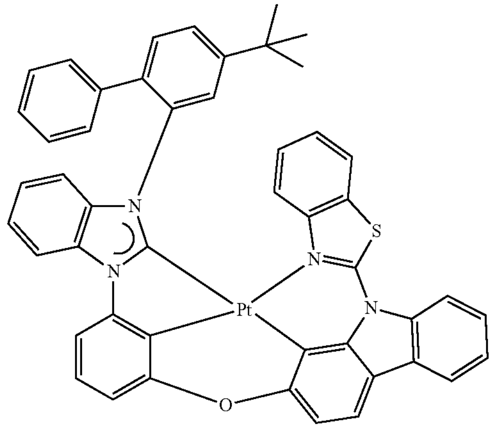
-continued
139
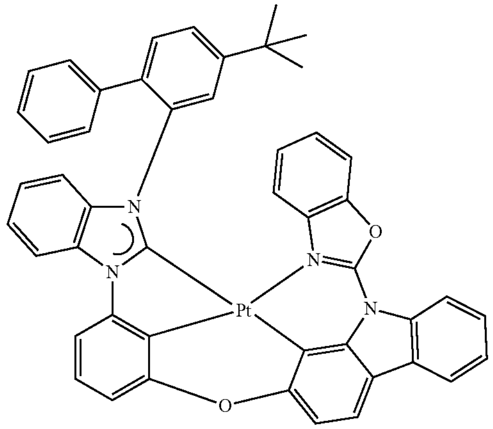
140
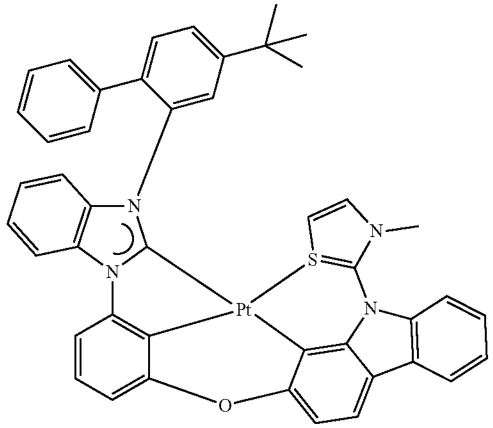
141
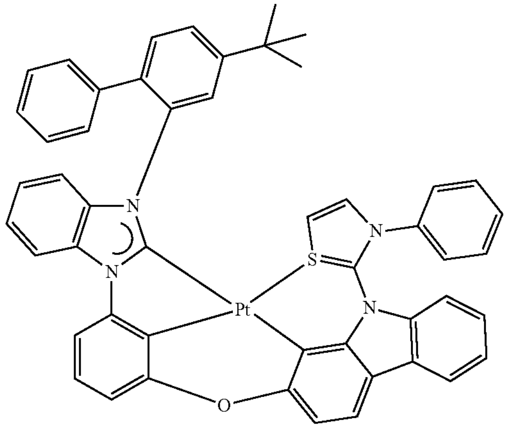

-continued
142
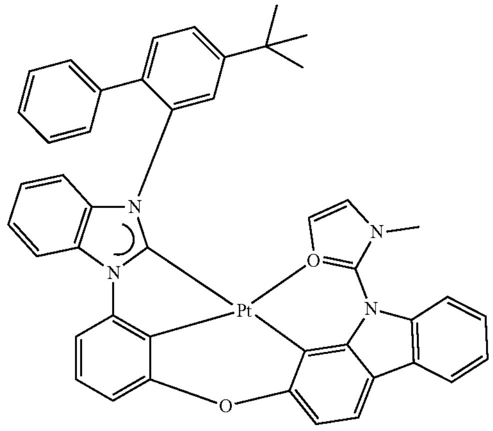
143
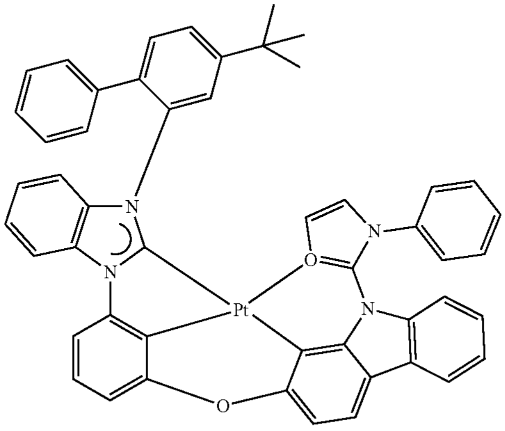
144
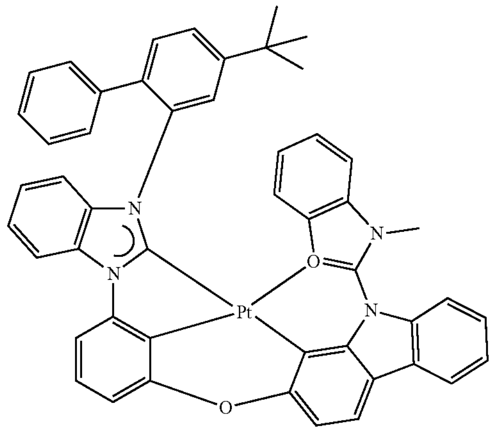
-continued
145
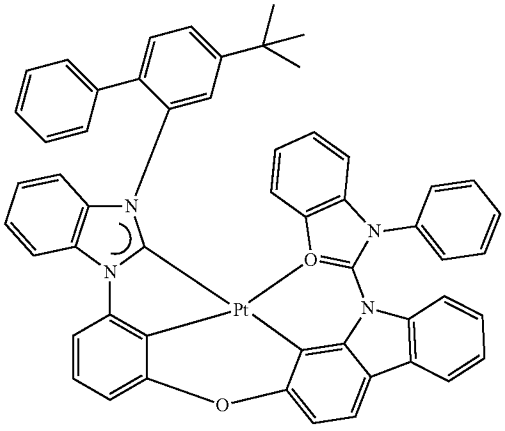
146
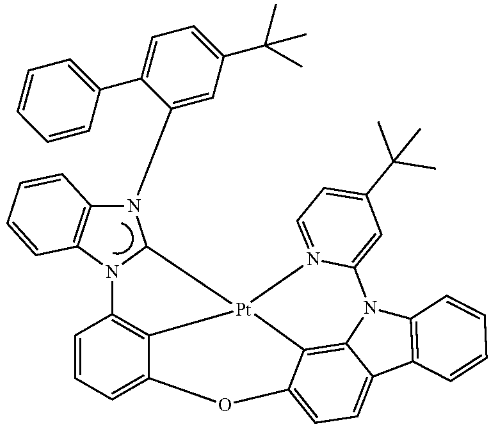

-continued
147
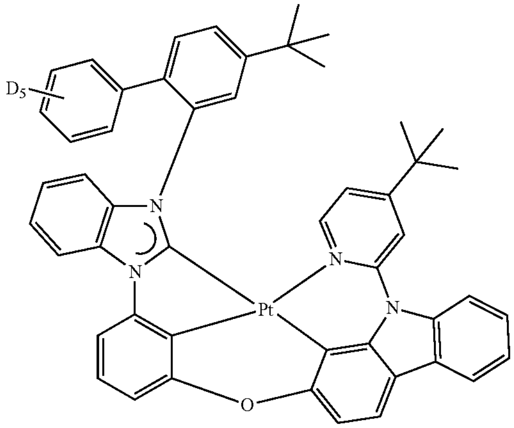
148
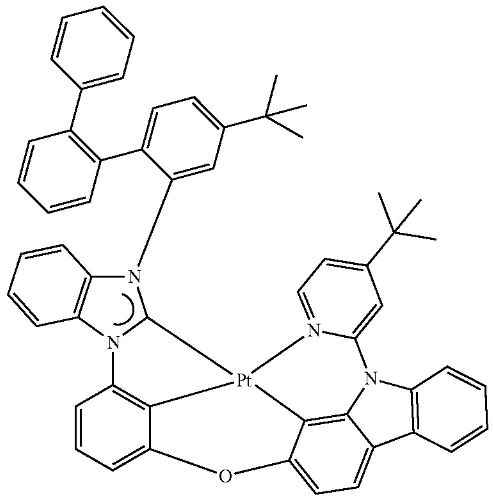
-continued
149
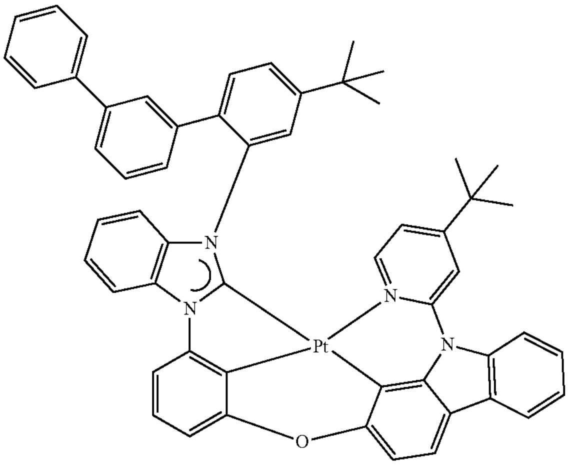
150
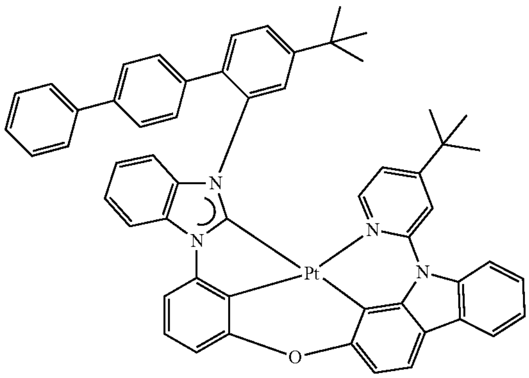
wherein in Compounds 1 to 150,
$D_5$ represents substitution with five deuterium atoms, and Ph is a phenyl group.
* * * * *